(12) United States Patent
De Brabander et al.

(10) Patent No.: US 10,082,496 B2
(45) Date of Patent: Sep. 25, 2018

(54) TARGETING EMOPAMIL BINDING PROTEIN (EBP) WITH SMALL MOLECULES THAT INDUCE AN ABNORMAL FEEDBACK RESPONSE BY LOWERING ENDOGENOUS CHOLESTEROL BIOSYNTHESIS

(71) Applicant: Board of Regents of the University of Texas System, Austin, TX (US)

(72) Inventors: Jef De Brabander, Flower Mound, TX (US); Jerry W. Shay, Dallas, TX (US); Wentian Wang, Irving, TX (US); Deepak Nijhawan, Dallas, TX (US); Pano Theodoropoulos, Dallas, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 15/201,667

(22) Filed: Jul. 5, 2016

(65) Prior Publication Data

US 2016/0313302 A1    Oct. 27, 2016

Related U.S. Application Data

(63) Continuation-in-part of application No. 14/482,659, filed on Sep. 10, 2014.

(60) Provisional application No. 62/193,019, filed on Jul. 15, 2015.

(51) Int. Cl.

| | |
|---|---|
| *G01N 33/50* | (2006.01) |
| *A61K 31/4545* | (2006.01) |
| *A61K 31/454* | (2006.01) |
| *A61K 31/496* | (2006.01) |
| *A61K 31/4725* | (2006.01) |
| *A61K 31/635* | (2006.01) |
| *A61K 31/5377* | (2006.01) |
| *A61K 31/655* | (2006.01) |
| *A61K 31/513* | (2006.01) |
| *A61K 31/55* | (2006.01) |
| *C07D 401/14* | (2006.01) |
| *C07D 405/14* | (2006.01) |
| *C07D 413/14* | (2006.01) |
| *C07D 413/04* | (2006.01) |
| *C07D 417/14* | (2006.01) |
| *C07D 453/02* | (2006.01) |
| *C07D 211/96* | (2006.01) |
| *G01N 33/48* | (2006.01) |

(52) U.S. Cl.
CPC ........ *G01N 33/5011* (2013.01); *A61K 31/454* (2013.01); *A61K 31/4545* (2013.01); *A61K 31/4725* (2013.01); *A61K 31/496* (2013.01); *A61K 31/513* (2013.01); *A61K 31/5377* (2013.01); *A61K 31/55* (2013.01); *A61K 31/635* (2013.01); *A61K 31/655* (2013.01); *C07D 211/96* (2013.01); *C07D 401/14* (2013.01); *C07D 405/14* (2013.01); *C07D 413/04* (2013.01); *C07D 413/14* (2013.01); *C07D 417/14* (2013.01); *C07D 453/02* (2013.01); *G01N 33/48* (2013.01); *G01N 2333/99* (2013.01)

(58) Field of Classification Search
CPC .................................................. G01N 33/5011
USPC ....................................................... 514/316
See application file for complete search history.

(56) References Cited

U.S. PATENT DOCUMENTS

| | | | |
|---|---|---|---|
| 4,105,027 | A | 8/1978 | Lundquist |
| 4,192,309 | A | 3/1980 | Poulsen |
| 4,227,522 | A | 10/1980 | Carris |
| 4,627,432 | A | 12/1986 | Newell et al. |
| 4,778,054 | A | 10/1988 | Newell et al. |
| 4,798,897 | A | 1/1989 | Hidaka et al. |
| 4,811,731 | A | 3/1989 | Newell et al. |
| 5,035,237 | A | 7/1991 | Newell et al. |
| 6,921,527 | B2 | 7/2005 | Platz et al. |
| 8,603,465 | B1 | 12/2013 | Yao |
| 8,642,660 | B2 | 2/2014 | Goldfarb |
| 2006/0035884 | A1 | 2/2006 | Neitzel et al. |
| 2010/0068708 | A1 | 3/2010 | Hood et al. |
| 2010/0197693 | A1 | 8/2010 | Zhang et al. |
| 2011/0076282 | A1 | 3/2011 | Ben-Neriah et al. |
| 2013/0330761 | A1 | 12/2013 | Laing et al. |

FOREIGN PATENT DOCUMENTS

| | | |
|---|---|---|
| WO | 199116038 A1 | 10/1991 |
| WO | 2013/119950 A2 * | 8/2013 |
| WO | 2015038644 A3 | 5/2015 |

OTHER PUBLICATIONS

Bae et al., Biochem. J. (2001), vol. 353, pp. 689-699.*
Tang et al., Clin. Sc., Lond. (2013), vol. 124(11), pp. 651-662.*
Acton, S. et al, "Identification of scavenger receptor SR-B1 as a high density lipoprotein receptor," Science 271: 518 (1996).
Bach, TJ, "Some new aspects of isoprenoid biosynthesis in plants—a review," Lipids 30: 191-202 (1995).
Baranowski, M., "Biological role of liver X receptors," J. Physiol. Pharmacology. 59 Suppl. 7: 31-55 (2008).
Berthois, Y. et al., "SR31747A is a sigma receptor ligand exhibiting antitumoural activity both in vitro and in vivo," Br. J. Cancer 88: 438-46 (2003).
Bhatia, B. et al, "Sonic hedgehog signaling and malignant transformation of the cerebellar granule neuron precursor cells," Oncogene 30(4): 410-22 (2011).
Bjorkhem, I., "Do oxysterols control choleseterol homeostasis," J. Clin. Invest. 110: 725-30 (2002).

(Continued)

*Primary Examiner* — Taofiq A Solola
(74) *Attorney, Agent, or Firm* — DLA Piper LLP (US)

(57) ABSTRACT

The described invention provides methods for targeting emopamil binding protein (EBP) with small molecules that induce an abnormal feedback response by lowering endogenous cholesterol biosynthesis.

19 Claims, 30 Drawing Sheets

(56) References Cited

OTHER PUBLICATIONS

Brown MI et al, A macrophage receptor for apolipoprotein B48: cloning, expression and atherosclerosis, Proc. Natl Acad. Sci. USA 97: 7488 (2000).
Brown, MS & Goldstein, JL, "The SREBP pathway: regulation of cholesterol metabolism by proteolysis of a membrane-bound transcription factor," Cell 89: 331-40 (1997).
Brown, MS and Goldstein, JL, "A proteolytic pathway that controls the cholesterol content of membranes, cells and blood,"Proc. Natl Acad. Sci. USA 96: 11041-48 (1999).
Burg, JS and Espenshade, PJ,"Regulation of HMG-CoA reductase in mammals and yeast," Prog. Lipid Res. 50: 403-410 (2011).
Cayuso, J. and Marti, E.; Morphogens in motion: Growth control of the neural tube; Journal of Neurobiology, 64:376-387 (2005).
Chen, W. et al, "Preferential ATP-binding cassette transporter A1-mediated cholesterol efflux from late endosomes/lysosomes," J. Biol. Chem. 276: 43564-69 (2001).
Cruz, PMR, et al, "The role of cholesterol metabolism and cholesterol transport in carcinogenesis: a review of scientific findings, relevant to future cancer therapeutics," Frontiers in Pharmacol. 4(119): doi:10.3369/phar.2013.00119.
Czarnecka, H. and Yokoyama, S., "Regulation of cellular cholesterol efflux by lecithin: cholesterol acyltransferase reaction through nonspecific lipid exchange," J. Biol. Chem. 271: 1023-27 (1996).
Daimiel, LA, et al, "Promoter analysis of the DHCR24 (3?-hydroxysterol ?24-reductase) gene: characterization of SREBP (sterol-regulatory element-binding-protein)-mediated activation," Biosci. Rep. (2013)/art:e000/doi 10.1042/BSR20120095.
Dang, H. et al, "Suppression of 2,3-oxidosqualene cyclase by high fat diet contributes to liver X receptor-?-mediated improvement of hepatic lipid profile," J. Biol. Chem. 284: 6218-26 (2009).
De La Grange, P., et al, "A new advance in alternative splicing databases from catalogue to detailed analysis of regulation of expression and function of human alternative splicing variants," BMC Bioinformatics 8: 180 (2007).
De La Llera-Moya, M. et al, "Scavenger receptor Bl (SR-B1) mediates free cholesterol flux independently of HDL tethering to the cell surface," J. Lipid Res. 40: 575-80 (1999).
De Man, FH et al, "Lipolysis of very low density lipoproteins by heparin sulfate proteoglycan-bound lipoprotein lipase," J. Lipid Res. 38: 2465 (1997).
De Medina, P. et al, "Dendrogenin A arises from cholesterol and histamine metabolism and shows cell differentiation and anti-tumour properties," Nature Communic. 4: 1840 (2013).
De Medina, P. et al, "Identification and pharmacological characterization of choleseterol-5,6-epoxide hydrolase as a target for tamoxifen and AEBS ligands," Proc. Natl. Acad. Sci. USA 107: 13520-5 (2010).
De Medina, P. et al, "Synthesis of new alkylaminooxysterols with potent cell differentiating activities: identification of leads for the treatment of cancer and neurodegenerative diseases," J. Med. Chem. 52: 7765-77 (2009).
Debose-Boyd, R. A. "Feedback Regulation of Cholesterol Synthesis: Sterol-accelerated ubiquitination and degradation of HMG CoA Reductase," Cell Res. 18 (6): 609-21 (2008).
Denis, M. et al, "ATP-binding cassette A-1-mediated lipidation of apolipoprotein A-1 occurs at the plasma membrane and not in the endocytic compartments," J. Biol. Chem. 283: 16178-186 (2008).
Dunlop, M. G., et al; "Common variation near CDKN1A, POLD3 and SHROOM2 influences colorectal cancer risk", Nature Genetics 44, 770-776 (2012).
Edwards, PA et al, "Purification and properties of rat liver 3-hydroxy-3-methylglutaryl coenzyme A reductase," Biochim. Biophys. Acta 574: 123-35 (1979).
Ehrenreiter, K., et al; "Raf-1 Addiction in Ras-Induced Skin Carcinogenesis", Cancer Cell 16, 149-160 (2009).
Ehrenreiter, K., et al; "Raf-1 regulates Rho signaling and cell migration"; J. Cell Biology; vol. 168, 955-964 (2005).
Elson, CE and Quereshi, AA, "Coupling the choleseterol- and tumor-suppressive actions of palm oil to the impact of its minor constituents on 3-hydroxy-3-methylglutaryl coenzyme A reductase activity," Prostaglandins Leukot. Essent. Fatty Acids 52: 205-207 (1995).
Endo, A., "A historical perspective on the discovery of statins," Proc. Jpn Acad, Ser. B Phys. Biol. Sci 86(5): 484-93 (2010).
Farber, M. J., et al; "Shroom2 regulates contractility to control endothelial morphogenesis"; Molecular Biology of the Cell; vol. 22, 795-805 (2011).
Faulkner, LE, et al, "An analysis of the role ofa retroendocytosis pathway in ABCA1-mediated cholesterol efflux from macrophages," J. Lipid Res. 49: 1322-32 (2008).
Fearon, E.R. & Vogelstein, B., A genetic model for colorectal tumorigenesis. Cell 61, 759-767 (1990).
Fernandez-Hernando, et al, "MicroRNAs in metabolic disease," Arterioscl. Thromb. Vasc. Biol. 33: 178-85 (2013).
Ferretti, R., et al, "Morgana/chp-1, a ROCK Inhibitor Involved in Centrosome Duplication and Tumorigenesis"; Developmental Cell 18, 486-495 (2010).
Freed-Pastor, WA, et al, "Mutant p53 disrupts mammary tissue architecture via the mevalonate pathway," Cell 148: 244-58 (2012).
Gabitova, L. et al., "Molecular Pathways: Sterols and receptor signaling in Cancer," Clin. Cancer Res. 19(23): 5344-50 (2013).
Garcia-Mata, R. et al. "The 'invisible hand': regulation of Rho GTPases by RHOGDIs." Nature Reviews Molecular Cell Biology. (2011) 12:493-504; at 494).
Gaylor, JL, "Membrane bound enzymes of cholesterol synthesis from lanosterol," Biochem. Biophys. Res. Communic., 292: 1139-46 (2002).
Gill, S. et al, "Cholesterol-dependent degradation of squalene monooxygenase, a control point in cholesterol synthesis beyond HMG-CoA reductase," Cell Metab. 13: 260-73 (2011).
Gillotte, KL, et al, "Removal of cellular cholesterol by pre-?-HDL involves plasma membrane microsolubilization," J. Lipid Res. 39: 1918-28 (1998).
Gong, Y. et al, "Sterol-regulated ubiquitination and degradation of Insig-1 creates a convergent mechanism for feedback control of cholesterol synthesis and uptake," Cell Metab. 3: 15-24 (2006).
Gonzalez, R. et al, "Two major regulatory steps in cholesterol synthesis by human renal cancer cells," Arch. Biochem. Biophys. 196: 574-80 (1979).
Gorin, A. et al., "Regulation of cholesterol biosynthesis and cancer signaling," Curr. Op. Pharmcol. 12(6) 710-16 (2012).
Green, R. A. and Kaplan, K. B., "Chromosome instability in colorectal tumor cells is associated with defects in -microtubule plus-end attachments caused by a dominant mutation in APC" Journal of Cell Biology, 163:949-961 (2003).
Greenwood, J et al, Statin therapy and autoimmune disease: from protein prenylation to immunomodulation, Nat. Rev. Immunol. 6: 358-70 (2006).
Gruenbacher, G. et al., "CD56+ human blood dendritic cells effectively promote TH1-type gammadelta T cell responses," Blood 114: 4422-31 (2009).
Gruenbacher, G. et al., "IL-2 costimulation enables statin-mediated activation of human NK cells, preferentially through a mechanism involving CD56+ dendritic cells," Cancer Res. 70: 9611-20 (2010).
Gu, X et al, "Scavenger receptor class B, type 1-mediated [3H]cholesterol efflux to high and alow density lipoproteins is dependent on lipoprotein binding to the receptor," J. Biol. Chem. 275: 29993-30001 (2000).
Guo, D et al, "Targeting SREBP-1 driven lipid metabolism to treat cancer," Curr. Pharm Des. 20(15): 2619-26 (2014).
Uddin, S. et al, "High prevalence of fatty acid synthase expression in colorectal cancers in Middle Eastern patients and its potential role as a therapeutic target," Am. J. Gastroenterol. 104(7): 1790-1801 (2009).
Vaughan, AM and Oram, JF, "ABCG1 redistributes cell cholesterol to domains removable by high density lipoprotein but not by lipid-depleted apolipoproteins," J. Biol. Chem. 280: 20150-57 (2005).
Wang, N. et al, "ATP-binding cassette transporters G1 and G4 mediate cellular cholesterol efflux to high-density lipoproteins," Proc. Natl Acad. Sci. USA 101: 9774-79 (2004).
Wang, Y. et al, "Regulation of cholesterologenesis by the oxysterol receptor, LXR?," J. Biol. Chem. 283: 26332-339 (2008).

(56) References Cited

OTHER PUBLICATIONS

Wang, Y., et al, "ROCK Isoform Regulation of Myosin Phosphatase and Contractility in Vascular Smooth Muscle Cells", Circ. Res. vol. 104, 531-540 (2009).
Ward Y., et al., The GTP binding proteins Gem and Rad are negative regulators of the Rho-Rho kinase pathway, J. Cell Biol. 157(2): 291-302 (2002).
Wheeler, A.P., Ridley, A.J., "Why three Rho proteins? RhoA, RhoB, RhoC and cell motility," Exp. Cell Res. 301(1): 43-49 (2004).
Williams, DL et al, "Binding and cross-linking studies show that scavenger receptor B1 interacts with multiple sites in apolipoprotein A-1 and identify the class A amphipathic ? helix as a recognition motif," J. Biol. Chem. 275: 18897-18904 (2000).
Williams, DL, et al, "Scavenger receptor B1 and cholesterol trafficking," Curr. Opin. Lipidol. 10: 329-39 (1999).
Williams,MT, et al, "Investigation of the rate-determining microsomal reaction of cholesterol biosynthesis from lanosterol in Morris hepatomas and liver," Cancer Res. 37 : 1377-83 (1977).
Willner, E. et al, Deficiency of acyl CoA:cholesterol aceyltransferase 2 prevents atherosclerosis in apolipoprotein E-deficient mice., Proc. Natl Acad. Sci. USA 100: 1262 (2003).
Wong, J. et al, "Endogenous 24(S),25-epoxycholesterol fine-tunes acute control of cellular cholesterol homeostasis," J. Biol. Chem. 283: 700-707 (2008).
Wong, WW et al, "HMG-CoA reductase inhibitors and the malignant cell: the statin family of drugs as triggers of tumor-specific apoptosis," Leukemia 16: 508-19 (2002).
Xu, J. et al, "Choleserol trafficking is required for mTPOR activation in endothelial cells," Proc. Natl Acad. Sci. USA 107(10): 4764-69 (2010).
Yabe, D. et al, "Insig-2, a second endoplasmic reticulum protein that binds SCAP and blocks export of sterol regulatory element-binding proteins," Proc. Natl. Acad. Sci. USA 99: 12753-758 (2002).
Yabe, D. et al, "Three mutations in sterol-sensing domain of SCAP block interaction with insig and render SREBP cleavage insensitive to sterols," Proc.Natl. Acad. Sci. USA 99: 16672-77 (2002).
Yancey, PG, et al, "High density lipoprotein phospholipid compositon is a major determinant of the bi-directional flux and net movement of cellular free cholesterol mediated by scavenger receptor B1," J. Biol. Chem. 275: 36596-36604 (2000).
Yang, C. et al, "Sterol intermediates from choleseterol biosynthetic pathway as liver X receptor ligands," J. Biol. Chem.. 281: 27816-826 (2006).
Yang, T. et al, "Crucial step in cholesterol homeostasis: sterols promote binding of SCAP to INSIG-1, a membrane protein that facilitates retention of SREBPs in ER," Cell 110: 489-500 (2002).
Yoneda, A., et al; "A Collapsin Response Mediator Protein 2 Isoform Controls Myosin II-Mediated Cell Migration and Matrix Assembly by Trapping ROCK II"; Mol. Cell. Biol. 1788-1804 (2012).
Yoshioka, K. et al., "Overexpression of Small GTP-binding protein RhoA promotes Invasion of Tumor Cells," J. Cancer Res. 59: 2004-2010 (1999).
Zannis, V. et al, "Role of apoA-1, ABCA1, LCAT and SR-B1 in the biogenesis of HDL," J. Mol. Med. 84: 276-94 (2006).
Zerenturk, EJ et al, "The endogenous regulator 24(S),25-epoxycholesterol inhibits cholesterol synthesis at DHCR24 (Seladin-1)," Biochim. Biophys. Acta 1821: 1269-77 (2012).
Zerenturk, EJ, et al, "Sterols regulate 3?-hydroxysterol?24-reductase (DHCR24) via dual sterol regulatory elements: cooperative induction of key enzymes in lipid synthesis by sterol regulatory element binding proteins," Biochim. Et Biophys. Acta 1821 (10): 1350-60 (2012).
Zhu, J. et al, "Effects of FoxO4 overexpression on cholesterol biosynthesis, triacylglycerol accumulation, and glucose uptake," J. Lipid Res. 51: 1312-24 (2010).
Zhuang, L. et al, "Cholesterol targeting alters lipid raft composition and cell survival in prostate cancer cells and zenografts," J. Clin. Invest. 115: 959-68 (2005).
Zumbrunn, J., et al., "Binding of the adenomatous polyposis coli protein to microtubules increases microtubule stability and is regulated by GSK3b phosphorylation", Current Biology, 11:44-49, (2001).
Mueller, B.K. et al., "Rho Kinase, a promising drug target for neurological disorders." Nat Rev Mol Cell Bio.l 4(6): 387-398 (2005).
Munz, C. et al, "Dendritic cell maturation by innate lymphocytes: coordinated stimulation of innate and adaptive immunity," J. Exptl Med. 202: 203-7 (2005).
Nagahashi, M. et al, "Sphingosine-1-phosphate produced by sphingosine kinase 1 promotes breast cancer progression by stimulating angiogenesis and lymphangiogenesis," Cancer Res. 72(3): 726-35 (2012).
Nakanishi, M. et al "Multivalent control of 3-hydroxy-3-methylglutaryl coenzyme A reductase. Mevalonate-derived product inhibits translation of mRNA and accelerates degradation of enzyme," J. Biol. Chem. 263: 8929-37 (1988).
Nguyen, AD et al,"Hypoxyia stimulates degradation of 3-hydroxy-3-methylglutaryl-coenzyme A reductase through accumulation of lanosterol and hypoxia-inducible factor-mediated induction of Insigs," J. Biol. Chem. 282: 27436-446 (2007).
Nguyen-Vu, T. et al, "Liver x receptor ligands disrupt breast cancer cell proliferation through an E2F-mediated mechanism," Breast Cancer Res. 15: R51 (2013).
Niault, T., et al; "From autoinhibition to inhibition in trans: the Raf-1 regulatory domain inhibits Rok-a kinase activity", J. Cell Biol., vol. 187(3), 335-342 (2009).
Nimph, J, and Schneider, WJ, The VLDL receptor: an LDL receptor relative with eight ligand binding repeats, LR8. Atherosclerosis 141: 191-202 (1998).
Nishimura, T., et al; "Shroom3-mediated recruitment of Rho kinases to the apical cell junctions regulates epithelial and neuroepithelial planar remodeling", Development, 135, 1493-1502 (2008).
Nohturfft, A. et al, "A substitution in a single codon of SREBP cleavage-activating protein causes sterol resistance in three mutant Chinese hamster ovary cell lines," Proc. Natl Acad. Sci. USA 93: 13709-714 (1996).
Nohturfft, A. et al, "Sterols regulate processing of carbohydrate chains of wild-type SREBP cleavage-activating protein (SCAP), but not sterol-resistant mutants Y298C o D443N," Proc. Natl Acad. Sci. USA 95: 12848-853 (1998).
Mohturfft, A. et al., "Topology of SREBP cleavage-activating protein, a polytopic membrane protein with a sterol sensing domain," J. Biol. Chem. 273: 17243-250 (1998).
Oliverase, G. et al, "Novel anti-fatty acid synthase compounds with anti-cancer activity in Her2+ breast cancer," Ann. N.Y. Acad. Sci. 1210: 86-92 (2010).
Olson, M.F. "Applications for ROCK kinase inhibition" Curr Opin Cell Biol. 20(2): 242-248, at 242-243 (2008).
Paul, R. et al., "Both the immunosuppressant SR31747 and the antiestrogen tamoxifen bind to an emopamil-insensative site of Mammalian D8-D7 sterol isomerase," J. Pharmacol. Exptl Thera. 285(3): 1296-1302 (1998).
Pehkonen, P. et al., "Genome-wide landscape of liver X receptor chromatin binding and gene regulation in human macrophages," BMC Genomics 13: 50 (2012).
Peterson, TR et al, "DEPTOR is an mTOR inhibitor frequently overexpressed in multiple myeloma cells and required for their survival," Cell 137: 873-86 (2009).
Peterson, TR, et al, "mTOR complex I regulates lipin 1 localization to control the SREBP pathway," Cell 146: 408-20 (2011).
Phillips, MC, "Molecular Mechanisms of Cellular Cholesterol Efflux," J. Biol. Chem. 289 (35): 24020-29 (2014).
Phillips, MC, "New insights into the determination of HDL structure by apolipoproteins," J. Lipid Res. 54: 2034-48 (2013).
Piazzolla, D., et al; "Raf-1 sets the threshold of Fas sensitivity by modulating Rok-a signaling"; J. Cell Biol. 171, 1013-1022 (2005).
Pinner, S. and Sahai, E., "PDK1 regulates cancer cell motility by antagonising inhibition of ROCK1 by RhoE"; Mature Cell Biology 10(2), (2008).

(56) References Cited

OTHER PUBLICATIONS

Quazi, F and Molday, RS, "Differential phospholipid substrates and directional transport by ATP-binding cassette proteins ABCA, ABCA7, and ABCA4 and disease-causing mutants," J. Biol. Chem. 288: 34414-26 (2013).
Radhakrishnan, A. et al, "Direct binding of cholesterol to the purified membrane region of SCAP: Mechanism for a sterol-sensing domain," Mol. Cell 15: 259-68 (2004).
Radhakrishnan, A. et al, "From the Cover: Sterol-regulated transport of SREBPs from endoplasmic reticulum to Golgi: Oxysterols block transport by binding to Insig," Proc. Natl Acad. Sci. USA 104: 6511-18 (2007).
Rana, M. K. and Worthylake, R. A., "Novel Mechanism for Negatively Regulating Rho-Kinase (ROCK) Signaling through Coronin1B Protein in Neuregulin 1 (NRG-1)-induced Tumor Cell Motility", The Journal of Biological Chemistry, vol. 287, No. 26, 21836-21845, Jun. 22, 2012.
Ravid, T. et al, "The ubiquitin proteasome pathway mediates the regulated degradation of mammalian 3-hydroxy-3-methylglutaryl-Coenzyme A reductase," J. Biol. Chem. 275: 35840-47 (2000).
Riento, K. and Ridley, A.J., "ROCKs: multifunction kinases in cell behavior." Nat Rev Mol Cell Biol. 4:446-456 (2003).
Roitelman, J. and Simoni, RD, "Distinct sterol and nonsterol signals for the regulated degradation of 3-hyudroxy-3-methylglutaryl-CoA reductase," J. Biol. Chem. 267: 25264-273 (1992).
Rosenson, RS et al, "Cholesterol efflux and atheroprotection: advancing the concept of reverse cholesterol transport," Circulation 125: 1905-19 (2012).
Rothblat, GH and Phillips, MC, "High-density lipoprotein heterogeneity and function in reverse cholesterol transport," Curr. Opin. Lipidol. 21: 229-38 (2010).
Russell, DW, "Oxsterol biosynthetic enzymes," Biochim. Biophys. Acta—Molec. Cell Biol. Lipids 1529: 126-135 (2000).
Sabatini, DM, "mTOR and cancer: insights into a complex relationship," Nat. Rev. Cancer 6: 729-34 (2006).
Sankaranarayanan, S. et al., "Effects of acceptor composition and mechanism of ABCG1-mediated cellular free cholesterol efflux," J. Lipid Res. 50: 275-84 (2009).
Sawamura, T. et al, "An endothelial receptor for oxidized low-density lipoprotein," Nature 386: 73 (1997).
Schroepfer, GJ, Jr., "Oxysterols: modulators of cholesterol metabolism and other processes," Physiol. Rev. 80: 361-554 (2000).
Sever, N. et al, "Accelerated degradation of HMG CoA reductase mediated by binding of insig-1 to its sterol-sensing domain," Mol. Cell 11: 25-33 (2003).
Sever, N. et al, "Insig-dependent ubiquitination and degradation of mammalian 3-hydroxy-3-methylglutaryl CoA reductase stimulated by sterols and geranylgeraniol," J. Biol. Chem. 278: 52479-90 (2003).
Sharpe, LJ and Brown, AJ, "Controlling cholesterol synthesis beyond 3-hydroxy-3-methylglutaryl CoA reductase (HMGCR)," J. Biol. Chem. 288 (26): 18707-715 (2013).
Smith, JD et al, "ABCA1 mediates concurrent cholesterol and phospholipid efflux to apolipoprotein A-1," J. Lipid Res. 45: 635-44 (2004).
Song, BL et al, "Gp8, a membrane-anchored ubiquitin ligase, associates with Insig-1 and couples sterol-regulated ubiquitination to degradation of HMG CoA reductase," Mol. Cell 19: 829-40 (2005).
Song, BL, et al, "Insig-mediated degradation of HMG-CoA reductase stimulated by lanosterol, an intermediate in the synthesis of cholesterol," Cell Meta. 1: 179-89 (2005).
Spann, NJ et al, "Regulated accumulation of desmosterol integrates macrophage lipid metabolism and inflammatory responses," Cell 151: 138-52 (2012).
Spencer, TA, et al, "24(S),25-epoxycholesterol. Evidence consistent with a role in the regulation of hepatic cholestrogenesis," J. Biol. Chem. 260: 13391-94 (1985).
Steinman, RM, Banchereau, J., "Taking dendritic cells into medicine," Nature 449: 419-26 (2007).
Street, C.A. and Bryan, B.A. "Rho Kinase Proteins-Pleiotropic Modulators of Cell Survival and Apoptosis" Anticancer Res., 31(11): 3645-3657 (2011).
Sun LP et al, "From the Cover: Sterol-regulated transport of SREBPs from endoplasmic reticulum to Golgi: Insig renders sorting signal in Scap inaccessible to COPII proteins," Proc. Natl Acad. Sci. USA 104: 6519-26 (2007).
Tapash K. Ghosh et al. Transdermal and Topical Drug Delivery Systems, eds., 1997, pp. 249-297.
Thuahnai, ST, et al, "SR-B1-mediated cholesteryl ester selective uptake and efflux of unesterified cholesterol: influence of HDL size and structure," J. Biol. Chem. 279: 12448-455 (2004).
Thumher, M., et al, "Novel aspects of mevalonate pathway inhibitors as antitumor agents," Clin. Cancer Res. 18: 3524-31 (2012).
International Preliminary Report on Patentability for PCT/US2016/040931 dated Jan. 16, 2018.
Guo, D. et al, "EGFR signaling through han Akt-SREBP-1-dependent, rapamycin-resistant pathway sensitizes glioblastomas to antilipogenic therapy," Science Signaling 2: ra82 (2009).
Hagiwara, et al, "Hepatic mTORC2 activates glycolysis and lipogenesis through Akt, glucokinase and SREBP1c," Cell Metab. 15: 725-38 (2012).
Hartman IZ, et al, "Sterol-inducd dislocation of 3-hydroxy-3-methylglutaryl coenzyme a reductase from endoplasmic reticulum membranes into the cytosol through a subcellular compartment resembling lipi droplets," J. Biol. Chem. 285: 19288-98 (2010).
He, M, et al, "Mutations in the human SC4MOL gene encoding a methyl sterol oxidase cause psoriasiform dermatitis, microcephaly, and developmental delay," J. Clin. Invest. 121: 97 6-984 (2011).
Hidaka, Y, et al, "Regulation of squalene epoxidase in HepG2 cells," J. Lipid Res. 31: 2087-94 (1990).
Hiltunen, TP et al, Expression of LDL receptor, VLDL receptor, LDL receptor-related protein, and scavenger receptor in rabbit atherosclerotic lesions: Marked induction of scavenger receptor and VLDL receptor expression during lesion development, Circulation 97: 1079 (1998).
Hirsch, HA et al, "A transcriptional signature and common gene networks link cancer with lipid metabolism and diverse human diseases," Cancer Cell. 17(4): 348-61 (2010).
Horton, JD, et al, "SREBPs: activators of the complete program of cholesterol and fatty acid synthesis in the liver," J. Clin. Invest. 109: 1125-31 (2002).
Hosono, Y., et al; Abstract LB-360: MYBPH, a novel transcriptional target of TTF-1/NKX2-1, inhibits ROCK1 and actomyosin assembly, and reduces cell motility and tumor metastasis; http://cancerres.aacrjournals.org/content/71/8_Supplement/LB-360; DOI: 10.1158/1538-7445.AM2011-LB-360 published Apr. 2011.
Hua, X et al, "Sterol resistance in CHO cells traced to point mutation in SREBP cleavage-activating protein," Cell 87: 415-26 (1996).
Hussein, D and Mo, H, "d-?-tocotrienol-mediated suppression of the proliferation of human PANC-1, M1A PaCa2 and BxPC-3 pancreatic carcinoma cells," Pancreas 38: e124-e136 (2009).
Inoue, S. et al, "Inhibition of degradation of 3-hydroxyl-3-methylglutaryl-coenzyme A reductase in vivo by cysteine protease inhibitors," J. Biol. Chem. 266: 13311-17 (1991).
Ji, Y, et al, "Scavenger receptor B1 promotes high density lipoprotein-mediated cellular cholesterol efflux," J. Biol. Chem. 272: 20982-985 (1997).
Jian, B. et al, "Scavenger receptor class B type 1 as a mediator of cellular cholesterol efflux to lipoproteins and phospholipid acceptors," J. Biol. Chem. 273: 5599-5606 (1998).
Jiang, W. and Song, B-L, "Ubiquitin Ligases in Cholesterol Metabolism," Diabetes Metab. 38: 171-80 (2014).
Jo, Y and Debose-Boyd, RA, "Control of cholesterol synthesis through regulated ER-associated degradation of HMG CoA reductase," Crit. Rev. Biochem. Mol. Bio. 445: 185-198 (2010).
Jo, Y et al, "ancient ubiquitous protein 1 mediates sterol-induced ubiquitination of 3-hydroxy-3-methylglutaryl CoA reductase in lipid droplet-associated endoplasmic reticulum membranes," Mol. Biol. Cell 24: 169-83 (2013).
Kastritis, E., et al., "Somatic mutations of adenomatous polyposis coli gene and nuclear b-catenin accumulation have prognostic

(56) References Cited

OTHER PUBLICATIONS significance in invasive urothelial carcinomas: evidence for Wnt pathway implication", International Journal of Cancer, 124:103-108 (2009).
Kawabata, S., et al; "Interaction of Rho-kinase with myosin II at stress fibres"; Genes to Cells, 9, 653-660 (2004).
Kennedy, MA et al, "ABCG1 has a critical role in mediating cholesterol efflux to HDL and preventing cellular lipid accumulation," Cell Metab. 1: 121-31 (2005).
Khaidakov, M.,et al., "Oxidized LDL receptor 1 (OLR1) as a possible link between obesity, dyslipidemia and cancer," PLoS One 6(5): e20277 (2011).
Kim, J. et al, "Itraconazole, a commonly used antifungal that inhibits Hedgehog pathway activity and cancer growth," Cancer Cell. 17(4): 388-99 (2010).
Kimura, K., et al, "Regulation of Myosin Phosphatase by Rho and Rho-Associated Kinase (Rho-Kinase)", Science, vol. 273, 245-248 (1996).
Konstantinopoulos, PA, et al, "Post translational modifications and regulation of the RAS superfamily of GTPases as anticancer targets," Nat. Rev. Drug Discov. 6: 541-55 (2007).
Krinbou, L. et al,"Biogenesis and speciation of nascent apo A1-containing particles in various cell lines," J. Lipid Res. 46: 1668 (2005).
Kuwabara, PE, "The sterol-sensing domain: multiple families, a unique role," Trends Genet. 18: 193-201 (2002).
Labit-Le Bouteiller, C. et al., "Antiproliferative effects of SR31747A in animal cell lines are mediated by inhibition of cholesterol biosynthesis at the sterol isomerase step," Eur. J. Biochem. 256: 342-49 (1998).
Landry, YD, et al, "ATP-binding cassette transporter A1 expression disrupts raft membrane microdomains through ts ATPase-related functions," J. Biol. Chem. 281: 36091-101 (2006).
Lange, Y. et al, "Effectors of rapid homeostatic responses of endoplasmic reticulum cholesterol and 3-hydroxy-3-methylglutaryl-CoA reductase," J. Biol. Chem. 283: 1445-55 (2008).
Lee, P.C. et al, "Isolation of sterol-resistant Chinese hamster ovary cells with genetic deficiencies in both Insig-1 and Insig-2," J. Biol. Chem. 280: 25242-249 (2005).
Lehmann, JM et al, "Activation of the nuclear receptor LXR by oxysterols defines a new hormone response pathway," J. Biol. Chem. 272: 3137-40 (1997).
Leichner, GS, et al, "Metabolically regulated endoplasmic reticulum-associated degradation of 3-hydroxy-3-methylglutaryl-CoA reductase. Evidence for requirement of a geranylgeranylated protein," J. Biol. Chem. 286: 32150-61 (2011).
Leung, T., et al, "p80 ROKa binding protein is a novel splice variant of CRMP-1 which associates with CRMP-2 and modulates RhoA-induced neuronal morphology"; FEBS Letters 532, 445-449 (2002).
Liu, Y, and Tang, C., "Regulation of ABCA1 functions by signaling pathways," Biochim. Biophys. Acta, 1821: 522-29 (2012).
Lo Sasso, G. et al., "Liver X receptors inhibit proliferation of human colorectal cancer cells and growth of intestinal tumors in mice," Gastroenterology 144(7): 1497-507 (2013).
Ma, Wei, et al; "RhoE is Frequently Down-regulated in Hepatocellular Carcinoma (HCC) and Suppresses HCC Invasion Through Antagonizing the Rho/Rho-Kinase/Myosin Phosphatase Target Pathway" Hepatology, Jan. 2013, vol. 57, 152-161.
Ma, Z., et al; "Interaction between ROCK II and Nucleophosmin/B23 in the Regulation of Centrosome Duplication", Molecular and Cellular Biology, 9016-9034 (2006).
Mahley, RW, Ji, ZS, "Remnant lipoprotein metabolism: key pathways involving cell-surface heparin sulfate proteoglycans and apolipoprotein E," J. Lipid Res. 40: 1-16 (1999).
Maniar, A. et al, "Human gammadelta T lymphocytes induce robust NK cell-mediated antitumor cytotoxicity through CD137 engagement," Blood 116: 1726-33 (2010).
Mashima, T. et al, "De novo fatty-acid synthesis and related pathways as molecular targets for cancer therapy," Br. J. Cancer 100 (9): 1369-72 (2009).

Mazein, A. et al., "A comprehensive machine-readable view of the mammalian cholesterol biosynthesis pathway," Biochemical Pharmacol. 86: 56-66 (2013).
McGee, TP et al, "Degradation of 3-hydroxy-3-methylglutaryl-CoA reductase in endoplasmic reticulum membranes is accelerated as a result of increased susceptibility to proteolysis," J. Biol. Chem. 271: 25630-638 (1996); Ravid, T. et al, "The ubiquitin proteasome pathway mediates the regulated degradation of mammalian 3-hydroxy-3-methylglutaryl-Coenzyme A reductase," J. Biol. Chem. 275: 35840-47 (2000).
Medina, M.W., et al, "Coordinately regulated alternative splicing of genes involved in cholesterol biosynthesis and uptake," PLosONE 6: e19420 (2011).
Menendez, JA and Lupu, R., Fatty acid synthase and the lipogenic phenotype in cancer pathogenesis, Nat. Rev. Cancer 7(10): 763-77 (2007).
Meyer, JM et al, "New developments in selective cholesteryl ester uptake," Curr. Opin. Lipidol. 24: 386-92 (2013).
Minde, D, et al., Messing up disorder: how do missense mutations in the tumor suppressor protein APC lead to cancer?, Molecular Cancer; 10:101 (2011).
Mineo, C. and Shaul, PW, "Regulation of signal transduction by HDL," J. Lipid Res. 54: 2315-24 (2013).
Mo H and Elfakhani, CE, Mevalonate-suppressive tocotrienols for cancer chemoprevention and adjuvant therapy, in Tocotrienols: Vitamin E beyond tocopherols, eds. RR. Wilson et al (Boca Raton: CRC Press), 135-149 (2013).
Mo, H and Elson, CE, "Studies of the isopreoid-mediated inhibition of mevalonate synthesis applied to cancer chemotherapy and chemoprevention," Exp. Biol. Med. (Maywood) 229: 567-85 (2004).
Morgan-Fisher, M. et al, Regulation of ROCK Activity in Cancer, Journal of Histochemistry & Cytochemistry, 61:185-198 (2013).
Banker et al. "Modern Pharmaceutics . . . " p. 596, 451 (1996).
Garattini "Active drug metabo . . . " Clin. Pharmacokinetics 10, 216-227 (1985).
Wolf "Burger's Medicinal . . . " p. 975-977 (1995).
Golbfarb et al. "Method using . . . " CA151:92839 (2009).
Aertgeerts et al. "Aryl sulfonyl-piperidines . . . " CA145:419173 (2006).
Coburn et al. "Preparation of . . . " CA162:670779 (2015).
Cui et al. "Preparation of 5-aralkyl . . . " CA138:14005 (2002).
Keldenich "Subsituted bipiperi . . . " CA163:145662 (2015).
Lee et al. "Preparation of 5-amino . . . " CA130:168237 (1999).
Hidaka et al. "Preparation of isoquinolin . . . " CA108:37665 (1988).
Golbfarb et al. "Method using . . . " CA151:92836 (2009).
Meltel et al. "Preparation of N-cyclic . . . " CA144:22719 (2005).
Golbfarb et al. "Method using . . . " CA151:115083 (2009).
Bae, et al., "Cholesterol biosynthesis from lanosterol: molecular cloning, chromosonal localization, functional expression and liver-specific gene regulation of rat sterol D8-isomerase, a cholesterogenic enzyme with mulitple functions", Biochem.J.,2001, vol. 353, pp. 689-699.
Tang, et al., "Histone deacetylases as targets for treatment of multiple diseases", Clin. Sci, 2013, vol. 124, pp. 351-662.
Chittur, et al., "Histone deacetylase inhibitors: A new mode for inhibition of cholesterol metabolism", BMC Genomics, 2008, vol. 9, pp. 1-14.
Aoki, K, et al., "Adenomatous polyposis coli (APC): a multi-functional tumor suppressor gene", Journal of Cell Science, 2007, vol. 120, pp. 3327-3335.
Bakhoum S.F., et al., "Deviant kinetochore microtuble dynamics underlie chromosomal instability", Current Biology, 2009, vol. 19, pp. 1937-1942, Elsevier Ltd.
Dikovskaya D., et al., "Loss of APC induces polyploidy as a result of a combination of defects in mitosis and apoptosis", The Journal of Cell Biology, 2016, vol. 176, pp. 183-195.
Eskiocak U., et al., "Functional parsing of driver mutations in the colorectal cancer genome reveals number suppressors of anchorage-independent growth", Cancer Research, 2011, vol. 71, pp. 4359-4365, American Association for Cancer Research.
Fodde R., et al., "Mutations in the APC tumour suppressor gene cause chromosomal instability", Nature Cell Biology, 2001, vol. 3, pp. 433-443.

(56) References Cited

OTHER PUBLICATIONS

Half E., et al., "Familial adenomatous polyposis, Orphanet Journal of Rare Diseases", 2009, vol. 4, pp. 1-23, BioMed Central.

Hinoi T., et al., "Mouse model of colonic adenoma-carcinoma progression based on somatic Apc inactivation", Cancer Res, 2007, vol. 67, pp. 9721-9730.

Kapplan K.B., et al., "A role for the adenomatous polyposis coli protein in chromsome segregation", Nature Cell Biology, 2001, vol. 3, pp. 429-432, Macmillan Magazines Ltd.

Kinzler K.W., et al., "Identification of FAP locus genes from chromosome 5q21", Science, 1991, vol. 253, pp. 661-664.

Kinzler K.W., et al., "Lessons from hereditary colorectal cancer", Cell, 1996, vol. 87, pp. 159-170.

Loberg R.D., et al., "Enhanced glyocen sythase kinase-3b activity mediates hypoxia-induced apoptosis of vascular smooth cells and is prevented by glucose transport and metabolixm", The Journal of Biological Chemistry, 2002, vol. 277, pp. 41667-41673, The American Society for Biochemistry and Molecular Biology, Inc.

Longin A., et al., "Comparison of antifading agents used in fluorescence microscopy: Image analysis and laser confocal microscopy study", The Journal of Histochemistry and Cytochemistry, 1993, vol. 41, pp. 1833-1840, The Histochemical Society, Inc.

Ly P., et al "RNAi screening of the human colorectal cancer genome identifies multifunctional tumor suppressors regulating epithelia cell invasion", Cell Research, 2012, vol. 22, pp. 1605-1608.d.

Phelps R.A., et al., "New perspectives on APC control of cell fate and proliferation in colorectal cancer", Cell Cycle, 2009, vol. 8, pp. 2549-2556.

Polakis P., "The many ways of Wnt in cancer", Current Opinion in Genetics & Development, 2007, vol. 17, pp. 45-51, www.sciencedirect.com.

Ren Y., et al., "Small molecule Wnt inhibitors enhance the efficiency of BMP-4-directed cardiac differentiation of human pluripotent stem cells", J Mol Cell Cardiol., 2011, vol. 51, pp. 280-287.

Roig A.I., et al., "Immortalized epithelial cells derived from human colon biopsies express stem cell markers and differentiate in vitro", Gastroentology, 2010, vol. 138, pp. 1012-1021.

Rusan N.M. et al., "Original CIN: reviewing roles for APC in chromosome instability", The Journal of Cell Biology, 2008, vol. 181, pp. 719-726.

Sato M., et al., "Multiple oncogenic changes (K-RAV v12, p53 knockdown, mutant EGFRs, p16 Bypass, Telomerase) are not sufficient to confer a full malignant phenotype on human bronchial epithelial cells", Cancer Res, 2006, vol. 66, pp. 2116-2128.

Sawhney A.S., et al., "Bioerodible hydrogels based on photopolymerized poly (ethylene glycol)-co-poly (a-hydroxy acid) diacrylate macromers", Macromolecus, 1993, vol. 26, vol. 581-587.

Schnekeirt J., et al., "Truncated APC regulates the transcriptional activity of B-catenin in a cell cycle dependent mannter", Human Molecular Genetics, 2007, vol. 16, pp. 199-209.

Shi Q., et al., "Chromosome nondisjunction yields tetraploid rather than aneuploid cells in human cell lines", Nature, 2005, vol. 437, pp. 1038-1043.

Scholl F.A., et al., "Mek1/2 MAPK inases are essential form mammalian development, homeostasis, and Raf-Induced hyperplasia", Development Cell, 2007, vol. 12, pp. 615-629.

Still W.C., et al., "Rapid chromatographic technique for preparative separations with moderate resolution", J. Org. Chem., 1978, vol. 43, pp. 2923-2925, American Chemical Society.

Zhang L., et al., "Idendilication of novel driver tumor suppressors through functional interrogataion of putative passenger mutations in colorectal cancer", International Journal of Cancer, 2012, vol. 132, pp. 732-737.

Pubchem. Compound Summary for CID 47305059. Create Date: Nov. 26, 2010. [retrieval on Feb. 3, 2015]. Retrived from the Internet.<URL: http://pubchem.ncbi.nim.nih.gov/compound/47305059>. entire.document.

Pubchem. Compound Summary for CID 2911561. Create Date: Jul. 29, 2005. [retrieval on Feb. 3, 2015]. Retrived from the Internet. <URL: http://pubchem.ncbi.nim.nih.gov/compound/2911561>. entire.document.

Pubchem. Compound Summary for CID 22721249. Create Date: Dec. 5, 2007. [retrieval on Feb. 3, 2015]. Retrived from the Internet. <URL: http://pubchem.ncbi.nim.nih.gov/compound/22721249>. entire.document.

Pubchem. Compound Summary for CID 57290202. Create Date: Jun. 15, 2012. [retrieval on Feb. 3, 2015]. Retrived from the Internet. <URL: http://pubchem.ncbi.nim.nih.gov/compound/57290202>. entire.document.

Pubchem. Compound Summary for CID 46851969. Create Date: Aug. 30, 2010. [retrieval on Feb. 3, 2015]. Retrived from the Internet. <URL: http://pubchem.ncbi.nim.nih.gov/compound/46851969>. entire.document.

Pubchem. Compound Summary for CID 61047227. Create Date: Oct. 19, 2012. [retrieval on Feb. 3, 2015]. Retrived from the Internet. <URL: http://pubchem.ncbi.nim.nih.gov/compound/61047227>. entire.document.

* cited by examiner

TARGETING EMOPAMIL BINDING PROTEIN (EBP) WITH SMALL MOLECULES THAT INDUCE AN ABNORMAL FEEDBACK RESPONSE BY LOWERING ENDOGENOUS CHOLESTEROL BIOSYNTHESIS

CROSS-REFERENCE TO RELATED APPLICATION

This application claims the benefit of priority to U.S. provisional application No. 62/193,019, filed on Jul. 15, 2015, the entire contents of which are hereby incorporated by reference. This application is a Continuation-In-Part of U.S. patent application Ser. No. 14/482,659, filed on Sep. 10, 2014, the entire contents of which are hereby incorporated by reference.

FIELD OF INVENTION

The described invention relates to small molecule cancer therapeutics.

BACKGROUND OF THE INVENTION

The major types of lipids that circulate in plasma include cholesterol and cholesteryl esters, phospholipids and triglycerides. Braunwald's Heart Disease, P. Libby, R. Bonow, D. Mann and D. Zipes, Eds., 8$^{th}$ Edition, Saunders Elsevier, Philadelphia, Pa. (2008) at 1071. Cholesterol contributes an essential component of mammalian cell membranes and furnishes substrate for steroid hormones and bile acids. Many cell functions depend critically on membrane cholesterol, and cells tightly regulate cholesterol content. Most of the cholesterol in plasma circulates in the form of cholesteryl esters in the core of lipoprotein particles. The enzyme lecithin cholesterol acyl transferase (LCAT) forms cholesteryl esters in the blood compartment by transferring a fatty acyl chain from phosphatidylcholine to cholesterol. Id.

Lipoproteins are complex macromolecular structures composed of an envelope of phospholipids and free cholesterol, a core of cholesteryl esters and triglycerides. Id. at 1072. Triglycerides consist of a three-carbon glycerol backbone covalently linked to three fatty acids. Their fatty acid composition varies in terms of chain length and degree of saturation. Triglyceride molecules are nonpolar and hydrophobic, and are transported in the core of the lipoprotein. Hydrolysis of triglycerides by lipases generates free fatty acids (FFAs) used for energy. Id. Phospholipids, constituents of all cellular membranes, consist of a glycerol molecule linked to two fatty acids. The fatty acids differ in length and in the presence of a single or multiple double bonds. The third carbon of the glycerol moiety carries a phosphate group to which one of four molecules is linked: choline (phosphatidylcholine or lecithin), ethanolamine (phosphatidylethanolamine), serine (phosphatidylserine), or inositol (phosphatidylinositol). Phospholipids, which are polar molecules, more soluble than triglycerides or cholesterol or its esters, participate in signal transduction pathways. Hydrolysis by membrane-associated phospholipases generates second messengers such as diacyl glycerols, lysophospholipids, phoshatidic acids and free fatty acids (FFAs) such as arachidonate that can regulate many cell functions. Id.

The apolipoproteins, which comprise the protein moiety of lipoproteins, vary in size, density in the aqueous environment of plasma, and lipid and apolipoprotein content. The classification of lipoproteins reflects their density in plasma (1.006 gm/mL) as gauged by flotation in the ultracentrifuge. For example, triglyceride-rich lipoproteins consisting of chylomicrons (meaning a class of lipoproteins that transport dietary cholesterol and triglycerides after meals from the small intestine to tissues for degradation) and very low density lipoprotein (VLDL) have a density less than 1.06 gm/mL. Id.

Apolipoproteins have four major roles: (1) assembly and secretion of the lipoprotein (apo B100 and B48); (2) structural integrity of the lipoprotein (apo B, apo E, apo A1, apo AII); (3) coactivators or inhibitors of enzymes (apo A1, C1, CII, CIII); and (4) binding or docking to specific receptors and proteins for cellular uptake of the entire particle or selective uptake of a lipid component (apoA1, B100, E). Id. The role of several apolipoproteins (AIV, AV, D, and J) remain incompletely understood. Id.

Low density lipoprotein (or LDL cholesterol) particles carry cholesterol throughout the body, delivering it to different organs and tissues. The excess keeps circulating in blood. LDL particles contain predominantly cholesteryl esters packaged with the protein moiety apoB 100. Id. at 1076.

High density lipoproteins (or HDL cholesterol) act as cholesterol scavengers, picking up excess cholesterol in the blood and taking it back to the liver where it is broken down. Apolipoprotein A1, the main protein of HDL, is synthesized in the intestine and liver. Lipid-free Apo A1 acquires phospholipids from cell membranes and from redundant phospholipids shed during hydrolysis of triglceride-rich lipoproteins. Lipid-free apo A1 binds to ABCA1 and promotes its phosphorylation via cAMP, which increases the net efflux of phospholipids and cholesterol onto apo A1 to form a nascent HDL particle. Id. These nascent HDL particles will mediate further cellular cholesterol efflux. Id.

The scavenger receptor class B (SR-B1; also named CLA-1 in humans (Id., citing Acton, S. et al, "Identification of scavenger receptor SR-B1 as a high density lipoprotein receptor," Science 271: 518 (1996)) and the adenosine triphosphate binding cassette transporter A1 (ABCA1) (Id., citing Krinbou, L. et al," Biogenesis and speciation of nascent apo A1-containing particles in various cell lines," J. Lipid Res. 46: 1668 (2005)) bind HDL particles. SR-B1, a receptor for HDL (also for LDL and VLDL, but with less affinity), mediates the selective uptake of HDL cholesteryl esters in steroidogenic tissues, hepatocytes and endothelium. ABCA1 mediates cellular phospholipid (and possibly cholesterol) efflux and is necessary and essential for HDL biogenesis. Id.

Cellular cholesterol homeostasis is achieved via at least four major routes: (1) cholesterol de novo biosynthesis from acetyl-CoA in the endoplasmic reticulum; (2) cholesterol uptake by low density lipoprotein (LDL) receptor-mediated endocytosis of LDL-derived cholesterol from plasma; 3) cholesterol efflux mediated by ABC family transporters such as ATP-binding cassette, sub-family A (ABC1), member 1 (ABCA1)/ATP-binding cassette, sub-family G, member 1 (ABCG1), and secretion mediated by apolipoprotein B (ApoB); and (4) cholesterol esterification with fatty acids to cholesterol esters (CE) by acyl-coenzyme A:cholesterol acyltransferase (ACAT) (see FIG. 1 (Jiang, W. and Song, B-L, "Ubiquitin Ligases in Cholesterol Metabolism," Diabetes Metab. 38: 171-80 (2014)).

Cholesterol Biosynthetic Pathways

Cholesterol synthesis takes place in four stages: (1) condensation of three acetate units to form a six-carbon intermediate, mevalonate; (2) conversion of mevalonate to activated isoprene units; (3) polymerization of six 5-carbon isoprene units to form the 30-carbon linear squalene; and (4)

cyclization of squalene to form the steroid nucleus, with a further series of changes to produce cholesterol. (Endo, A., "A historical perspective on the discovery of statins," Proc. Jpn Acad, Ser. B Phys. Biol. Sci 86(5): 484-93 (2010)).

The mevalonate arm of the cholesterol biosynthesis pathway, which includes enzymatic activity in the mitochondria, peroxisome, cytoplasm and endoplasmic reticulum, starts with the consumption of acetyl-CoA, which occurs in parallel in three cell compartments (the mitochondria, cytoplasm, and peroxisome) and terminates with the production of squalene in the endoplasmic reticulum (Mazein, A. et al., "A comprehensive machine-readable view of the mammalian cholesterol biosynthesis pathway," Biochemical Pharmacol. 86: 56-66 (2013)). The following are enzymes of the mevalonate arm:

Acetyl-CoA acetyltransferase (ACAT1; ACAT2; acetoacetyl-CoA thiolase; EC 2.3.1.9) catalyzes the reversible condensation of two molecules of acetylcoA and forms acetoacetyl-CoA. Id.

Hydroxymethylglutaryl-CoA synthase (HMGCS1 (cytoplasmic); HMGCS2 (mitochondria and peroxisome); EC 2.3.3.10 catalyzes the formation of 3-hydroxy-3-methylglutaryl CoA (3HMG-CoA) from acetyl CoA and acetoacetyl Co A. Id.

Hydroxymethylglutaryl-CoA lysase (mitochondrial, HMGCL; EC 4.1.3.4) transforms HMG-CoA into Acetyl-CoA and acetoacetate.

3-hydroxy-3-methylglutaryl-coenzyme A reductase (HMGCR; EC 1.1.34) catalyzes the conversion of 3HMG-CoA into mevalonic acid. This step is the committed step in cholesterol formation. HMGCR is highly regulated by signaling pathways, including the SREBP pathway.Id.

Mevalonate kinase (MVK; ATP:mevalonate 5-phosphotransferase; EC 2.7.1.36) catalyzes conversion of mevalonate into phosphomevalonate. Id.

Phosphomevalonate kinase (PMVK; EC 2.7.4.2) catalyzes formation of mevalonate 5-diphosphate from mevalonate 5-phosphate. Id.

Diphosphomevalonate decarboxylase (MVD; mevalonate (diphospho) decarboxylase; EC 4.1.1.33) decarboxylates mevalonate 5-diphosphate, forming isopentenyldiphosphate while hydrolyzing ATP. Id.

Isopentenyl-diphosphate delta-isomerases (ID11; ID12; EC 5.3.3.2) isomerize isopentenyl diphosphate into dimethylallyl diphosphate, the fundamental building blocks of isoprenoids. Id.

Farnesyl diphosphate synthase (FDPS; EC2.5.1.10; EC 2.5.1.1; dimethylallyltranstransferase) catalyzes two reactions that lead to farnesyl diphosphate formation. In the first (EC 2.5.1.1 activity), isopentyl diphosphate and dimethylallyl diphosphate are condensed to form geranyl disphosphate. Next, geranyl diphosphate and isopentenyl diphosphate are condensed to form farnesyl diphosphate (EC 2.5.1.10 activity). Id.

Geranylgeranyl pyrophosphate synthase (GGPS1; EC 1.5.1.29; EC 2.5.1.10; farnesyl diphosphate synthase; EC 2.5.1.1; dimethylallyltranstransferase) catalyzes the two reactions of farnesyl diphosphate formation and the addition of three molecules of isopentenyl diphosphate to dimethylallyl diphosphate to form geranylgeranyl diphosphate. Id.

Farnesyl-diphosphate farnesyltransferase 1 (FDFT1; EC 2.5.1.21; squalene synthase) catalyzes a two-step reductive dimerization of two farnesyl diphosphate molecules (C15) to form squalene (C30). The FDFT1 expression level is regulated by cholesterol status; the human FDFT1 gene has a complex promoter with multiple binding sites for SREBP-1a and SREBP-2. Id.

The sterols arms of the pathway start with Squalene and terminate with cholesterol production on the Bloch and Kandutsch-Russell pathways and with 24 (S),25-epoxycholesterol on the shunt pathway. Id. The following are enzymes of the sterol arms:

Squalene epoxidase (SQLE; EC 1.14.13.132, squalene monooxygenase) catalyzes the conversion of squalene into squalene-2,3-epoxide and the conversion of squalene-2,3-epoxide (2,3-oxidosqualene) into 2,3:22,23-diepoxysqualene (2,3:22,23-dioxidosqualene). The first reaction is the first oxygenation step in the cholesterol biosynthesis pathway. The second is the first step in 24(S),25-epoxycholesterol formation from squalene 2,3-epoxide. Id.

Lanosterol synthase (LSS; OLC; OSC; 2,3-oxidosqualene:lanosterol cyclase; EC 5.4.99.7) catalyzes cyclization of squalene-2,3-epoxide to lanosterol and 2,3:22,23-depoxysqualene to 24(S),25-epoxylanosterol. Id.

Delta(24)-sterol reductase (DHCR24; 24-dehydrocholesterol reductase; EC 1.3.1.72) catalyzes the reduction of the delta-24 double bond of intermediate metabolites. In particular it converts lanosterol into 24, 25-dihydrolanosterol, the initial metabolite of the Kandutsch-Russel pathway and also provides the last step of the Bloch pathway converting desmosterol into cholesterol. Intermediates of the Bloch pathway are converted by DHCR24 into intermediates of the Kandutsch-Russell pathway. Id.

Lanosterol 14-alpha demethylase (CYP51A1; cytochrome P450, family 51, subfamily A, polypeptide 1; EC 1.14.13.70) converts lanosterol into 4,4-dimethyl-5α-cholesta-8,14,24-trien-3β-ol and 24,25-dihydrolanosterol into 4,4-dimethyl-5α-cholesta-8,14-dien-3β-ol in three steps. Id.

Delta (14)-sterol reductase (TM7F2; transmembrane 7 superfamily member 2, EC 1.3.1.70) catalyzes reactions on the three branches of the cholesterol and 24(S),25-epoxycholesterol pathways. Id.

Methylsterol monooxygenase 1 (MSM01; SC4MOL; C-4 methylsterol oxidase; EC 1.14.13.72) catalyzes demethylation of C4 methylsterols. Id.

Sterol-4-alpha-carboxylate 3-dehydrogenase, decarboxylating (NSDHL; NAD(P) dependent steroid dehydrogenase-like; EC 1.1.1.170) participates in several steps of post-squalene cholesterol and 24(S),25-epoxycholeseterol synthesis. Id.

3-keto-steroid reductase (HSD17B7; 17-beta-hydroxysteroid dehydrogenase 7; EC 1.1.1.270) converts zymosterone into zymosterol in the Bloch pathway. Id.

3-Beta-hydroxysteroid-delta(8),delta(7)-isomerase (EBP; emopamil-binding protein; EC5.3.3.5) catalyzes the conversion of delta(8)-sterols into delta(7)-sterols. Id.

Lathosterol oxidase (SC5DL; sterol-C5-desaturase (ERG3 delta-5-desaturase homolog, S. cerevisiae-like; EC 1.14.21.6) catalyzes the production of 7-dehydrocholesterol, 7-dehydrodesmosterol and 24(S),25-epoxy-7-dehydrocholesterol. Id.

7-dehydrocholesterol reductase (DHCR7; EC 1.3.1.21) catalyzes reduction of the C7-C8 double bond of 7-dehydrocholesterol and formation of cholesterol, and produces desmosterol from 7-dehydrodesmosterol and 24(S),25-epoxycholesterol from 24(S),25-epoxy-7-dehydrocholesterol. Id.

Cytochrome P450, family 3, subfamily A, polypeptide 4 (CYP3A4; 1,8-cineole 2-exo-monooxygenase; taurochenodeoxycholate 6α-hydroxylase; EC 1.14.13.97)) catalyzes the hydroxylation of cholesterol leading to 25-hydroxycholesterol and 4β-hydroxycholesterol. Id.

Cholesterol 25-hydroxylase (CH25H; cholesterol 25-monooxygenase; EC 1.14.99.38) uses di-iron cofactors to catalyze the hydroxylation of cholesterol to produce 25-hydroxycholesterol, and has the capacity to catalyze the transition of 24-hydroxycholesterol to 24, 25-dihydroxycholesterol. Id.

Cytochrome P450, family 7, subfamily A, polypeptide 1 (CYP7A1; cholesterol 7-alpha-hydroxylase; EC 1.14.13.17) is responsible for introducing a hydrophilic moiety at position 7 of cholesterol to form 7α-hydroxycholesterol. Id.

Cytochrome P450, family 27, subfamily A, polypeptide 1 (CYP27A1; Sterol 27-hydroxylase; EC 1.14.13.15) catalyzes the transition of mitochondrial cholesterol to 27-hydroxycholesterol and 25-hydroxycholesterol. Id.

Cytochrome P450 46A1 (CYP46A1, cholesterol 24-hydroxylase, EC 1.14.13.98) catalyzes transformation of cholesterol into 24(S)-hydroxycholesterol. Id.

Intermediates in Cholesterol Synthesis as Physiological Regulators

Intermediates in cholesterol synthesis, mostly sterols (e.g. 7-dehydrocholesterol, which is converted to cholesterol by DHCR7 (7-dehydrocholesterol reductase), but which also is a precursor for vitamin D), have been credited with having regulatory functions distinct from those of cholesterol. (Sharpe, L J and Brown, A J, "Controlling cholesterol synthesis beyond 3-hydroxy-3-methylglutaryl CoA reductase (HMGCR)," J. Biol. Chem. 288 (26): 18707-715 (2013)).

C4-methylsterols are produced by lanosterol 14α-demethylase (encoded by CYP51A1 (cytochrome P450, family 51, subfamily A, polypeptide 1) and demethylated by SC4MOL (sterol-C4-methyl oxidase like 1; methylsterol monooxygenase 1) and its partner, NSDHL (NAD(P)-dependent steroid dehydrogenase-like; sterol-4-α-carboxylate 3-dehydrogenase, decarboxylating).Id.

24, 25-dihydrolanosterol purportedly is the primary degradation signal for 3-hydroxy-3-methylglutaryl-CoA reductase (HMGCR) (Id., citing Song, B L, et al, "Insig-mediated degradation of HMG-CoA reductase stimulated by lanosterol, an intermediate in the synthesis of choleseterol," Cell Meta. 1: 179-89 (2005); Lange, Y. et al, "Effectors of rapid homeostatic responses of endoplasmic reticulum cholesterol and 3-hydroxy-3-methylglutaryl-CoA reductase," J. Biol. Chem. 283: 1445-55 (2008)).

The nonsterol intermediate squalene has been implicated in stimulating HMGCR degradation (Id., citing Leichner, G S, et al, "Metabolically regulated endoplasmic reticulum-associated degradation of 3-hydroxy-3-methylglutaryl-CoA reductase. Evidence for requirement of a geranylgeranylated protein," J. Biol. Chem. 286: 32150-61 (2011)).

A number of cholesterol synthesis intermediates can serve as activating ligands of the nuclear liver X receptor (LXR), which up-regulates cholesterol export genes and represses inflammatory genes. These sterols include 24,25-dihydrolanosterol (Id., citing Zhu, J. et al, "Effects of FoxO4 overexpression on cholesterol biosynthesis, triacylglycerol accumulation, and glucose uptake," J. Lipid Res. 51: 1312-24 (2010)), meiosis-activating sterols (MASs) (Id., citing He, M, et al, "Mutations in the human SC4MOL gene encoding a methyl sterol oxidase cause psoriasiform dermatitis, microcephaly, and developmental delay," J. Clin. Invest. 121: 97 6-984 (2011)) and desmosterol (Id., citing Yang, C. et al, "Sterol intermediates from cholesterol biosynthetic pathway as liver X receptor ligands," J. Biol. Chem. 281: 27816-826 (2006); Spann, N J et al, "Regulated accumulation of desmosterol integrates macrophage lipid metabolism and inflammatory responses," Cell 151: 138-52 (2012)).

The oxysterol 24(S),25-epoxycholesterol (24,25-EC), a potent LXR agonist (Id., citing Lehmann, J M et al, "Activation of the nuclear receptor LXR by oxysterols defines a new hormone response pathway," J. Biol. Chem. 272: 3137-40 (1997)), is produced in a shunt pathway in sterol synthesis (Id., citing Spencer, T A, et al, "24(S),25-epoxyscholesterol. Evidence consistent with a role in the regulation of hepatic cholestrogenesis," J. Biol. Chem. 260: 13391-94 (1985)), and its production is determined by the relative activities of squalene monooxygenase (SM) and lanosterol synthase (LS). Partial inhibition or knockdown of LS diverts more flux into the shunt pathway, producing more 14,15-epoxycholesterol (14,15-EC) (Id., citing Dang, H. et al, "Suppression of 2,3-oxidosqualene cyclase by high fat diet contributes to liver X receptor-α-mediated improvement of hepatic lipid profile," J. Biol. Chem. 284: 6218-26 (2009)), whereas overexpression of LS abolishes 24,25-EC production (Id., citing Wong, J. et al, "Endogenous 24(S),25-epoxycholesterol fine-tunes acute control of cellular cholesterol homeostasis," J. Biol. Chem. 283: 700-707 (2008)). Conversely, overexpression of SM increases 24,25-EC production (Id., citing Zerenturk, E J et al, "The endogenous regulator 24(S),25-epoxycholesterol inhibits cholesterol synthesis at DHCR24 (Seladin-1)," Biochim. Biophys. Acta 1821: 1269-77 (2012)). The extent to which SM and LS are differentially regulated to alter 14,15-EC production is not known.

Cholesterol Uptake by Low Density Lipoprotein (LDL) Receptor-mediated Endocytosis of LDL-derived Cholesterol from Plasma The LDL receptor regulates the entry of cholesterol into cells; tight control mechanisms alter its expression on the cell surface, depending on need. Braunwald's Heart Disease, P. Libby, R. Bonow, D. Mann and D. Zipes, Eds., 8th Edition, Saunders Elsevier, Philadelphia, Pa. (2008) at 1072. Other receptors for lipoproteins include several that bind VLDL, but not LDL. Id. The LDL receptor-related peptide, which mediates the uptake of chylomicron remnants and VLDL, preferentially recognizes apolipoprotein E (apo E) (Id., citing Hiltunen, T P et al, Expression of LDL receptor, VLDL receptor, LDL receptor-related protein, and scavenger receptor in rabbit atherosclerotic lesions: Marked induction of scavenger receptor and VLDL receptor expression during lesion development," Circulation 97: 1079 (1998)). The LDL receptor-related peptide interacts with hepatic lipase. A specific VLDL receptor also exists (Id., citing Nimph, J, and Schneider, W J, "The VLDL receptor: an LDL receptor relative with eight ligand binding repeats, LR8. Atherosclerosis 141: 191-202 (1998)). The interaction between hepatocytes and the various lipoproteins containing apo E is complex and involves cell surface proteoglycans that provide a scaffolding for lipolytic enzymes (lipoprotein lipase and hepatic lipase) involved in remnant lipoprotein recognition (Id., citing Mahley, R W, Ji, Zs, "Remnant lipoprotein metabolism: key pathways involving cell-surface heparin sulfate proteoglycans and apolipoprotein E," J. Lipid Res. 40: 1-(1999); Barown M I et al, "A macrophage receptor for apolipoprotein B48: cloning, expression and atherosclerosis, Proc. Natl Acad. Sci. USA 97: 7488 (2000); de Man, F H et al, "Lipolysis of very low density lipoproteins by heparin sulfate proteoglycan-bound lipoprotein lipase," J. Lipid Res. 38: 2465 (1997)).

Macrophages express receptors that bind modified (especially oxidized) lipoproteins. These scavenger lipoprotein receptors mediate the uptake of oxidized LDL into macrophages. In contrast to the regulated LDL receptor, high cellular cholesterol content does not suppress scavenger receptors, enabling the intimal macrophages to accumulate abundant cholesterol, become foam cells, and form fatty streaks. Endothelial cells also can take up modified lipoproteins through a specific receptor, such as Lox-1 (Sawamura, T. et al, "an endothelial receptor for oxidized low-density lipoprotein," Nature 386: 73 (1997)).

Cholesterol Efflux is Mediated by ABC Family Transporters Such as ATP-binding cassette, Sub-family a (ABC1), Member 1 (ABCA1)/ATP-binding Cassette, Sub-family G, Member 1 (ABCG1), and Secretion Mediated by Apolipoprotein B (ApoB);

Because most cells in the body do not express pathways for catabolizing cholesterol, efflux of cholesterol is critical for maintaining homeostasis. (Phillips, M C, "Molecular Mechanisms of Cellular Cholesterol Efflux," J. Biol. Chem. 289 (35): 24020-29 (2014)). High density lipoprotein (HDL) comprises a heterogeneous population of microemulsion particles 7-12 nm in diameter containing a core of cholesterol ester (CE) and triglyceride (TG) molecules stabilized by a monomolecular layer of phospholipid (PL) and apolipoprotein (apo), of which apo1 is the principal component (Id. citing Phillips, M C, "New insights into the determination of HDL structure by apolipoproteins," J. Lipid Res. 54: 2034-48 (2013)). The presence of PL in the particles enables HDL to solubilize and transport unesterified (free) cholesterol (FC) released from cells, thereby mediating removal of cholesterol from cholesterol-loaded arterial macrophages and transport to the liver for catabolism and elimination from the body ("reverse cholesterol transport") (Id., citing Rothblat, G H and Phillips, M C, "High-density lipoprotein heterogeneity and function in reverse cholesterol transport," Curr. Opin. Lipidol. 21: 229-38 (2010); Rosenson, R S et al, "Cholesterol efflux and atheroprotection: advancing the concept of reverse cholesterol transport," Circulation 125: 1905-19 (2012)).

The first step in reverse cholesterol transport is efflux of FC from the cell plasma membrane to HDL. Id. In the case of macrophages, four efflux pathways have been identified: the aqueous diffusion efflux pathway, the scavenger receptor class B, type 1 (SR-B1) pathway; the ATP binding cassette transporter G1 (ABCG1) pathway and the ATP-binding cassette transporter A1 (ABCA1) pathway. Id. The first two processes, which are passive, involve simple diffusion (aqueous diffusion pathway) and facilitated diffusion (SR-B1-mediated pathway). Id. The two active processes involve members of the ATP-binding cassette (ABC) family of transmembrane transporters, namely ABCA1 and ABCG1. Id. The efficiency of an individual serum sample in accepting cellular cholesterol depends upon both the distribution of HDL particles present and the levels of cholesterol transporters expressed in the donor cells. Id.

Aqueous Diffusion Efflux Pathway

HDL is the component of serum responsible for mediating FC efflux from monolayers of mouse L-cell fibroblasts. Id. Transfer occurs by an aqueous phase intermediate where monomeric FC molecules desorb from a donor particle and diffuse until they are absorbed by an acceptor particle. The rate of transfer of the highly hydrophobic cholesterol molecule from donor to acceptor is limited by the rate of desorption into the aqueous phase, which is sensitive to the physical state of the phospholipid (PL) milieu in which the transferring FC molecules are located. The net mass FC efflux from cells to HDL in the extracellular medium is promoted by metabolic trapping in which return of released FC to the cell is prevented by esterification, when lecithin-cholesterol aceyltransferase acts on HDL (Id., citing Czarnecka, H. and Yokoyama, S., "Regulation of cellular cholesterol efflux by lecithin: cholesterol acyltransferase reaction through nonspecific lipid exchange," J. Biol. Chem. 271: 1023-27 (1996)).

SR-B1 Efflux Pathway

SR-B1 is a member of the CD36 superfamily of scavenger receptor proteins that also includes lysosomal integral membrane protein-2 (LIMP-2). Id. The receptor is most abundantly expressed in liver, where it functions in the reverse cholesterol transport pathway and in steroidogenic tissue, where it mediates cholesterol delivery (Id., citing Zannis, V. et al, "Role of apoA-1, ABCA1, LCAT and SR-B1 in the biogenesis of HDL," J. Mol. Med. 84: 276-94 (2006)). It is a homo-oligomeric glycoprotein located in the plasma membrane with two N- and C-terminal transmembrane domains and a large central extracellular domain (Id., citing Williams, D L, et al, "Scavenger receptor B1 and cholesterol trafficking," Curr. Opin. Lipidol. 10: 329-39 (1999); Meyer, J M et al, "New developments in selective cholesteryl ester uptake," Curr. Opin. Lipidol. 24: 386-92 (2013)). In 1996, it was established that SR-B1 is an HDL receptor that mediates cholesterol uptake into cells. This process involves selective transfer of the cholesterol ester (CE) in an HDL particle into the cell without endocytic uptake and degradation of the HDL particle itself. In addition to promoting delivery of HDL cholesterol to cells, SR-B1 also enhances efflux of cellular cholesterol to HDL (Id., citing Ji, Y et al, "Scavenger receptor B1 promotes high density lipoprotein-mediated cellular cholesterol efflux," J. Biol. Chem. 272: 20982-985 (1997); Jian, B. et al, "Scavenger receptor class B type 1 as a mediator of cellular cholesterol efflux to lipoproteins and phospholipid acceptors," J. Biol. Chem. 273: 5599-5606 (1998)) with the two processes being related (Id., citing Gu, X et al, "Scavenger receptor class B, type 1-mediated [3H]cholesterol efflux to high and a low density lipoproteins is dependent on lipoprotein binding to the receptor," J. Biol. Chem. 275: 29993-30001 (2000)). For CE selective uptake via SR-B1, HDL binding and CE uptake are tightly coupled. The mechanism for CE uptake from HDL involves a two-step process in which HDL first binds to the receptor and then CE molecules transfer from the bound HDL particle into the cell plasma membrane, with enhanced binding of larger HDL particles to SR-B1 increasing the selective delivery of CE (Id., citing Thuahnai, S T, et al, "SR-B1-mediated cholesteryl ester selective uptake and efflux of unesterified cholesterol: influence of HDL size and structure, "" J. Biol. Chem. 279: 12448-455 (2004)). The binding of HDL to the extracellular domain of SR-B1 involves direct protein-protein contact with a recognition motif being the amphipathic a helix characteristic of HDL apolipoproteins (Id., citing Williams, D L et al, "Binding and cross-linking studies show that scavenger receptor B1 interacts with multiple sites in apolipoprotein A-1 and identify the class A amphipathic a helix as a recognition motif," J. Biol. Chem. 275: 18897-18904 (2000). Consistent with CE selective uptake being a passive process, the rate of uptake is proportional to the amount of CE initially present in the HDL particles.

FC efflux and HDL binding are not completely coupled, and the FC efflux mechanism proceeds by different pathways at low and high extracellular HDL concentrations (Id., citing Thuahnai, S T, et al, "SR-B1-mediated cholesteryl ester selective uptake and efflux of unesterified cholesterol: influence of HDL size and structure,"" J. Biol. Chem. 279: 12448-455 (2004); de la Llera-Moya, M. et al, "Scavenger receptor B1 (SR-B1) mediates free cholesterol flux independently of HDL tethering to the cell surface," J. Lipid Res. 40: 575-80 (1999)). At low HDL concentrations, binding of HDL to SR-B1 is critical, allowing bidirectional FC transit through the hydrophobic tunnel present in the extracellular domain of the receptor. Because the FC concentration gradient between the bound HDL particle and the cell plasma membrane is opposite to that of CE, the relatively high FC/PL ratio in the plasma membrane causes the direction of net mass FC transport to be out of the cell. Consistent with this concept, enhancing the PL content of HDL promotes FC efflux from cells (Id., citing Yancey, P G, et al, "High density lipoprotein phospholipid composition is a major determinant of the bi-directional flux and net movement of cellular free cholesterol mediated by scavenger receptor B1," J. Biol. Chem. 275: 36596-36604 (2000)). Larger HDL particles promote more FC efflux than smaller HDL, because they bind better to SR-B1 (Id., citing Thuahnai, S T, et al, "SR-B1-mediated cholesteryl ester selective uptake and efflux of unesterified cholesterol: influence of HDL size and structure,"" J. Biol. Chem. 279: 12448-455 (2004)). At higher HDL concentrations where binding to the receptor is saturated, FC efflux still increases with increasing HDL concentration (Id., citing Thuahnai, S T, et al, "SR-B1-mediated cholesteryl ester selective uptake and efflux of unesterified cholesterol: influence of HDL size and structure, "" J. Biol. Chem. 279: 12448-455 (2004)), because SR-B1 induces reorganization of the FC in the cell plasma membrane.

ABCG1 Efflux Pathway

ABCG1 functions as a homodimer, and is expressed in several types, where it mediates cholesterol transport through its ability to translocate cholesterol and oxysterols across membranes. Id. Expression of ABCG1 enhances FC and PL efflux to HDL (Id., citing Wang, N. et al, "ATP-binding cassette transporters G1 and G4 mediate cellular cholesterol efflux to high-density lipoproteins," Proc. Natl Acad. Sci. USA 101: 9774-79 (2004); Kennedy, M A et al, "ABCG1 has a critical role in mediating cholesterol efflux to HDL and preventing cellular lipid accumulation," Cell Metab. 1: 121-31 (2005)), but not to lipid-free apoA-1 (Id., citing Vaughan, A M and Oram, J F, "ABCG1 redistributes cell cholesterol to domains removable by high density lipoprotein but not by lipid-depleted apolipoproteins," J. Biol. Chem. 280: 20150-57 (2005); Sankaranarayanan, S. et al., "Effects of acceptor composition and mechanism of ABCG1-mediated cellular free cholesterol efflux," J. Lipid Res. 50: 275-84 (2009)). The presence of the transporter induces reorganization of plasma membrane cholesterol so that it becomes accessible to cholesterol oxidase (Id., citing Vaughan, A M and Oram, J F, "ABCG1 redistributes cell cholesterol to domains removable by high density lipoprotein but not by lipid-depleted apolipoproteins," J. Biol. Chem. 280: 20150-57 (2005)), creating an activated pool of plasma membrane FC, and desorption of FC molecules from this environment into the extracellular medium is facilitated. Increased expression of ABCG1 enhances FC efflux to HDL2 and HDL3 similarly, but has no effect on the influx of FC from these lipoprotein particles.

ABCA1 Efflux Pathway

ABCA1 is a full transporter whose expression is up-regulated by cholesterol loading, which leads to enhanced FC efflux. Id. Binding and hydrolysis of ATP by the two cytoplasmic, nucleotide-binding domains control the conformation of the transmembrane domains so that the extrusion pocket is available to translocate substrate from the cytoplasmic leaflet to the exofacial leaflet of the bilayer membrane. Id. ABCA1 actively transports phosphatidylcholine, phosphatidylserine, and sphingomyelin with a preference for phosphatidylcholine (Id., citing Quazi, F and Molday, R S, "Differential phospholipid substrates and directional transport by ATP-binding cassette proteins ABCA, ABCA7, and ABCA4 and disease-causing mutants," J. Biol. Chem. 288: 34414-26 (2013)). This PL translocase activity leads to the simultaneous efflux of PL and FC (Id., citing Gillotte, K L, et al, "Removal of cellular cholesterol by pre-β-HDL involves plasma membrane microsolubilization," J. Lipid Res. 39: 1918-28 (1998); Smith, J D et al, "ABCA1 mediates concurrent cholesterol and phospholipid efflux to apolipoprotein A-1," J. Lipid Res. 45: 635-44 (2004)) to lipid-free apoA-1 (plasma pre-β1-HDL). The cellular FC released to apoA-1 originates from both the plasma membrane and the endosomal compartment (Id., citing Chen, W. et al, "Preferential ATP-binding cassette transporter A1-mediated cholesterol efflux from late endosomes/lysosomes," J. Biol. Chem. 276: 43564-69 (2001)).

The PL translocase activity of ABCA1 induces reorganization of lipid domains in the plasma membrane (Id., citing Landry, Y D, et al, "ATP-binding cassette transporter A1 expression disrupts raft membrane microdomains through its ATPase-related functions," J. Biol. Chem. 281: 36091-101 (2006)). ABCA1 exports PL and FC to various plasma apolipoproteins. Besides FC efflux, intracellular signaling pathways are activated by the interaction of apoA-1 with ABCA1 (Id., citing Mineo, C. and Shaul, P W, "Regulation of signal transduction by HDL," J. Lipid Res. 54: 2315-24 (2013); Liu, Y, and Tang, C., "Regulation of ABCA1 functions by signaling pathways," Biochim. Biophys. Acta, 1821: 522-29 (2012)).

It is well established that the activity of ABCA1 in the plasma membrane enhances binding of apoA-1 to the cell surface, but there has been controversy about the role of this binding in the acquisition of membrane PL by apo-A1. Id. It has been proposed that apoA-1 acquires PL either directly from ABCA1 while it is bound to the transporter, or indirectly at a membrane lipid-binding site created by ABCA1 activity. Id.

The ABCA1-mediated assembly of nascent HDL particles occurs primarily at the cell surface (Id., citing Faulkner, L E, et al, "An analysis of the role of a retroendocytosis pathway in ABCA1-mediated cholesterol efflux from macrophages," J. Lipid Res. 49: 1322-32 (2008); Denis, M. et al, "ATP-binding cassette A-1-mediated lipidation of apolipoprotein A-1 occurs at the plasma membrane and not in the endocytic compartments," J. Biol. Chem. 283: 16178-186 (2008)), where extracellular apoA-1 for HDL particle formation is available. The FC/PL ratio in nascent HDL particles created by ABCA1 activity is dependent upon the cell type and metabolic status of the cell, but the population of larger particles is always relatively FC-rich as compared with the smaller particles.

Regulation of cholesterol efflux depends in part on the ABCA1 pathway, controlled in turn by hydroxysterols (especially 24 and 27-OH cholesterol, which act as ligands for the liver-specific receptor (LXR) family of transcriptional regulatory factors. Braunwald's Heart Disease, P. Libby, R. Bonow, D. Mann and D. Zipes, Eds., 8th Edition, Saunders Elsevier, Philadelphia, Pa. (2008) at 1076.

Cholesterol Esterification with Fatty Acids to Cholesterol Esters (CE) by Acyl-coenzyme A:cholesterol Acyltransferase (ACAT)

Cholesterol content in membranes regulates the cholesterol acyltransferase (CAT) pathway at the level of protein regulation. (Braunwald's Heart Disease, P. Libby, R. Bonow, D. Mann and D. Zipes, Eds., 8th Edition, Saunders Elsevier, Philadelphia, Pa. (2008) at 1076, citing Willner, E. et al, "Deficiency of acyl CoA:cholesterol aceyltransferase 2 prevents atherosclerosis in apolipoprotein E-deficient mice., Proc. Natl Acad. Sci. USA 100: 1262 (2003). Humans express two separate forms of ACAT (ACT1 and ACAT2), which derive from different genes and mediate cholesterol esterification in cytoplasm and in the endoplasmic reticulum lumen for lipoprotein assembly and secretion.

Regulation of Cholesterol Content

Under conditions of cell cholesterol sufficiency, the cell can decrease its input of cholesterol by decreasing the de novo synthesis of cholesterol. The cell can also decrease the amount of cholesterol that enters the cell via the LDL-R, increase the amount stored as cholesteryl esters, and promote the removal of cholesterol by increasing its movement to the plasma membrane for efflux.

The regulation of HMG CoA reductase, the rate limiting step in cholesterol biosynthesis, has been investigated in detail. However, this enzyme acts very early in the cholesterol synthesis pathway. There is accumulating evidence that enzymes beyond HMG CoA reductase serve as flux controlling points, and that regulation of cholesterol synthesis can occur at multiple levels throughout the pathway. (Sharpe, L J and Brown, A J, "Controlling cholesterol synthesis beyond 3-hydroxy-3-methylglutaryl CoA reductase (HMGCR)," J. Biol. Chem. 288 (26): 18707-715 (2013)).

Transcriptional Regulation

Sterol Regulatory Element-binding Proteins (SREBPs)

SREBPs, membrane bound transcription factors that coordinate the synthesis of fatty acids and cholesterol, the two major building blocks of membranes (Brown, M S & Goldstein, J L, "The SREBP pathway: regulation of cholesterol metabolism by proteolysis of a membrane-bound transcription factor," Cell 89: 331-40 (1997)), belong to the basic helix-loop-helix-leucine zipper (bHLH-Zip) family of transcription factors. There are three SREBP proteins (SREB-1a, SREBP-1c, and SREBP-2) from two srebp genes designated srebp1 and srebp2. Id. The SREBP2 isoform plays a major role in regulating cholesterol synthetic genes.

As shown in Table 1, nearly all of the genes encoding cholesterol synthesis enzymes are SREBP targets.

TABLE 1

Genes Encoding Cholesterol Syhnthesis Enzymes that are SREBP Targets

| Gene Name | Gene Symbol | SREBP Target |
|---|---|---|
| Acetyl-CoA acetyltransferase, cytosolic | ACAT2 | Yes |
| 3-hydroxy-3-methylglutaryl-CoA synthase 1 (soluble) | MHGCS1 | Yes |
| 3-hydroxy-3-methylglutaryl-CoA reductase | HMGCR | Yes |
| Mevalonate kinase | MVK | Yes |
| Phosphomevalonate kinase | PMVK | Yes |
| Mevalonate (diphospho)decarboxylase | MVD | Yes |
| Isopentenyl-diphosphate Δ-isomerase ½ | ID11/ID12 | Yes |
| Farnesyl-diphosphate synthase | FDFS | Yes |
| Geranylgeranyl-diphosphate synthase 1 | GGPS1 | Yes |
| Farnesyl-diphosphate farnesyltransferase 1 | FDFT1 | Yes |
| Squalene epoxidase | SQLE | Yes |
| Lanosterol synthase (2,3-oxidosqualene-lanosterol cyclase) | LSS | Yes |
| Cytochrome P450, family 51, subfamily A, polypeptide 1 | CYPS1A1 | Yes |
| Transmembrane 7 superfamily member 2 | TM75F2 | Yes |
| Lamin B receptor | LBR | No |
| Methylsterol monooxygenase 1 | SCAMOL | Yes |
| NAD(P)-dependent steroid dehydrogenase-like | NSDHL | Yes |
| Hydroxysteroid 17β-dehydrogenase 7 | HSD17B7 | Yes |
| Emopamil-binding protein (sterol isomerase) | EBP | Yes |
| Sterol C5-desaturase | SC5D | Yes |
| 7-Dehydrocholesterol reductase | DHCR7 | Yes |
| 24 Dehydrocholesterol reductase | DHCR24 | Yes |

Taken from Sharpe, L J and Brown, A J, "Controlling cholesterol synthesis beyond 3-hydroxy-3-methylglutaryl CoA reductase (HMGCR)," J. Biol. Chem. 288 (26): 18707-715 (2013))

SREBPs coordinately regulate the cholesterol biosynthetic pathway and receptor-mediated endocytosis of LDL at the level of gene transcription. (Brown, M S and Goldstein, J L, "A proteolytic pathway that controls the cholesterol content of membranes, cells and blood,"Proc. Natl Acad. Sci. USA 96: 11041-48 (1999)). In the cholesterol biosynthetic pathway, SREBPs regulate transcription of HMG CoA reductase as well as transcription of genes encoding many other enzymes in the cholesterol biosynthetic pathway, including HMG CoA synthase, farnesyl diphosphate synthase and squalene synthase. Id. Studies investigating regulation of the DHCR24 promoter provided evidence of binding sites for SREBP-2 [Daimiel, L A, et al, "Promoter analysis of the DHCR24 (3β-hydroxysterol Δ24-reductase) gene: characterization of SREBP (sterol-regulatory element-binding-protein)-mediated activation," Biosci. Rep. (2013)/art:e000/doi 10.1042/BSR20120095); Zerenturk, E J, et al, "Sterols regulate 3β-hydroxysterolΔ24-reductase (DHCR24) via dual sterol regulatory elements: cooperative induction of key enzymes in lipid synthesis by sterol regulatory element binding proteins," Biochim. Et Biophys. Acta 1821 (10): 1350-60 (2012)). The SREBPs also regulate the LDL receptor, which supplies cholesterol through receptor mediated endocytosis, and modulate transcription of genes encoding enzymes of fatty acid synthesis and uptake, including acetyl CoA carboxylase, fatty acid synthase, stearoyl CoA desaturase-1 and lipoprotein lipase. (Brown, M S & Goldstein, J L, "The SREBP pathway: regulation of cholesterol metabolism by proteolysis of a membrane-bound transcription factor," Cell 89: 331-40 (1997)).

Nascent SREBPs are targeted to the endoplasmic reticulum (ER) membrane without any transcription activity, because they are not available for their target genes, which are located in the nucleus. (Brown, M S & Goldstein, J L, "The SREBP pathway: regulation of cholesterol metabolism by proteolysis of a membrane-bound transcription factor," Cell 89: 331-40 (1997)). To enhance transcription when cellular sterol is low, the active NH2-terminal domains of SREBPs are released from endoplasmic reticulum membranes by two sequential cleavages that must occur in the proper order. The first is catalyzed by Site-1 protease (S1P), a membrane bound subtilisin-related serine protease that cleaves the hydrophilic loop of SREBP that projects into the endoplasmic reticulum lumen. (Brown, M S and Goldstein, J L, "A proteolytic pathway that controls the cholesterol content of membranes, cells and blood," Proc. Natl Acad. Sci. USA 96: 11041-48 (1999)). The second cleavage, at Site-2, requires the action of S2P, a hydrophobic protein that appears to be a zinc metalloprotease, and takes place within a membrane-spanning domain of SREBP. Id. Sterols block SREBP processing by inhibiting S1P. Id. Sterols block the proteolytic release process by selectively inhibiting cleavage by S1P; S2P is regulated indirectly because it cannot act until SREBP has been processed by S1P. Id.

SREBP cleavage-activating protein (SCAP), an integral ER membrane regulatory protein, is required for cleavage at Site 1 and is the target for sterol suppression of this cleavage, i.e., SCAP loses its activity when sterols overaccumulate in cells. Id. Within cells, SCAP is found in a tight complex with SREBPs. Id. SCAP contains two distinct domains: a hydrophobic N-terminal domain that spans the membrane eight times and a hydrophilic C-terminal domain that projects into the cytosol. (DeBose-Boyd, R. A. "Feedback Regulation of Cholesterol Synthesis: Sterol-accelerated ubiquitination and degradation of HMG CoA Reductase," Cell Res. 18 (6): 609-21 (2008)) A 160 amino acid segment of the membrane domain of SCAP has been termed the sterol-sensing domain. (Brown, M S and Goldstein, J L, "A proteolytic pathway that controls the cholesterol content of membranes, cells and blood," Proc. Natl Acad. Sci. USA 96: 11041-48 (1999)). The C-terminal domain of SCAP mediates a constitutive association with SREBPs, which is required for SCAP-dependent translocation of SREBPs from the ER to Golgi in sterol-deprived cells. (DeBose-Boyd, R. A. "Feedback Regulation of Cholesterol Synthesis: Sterol-accelerated ubiquitination and degradation of HMG CoA Reductase," Cell Res. 18 (6): 609-21 (2008)). The NH2-terminal bHL-Zip domain with full transcription activity is released from the membrane to reach the nucleus and act as a transcription factor to activate genes responsible for cholesterol and fatty acid biosynthesis and LDL uptake (Brown, M S and Goldstein, J L, "A proteolytic pathway that controls the cholesterol content of membranes, cells and blood,"Proc. Natl Acad. Sci. USA 96: 11041-48 (1999)).

When sterols build up within cells, the proteolytic release of SREBPs from ER membranes is blocked, the NH2-terminal domains that have already entered the nucleus are rapidly degraded, and, as a result, transcription of all of the target genes declines. (Id). This decline is complete for the cholesterol biosynthetic enzymes whose transcription is entirely dependent on SREBPs, but less complete for the fatty acid biosynthetic enzymes whose basal transcription can be maintained by other factors.

Other Factors

Besides SREBP, numerous other transcription factors have been implicated in the transcriptional control of the various enzymes in cholesterol biosynthesis. (Sharpe, L J and Brown, A J, "Controlling cholesterol synthesis beyond 3-hydroxy-3-methylglutaryl CoA reductase (HMGCR)," J. Biol. Chem. 288 (26): 18707-715 (2013)).

Liver X Receptors (LXRs)

Liver X receptors (LXRs) are ligand-activated transcription factors of the nuclear receptor superfamily. (Baranowski, M., "Biological role of liver X receptors," J. Physiol. Pharmacology. 59 Suppl. 7: 31-55 (2008)). There are two LXR isoforms (termed alpha and beta), which, upon activation, form heterodimers with retinoid X receptor and bind to LXR response elements found in the promoter region of the target genes. Id. High expression levels of LXRα in metabolically active tissues fit with a central role of the receptor in lipid metabolism, while LXRβ is more ubiquitously expressed. (Pehkonen, P. et al., "Genome-wide landscape of liver X receptor chromatin binding and gene regulation in human macrophages," BMC Genomics 13: 50 (2012)). Both LXRs are found in various cells of the immune system, such as macrophages, dendritic cells and lymphocytes. Id. In macrophages, the accumulation of excess lipoprotein-derived cholesterol activates LXR and triggers the induction of a transcriptional program for cholesterol efflux, such as ATP-binding cassette transporter (ABC) A1 (ABCA1) and ABCG1, while in parallel the receptor transrepresses inflammatory genes, such as inducible nitric oxide synthase, interleukin 1β, and monocyte chemotactic protein-1. Id. LXR has been reported to regulate cholesterol biosynthesis by directly silencing the gene expression of two cholesterogenic enzymes (FDFT1 and CYP51A1). (Sharpe, L J and Brown, A J, "Controlling cholesterol synthesis beyond 3-hydroxy-3-methylglutaryl CoA reductase (HMGCR)," J. Biol. Chem. 288 (26): 18707-715 (2013), citing Wang, Y. et al, "Regulation of cholesterologenesis by the oxysterol receptor, LXRα," J. Biol. Chem. 283: 26332-339 (2008)).

Endogenous agonists of the LXRs include oxysterols, which are oxidized cholesterol derivatives. (Baranowski, M., "Biological role of liver X receptors," J. Physiol. Pharmacol. 59 Suppl. 7: 31-55 (2008)). LXRs have been characterized as key transcriptional regulators of lipid and carbohydrate metabolism, and were shown to function as sterol sensors protecting the cells from cholesterol overload by stimulating reverse cholesterol transport and activating its conversion to bile acids in the liver. Id. This finding led to identification of LXR agonists as potent anti-atherogenic agents in rodent models of atherosclerosis. Id. However, first-generation LXR activators were also shown to stimulate lipogenesis via SREBP1c leading to liver steatosis and hypertriglyceridemia. Id.

Despite their lipogenic action, LXR agonists possess antidiabetic properties. Id. LXR activation normalizes glycemia and improves insulin sensitivity in rodent models of type 2 diabetes and insulin resistance. Id. Although antidiabetic action of LXR agonists is thought to result predominantly from suppression of hepatic gluconeogenesis, some studies suggest that LXR activation may also enhance peripheral glucose uptake. Id.

Published reports of anti-proliferative effects of synthetic LXR ligands on breast, prostate, ovarian, lung, skin, and colorectal cancer cells suggest that LXRs are potential targets in cancer prevention and treatment. Nguyen-Vu, T. et al, "Liver x receptor ligands disrupt breast cancer cell proliferation through an E2F-mediated mechanism," Breast Cancer Res. 15: R51 (2013). Cell line-specific transcriptional responses and a set of common responsive genes were shown by microarray analysis of gene expression in four breast cell lines [MCF-7 (ER+), T-47D (ER+), SK-BR-3 (ER−), and MDA-MB-231] following treatment with the synthetic LXR ligand GW3965. Id. In the common responsive gene set, upregulated genes tend to function in the known metabolic effects of LXR ligands and LXRs whereas the downregulated genes mostly include those which function in cell cycle regulation, DNA replication, and other cell proliferation-related processes. Id. Transcription factor binding site analysis of the downregulated genes revealed an enrichment of E2F binding site sequence motifs. Id. Correspondingly, E2F2 transcript levels are downregulated following LXR ligand treatment. Id. Knockdown of E2F2 expression, similar to LXR ligand treatment, resulted in a significant disruption of estrogen receptor positive breast cancer cell proliferation. Id. Ligand treatment also decreased E2F2 binding to cis-regulatory regions of target genes.

Expression of activated LXRα blocks proliferation of human colorectal cancer cells and slows the growth of xenograft tumors in mice, and reduces intestinal tumor formation after administration of chemical carcinogens in Apc(min/+) mice. Lo Sasso, G. et al., "Liver X receptors inhibit proliferation of human colorectal cancer cells and growth of intestinal tumors in mice," Gastroenterology 144(7): 1497-507 (2013). A link of LXRs to apoptosis has been reported. (Pehkonen, P. et al, "Genome-wide landscape of liver X receptor chromatin binding and gene regulation in human macrophages," BMC Genomics 13: 50 (2012)).

MicroRNAs and Alternative Splicing

Overall, relatively little has been reported on miRNAs in the context of cholesterol synthesis. (Sharpe, L J and Brown, A J, "Controlling cholesterol synthesis beyond 3-hydroxy-3-methylglutaryl CoA reductase (HMGCR)," J. Biol. Chem. 288 (26): 18707-715 (2013)) In the context of cholesterol metabolism, perhaps the best studied microRNA (miRNA) is miR-33, an intronic miRNA encoded in the SREBP genes that controls cellular cholesterol export, whereas its SREBP host genes stimulate cholesterol synthesis (Id., citing Fernandez-Hernando, et al, "MicroRNAs in metabolic disease," Arterioscl. Thromb. Vasc. Biol. 33: 178-85 (2013)).

Alternative splicing of HMGCR is regulated by sterols, with proportionally less of an unproductive transcript present when sterol levels are low and more when sterol levels are higher (Id., citing Medina, M. W., et al, "Coordinately regulated alternative splicing of genes involved in cholesterol biosynthesis and uptake," PLosONE 6: e19420 (2011)). This effect also extends to other cholesterogenic genes, including HMGSC1 and MVK (Id citing Medina, M. W., et al, "Coordinately regulated alternative splicing of genes involved in cholesterol biosynthesis and uptake," PLosONE 6: e19420 (2011)). Because the effect is mediated via SREBP-2 and alternative transcripts occur for all cholesterol synthesis enzymes beyond HMGCR (Id., citing de la Grange, P., et al, "a new advance in alternative splicing databases from catalogue to detailed analysis of regulation of expression and function of human alternative splicing variants," BMC Bioinformatics 8: 180 (2007)), this effect may involve the entire cholesterol synthesis pathway.

Post-translational Regulation

Because transcriptional down-regulation via the SREBP pathway is relatively slow, with mRNA of target genes decreasing only after several hours, rapid shutdown of cholesterol synthesis requires post-transcriptional control. Turnover of 3-hydroxy-3-methylglutaryl-CoA reductase (HMGCR) is accelerated by non-sterol and sterol products of the mevalonate pathways (Id., citing Roitelman, J. and Simoni, R D, "Distinct sterol and nonsterol signals for the regulated degradation of 3-hydroxy-3-methylglutaryl-CoA reductase," J. Biol. Chem. 267: 25264-273 (1992)), with physiological sterol degradation signals, such as 24,25-dihydrolanosterol, and side chain oxysterols, such as 24,25-EC and 27-hydroxycholeseterol (generated from cholesterol itself (Id., citing Lange, Y. et al, "Effectors of rapid homeostatic responses of endoplasmic reticulum cholesterol and 3-hydroxy-3-methylglutaryl-CoA reductase," J. Biol. Chem. 283: 1445-55 (2008); Nguyen, A D et al, "Hypoxyia stimulates degradation of 3-hydroxy-3-methylglutaryl-coenzyme A reductase through accumulation of lanosterol and hypoxia-inducible factor-mediated induction of Insigs," J. Biol. Chem. 282: 27436-446 (2007)). The regulated turnover is proteosomal, and requires the Insig proteins, which also act to suppress SREBP activation (Jo, Y and Debose-Boyd, R A, "Control of cholesterol synthesis through regulated ER-associated degradation of HMG CoA reductase," Crit. Rev. Biochem. Mol. Bio. 445: 185-198 (2010); Burg, J S and Espenshade, P J, "Regulation of HMG-CoA reductase in mammals and yeast," Prog. Lipid Res. 50: 403-410 (2011)).

Regulated ER-associated degradation also occurs for a later step in cholesterol synthesis, catalyzed by squalene monooxygenase (SM), albeit by a mechanism distinct from HMGCR. Squalene monooxygenase has been proposed as a second rate-limiting enzyme in cholesterol synthesis (Id., citing Gonzalez, R. et al, "Two major regulatory steps in cholesterol synthesis by human renal cancer cells," Arch. Biochem. Biophys. 196: 574-80 (1979); Hidaka, Y, et al, "Regulation of squalene epoxidase in HepG2 cells," J. Lipid Res. 31: 2087-94 (1990)). Cholesterol itself accelerates SM degradation, an example of end product inhibition (Id., citing Gill, S. et al, "Cholesterol-dependent degradation of squalene monooxygenase, a control point in cholesterol synthesis beyond HMG-CoA reductase," Cell Metab. 13: 260-73 (2011)), and unlike HMGCR, SM turnover does not require the Insig proteins.

Feedback Regulation of Cholesterol Synthesis

Cholesterol accumulation lowers the activity of HMG CoA reductase and several other enzymes in the cholesterol biosynthetic pathway, thereby limiting the production of cholesterol.

HMG CoA reductase, the rate-limiting enzyme in cholesterol synthesis, and the target of statins, is subject to feedback control through multiple mechanisms that are mediated by sterol and nonsterol end-products of mevalonate metabolism such that essential nonsterol isoprenoids can be constantly supplied without risking the potentially toxic overproduction of cholesterol or one of its sterol precursors. (DeBose-Boyd, R. A. "Feedback Regulation of Cholesterol Synthesis: Sterol-accelerated ubiquitination and degradation of HMG CoA Reductase," Cell Res. 18 (6): 609-21 (2008)). For example, treatment of cultured cells with the statin Compactin, a competitive inhibitor of HMG-CoA reductase, blocks production of mevalonate, thereby reducing levels of sterol and nonsterol isoprenoids that normally govern this feedback regulation. Id. Cells respond to the inhibition of HMG-CoA reductase with a compensatory increase in the reductase due to the combined effects of enhanced transcription of the reductase gene, efficient translation of mRNA, and extended half-life of reductase protein. Id. Complete reversal of this compensatory increase in reductase requires regulatory actions of both sterol and nonsterol end-products of mevalonate metabolism. Id.

Sterols inhibit the activity of sterol regulatory element-binding proteins (SREBPs) and the low density lipoprotein (LDL)-receptor (Id., citing Horton, J D, et al, "SREBPs: activators of the complete program of cholesterol and fatty acid synthesis in the liver," J. Clin. Invest. 109: 1125-31 (2002)). A nonsterol mevalonate-derived product(s) control(s) the translational effects through a poorly understood mechanism that may be mediated by the complex 5'-untranslated region of the reductase mRNA (Id., citing Nakanishi, M. et al, "Multivalent control of 3-hydroxy-3-methylglutaryl coenzyme A reductase. Mevalonate-derived product inhibits translation of mRNA and accelerates degradation of enzyme," J. Biol. Chem. 263: 8929-37 (1988)). Both sterol and nonsterol end-products of mevalonate metabolism combine to accelerate degradation of reductase protein through a mechanism mediated by the ubiquitin-proteosome pathway (Id., citing Roitelman, J. and Simoni, R D, "Distinct sterol and nonsterol signals for the regulated degradation of 3-hydroxy-3-methylglutaryl-CoA reductase," J. Biol. Che. 267: 25264-273 (1992); McGee, T P et al, "Degradation of 3-hydroxy-3-methylglutaryl-CoA reductase in endoplasmic reticulum membranes is accelerated as a result of increased susceptibility to proteolysis," J. Biol. Chem. 271: 25630-638 (1996); Ravid, T. et al, "The ubiquitin proteasome pathway mediates the regulated degradation of mammalian 3-hydroxy-3-methylglutaryl-Coenzyme A reductase," J. Biol. Chem. 275: 35840-47 (2000)).

Inhibition of ER to Golgi transport of SREBPs results from sterol-induced binding of SCAP to ER retention proteins called insulin-induced gene 1 and 2 proteins (Insig-1 and Insig-2) (DeBose-Boyd, R. A. "Feedback Regulation of Cholesterol Synthesis: Sterol-accelerated ubiquitination and degradation of HMG CoA Reductase," Cell Res. 18 (6): 609-21 (2008., citing Yang, T. et al, "Crucial step in cholesterol homeostasis: sterols promote binding of SCAP to INSIG-1, a membrane protein that facilitates retention of SREBPs in ER," Cell 110: 489-500 (2002); Yabe, D. et al, "Insig-2, a second endoplasmic reticulum protein that binds SCAP and blocks export of sterol regulatory element-binding proteins," Proc. Natl. Acad. Sci. USA 99: 12753-758 (2002)). Insig binding occludes a cytosolic binding site in SCAP recognized by COPII proteins, which incorporate cargo molecules into vesicles that deliver ER-derived proteins to the Golgi (Id., citing Sun L P et al, "From the Cover: Sterol-regulated transport of SREBPs from endoplasmic reticulum to Golgi: Insig renders sorting signal in Scap inaccessible to COPII proteins," Proc. Natl Acad. Sci. USA 104: 6519-26 (2007)). SCAP-Insig binding is mediated by a segment of SCAP's membrane domain that includes transmembrane helices 2-6 (Id., citing Hua, X et al, "Sterol resistance in CHO cells traced to point mutation in SREBP cleavage-activating protein," Cell 87: 415-26 (1996); Yang, T. et al, "Crucial step in cholesterol homeostasis: sterols promote binding of SCAP to INSIG-1, a membrane protein that facilitates retention of SREBPs in ER," Cell 110: 489-500 (2002)), i.e., the sterol-sensing domain (Id., citing Kuwabara, P E, "The sterol-sensing domain: multiple families, a unique role," Trends Genet. 18: 193-201 (2002)), since a similar stretch of transmembrane helices is found in at least four other polytopic proteins, including the Niemann Pick C1 protein (part of an intestinal cholesterol transporter complex), Patched, Dispatched and reductase) that have been postulated to interact with sterols. Point mutations within this region disrupt Insig binding, which relieves sterol-mediated retention of mutant SCAP-SREBP complexes in the ER (Id., citing Yang, T. et al, "Crucial step in cholesterol homeostasis: sterols promote binding of SCAP to INSIG-1, a membrane protein that facilitates retention of SREBPs in ER," Cell 110: 489-500 (2002); Yabe, D., "Insig-2, a second endoplasmic reticulum protein that binds SCAP and blocks export of sterol regulatory element-binding proteins," Proc. Natl. Acad. Sci. USA 99: 12753-758 (2002); Yabe, D. et al, "Three mutations in sterol-sensing domain of SCAP block interaction with insig and render SREBP cleavage insensitive to sterols," Proc. Natl Acad. Sci. USA 99: 16672-77 (2002); Nohturfft, A. et al, "A substitution in a single codon of SREBP cleavage-activating protein causes sterol resistance in three mutant Chinese hamster ovary cell lines," Proc. Natl. Acad. Sci. USA 93: 13709-714 (1996); Nohturfft, A. et al, "Sterols regulate processing of carbohydrate chains of wild-type SREBP cleavage-activating protein (SCAP), but not sterol-resistant mutants Y298C o D443N," Proc. Natl. Acad. Sci. USA 95: 12848-853 (1998)).

The following observations suggest that Insigs may play a role in degradation of HMG CoA reductase. First, when Insigs are overexpressed by transfection in Chinese hamster ovary (CHO) cells, HMG CoA reductase cannot be degraded when the cells are treated with sterols (Id., citing Sever, N. et al, "Accelerated degradation of HMG CoA reductase mediated by binding of insig-1 to its sterol-sensing domain," Mol. Cell 11: 25-33 (2003)). Co-expression of Insig-1 restores sterol-accelerated degradation of HMG CoA reductase, suggesting the saturation of endogenous Insigs by the overexpressed reductase. Id. Second, reduction of both Insig-1 and Insig-2 by RNA interference (RNAi) abolishes sterol-accelerated degradation of endogenous HMG CoA reductase (Id., citing Sever, N. et al, "Insig-dependent ubiquitination and degradation of mammalian 3-hydroxy-3-methylglutaryl CoA reductase stimulated by sterols and geranylgeraniol," J. Biol. Chem. 278: 52479-90 (2003)). Third, mutant CHO cells lacking both Insigs are impervious to sterol-stimulated degradation of HMG CoA reductase as well as sterol-mediated inhibition of SREBP processing (Id., citing Lee, P. C. et al, "Isolation of sterol-resistant Chinese hamster ovary cells with genetic deficiencies in both Insig-1 and Insig-2," J. Biol. Chem. 280: 25242-249 (2005)).

Degradation of HMG CoA reductase coincides with sterol-induced binding of its membrane domain to Insigs (Id., citing Sever, N. et al, "Accelerated degradation of HMG CoA reductase mediated by binding of insig-1 to its sterol-sensing domain," Mol. Cell 11: 25-33 (2003)), an action that requires a tetrapeptide sequence (YIYF) located in the second transmembrane segment of HMG CoA reductase. A mutant form of HMG CoA reductase in which the YIYF sequence is mutated to alanine residues no longer binds to Insigs, and the enzyme is not subject to rapid degradation. The YIYF sequence is also present in the second transmembrane domain of SCAP, where it mediates sterol-dependent formation of SCAP-Insig complexes (Id., citing Yang, T. et al, "Crucial step in cholesterol homeostasis: sterols promote binding of SCAP to INSIG-1, a membrane protein that facilitates retention of SREBPs in ER," Cell 110: 489-500 (2002); Yabe, D., "Insig-2, a second endoplasmic reticulum protein that binds SCAP and blocks export of sterol regulatory element-binding proteins," Proc. Natl. Acad. Sci. USA 99: 12753-758 (2002)). Overexpressing the sterol-sensing domain of SCAP in cells blocks Insig-mediated, sterol-accelerated degradation of HMG CoA reductase; mutation of the YIYF sequence in the SCAP sterol-sensing domain ablates this inhibition, suggesting that SCAP and HMG CoA reductase bind to the same site on Insigs and that the two proteins compete for limiting amounts of Insigs when intracellular sterol levels rise. Id.

Glycoprotein 78 (Gp78), an E3 ubiquitin ligase, mediates ubiquitination of ApoB-100, Insig 1 and 2 proteins, and HMG-CoA reductase (Jiang, W., Song, B-L, "Ubiquitin Ligases in Cholesterol Metabolism," Diabetes Metab. 38: 171-80 (2014)). High concentration of sterol (lanosterol) promote the NH2-terminal transmembrane domain of 3-hydroxy-3-methylglutaryl CoA reductase to interact with Insigs (Id., citing Sever, N. et al, "Accelerated degradation of HMG CoA reductase mediated by binding of insig-1 to its sterol-sensing domain," Mol. Cell 11: 25-33 (2003); Song, B L, et al, "Insig-mediated degradation of HMG CoA reductase stimulated by lanosterol, an intermediate in the synthesis of cholesterol," Cell Metab. 1: 179-89 (2005)), and sterol-dependent Insig binding results in recruitment of ubiquitin ligase.

Gp78 binds Insig-1 constitutively in the ER membrane.Id. When the cellular sterol level is high, the insig-1/gp78 complex binds the transmembrane domain of 3-hydroxy-3-methylglutaryl CoA reductase. Id. With the assistance of at least two proteins associated with gp78, p97/VCP and Aup1 (Id., citing Song, B L et al, "Gp8, a membrane-anchored ubiquitin ligase, associates with Insig-1 and couples sterol-regulated ubiquitination to degradation of HMG CoA reductase," Mol. Cell 19: 829-40 (2005); Jo, Y et al, "ancient ubiquitous protein 1 mediates sterol-induced ubiquitination of 3-hydroxy-3-methylglutaryl CoA reductase in lipid droplet-associated endoplasmic reticulum membranes," Mol. Biol. Cell 24: 169-83 (2013)), the ubiquitinated reductase is translocated to lipid droplet-associated ER membrane and dislocated from membrane into cytosol for proteosomal degradation (Id., citing Jo, Y et al, "ancient ubiquitous protein 1 mediates sterol-induced ubiquitination of 3-hydroxy-3-methylglutaryl CoA reductase in lipid droplet-associated endoplasmic reticulum membranes," Mol. Biol. Cell 24: 169-83 (2013); Hartman I Z, et al, "Sterol-induced dislocation of 3-hydroxy-3-methylglutaryl coenzyme A reductase from endoplasmic reticulum membranes into the cytosol through a subcellular compartment resembling lipi droplets," J. Biol. Chem. 285: 19288-98 (2010)). This post-ubiquitination process can be promoted by geranylgeraniol or its metabolically active geranyl-geranyl-pyrophosphate (Id., citing Sever, N. et al, "Insig-dependent ubiquitination and degradation of mammalian 3-hydroxy-3-methylglutaryl CoA reductase stimulated by sterols and geranylgeraniol," J. Biol. Chem. 278: 52479-90 (2003)).

In short, the ubiquitination of Insig-1 is mediated by gp78 and regulated by sterols. Id. Insig-1 is modified by gp78 under low sterol conditions. Id. High sterol promotes SCAP to bind Insig and gp78 is competed off, thereby stabilizing Insig-1. Id.

Gp78-mediated ubiquitination and degradation of Insig-1 provides a mechanism for convergent feedback inhibition, whereby inhibition of SREBP processing requires convergence of newly synthesized Insig-1 and newly acquired sterols (DeBose-Boyd, R. A. "Feedback Regulation of Cholesterol Synthesis: Sterol-accelerated ubiquitination and degradation of HMG CoA Reductase," Cell Res. 18 (6): 609-21 (2008); citing Gong, Y. et al, "Sterol-regulated ubiquitination and degradation of Insig-1 creates a convergent mechanism for feedback control of cholesterol synthesis and uptake," Cell Metab. 3: 15-24 (2006)). In sterol-depleted cells, SCAP-SREBP complexes no longer bind Insig-1, which in turn becomes ubiquitinated and degraded. Id. These SCAP-SREBP complexes are free to exit the ER and translocate to the Golgi, where the SREBPs are processed to the nuclear form that stimulates transcription of target genes, including the Insig-1 gene. Id. Increased transcription of the Insig-1 gene leads to increased synthesis of Insig-1 protein, but the protein is ubiquitinated and degraded until sterols build up to levels sufficient to trigger SCAP binding. Id.

Insig-2 has been defined as a membrane-bound oxysterol binding protein with binding specificity that correlates with the ability of oxysterols to inhibit SREBP processing (Id., citing Sun, L P, et al, "Sterol-regulated transport of SREBPs from endoplasmic reticulum to Golgi: Insig renders sorting signal in Scap inaccessible to COPII proteins," Proc. Natl Acad. Sci. USA 104: 6519-26 (2007); Radhakrishnan, A. et al, "From the Cover: Sterol-regulated transport of SREBPs from endoplasmic reticulum to Golgi: Oxysterols block transport by binding to Insig," Proc. Natl Acad. Sci. USA 104: 6511-18 (2007)). Oxysterols, cholesterol derivatives that contain hydroxyl groups at various positions in the iso-octyl side chain (e.g., 24-hydroxycholesterol, 25-hydroxycholesterol, 27-hydroxycholesterol), are synthesized in many tissues by specific hydrolases; oxysterols play key roles in cholesterol export, and are intermediates in the synthesis of bile acids (Id., citing Russell, D W, "Oxsterol biosynthetic enzymes," Biochim. Biophys. Acta—Molec. Cell Biol. Lipids 1529: 126-135 (2000)). Oxysterols, which are significantly more soluble than cholesterol in aqueous solution, can readily pass across the plasma membrane and enter cells, and are extremely potent in inhibiting cholesterol synthesis by stimulating binding of both HMG Co A reductase and SCAP to Insigs. Id. Thus, formation of the SCAP-Insig complex can be initiated by either binding of cholesterol to the membrane domain of SCAP or by binding of oxysterols to Insigs, both of which prevent incorporation of SCAP-SREBP into vesicles that bud from the ER en route to the Golgi. Id.

Insig-mediated regulation of HMG Co A reductase is controlled by three classes of sterols: oxysterols, cholesterol, and methylated sterols (e.g., lanosterol and 24, 25-dihydrolanosterol). Id. Oxysterols both accelerate degradation of HMG Co A reductase and block ER to Golgi transport of SCAP-SREBP through their direct binding to Insigs. Id. Cholesterol does not regulate HMG Co A reductase stability directly, but binds to SCAP and triggers Insig binding, thereby preventing escape of SCAP-SREBP from the ER.Id. Lanosterol selectively accelerates degradation of HMG Co A reductase without an effect on ER to Golgi transport of SCAP-SREBP. Id. However, the demethylation of lanosterol has been implicated as a rate-limiting step in the post-squalene portion of cholesterol synthesis (Id., citing Gaylor, J L, "Membrane bound enzymes of cholesterol synthesis from lanosterol," Biochem. Biophys. Res. Communic., 292: 1139-46 (2002); Williams, M T, et al, "Investigation of the rate-determining microsomal reaction of cholesterol biosynthesis from lanosterol in Morris hepatomas and liver," Cancer Res. 37: 1377-83 (1977)). The accumulation of lanosterol is avoided; its inability to block SREBP processing through SCAP assures that mRNAs encoding enzymes catalyzing reactions subsequent to lanosterol remain elevated, and lanosterol is metabolized to cholesterol.

It is a paradox that gp78 deficiency increases both the 3-hydroxy-3-methylglutaryl CoA reductase and Insig protein levels in mouse liver, because Insigs not only negatively regulate 3-hydroxy-3-methylglutaryl CoA reductase post-transcriptionally, but also inhibit SREBPs processing through binding to SCAP (Jiang, W. and Song, B-L, "Ubiquitin Ligases in Cholesterol Metabolism," Diabetes Metab. 38: 171-80 (2014) citing Nohturfft, A. et al., "Topology of SREBP cleavage-activating protein, a polytopic membrane protein with a sterol sensing domain," J. Biol. Chem. 273: 17243-250 (1998)). These two outcomes are contradictory regarding cholesterol biosynthesis. Studies from L-gp78+ mice have shown that the biosynthesis of cholesterol and fatty acids is decreased in gp78-deficient mouse liver (Id., citing Edwards, P A et al, "Purification and properties of rat liver 3-hydroxy-3-methylglutaryl coenzyme A reductase," Biochim. Biophys. Acta 574: 123-35 (1979)). This has been interpreted to mean that the Insig-SCAP-SREBP axis dominates, even though 3-hydroxy-3-methylglutaryl CoA (HMG CoA) reductase is elevated. Id.

ApoB-100, an essential protein component of very low density lipoproteins (VLDL) and low density lipoproteins (LDL), which plays critical roles in plasma cholesterol transportation, is another substrate of g78. Id. Under normal conditions, ApoB-100 is one of the committed secretory proteins.Id. However, when the cellular lipid availability is limited (e.g., the new synthesized core lipids (triglyceride, cholesterol ester) or microsomal triglyceride transfer protein activity is decreased), the nascent ApoB-100 is subjected to ER-associated degradation mediated by gp78. Id. When gp78 is overexpressed, ubiquitination and degradation through the 26S proteosome of apoB-100 is decreased (Id., citing Ravid, T. et al, "The ubiquitin-proteasome pathway mediates the regulated degradation of mammalian 3-hydroxy-3-methylglutaryl-coenzyme A reductase," J. Biol. Chem. 275: 35840-847 (2000)). When gp78 is knocked down, the secretion of apoB-100 and the assembly of VLDL are increased in HepG2 cells (Id., citing Hua, X., et al, "Sterol resistance in CHO cells traced to point mutation in SREBP cleavage-activating protein," Cell 87: 415-426 (1996)). The retrotranslocation of ApoB-100 also requires p97/VCP, similar to HMG CoA reductase (Id, citing Nakanishi, M. et al, "multivalent control of 3-hydroxy-3-methylglutaryl coenzyme A reductase. Mevalonate-derived product inhibits translation of mRNA and accelerates degradation of enzyme," J. Biol. Chem. 263: 8929-37 (1988); Hua, X., et al, "Sterol resistance in CHO cells traced to point mutation in SREBP cleavage-activating protein," Cell 87: 415-426 (1996)).

TRC8

Human TRC8 is a multi-pass membrane protein located in the ER membrane that binds both Insig-1 and Insig-2. (Id., citing Inoue, S. et al, "Inhibition of degradation of 3-hydroxyl-3-methylglutaryl-coenzyme A reductase in vivo by cysteine protease inhibitors," J. Biol. Chem. 266: 13311-17 (1991)). It contains a conserved sterol sensing domain and C-terminal RING domain with ubiquitin ligase activity (Id., citing Yabe, D. et al, "Insig-2, a second endoplasmic reticulum protein that binds SCAP and blocks export of sterol regulatory element-binding proteins," Proc. Natl. Acad. Sci. USA 99: 12753-758 (2002); Sun L P et al, "From the Cover: Sterol-regulated transport of SREBPs from endoplasmic reticulum to Golgi: Insig renders sorting signal in Scap inaccessible to COPII proteins," Proc. Natl Acad. Sci. USA 104: 6519-26 (2007)). RNAi studies in SV-589 cells showed that knockdown of TRC8 combined with gp78 can dramatically decrease the sterol-regulated ubiquitination as well as degradation of HMG CoA reductase, suggesting that both gp78 and TRC8 are involved in the sterol-accelerated ubiquitination of HMG CoA reductase in CHO-7 and SV-589 cells. (Id., citing Inoue, S. et al, "Inhibition of degradation of 3-hydroxyl-3-methylglutaryl-coenzyme A reductase in vivo by cysteine protease inhibitors," J. Biol. Chem. 266: 13311-17 (1991)).

TEB4

Human TEB4 is a 910 amino acid ER membrane-resident ubiquitin ligase. In mammalian cells, cholesterol stimulates the degradation of squalene monooxygenase (SM), the enzyme that catalyzes the first oxygenation step in cholesterol synthesis by which squalene is converted to the squalene-2,3-epoxide (37) mediated by TEB4 (Id., citing Sever, N. et al, "Accelerated degradation of HMG CoA reductase mediated by binding of insig-1 to its sterol-sensing domain," Mol. Cell 11: 25-33 (2003)). As one of the target genes of SREBP-2, both the transcription of SM and the stability of SM protein are regulated by sterols (Id., citing Sever, N. et al, Insig-dependent ubiquitination and degradation of mammalin 3-hydroxy-3-methylglutaryl-CoA reductase stimulated by sterols and geranylgeraniol," J. Biol. Chem. 278: 52479-490 (2003)). SM protein level is negatively regulated by cholesterol in mammalian cells (Id., citing Lee, P C, et al, "Isolation of sterol-resistant Chinese hamster ovary cells with genetic deficiencies in both Insig-1 and Insig-2," J. Biol. Chem. 280: 25242-249 (2005)). When cholesterol, but not 24, 25-dihydrolanosterol, or side chain oxysterols, such as 27-hydroxycholesterol, is/are present, SM is ubiquitinated by TEB4 (Id., citing Sever, N. et al, "Accelerated degradation of HMG CoA reductase mediated by binding of insig-1 to its sterol-sensing domain," Mol. Cell 11: 25-33 (2003); Lee, P C, et al, "Isolation of sterol-resistant Chinese hamster ovary cells with genetic deficiencies in both Insig-1 and Insig-2," J. Biol. Chem. 280: 25242-249 (2005)).

IDOL

The low density lipoprotein receptor (LDL-R) gene family consists of cell surface proteins involved in receptor-mediated endocytosis of specific ligands. Low density lipoprotein (LDL) is normally bound at the cell membrane and taken into the cell, ending up in lysosomes where the protein is degraded and the cholesterol is made available for repression of microsomal enzyme HMG CoA reductase. At the same time, a reciprocal stimulation of cholesterol ester synthesis takes place.

Inducible degrader of LDL-R (IDOL) moderates the degradation of LDL-R and requires the E2 enzyme UBE2D (Id., citing Schroepfer, G J, Jr., "Oxysterols: modulators of cholesterol metabolism and other processes," Physiol. Rev. 80: 361-554 (2000); Bjorkhem, I., "Do oxysterols control choleseterol homeostasis," J. Clin. Invest. 110: 725-30 (2002)).

Transcription of the LDL-R gene is regulated primarily by SREBP in a sterol responsive manner. (Id.) The LDL-R is also regulated at the posttranscriptional level by protoprotein convertase subtilisin/kexin type 9 (PCSK9)-mediated degradation of LDLR in the lysosome. (Id., citing Radhakrishnan, A. et al, "Direct binding of cholesterol to the purified membrane region of SCAP: Mechanism for a sterol-sensing domain," Mol. Cell 15: 259-68 (2004)). PCSK9 is synthesized as an about 74 kD soluble zymogen in the endoplasmic reticulum (ER), where it undergoes autocatalytic processing to release a processing enzyme of about 60 kDa to secrete from cells. (Id.) PCSK9 binds the extracellular domain of LDLR, which leads to lysosomal degradation of LDLR. (Id.)

IDOL also is a post-transcriptional regulator of LDL-R (Id., citing Schroepfer, G J, Jr., "Oxysterols: modulators of cholesterol metabolism and other processes," Physiol. Rev. 80: 361-554 (2000)). Activation of LXR can decrease the abundance of LDLR without changing its mRNA level and subsequently inhibited uptake of LDL in different cells (Id., citing Schroepfer, G J, Jr., "Oxysterols: modulators of cholesterol metabolism and other processes," Physiol. Rev. 80: 361-554 (2000)). IDOL can increase plasma cholesterol level by ubiquitination and degradation of LDL-R dependent on its cytosolic domain. The decrease or ablation of IDOL can elevate the LDL-R protein level and promote LDL uptake. The expression of Idol in liver is relatively low, and it is not regulated by LXR, while the LXR-IDOL pathway seems to be more active in peripheral cells, e.g., macrophages, small intestine, adrenals.

Cholesterol Biosynthesis Pathway Inhibitors as Antitumor Agents

Statins, which were developed as lipid-lowering drugs to control hypercholesterolemia, competitively inhibit HMG-CoA reductase, and have been proposed as anticancer agents, because of their ability to trigger apoptosis in a variety of tumor cells in a manner that is sensitive and specific to the inhibition of HMG-CoA reductase (Thumher, M., et al., "Novel aspects of mevalonate pathway inhibitors as antitumor agents," Clin. Cancer Res. 18: 3524-31 (2012) citing Wong, W W et al, "HMG-CoA reductase inhibitors and the malignant cell: the statin family of drugs as triggers of tumor-specific apoptosis," Leukemia 16: 508-19 (2002)). This apoptotic response is in part due to the downstream depletion of geranylgeranyl pyrophosphate (GGPP), and thus due to inhibition of protein prenylation. Protein prenylation creates a lipidated hydrophobic domain and plays a role in membrane attachment or protein-protein interactions. Prenylation occurs on many members of the Ras and Rho family of small guanosine triphosphatases (GTPases). Three enzymes (farnesyltransferase (FTase), geranylgeranyltransferase (GGTase) I and GGTase II can catalyze protein prenylation.

While statin therapy blocks the intracellular synthesis of cholesterol, it also alters the cholesterol content of tumor cell membranes, interfering with key signaling pathways. (Cruz, P M R, et al, "The role of cholesterol metabolism and cholesterol transport in carcinogenesis: a review of scientific findings, relevant to future cancer therapeutics," Frontiers in Pharmacol. 4(119): doi:10.3369/phar.2013.00119, citing Zhuang, L. et al, "Cholesterol targeting alters lipid raft composition and cell survival in prostate cancer cells and zenografts," J. Clin. Invest. 115: 959-68 (2005)).

Statins have been shown to have immunomodulatory activity (Thumher, M., et al., "Novel aspects of mevalonate pathway inhibitors as antitumor agents," Clin. Cancer Res. 18: 3524-31 (2012), citing Greenwood, J et al, Statin therapy and autoimmune disease: from protein prenylation to immunomodulation," Nat. Rev. Immunol. 6: 358-70 (2006)), and to induce the depletion of prenyl pyrophosphates in human dendritic cells [Gruenbacher, G. et al., "CD56+ human blood dendritic cells effectively promote TH1-type gammadelta T cell responses," Blood 114: 4422-31 (2009); Steinman, R M, Banchereau, J., "Taking dendritic cells into medicine," Nature 449: 419-26 (2007)). Prenyl pyrophosphate deprivation translated into activation of caspase I, which cleaved the preforms of IL-1β and IL-18 and enabled the release of bioactive cytokines. The statin-treated dendritic cells (DCs) thus acquired the capability to potentially activate IL-2 primed natural killer (NK) cells (Id., citing Gruenbacher, G. et al., "IL-2 costimulation enables statin-mediated activation of human NK cells, preferentially through a mechanism involving CD56+ dendritic cells," Cancer Res. 70: 9611-20 (2010)). NK cells, which recognize and attack tumor cells that lack MHC class I molecules (Id., citing Munz, C. et al, "Dendritic cell maturation by innate lymphocytes: coordinated stimulation of innate and adaptive immunity," J. Exptl Med. 202: 203-7 (2005); Maniar, A. et al, "Human gammadelta T lymphocytes induce robust NK cell-mediated antitumor cytotoxicity through CD137 engagement," Blood 116: 1726-33 (2010)) contribute to innate immune responses against neoplastic cells. The statin-induced response of IL-2-primed NK cells could be abolished completely when cell cultures were reconstituted with the isoprenoid pyrophosphate GGPP, which allows protein geranylgeranylation to occur despite statin-mediated inhibition of HMB-CoA reductase. Statins also acted directly on human carcinoma cells to induce apoptosis, and IFN-γ produced by NK cells cooperated with statins to enhance tumor cell death synergistically (Id., citing Gruenbacher, G. et al., "IL-2 costimulation enables statin-mediated activation of human NK cells, preferentially through a mechanism involving CD56+ dendritic cells," Cancer Res. 70: 9611-20 (2010)).

Mutant p53, which is present in more than half of all human cancers, can significantly upregulate mevalonate pathway activity in cancer cells, which contributes to maintenance of the malignant phenotype. (Id., citing Freed-Pastor, W A, et al, "Mutant p53 disrupts mammary tissue architecture via the mevalonate pathway," Cell 148: 244-58 (2012)). Simvastatin was shown to reduce 3-dimensional growth of cancer cells expressing a single mutant p53 allele, and was able to induce extensive cancer cell death and a significant reduction of their invasive phenotype. In isoprenoid add-back experiments, supplementation with GGPP was sufficient to restore the invasive phenotype in the presence of HMG-CoA reductase inhibition, showing that upregulation of protein geranylgeranylation is an important effect of mutant p53 (Id., citing Freed-Pastor, W A, et al, "Mutant p53 disrupts mammary tissue architecture via the mevalonate pathway," Cell 148: 244-58 (2012)).

Bisphosphonates, drugs that prevent bone resorption, act downstream of HMG-CoA reductase to inhibit farnesyl pyrophosphate (FPP) synthase. Both bisphosphonates and statins eventually cause FPP and GGPP deprivation and thus failure to perform farnesylation and geranylgeranylation of small GTPases of the Ras superfamily. With regard to bisphosphonates, the inhibition of Ras signaling due to the disruption of membrane anchoring of these GTPases eventually stops osteoclast-mediated bone resorption (Id., citing Konstantinopoulos, P A, et al, "Post translational modifications and regulation of the RAS superfamily of GTPases as anticancer targets," Nat. Rev. Drug Discov. 6: 541-55 (2007)).

Suppressors of the mevalonate pathway also include the diverse isoprenoids (Cruz, P M R, et al, "The role of cholesterol metabolism and cholesterol transport in carcinogenesis: a review of scientific findings, relevant to future cancer therapeutics," Frontiers in Pharmacol. 4(119): doi: 10.3369/phar.2013.00119, Id., citing Mo, H and Elson, C E, "Studies of the isopreoid-mediated inhibition of mevalonate synthesis applied to cancer chemotherapy and chemoprevention," Exp. Biol. Med. (Maywood) 229: 567-85 (2004)), mevalonate-derived secondary metabolites of plants (Bach, T J, "Some new aspects of isoprenoid biosynthesis in plants—a review," Lipids 30: 191-202 (1995)). The potencies of isoprenoids in suppressing hepatic HMG-CoA reductase activity was found to be strongly correlated to their potencies in tumor suppression (Id., citing Elson, C E and Quereshi, A A, "Coupling the cholesterol—and tumor-suppressive actions of palm oil to the impact of its minor constituents on 3-hydroxy-3-methylglutaryl coenzyme A reductase activity," Prostaglandins Leukot. Essent. Fatty Acids 52: 205-207 (1995)). The tocotrienols, vitamin E molecules, and "mixed isoprenoids" with a farnesol side chain, down-regulate HMG-CoA reductase activity in tumors and consequently induce cell cycle arrest and apoptosis (Id., citing Mo H and Elfakhani, C E, "Mevalonate-suppressive tocotrienols for cancer chemoprevention and adjuvant therapy, in Tocotrienols: Vitamin E beyond tocopherols, eds. R R. Wilson et al (Boca Raton: CRC Press), 135-149 (2013)). The growth-suppressive effect of tocotrienols was attenuated by supplemental mevalonate (Id., citing Hussein, D and Mo, H, "d-δ-tocotrienol-mediated suppression of the proliferation of human PANC-1, M1A PaCa2 and BxPC-3 pancreatic carcinoma cells," Pancreas 38: e124-e136 (2009)).

Activity of azole antifungal compounds, such as ketoconazole, to block the function of several cytochrome P450 enzymes involved in cholesterol biosynthesis (e.g., CYP51A1, which catalyzes demethylation of lanosterol) and CYP17A1 (which mediates a step in the synthesis of androgens) has been utilized clinically to treat hormone refractory prostate cancer, and recently has been surpassed by abiraterone, a CYP17A1 antagonist. Gorin, A. et al., "Regulation of cholesterol biosynthesis and cancer signaling," Curr. Op. Pharmcol. 12(6) 710-16 (2012); citing (4). Itraconazole has shown activity against medulloblastoma, via its inhibitory effects on Smoothened in the hedgehog pathway. (Id., citing Kim, J. et al, "Itraconazole, a commonly used antifungal that inhibits Hedgehog pathway activity and cancer growth," Cancer Cell. 17(4): 388-99 (2010)), and suppression of angiogenesis via its interference with lysosomal cholesterol trafficking (Id., citing Xu, J. et al, "Cholesterol trafficking is required for mTPOR activation in endothelial cells," Proc. Natl Acad. Sci. USA 107(10): 4764-69 (2010)). The anti-angiogenic effect of itraconazole, a well-established CYP51/ERG11 antifungal antibiotic, is exerted via inhibition of endosomal cholesterol trafficking and suppression of mTOR signaling (Id.).

In tumor cells, increased signaling activity of growth factor or steroid hormone receptors via PI3K/AKT and MAPK/ERK1/2 (Gorin, A. et al., Regulation of cholesterol biosynthesis and cancer signaling, Curr. Opin. Pharmacol. 12(6): 710-16 (2012), citing Menendez, J A and Lupu, R., Fatty acid synthase and the lipogenic phenotype in cancer pathogenesis," Nat. Rev. Cancer 7(10): 763-77 (2007)), HIF-1α, p53 (Id., citing Oliverase, G. et al, "Novel anti-fatty acid synthase compounds with anti-cancer activity in Her2+ breast cancer," Ann. N.Y. Acad. Sci. 1210: 86-92 (2010) and sonic hedgehog (SHH) (Id., citing Bhatia, B. et al, "Sonic hedgehog signaling and malignant transformation of the cerebellar granule neuron precursor cells," Oncogene 30(4): 410-22 (2011)) pathways modulate and activate SREBP-1, the main regulatory component of lipogenesis. It has been reported that inhibiting mTORC1 using rapamycin has little effect on SREBP-1 nuclear localization and its abundance, but inhibiting its upstream factors, like EGFR, PI3K and Akt, significantly decreases SREBP-1 N-terminal levels and diminishes its abundance in the nucleus (Guo, D et al, "Targeting SREBP-1 driven lipid metabolism to treat cancer," Curr. Pharm Des. 20(15): 2619-26 (2014) citing Guo, D. et al, "EGFR signaling through han Akt-SREBP-1-dependent, rapamycin-resistant pathway sensitizes glioblastomas to antilipogenic therapy," Science Signaling 2: ra82 (2009)). mTOR kinase inhibitor Torin-1 (Id., citing Peterson, T R et al, "DEPTOR is an mTOR inhibitor frequently overexpressed in multiple myeloma cells and required for their survival," Cell 137: 873-86 (2009)), which inhibits both mTORC1 and mTORC2 activity (Id., citing Sabatini, D M, "mTOR and cancer: insights into a complex relationship," Nat. Rev. Cancer 6: 729-34 (2006)), significantly decreased SREBP-1 abundance in the nucleus compared to the inhibition of mTORC1 alone by rapamycin (Id., citing Peterson, T R, et al, "mTOR complex I regulates lipin 1 localization to control the SREBP pathway," Cell 146: 408-20 (2011), Hagiwara, et al, "Hepatic mTORC2 activates glycolysis and lipogenesis through Akt, glucokinase and SREBP1c," Cell Metab. 15: 725-38 (2012)).

Overexpression of lipogenic enzymes has been observed in a number of carcinomas (Gorin, A. et al., Regulation of cholesterol biosynthesis and cancer signaling, Curr. Opin. Pharmacol. 12(6): 710-16 (2012), citing Nagahashi, M. et al, "Sphingosine-1-phosphate produced by sphingosine kinase 1 promotes breast cancer progression by stimulating angiogenesis and lymphangiogenesis," Cancer Res. 72(3): 726-35 (2012)) and has been described to correlate with disease severity, increased risk of recurrence and a lower chance of survival (Id., citing Uddin, S. et al, "High prevalence of fatty acid synthase expression in colorectal cancers in Middle Eastern patients and its potential role as a therapeutic target," Am. J. Gastroenterol. 104(7): 1790-1801 (2009; Mashima, T. et al, "De novo fatty-acid synthesis and related pathways as molecular targets for cancer therapy," Br. J. Cancer 100 (9): 1369-72 (2009)).

Accelerated synthesis of lipids and sterols also is an essential mechanistic component of malignant transformation. Oxidized LDL receptor 1 (OLR1) is required for Src kinase transformation of immortalized MCF10A mammary epithelial cells (Id., citing Hirsch, H A et al, "A transcriptional signature and common gene networks link cancer with lipid metabolism and diverse human diseases," Cancer Cell. 17(4): 348-61 (2010)). OLR1 is significantly induced during transformation, and depletion of OLR1 by siRNA blocks morphological transformation and inhibits cell migration and invasion, and results in reduction of tumor growth in vivo (Id.). Conversely, overexpression of ORL1 protein in MCF10A and HCC 1143 mammary epithelial cells leads to significant upregulating of BCL2, a negative regulator of apoptosis (Id., citing Khaidakov, M., et al., "Oxidized LDL receptor 1 (OLR1) as a possible link between obesity, dyslipidemia and cancer," PLoS One 6(5): e20277 (2011)).

EBP in complex with dihydrocholesterol-7 reductase (DHCR7) catalyzes isomerization of the double-bond between C7 and C8 in the second cholesterol ring. (Gabitova, L. et al., "Molecular Pathways: Sterols and receptor signaling in Cancer," Clin. Cancer Res. 19(23): 6344-50 (2013)). This complex mediates the activity of cholesterol epoxide hydrolase (Id., citing de Medina, P. et al, "Identification and pharmacological characterization of cholesterol-5,6-epoxide hydrolase as a target for tamoxifen and AEBS ligands," Proc. Natl. Acad. Sci. USA 107: 13520-5 (2010)).

There are several known inhibitors of EBP, and some have been described as anti-cancer agents. For example, a sterol conjugate of a naturally occurring steroidal alkaloid, 5alpha-hydroxy-6beta-[2-(1H-imidazol-4-yl)ethylamino]cholestan-3beta-ol (dendrogenin A) which is produced in normal, but not in cancer cells, and 5,6 alpha-epoxy-cholesterol and histamine (Id., citing de Medina, P. et al, "Dendrogenin A arises from cholesterol and histamine metabolism and shows cell differentiation and anti-tumour properties," Nature Communic. 4: 1840 (2013); de Medina, P. et al, "Synthesis of new alkylaminooxysterols with potent cell differentiating activities: identification of leads for the treatment of cancer and neurodegenerative diseases," J. Med. Chem. 52: 7765-77 (2009)), has been shown to suppress cancer cell growth and to induce differentiation in vitro in various tumor cell lines of different types of cancers (Id., citing de Medina, P. et al, "Synthesis of new alkylaminooxysterols with potent cell differentiating activities: identification of leads for the treatment of cancer and neurodegenerative diseases," J. Med. Chem. 52: 7765-77 (2009)). It also inhibited tumor growth in melanoma xenograft studies in vivo and prolonged animal survival. (Id., citing de Medina, P. et al, "Dendrogenin A arises from cholesterol and histamine metabolism and shows cell differentiation and anti-tumour properties," Nature Communic. 4: 1840 (2013);).

SR31747A (cis-N-cyclohexyl-N-ethyl-3-(3-chloro-4-cyclohexyl-phenyl)propen-2-ylamine hydrochloride), a selective peripheral sigma binding site ligand whose biological activities include immunoregulation and inhibition of cell proliferation, binds to SR31747A-binding protein 1 (SR-BP) and EBP with nanomolar affinity. Berthois, Y. et all., "SR31747A is a sigma receptor ligand exhibiting antitumoural activity both in vitro and in vivo," Br. J. Cancer 88: 438-46 (2003). The effect of SR31747A on proliferative activity was evaluated in vitro on the following breast and prostate cancer cell lines: breast (hormone responsive MCF-7 cells from a breast adenocarcinoma pleural effusion;

MCF-7AZ; Hormone independent MCF-7/LCC1 cells derived from MCF-7 cell lines; MCF-7LY2, resistant to the growth-inhibitory effects of the antiestrogen LY117018; Hormone unresponsive MDA-MB-321 and BT20 established from a metastatic human breast cancer tumor); and prostate (Hormone responsive prostate cancer cell line LNCaP; hormone-unresponsive PC3 cell line established from bone marrow metastasis; hormone-unresponsive DU145 established from brain metastasis). Id. SR31747A induced concentration-dependent inhibition of cell proliferation, regardless of whether the cells were hormone responsive or unresponsive. Id. The antiproliferative effect of SR31747A was partially reduced by adding cholesterol (Id.; Labit-Le Bouteiller, C. et al., "Antiproliferative effects of SR31747A in animal cell lines are mediated by inhibition of cholesterol biosynthesis at the sterol isomerase step," Eur. J. Biochem. 256: 342-49 (1998)), thus demonstrating the involvement of EBP. Sensitivity to SR31747A did not correlate with cellular levels of EBP. Berthois, Y. et all., "SR31747A is a sigma receptor ligand exhibiting antitumoural activity both in vitro and in vivo," Br. J. Cancer 88: 438-46 (2003). SR31747A also inhibited proliferation in vivo in the mouse xenograft model. Id. Murine EBP cDNA overexpression in CHO cells increased resistance of these cells to SR31747A-induced inhibition of proliferation. Labit-Le Bouteiller, C. et al., "Antiprolifertive effects of SR31747A in animal cell lines are mediated by inhibition of cholesterol biosynthesis at the sterol isomerase step," Eur. J. Biochem. 256: 342-49 (1998)), Tamoxifen, inhibited SR31747 binding in a competitive manner and induced the accumulation of Δ8-sterols, while Emopamil, a high affinity ligand of human sterol isomerase, and verapamil, another calcium channel-blocking agent, are inefficient in inhibiting SR31747 binding to its mammalian target, suggesting that their binding sites do not overlap. Paul, R. et al., "Both the immunosuppressant SR31747 and the antiestrogen tamoxifen bind to an emopamil-insensative site of Mammalian Δ8-47 sterol isomerase," J. Pharmacol. Exptl Thera. 285(3): 1296-1302 (1998)). Some drugs, e.g., cis-flupentixol, trifluoroperazine, 7-=ketocholestanol and tamoxifen, inhibit SR31747 binding only with mammalian EBP enzymes, whereas other drugs, e.g., haloperidol and fenpropimorph, are more effective with the yeast enzyme than with the mammalian ones. Id.

While some cancer cell lines are highly sensitive to small molecule EBP inhibition, other cancer cell lines, as well as normal cell lines, do not respond to EBP inhibition, even when up to 10,000-fold higher concentrations of the EBP inhibitors are used. A determination of which cancer will respond to which inhibitor therefore has required an empirical hit or miss, impractical and expensive, approach.

The described invention establishes that EBP inhibition is only toxic to cancer cells that paradoxically respond to small molecule EBP inhibitors via downregulation of endogenous cholesterol biosynthesis, and provides a method for identifying such EBP inhibitors and for cancer cells that are sensitive to treatment with such inhibitors.

SUMMARY OF THE INVENTION

According to one aspect, the described invention provides a method for identifying a subject who will benefit from treatment with a pharmaceutical composition comprising an EBP-modulating anti-cancer compound, the method comprising (a) isolating a tumor sample comprising a population of cancer cells from the subject; (b) providing (i) an aliquot of the tumor sample in (a) as a test population of cancer cells, (ii) a known population of cancer cells sensitive to an EBP-modulating anticancer compound (positive control), and (iii) a known population of cancer cells insensitive to an EBP-modulating anticancer compound (negative control); (c) determining whether the aliquot of the tumor sample contains a subpopulation of cancer cells sensitive to a composition comprising an EBP-modulating anti-cancer compound by (1) contacting the known EBP-modulating anticancer compound to the populations of cancer cells in (b); (2) measuring EBP enzyme activity and a parameter of endogenous cholesterol synthesis for each population of cancer cells, wherein an amount of the EBP-modulating anti-cancer compound is effective to decrease EBP enzyme activity and to decrease endogenous cholesterol synthesis in a cancer cell sensitive to the known EBP modulating anti-cancer compound, while an amount of the EBP-modulating anti-cancer compound is effective to increase EBP activity and to increase endogenous cholesterol synthesis in a cancer cell insensitive to the EBP modulating anti-cancer compound; (3) distinguishing the sensitive population of cancer cells from the insensitive population of cancer cells in the test population of cancer cells; and (d) if the test population of cancer cells contains a population of cancer cells sensitive to the EBP modulating anti-cancer compound, treating the tumor by administering to the subject a pharmaceutical composition containing a therapeutic amount of the EBP modulating anti-cancer compound. According to one embodiment of the method, in a cancer cell sensitive to the EBP modulating anti-cancer compound, the effective amount of the EBP-modulating anti-cancer compound is effective to cause accumulation of a Δ8 sterol intermediate. According to another embodiment, the Δ8 sterol intermediate is 5α-cholest-8-(9)-en-3β-ol (Δ8-choleseteenol). According to another embodiment, in the cancer cell sensitive to the EBP-modulating anticancer compound, the effective amount of the EBP modulating anti-cancer compound is effective to cause downregulation of SREBP-2. According to another embodiment, in the cancer cell sensitive to the EBP-modulating anticancer compound, the effective amount of the EBP modulating anti-cancer compound is effective to cause downregulation of SREBP-2 genes. According to another embodiment, in the cancer cell sensitive to the EBP-modulating anticancer compound, the effective amount of the EBP modulating anti-cancer compound is effective to cause downregulation of SREBP-2 and one or more SREBP-2 target genes of the cholesterol biosynthetic pathway selected from the group consisting of ACAT2; MHGCS1; HMGCR; MVK; PMVK; MVD; ID11/ID12; FDFS; GGPS1; FDFT1; SQLE; LSS; CYPS1A1; TM75F2; SCAMOL; NSDHL; HSD17B7; EBP; SC5D; DHCR7; and DHCR24. According to another embodiment, the cancer cell sensitive to the EBP-modulating anti-cancer compound comprises a truncated APC protein. According to another embodiment, the therapeutic amount of the EBP-modulating anti-cancer compound is effective to reduce proliferation of the cancer cell sensitive to the EBP modulating anti-cancer compound, to reduce invasiveness of the cancer cell sensitive to the EBP modulating anti-cancer compound, increase apoptosis of the cancer cell sensitive to the EBP modulating anti-cancer compound, reduce growth of a tumor comprising the cancer cell sensitive to the EBP modulating anti-cancer compound, reduce tumor burden, improve progression free survival, improve overall survival, achieve remission of disease, or a combination thereof. According to another embodiment, the EBP-modulating anti-cancer compound is selected from the group consisting of TASIN-1 and functional equivalents thereof, dendrogenin A, SR31747A, tamoxifen, emopamil, verapamil, cis-flupentixol, trifluoroperazine, 7-ketocholestenol, haloperidol, and fenpropimorph.
According to another embodiment, a functional equivalent of TASIN-1 is selected from the group consisting of:
1.
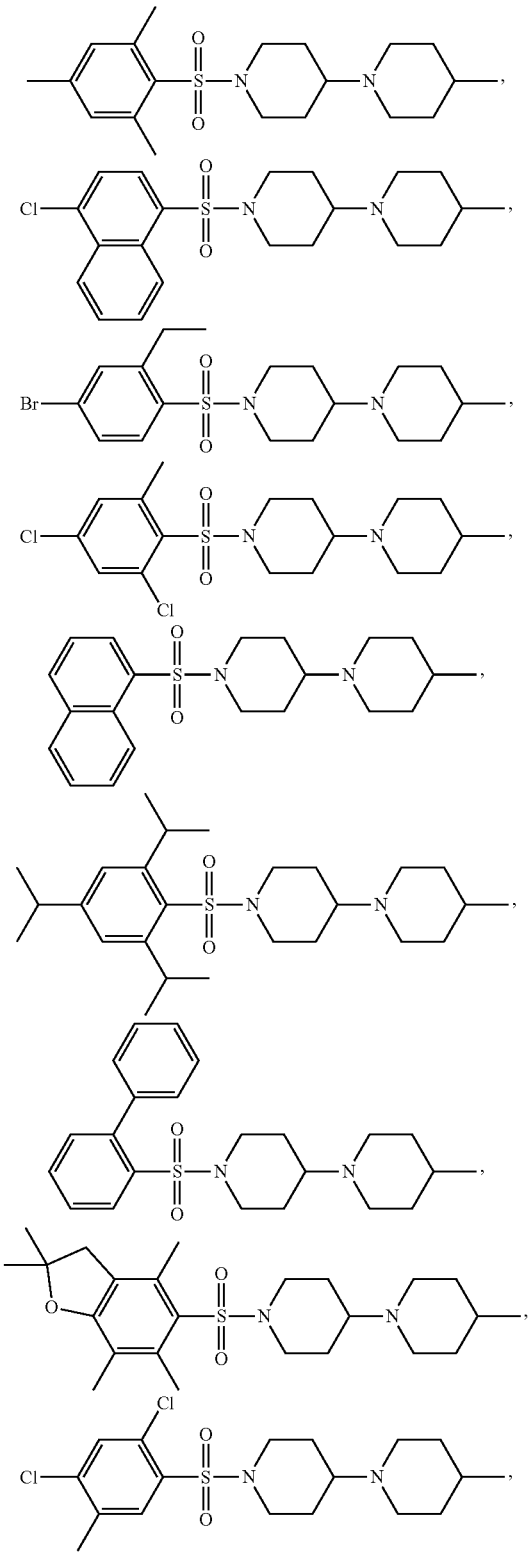
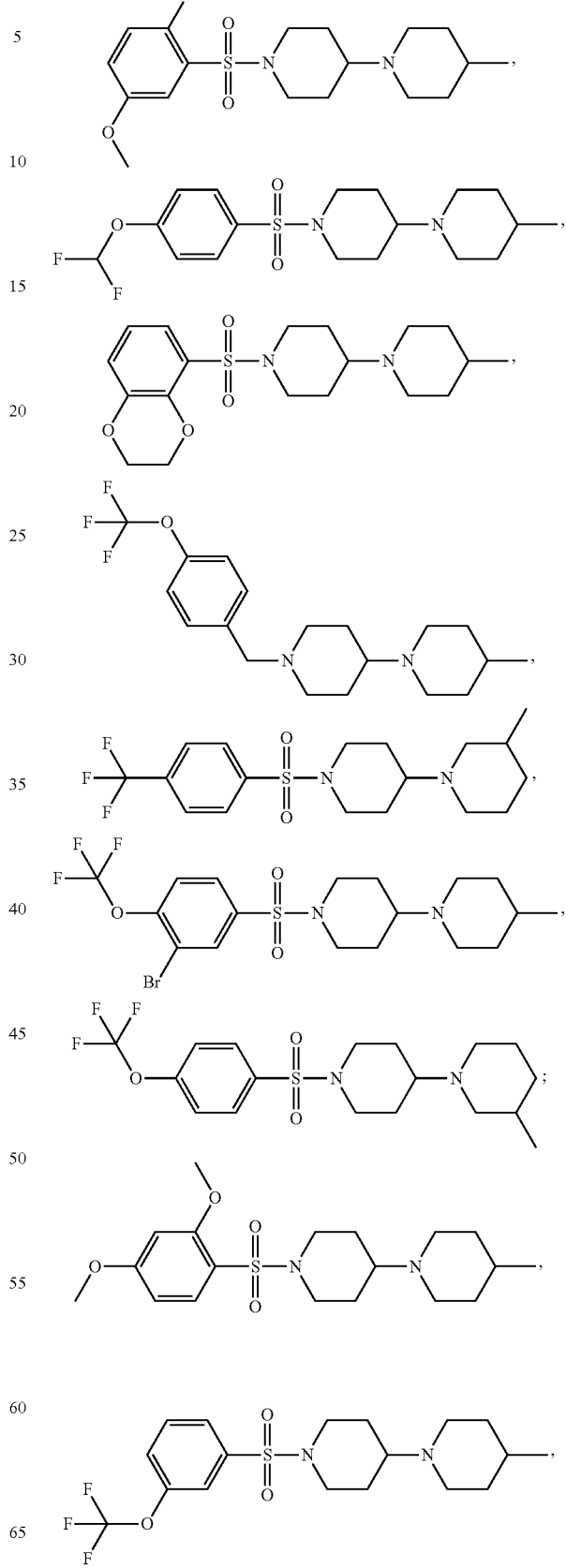

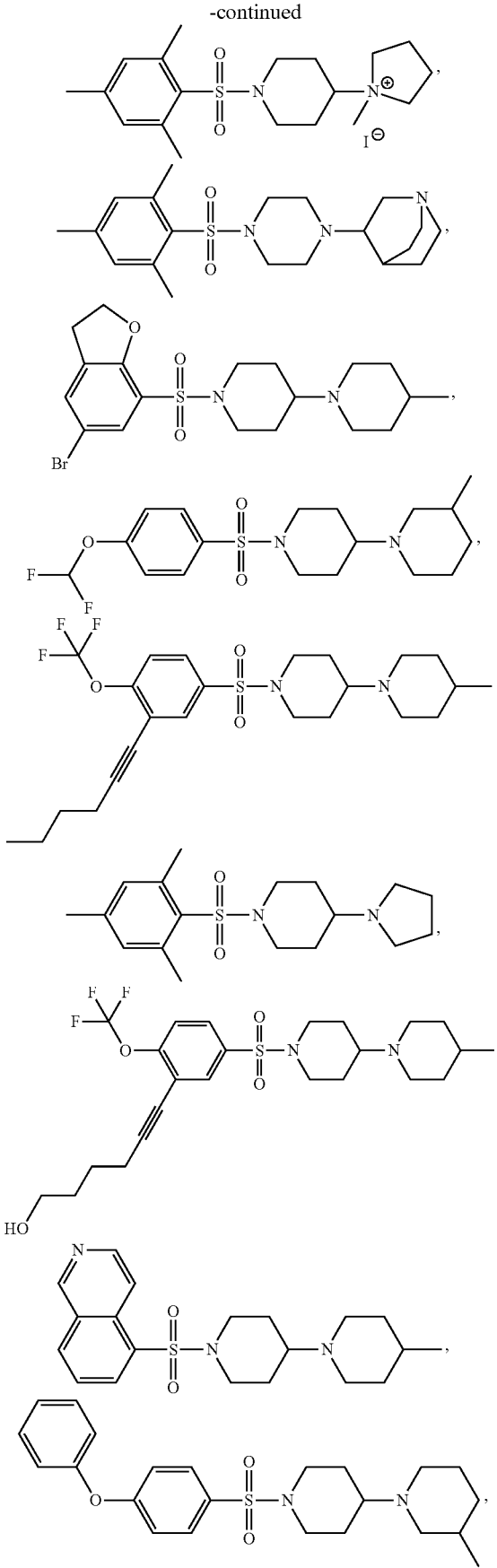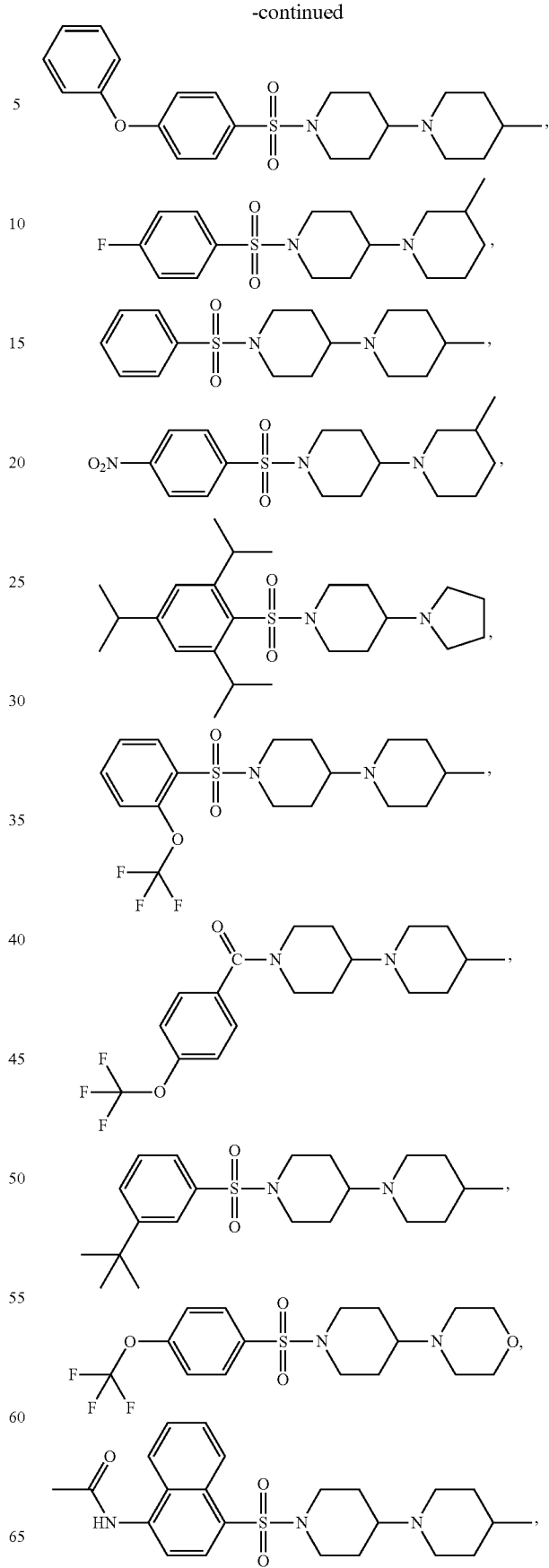

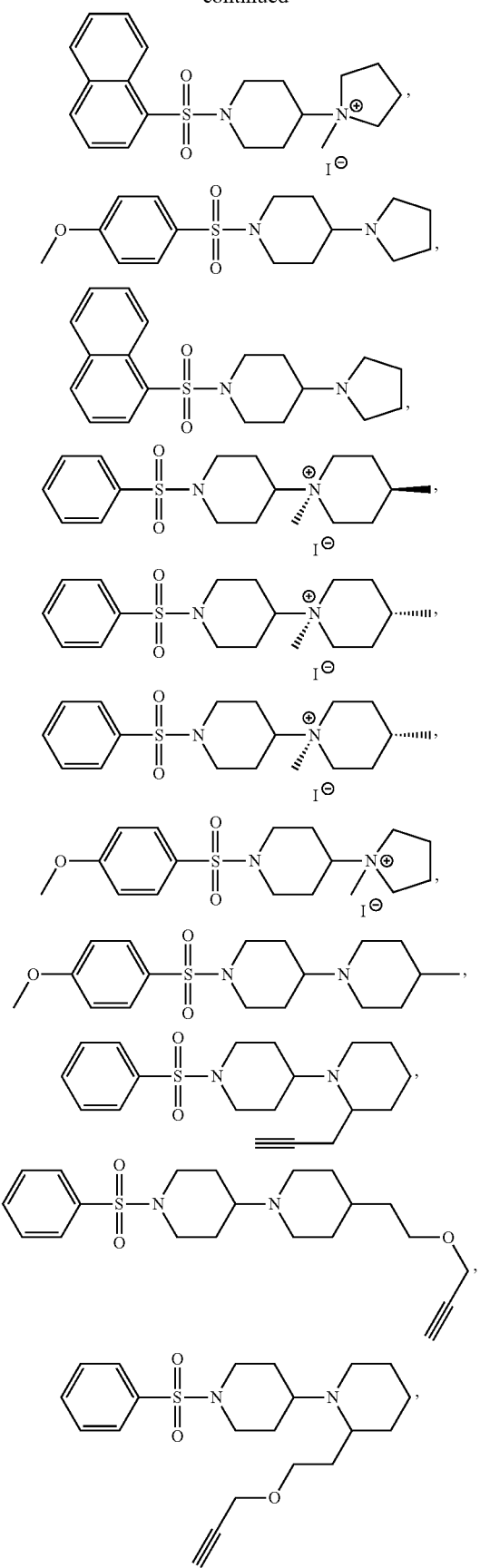
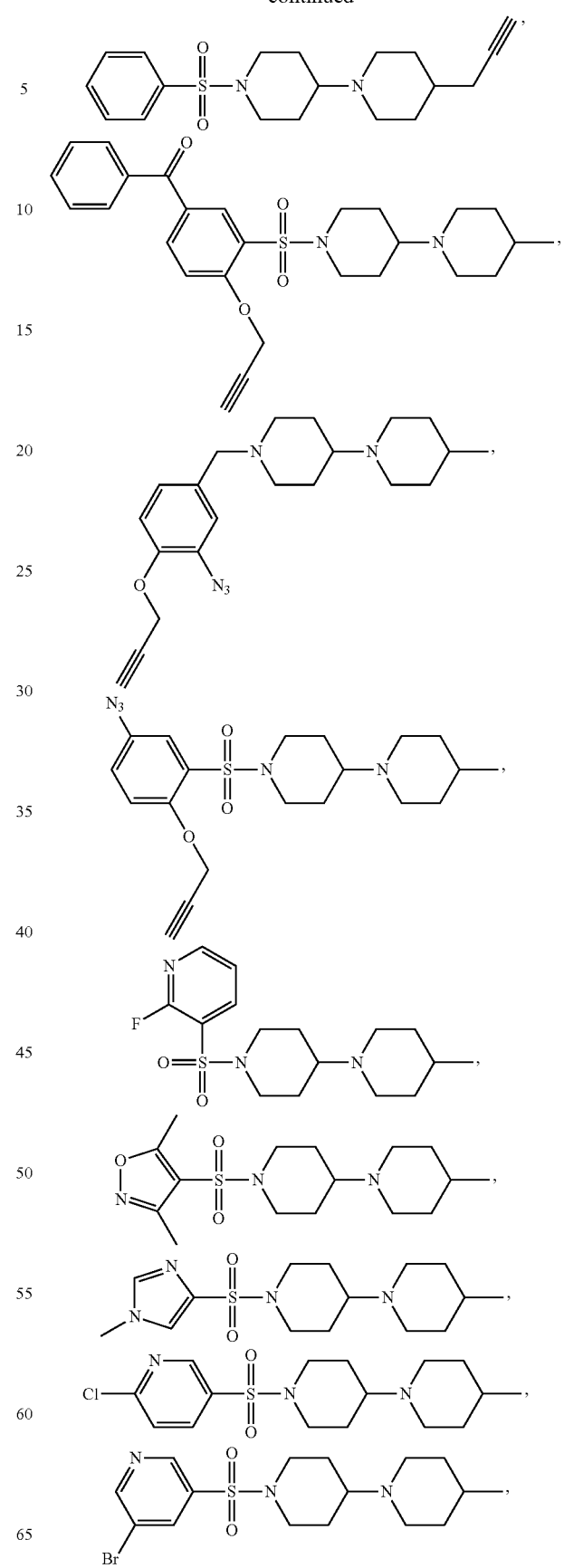

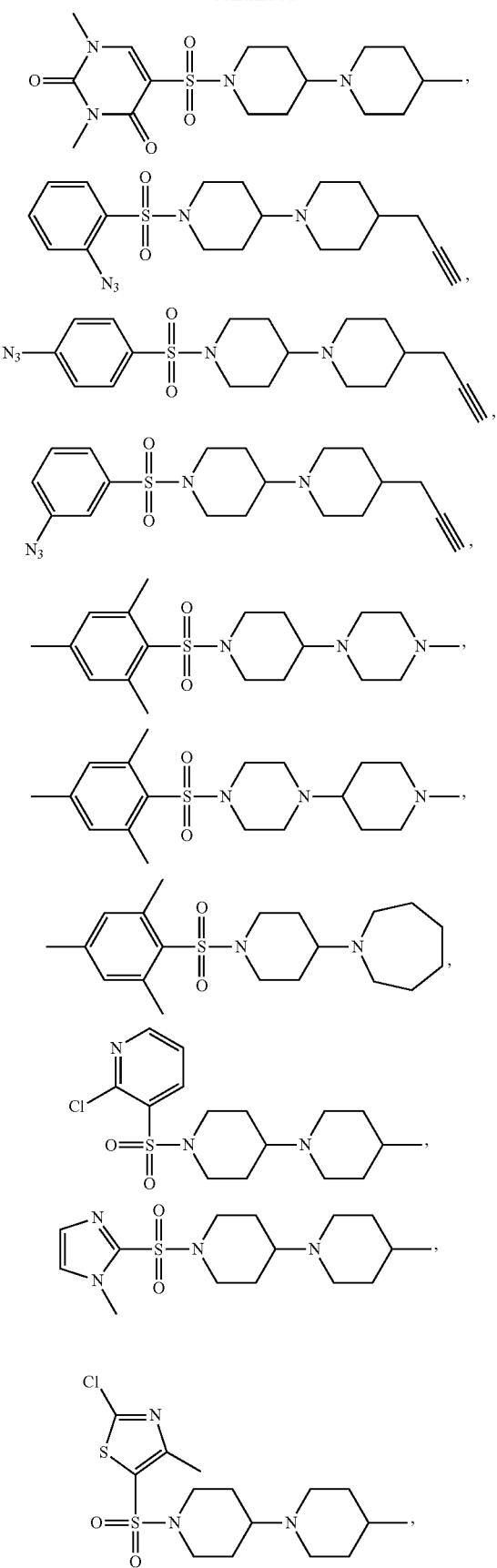
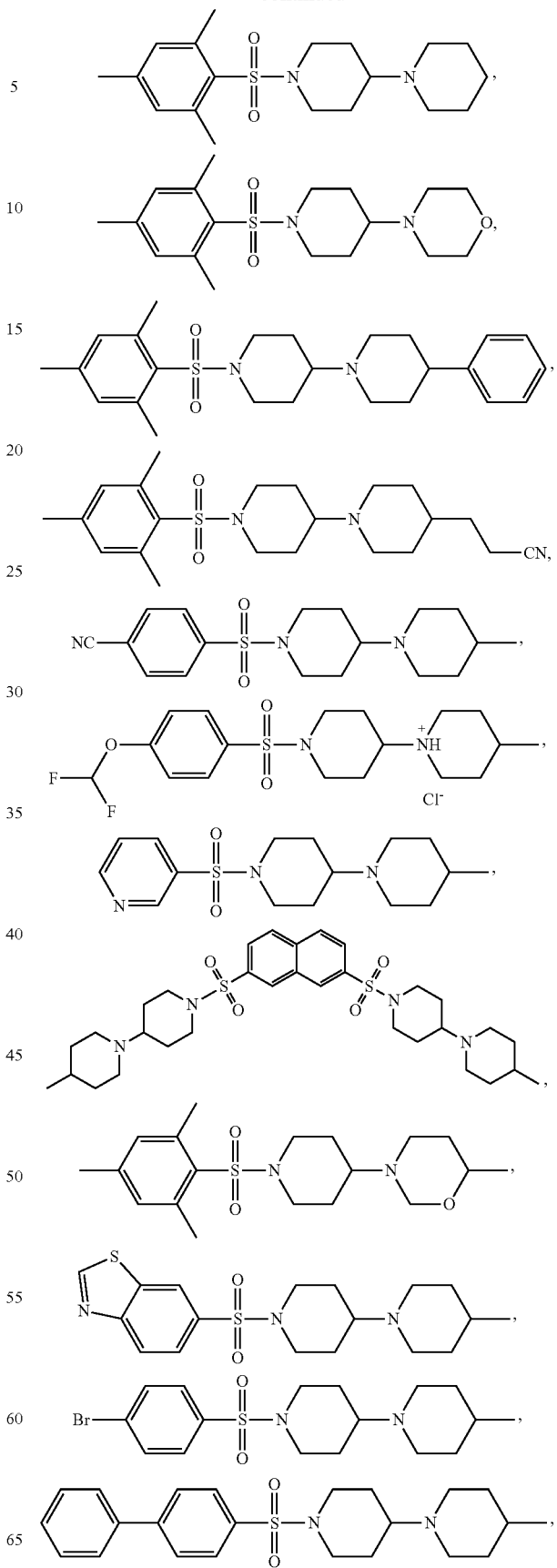

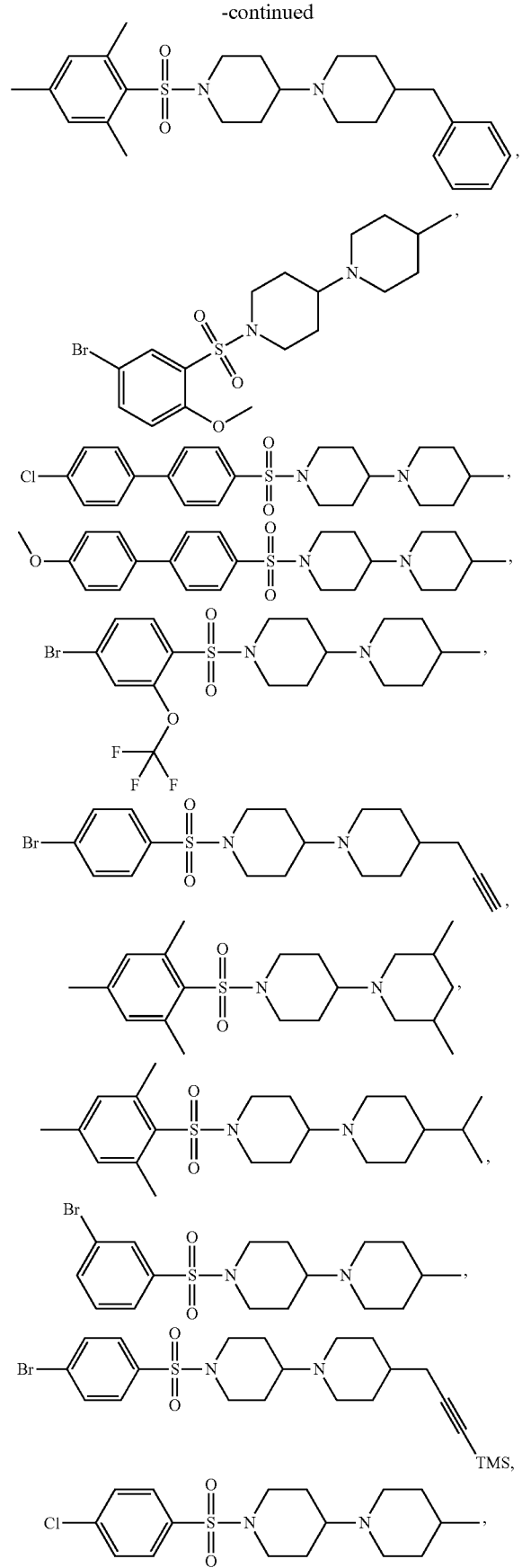
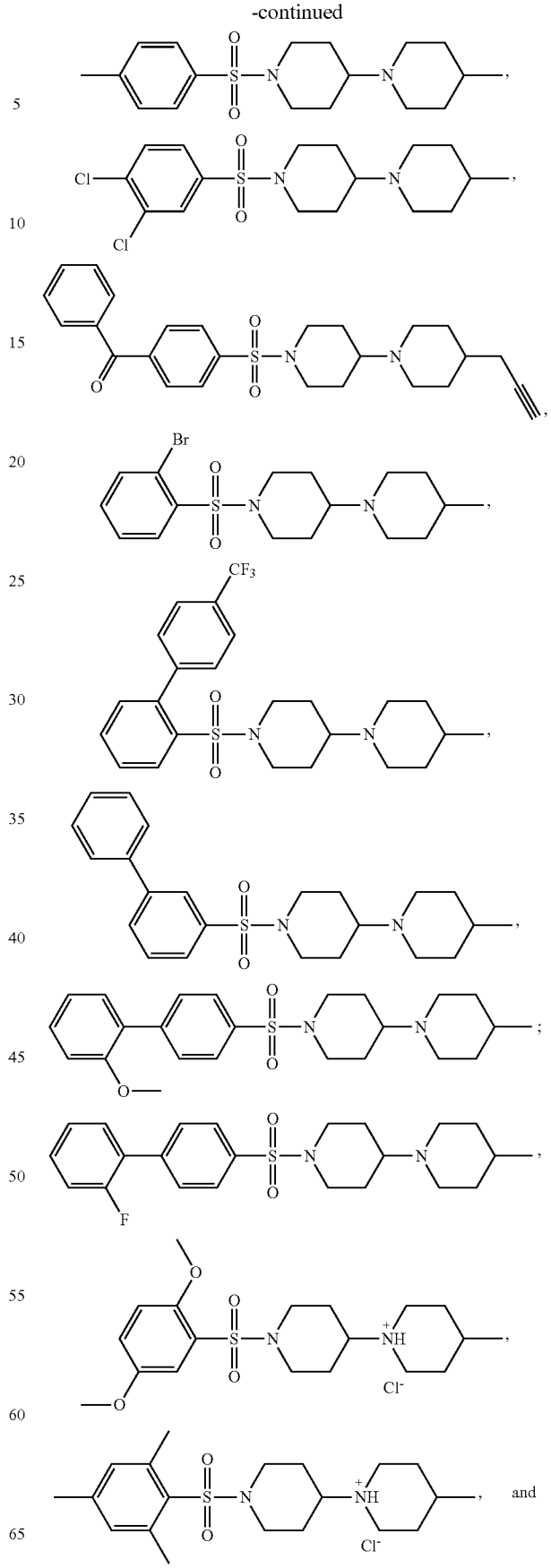

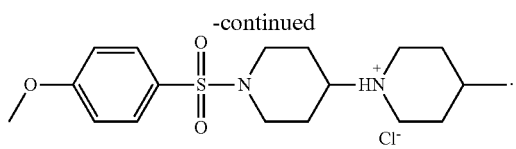

According to another embodiment, the known population of cancer cells insensitive to the EBP-modulating anticancer compound is a population of HCT116 cells or RKO cells. According to another embodiment, the known population of cancer cells sensitive to the EBP modulating anti-cancer compound is a population of DLD1 cells, HT29 cells, SW620 cells, SE480 cells, Caco-2 cells, Lovo cells or HC116 p53−/−A1309 cells.

According to another aspect, the described invention provides a method for identifying a therapeutic EBP-modulating anticancer compound comprising (a) dividing a population of cancer cells sensitive to a known EBP-modulating anti-cancer compound into aliquoted samples of the population of cancer cells; (b) contacting one sample of the population of sensitive cancer cells with a candidate EBP-modulating anti-cancer compound, contacting a second sample of the sensitive population of cancer cells with a known EBP-modulating anticancer compound (positive control), and contacting a third sample of the sensitive population of cancer cells with a negative control; (c) measuring EBP activity and a parameter of endogenous cholesterol synthesis for the candidate EBP-modulating compound, the positive control and the negative control in (b), wherein an amount of the known EBP-modulating anti-cancer compound is effective to decrease EBP activity and to decrease endogenous cholesterol synthesis in a sensitive cancer cell, while an amount of the known EBP-modulating anti-cancer compound is effective to increase EBP activity and to increase endogenous cholesterol synthesis in a cancer cell insensitive to the known EBP modulating anti-cancer compound; (d) ranking a plurality of candidate EBP-modulating anti-cancer compounds according to the measured effect on EBP activity and the parameter of endogenous cholesterol synthesis in (c); and (e) selecting a top-ranked candidate EBP-modulating anti-cancer compound in (d) as a new EBP-modulating anti-cancer compound for treating a subject in need thereof. According to one embodiment of the method, the population of cancer cells known to be sensitive to the EBP modulating compound is a population of DLD1 cells or HT29 cells. According to another embodiment, the EBP-modulating anti-cancer compound is selected from TASIN-1 or a functional equivalent thereof, dendrogenin A, SR31747A, tamoxifen, emopamil, verapamil, cis-flupentixol, trifluoroperazine, 7-ketocholestenol, haloperidol, and fenpropimorph.

According to another embodiment, the functional equivalent of TASIN-1 is selected from the group consisting of:

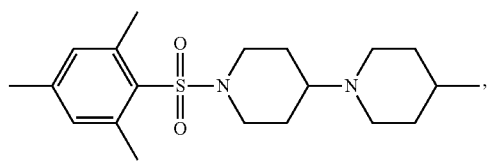

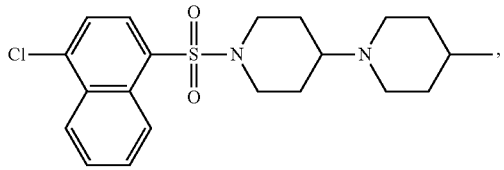

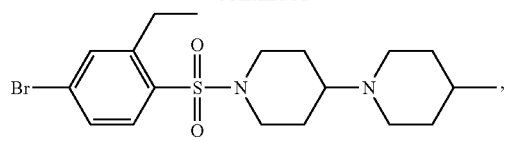

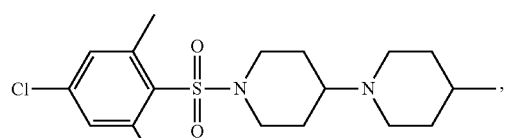

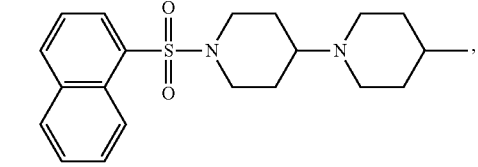

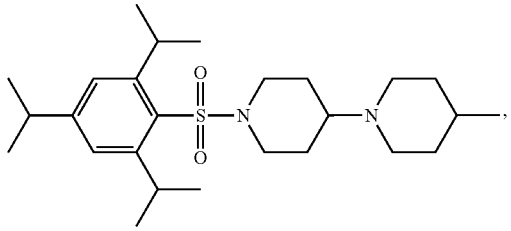

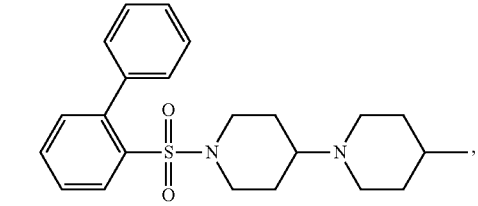

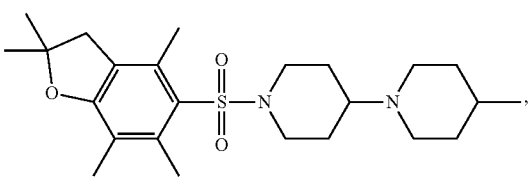

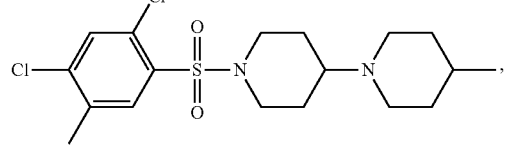

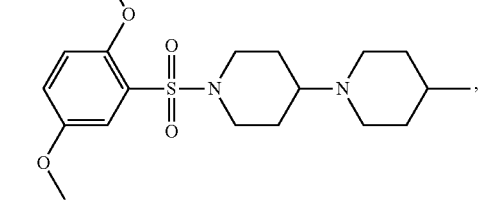

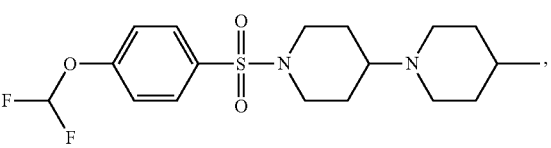

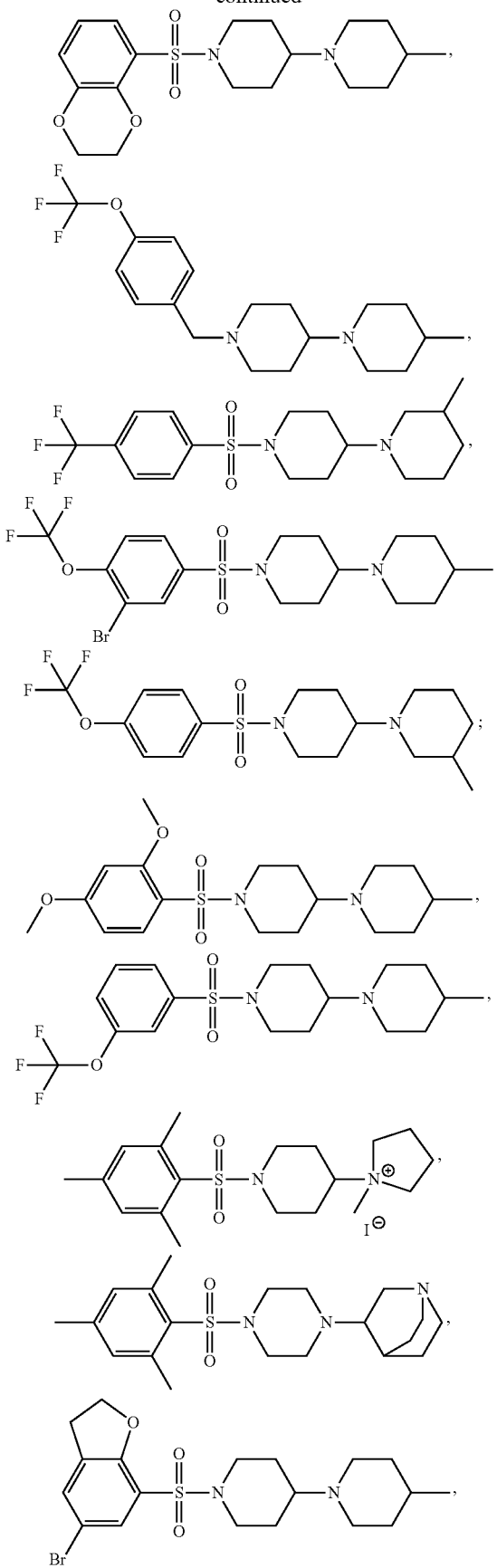
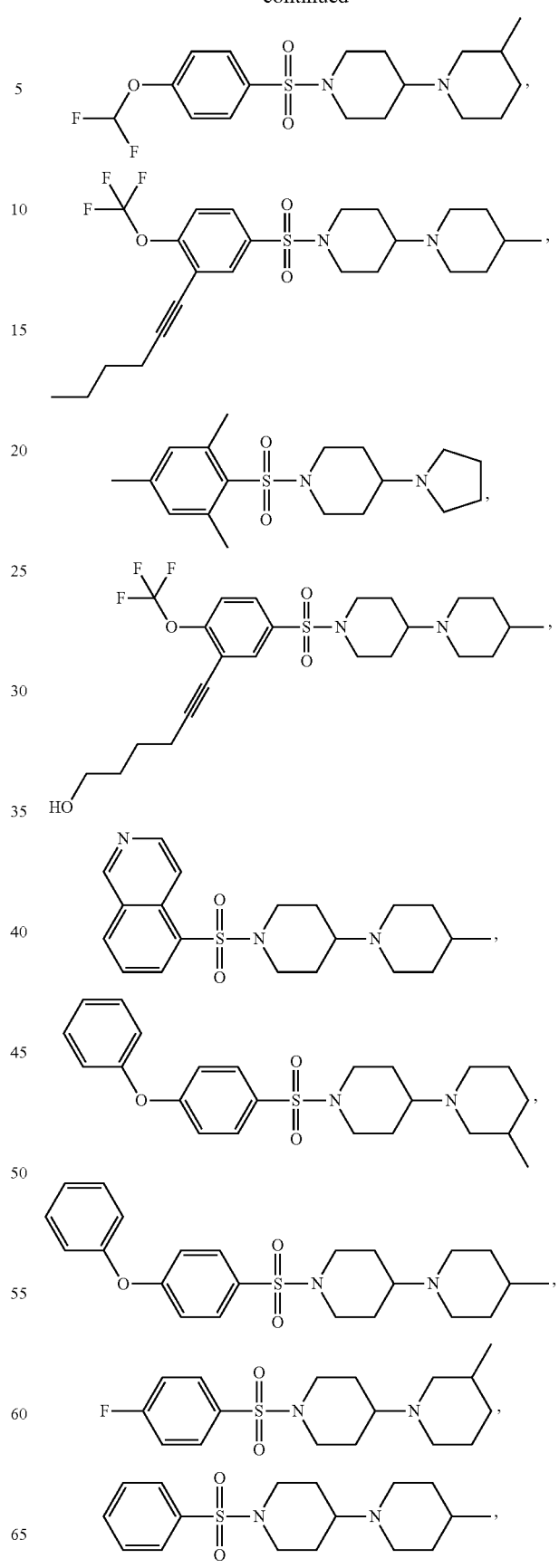

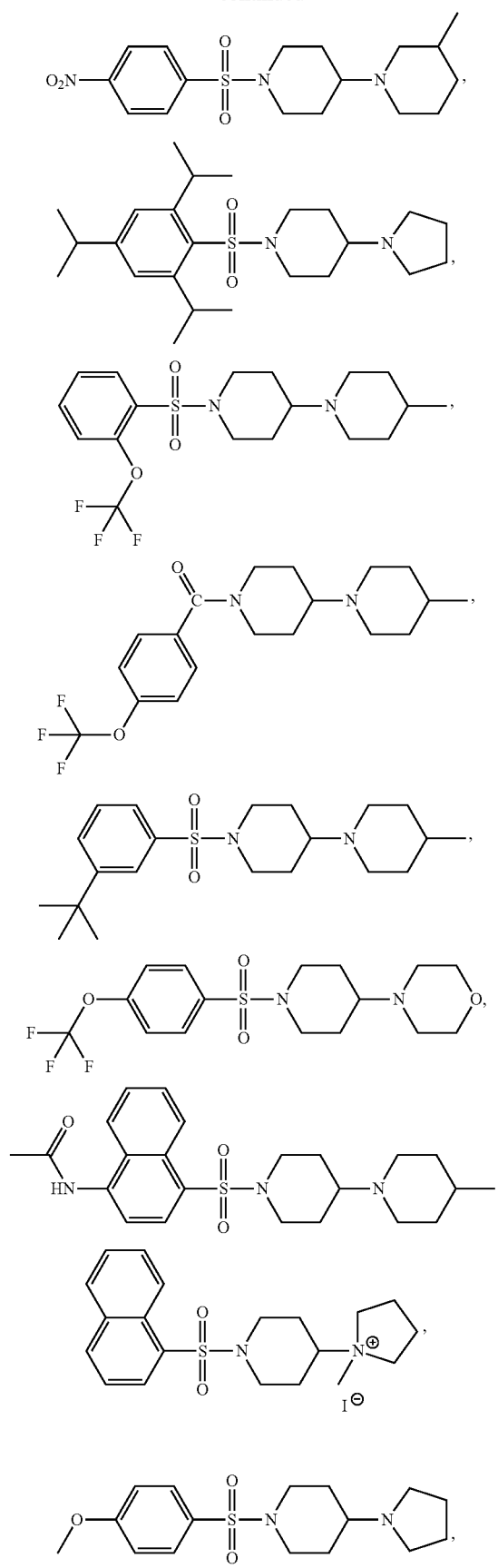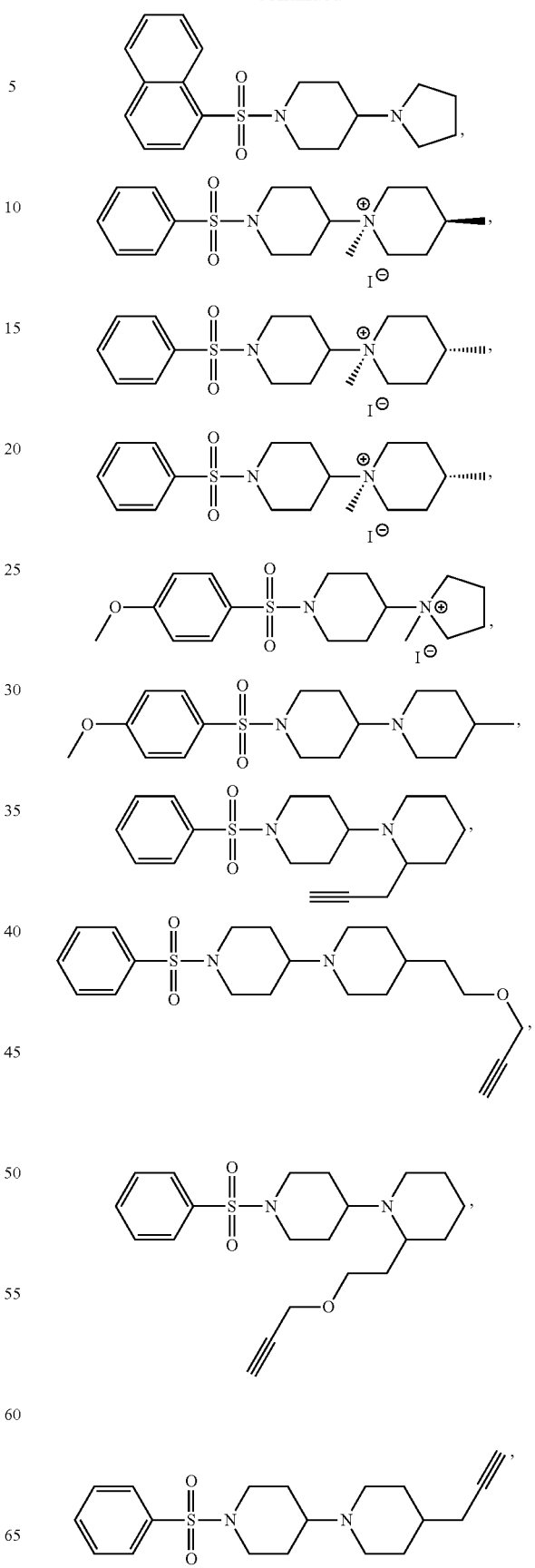

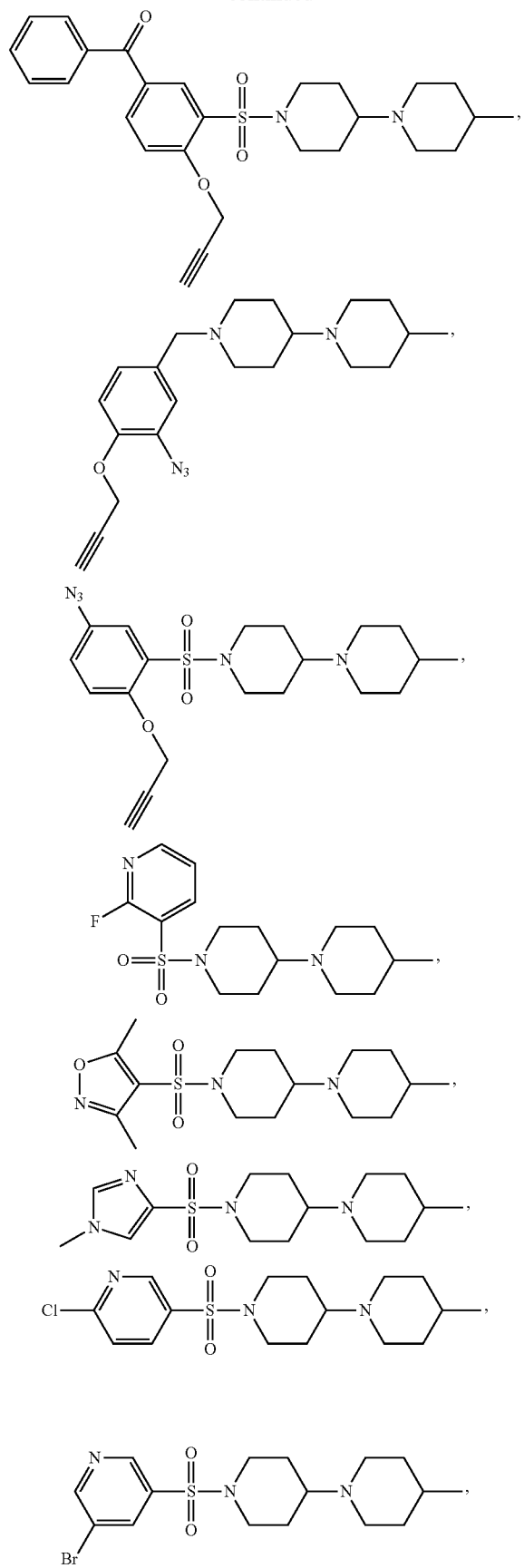
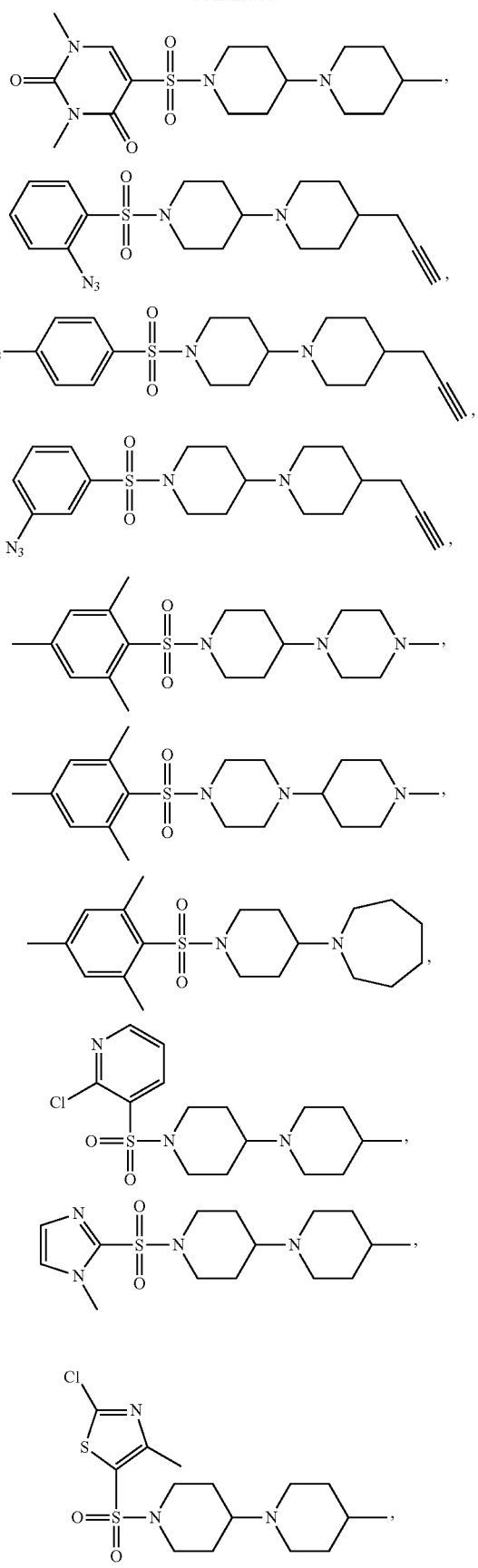

-continued
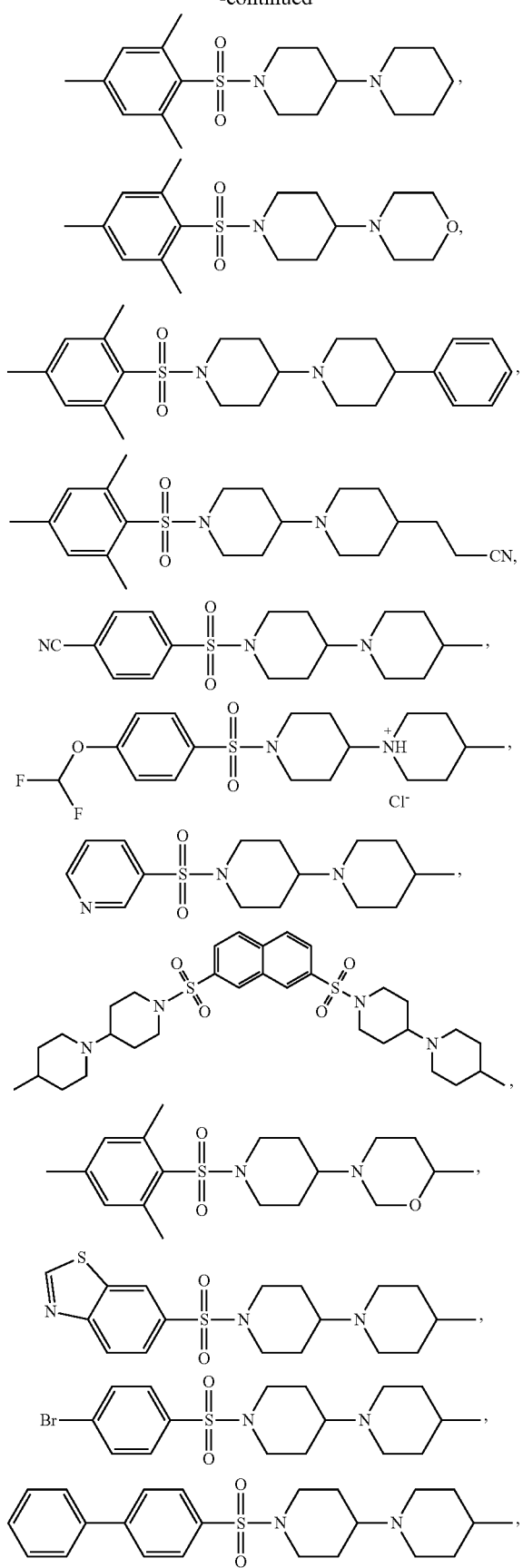
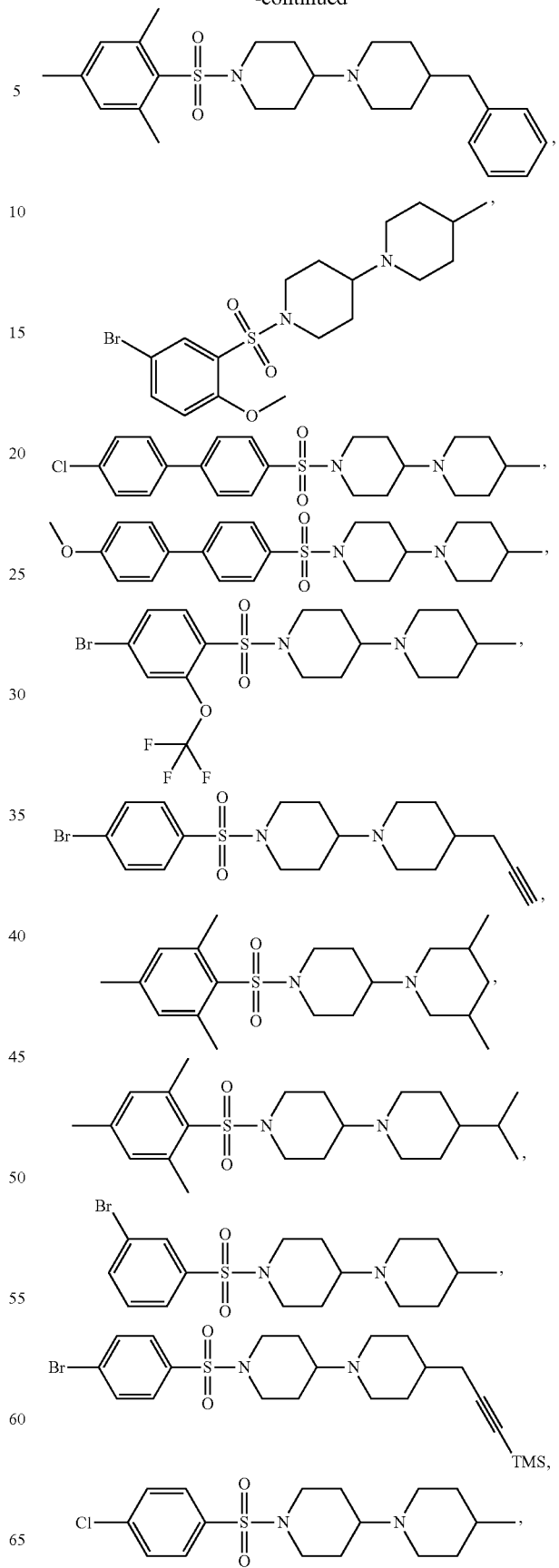

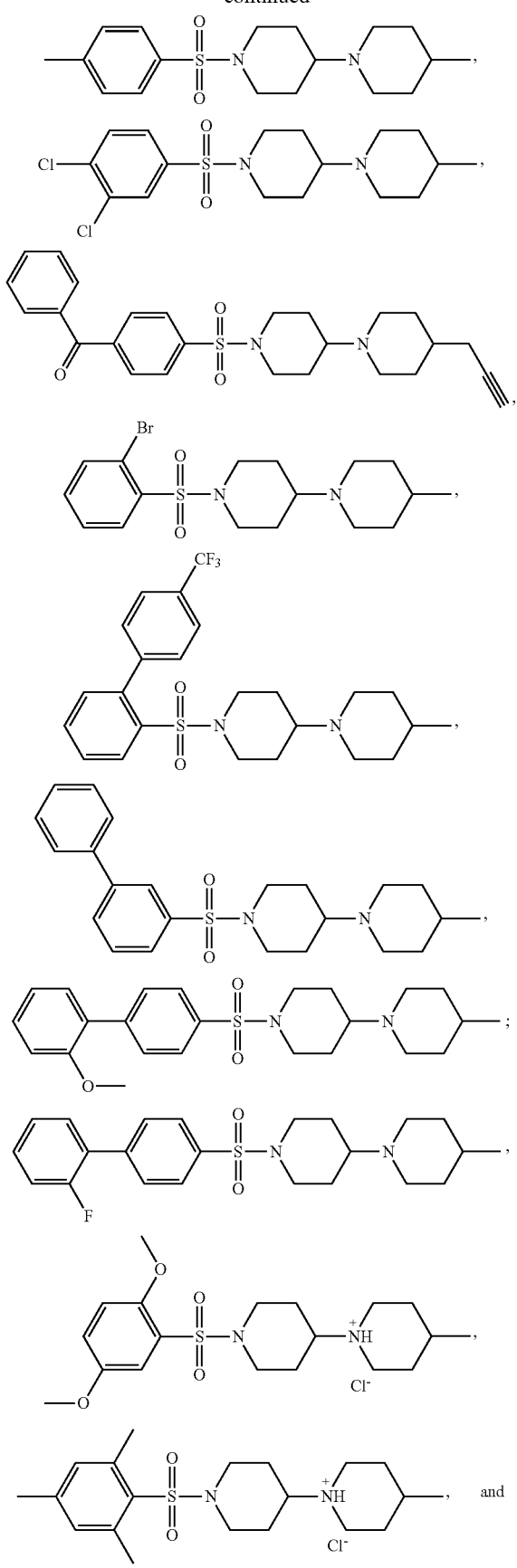

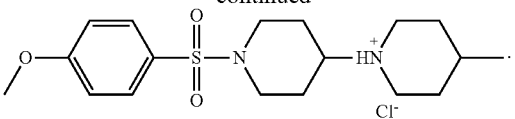

According to another embodiment, the decrease in EBP activity is measured as an accumulation of a Δ8 sterol intermediate. According to another embodiment, the Δ8 sterol intermediate is 5α-cholest-8-(9)-en-3β-ol (Δ8-cholesetenol). According to another embodiment, the effective amount of the new EBP modulating anti-cancer compound is effective to cause downregulation of SREBP-2. According to another embodiment, the effective amount of the new EBP modulating anti-cancer compound is effective to cause downregulation of one or more SREBP-2 target genes of the cholesterol biosynthetic pathway selected from the group consisting of ACAT2; MHGCS1; HMGCR; MVK; PMVK; MVD; ID11/ID12; FDFS; GGPS1; FDFT1; SQLE; LSS; CYPS1A1; TM75F2; SCAMOL; NSDHL; HSD17B7; EBP; SC5D; DHCR7; and DHCR24. According to another embodiment, the effective amount of the new EBP modulating anti-cancer compound is effective to cause downregulation of SREBP-2 and one or more SREBP-2 target genes of the cholesterol biosynthetic pathway selected from the group consisting of ACAT2; MHGCS1; HMGCR; MVK; PMVK; MVD; ID11/ID12; FDFS; GGPS1; FDFT1; SQLE; LSS; CYPS1A1; TM75F2; SCAMOL; NSDHL; HSD17B7; EBP; SC5D; DHCR7; and DHCR24.

DETAILED DESCRIPTION OF THE INVENTION

Definitions

Figure 1:
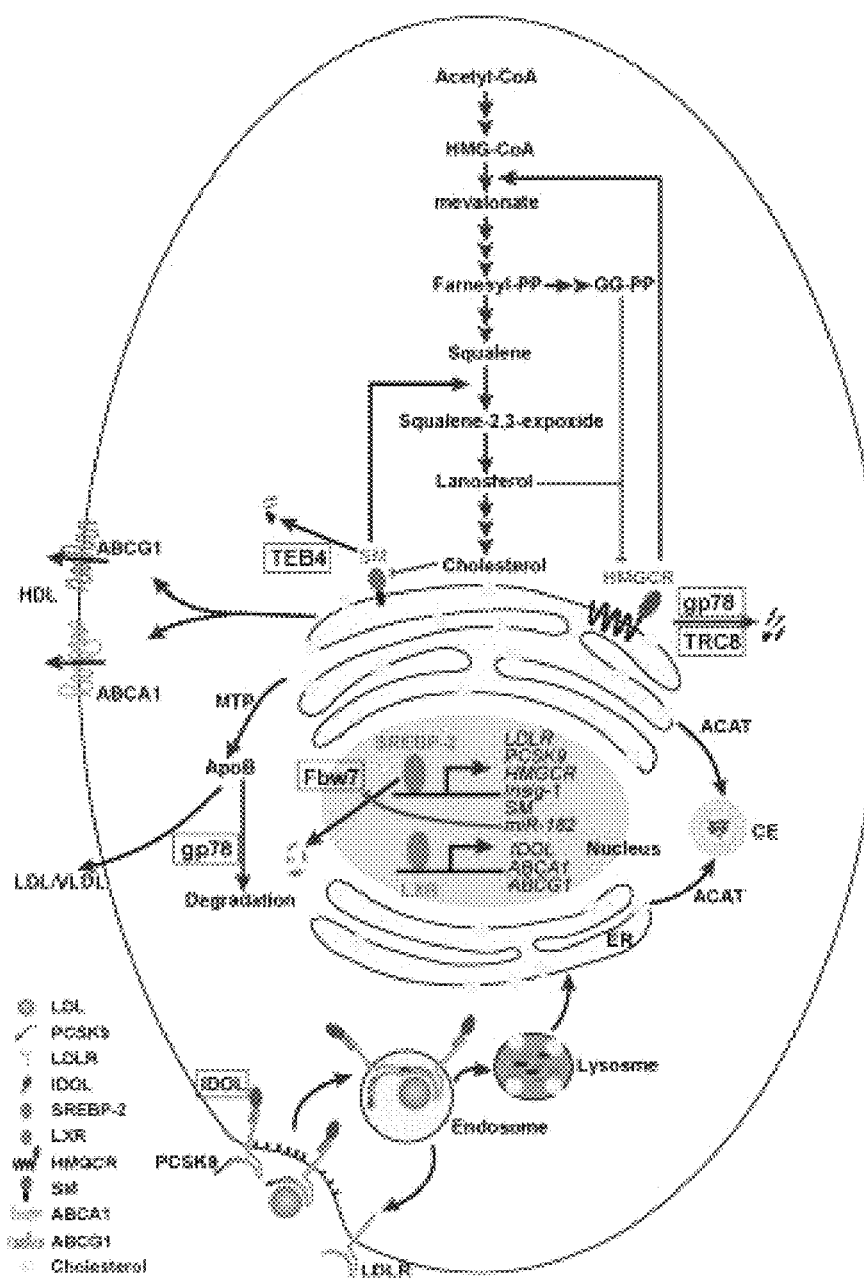
FIG. 1 is an illustration of cholesterol homeostasis in a typical mammalian cell. Taken from Jiang, W. and Song, B-L, Diabetes Meta. J. 38(3): 171-80 (2014)

Various terms used throughout this specification shall have the definitions set out herein.

The term "Adenomatous polyposis *coli* gene" or "APC gene" or "APC" as used herein refers to a mammalian DNA sequence coding for an APC protein. An example of a human APC gene is located at 5q21-q22 on chromosome 5, GenBank: M74088.1. Synonyms for the human APC gene include: BTPS2, DP2, DP2.5, DP3, PPP1R46 and "protein phosphatase 1, regulatory subunit 46". An example of a mouse APC gene is located at chromosome 18 B1, MGI: 88039. Synonyms for the mouse APC gene include: CC2, Min, mAPC, AAI10147805, AU020952 and AW124434.

The term "Adenomatous polyposis *coli* protein" or "APC protein" or "APC" as used herein refers to a mammalian protein sequence of 2843 amino acids. An example of a human APC sequence is GenBank: AAA03586. An example of a mouse APC sequence is GenBank: AAB59632.

The term "APC truncation" or "APC truncation mutant" or "APC truncation mutation" refers to a truncated protein product resulting from a mutation occurring within the APC gene. An APC truncation can be, for example, but not limited to, a 1309 amino acid product or a 1450 amino acid product.

The term "adjuvant therapy" refers to a treatment added to a primary treatment to prevent recurrence of a disease, or the additional therapy given to enhance or extend the primary therapy's effect, as in chemotherapy's addition to a surgical regimen.

The term "agonist" as used herein refers to a chemical substance capable of activating a receptor to induce a full or partial pharmacological response. Receptors can be activated or inactivated by either endogenous or exogenous agonists and antagonists, resulting in stimulating or inhibiting a biological response. A physiological agonist is a substance that creates the same bodily responses, but does not bind to the same receptor. An endogenous agonist for a particular receptor is a compound naturally produced by the body which binds to and activates that receptor. A superagonist is a compound that is capable of producing a greater maximal response than the endogenous agonist for the target receptor, and thus an efficiency greater than 100%. This does not necessarily mean that it is more potent than the endogenous agonist, but is rather a comparison of the maximum possible response that can be produced inside a cell following receptor binding. Full agonists bind and activate a receptor, displaying full efficacy at that receptor. Partial agonists also bind and activate a given receptor, but have only partial efficacy at the receptor relative to a full agonist. An inverse agonist is an agent which binds to the same receptor binding-site as an agonist for that receptor and reverses constitutive activity of receptors. Inverse agonists exert the opposite pharmacological effect of a receptor agonist. An irreversible agonist is a type of agonist that binds permanently to a receptor in such a manner that the receptor is permanently activated. It is distinct from a mere agonist in that the association of an agonist to a receptor is reversible, whereas the binding of an irreversible agonist to a receptor is believed to be irreversible. This causes the compound to produce a brief burst of agonist activity, followed by desensitization and internalization of the receptor, which with long-term treatment produces an effect more like an antagonist. A selective agonist is specific for one certain type of receptor.

The term "antagonist" as used herein refers to a small molecule, peptide, protein, or antibody that can bind to an enzyme, a receptor or a co-receptor, competitively or non-competitively through a covalent bond, ionic bond, hydrogen bond, hydrophobic interaction, or a combination thereof and either directly or indirectly deactivate a related downstream signaling pathway.

The term "anti-cancer compounds" as used herein refers to small molecule compounds that selectively target cancer cells and reduce their growth, proliferation, or invasiveness, or tumor burden of a tumor containing such cancer cells The term "administering" as used herein includes in vivo administration, as well as administration directly to tissue ex vivo. Generally, compositions may be administered systemically either orally, buccally, parenterally, topically, by inhalation or insufflation (i.e., through the mouth or through the nose), or rectally in dosage unit formulations containing conventional nontoxic pharmaceutically acceptable carriers, adjuvants, and vehicles as desired, or may be administered by means such as, but not limited to, injection, implantation, grafting, topical application, or parenterally.

The terms "analog" and "derivative" are used interchangeably to mean a compound produced from another compound of similar structure in one or more steps. A "derivative" or "analog" of a compound retains at least a degree of the desired function of the reference compound. Accordingly, an alternate term for "derivative" may be "functional derivative." Derivatives can include chemical modifications, such as akylation, acylation, carbamylation, iodination or any modification that derivatives the compound. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formal groups. Free carboxyl groups can be derivatized to form salts, esters, amides, or hydrazides. Free hydroxyl groups can be derivatized to form O-acyl or O-alkyl derivatives.

The term "allosteric modulation" as used herein refers to the process of modulating a receptor by the binding of allosteric modulators at a different site (i.e., regulatory site) other than of the endogenous ligand (orthosteric ligand) of the receptor and enhancing or inhibiting the effects of the endogenous ligand. It normally acts by causing a conformational change in a receptor molecule, which results in a change in the binding affinity of the ligand. Thus, an allosteric ligand "modulates" its activation by a primary "ligand" and can adjust the intensity of the receptor's activation. Many allosteric enzymes are regulated by their substrate, such a substrate is considered a "homotropic allosteric modulator." Non-substrate regulatory molecules are called "heterotropic allosteric modulators."

The term "allosteric regulation" is the regulation of an enzyme or other protein by binding an effector molecule at the proteins allosteric site (meaning a site other than the protein's active site). Effectors that enhance the protein's activity are referred to as "allosteric activators", whereas those that decrease the protein's activity are called "allosteric inhibitors." Thus, "allosteric activation" occurs when the binding of one ligand enhances the attraction between substrate molecules and other binding sites; "allosteric inhibition" occurs when the binding of one ligand decrease the affinity for substrate at other active sites. The term "antagonist" as used herein refers to a substance that counteracts the effects of another substance.

The terms "apoptosis" or "programmed cell death" refer to a highly regulated and active process that contributes to biologic homeostasis comprised of a series of biochemical events that lead to a variety of morphological changes, including blebbing, changes to the cell membrane, such as loss of membrane asymmetry and attachment, cell shrinkage, nuclear fragmentation, chromatin condensation, and chromosomal DNA fragmentation, without damaging the organism.

Apoptotic cell death is induced by many different factors and involves numerous signaling pathways, some dependent on caspase proteases (a class of cysteine proteases) and others that are caspase independent. It can be triggered by many different cellular stimuli, including cell surface receptors, mitochondrial response to stress, and cytotoxic T cells, resulting in activation of apoptotic signaling pathways The caspases involved in apoptosis convey the apoptotic signal in a proteolytic cascade, with caspases cleaving and activating other caspases that then degrade other cellular targets that lead to cell death. The caspases at the upper end of the cascade include caspase-8 and caspase-9. Caspase-8 is the initial caspase involved in response to receptors with a death domain (DD) like Fas.

Receptors in the TNF receptor family are associated with the induction of apoptosis, as well as inflammatory signaling. The Fas receptor (CD95) mediates apoptotic signaling by Fas-ligand expressed on the surface of other cells. The Fas-FasL interaction plays an important role in the immune system and lack of this system leads to autoimmunity, indicating that Fas-mediated apoptosis removes self-reactive lymphocytes. Fas signaling also is involved in immune surveillance to remove transformed cells and virus infected cells. Binding of Fas to oligimerized FasL on another cell activates apoptotic signaling through a cytoplasmic domain termed the death domain (DD) that interacts with signaling adaptors including FAF, FADD and DAX to activate the caspase proteolytic cascade. Caspase-8 and caspase-10 first are activated to then cleave and activate downstream caspases and a variety of cellular substrates that lead to cell death.

Mitochondria participate in apoptotic signaling pathways through the release of mitochondrial proteins into the cytoplasm. Cytochrome c, a key protein in electron transport, is released from mitochondria in response to apoptotic signals, and activates Apaf-1, a protease released from mitochondria. Activated Apaf-1 activates caspase-9 and the rest of the caspase pathway. Smac/DIABLO is released from mitochondria and inhibits IAP proteins that normally interact with caspase-9 to inhibit apoptosis. Apoptosis regulation by Bcl-2 family proteins occurs as family members form complexes that enter the mitochondrial membrane, regulating the release of cytochrome c and other proteins. TNF family receptors that cause apoptosis directly activate the caspase cascade, but can also activate Bid, a Bcl-2 family member, which activates mitochondria-mediated apoptosis. Bax, another Bcl-2 family member, is activated by this pathway to localize to the mitochondrial membrane and increase its permeability, releasing cytochrome c and other mitochondrial proteins. Bcl-2 and Bcl-xL prevent pore formation, blocking apoptosis. Like cytochrome c, AIF (apoptosis-inducing factor) is a protein found in mitochondria that is released from mitochondria by apoptotic stimuli. While cytochrome C is linked to caspase-dependent apoptotic signaling, AIF release stimulates caspase-independent apoptosis, moving into the nucleus where it binds DNA. DNA binding by AIF stimulates chromatin condensation, and DNA fragmentation, perhaps through recruitment of nucleases.

The mitochondrial stress pathway begins with the release of cytochrome c from mitochondria, which then interacts with Apaf-1, causing self-cleavage and activation of caspase-9. Caspase-3, -6 and -7 are downstream caspases that are activated by the upstream proteases and act themselves to cleave cellular targets.

Granzyme B and perforin proteins released by cytotoxic T cells induce apoptosis in target cells, forming transmembrane pores, and triggering apoptosis, perhaps through cleavage of caspases, although caspase-independent mechanisms of Granzyme B mediated apoptosis have been suggested.

Fragmentation of the nuclear genome by multiple nucleases activated by apoptotic signaling pathways to create a nucleosomal ladder is a cellular response characteristic of apoptosis. One nuclease involved in apoptosis is DNA fragmentation factor (DFF), a caspase-activated DNAse (CAD). DFF/CAD is activated through cleavage of its associated inhibitor ICAD by caspases proteases during apoptosis. DFF/CAD interacts with chromatin components such as topoisomerase II and histone H1 to condense chromatin structure and perhaps recruit CAD to chromatin. Another apoptosis activated protease is endonuclease G (EndoG). EndoG is encoded in the nuclear genome but is localized to mitochondria in normal cells. EndoG may play a role in the replication of the mitochondrial genome, as well as in apoptosis. Apoptotic signaling causes the release of EndoG from mitochondria. The EndoG and DFF/CAD pathways are independent since the EndoG pathway still occurs in cells lacking DFF.

Hypoxia, as well as hypoxia followed by reoxygenation can trigger cytochrome c release and apoptosis. Glycogen synthase kinase (GSK-3) a serine-threonine kinase ubiquitously expressed in most cell types, appears to mediate or potentiate apoptosis due to many stimuli that activate the mitochondrial cell death pathway. Loberg, R D, et al., J. Biol. Chem. 277 (44): 41667-673 (2002). It has been demonstrated to induce caspase 3 activation and to activate the proapoptotic tumor suppressor gene p53. It also has been suggested that GSK-3 promotes activation and translocation of the proapoptotic Bcl-2 family member, Bax, which, upon aggregation and mitochondrial localization, induces cytochrome c release. Akt is a critical regulator of GSK-3, and phosphorylation and inactivation of GSK-3 may mediate some of the antiapoptotic effects of Akt.

The term "assay marker" or "reporter gene" (or "reporter") refers to a gene that can be detected, or easily identified and measured. The expression of the reporter gene may be measured at either the RNA level, or at the protein level. The gene product, which may be detected in an experimental assay protocol, includes, but is not limited to, marker enzymes, antigens, amino acid sequence markers, cellular phenotypic markers, nucleic acid sequence markers, and the like. Researchers may attach a reporter gene to another gene of interest in cell culture, bacteria, animals, or plants. For example, some reporters are selectable markers, or confer characteristics upon on organisms expressing them allowing the organism to be easily identified and assayed. To introduce a reporter gene into an organism, researchers may place the reporter gene and the gene of interest in the same DNA construct to be inserted into the cell or organism. For bacteria or eukaryotic cells in culture, this may be in the form of a plasmid. Commonly used reporter genes may include, but are not limited to, fluorescent proteins, luciferase, beta-galactosidase, and selectable markers, such as chloramphenicol and kanomycin.

As used herein, the term "bioavailability" refers to the rate and extent to which the active drug ingredient or therapeutic moiety is absorbed into the systemic circulation from an administered dosage form as compared to a standard or control.

The term "biomarkers" (or "biosignatures") as used herein refers to peptides, proteins, nucleic acids, antibodies, genes, metabolites, or any other substances used as indicators of a biologic state. It is a characteristic that is measured objectively and evaluated as a cellular or molecular indicator of normal biologic processes, pathogenic processes, or pharmacologic responses to a therapeutic intervention. The term "indicator" as used herein refers to any substance, number or ratio derived from a series of observed facts that may reveal relative changes as a function of time; or a signal, sign, mark, note or symptom that is visible or evidence of the existence or presence thereof. Once a proposed biomarker has been validated, it may be used to diagnose disease risk, presence of disease in an individual, or to tailor treatments for the disease in an individual (choices of drug treatment or administration regimes). In evaluating potential drug therapies, a biomarker may be used as a surrogate for a natural endpoint, such as survival or irreversible morbidity. If a treatment alters the biomarker, and that alteration has a direct connection to improved health, the biomarker may serve as a surrogate endpoint for evaluating clinical benefit. Clinical endpoints are variables that can be used to measure how patients feel, function or survive. Surrogate endpoints are biomarkers that are intended to substitute for a clinical endpoint; these biomarkers are demonstrated to predict a clinical endpoint with a confidence level acceptable to regulators and the clinical community.

The term "bound" or any of its grammatical forms as used herein refers to the capacity to hold onto, attract, interact with or combine with.

The terms "cancer" or "malignancy" as used herein refer to diseases in which abnormal cells divide without control and can invade nearby tissues. Cancer cells also can spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue such as the bone marrow, and causes large numbers of abnormal blood cells to be produced and enter the blood. Lymphoma and multiple myeloma are cancers that begin in cells of the immune system. Central nervous system cancers are cancers that begin in the tissues of the brain and spinal cord.

The term "carrier" as used herein describes a material that does not cause significant irritation to an organism and does not abrogate the biological activity and properties of the active compound of the composition of the described invention. Carriers must be of sufficiently high purity and of sufficiently low toxicity to render them suitable for administration to the mammal being treated. The carrier can be inert, or it can possess pharmaceutical benefits, cosmetic benefits or both. The terms "excipient", "carrier", or "vehicle" are used interchangeably to refer to carrier materials suitable for formulation and administration of pharmaceutically acceptable compositions described herein. Carriers and vehicles useful herein include any such materials know in the art which are nontoxic and do not interact with other components.

The term "cell" is used herein to refer to the structural and functional unit of living organisms and is the smallest unit of an organism classified as living.

The term "cell line" as used herein refers to a population of immortalized cells, which have undergone transformation and can be passed indefinitely in culture.

The term "chemoresistance" as used herein refers to the development of a cell phenotype resistant to a variety of structurally and functionally distinct agents. Tumors can be intrinsically resistant prior to chemotherapy, or resistance may be acquired during treatment by tumors that are initially sensitive to chemotherapy. Drug resistance is a multifactorial phenomenon involving multiple interrelated or independent mechanisms. A heterogeneous expression of involved mechanisms may characterize tumors of the same type or cells of the same tumor and may at least in part reflect tumor progression. Exemplary mechanisms that can contribute to cellular resistance include: increased expression of defense factors involved in reducing intracellular drug concentration; alterations in drug-target interaction; changes in cellular response, in particular increased cell ability to repair DNA damage or tolerate stress conditions, and defects in apoptotic pathways.

The term "chemosensitive", "chemosensitivity" or "chemosensitive tumor" as used herein refers to a tumor that is responsive to a chemotherapy or a chemotherapeutic agent. Characteristics of a chemosensitive tumor include, but are not limit to, reduced proliferation of the population of tumor cells, reduced tumor size, reduced tumor burden, tumor cell death, and slowed/inhibited progression of the population of tumor cells.

The term "chemotherapeutic agent" as used herein refers to chemicals useful in the treatment or control of a disease, e.g., cancer The term "chemotherapy" as used herein refers to a course of treatment with one or more chemotherapeutic agents. In the context of cancer, the goal of chemotherapy is, e.g., to kill cancer cells, reduce proliferation of cancer cells, reduce growth of a tumor containing cancer cells, reduce invasiveness of cancer cells, increase apoptosis of cancer cells.

The term "chemotherapy regimen" ("combination chemotherapy") means chemotherapy with more than one drug in order to benefit from the dissimilar toxicities of the more than one drug. A principle of combination cancer therapy is that different drugs work through different cytotoxic mechanisms; since they have different dose-limiting adverse effects, they can be given together at full doses.

The term "compatible" as used herein means that the components of a composition are capable of being combined with each other in a manner such that there is no interaction that would substantially reduce the efficacy of the composition under ordinary use conditions.

The term "condition", as used herein, refers to a variety of health states and is meant to include disorders or diseases caused by any underlying mechanism or injury.

The term "contact" and its various grammatical forms as used herein refers to a state or condition of touching or of immediate or local proximity. Contacting a composition to a target destination, such as, but not limited to, an organ, a tissue, a cell, or a tumor, may occur by any means of administration known to the skilled artisan.

The term "derivative" as used herein means a compound that may be produced from another compound of similar structure in one or more steps. A "derivative" or "derivatives" of a peptide or a compound retains at least a degree of the desired function of the peptide or compound. Accordingly, an alternate term for "derivative" may be "functional derivative." Derivatives can include chemical modifications of the peptide, such as akylation, acylation, carbamylation, iodination or any modification that derivatizes the peptide. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formal groups. Free carboxyl groups can be derivatized to form salts, esters, amides, or hydrazides. Free hydroxyl groups can be derivatized to form O-acyl or O-alkyl derivatives. The imidazole nitrogen of histidine can be derivatized to form N-im-benzylhistidine. Also included as derivatives or analogues are those peptides that contain one or more naturally occurring amino acid derivative of the twenty standard amino acids, for example, 4-hydroxyproline, 5-hydroxylysine, 3-methylhistidine, homoserine, ornithine or carboxyglutamiate, and can include amino acids that are not linked by peptide bonds. Such peptide derivatives can be incorporated during synthesis of a peptide, or a peptide can be modified by wellknown chemical modification methods (see, e.g., Glazer et al., Chemical Modification of Proteins, Selected Methods and Analytical Procedures, Elsevier Biomedical Press, New York (1975)).

The term "detectable marker" encompasses both selectable markers and assay markers. The term "selectable markers" refers to a variety of gene products to which cells transformed with an expression construct can be selected or screened, including drug-resistance markers, antigenic markers useful in fluorescence-activated cell sorting, adherence markers such as receptors for adherence ligands allowing selective adherence, and the like. When a nucleic acid is prepared or altered synthetically, advantage can be taken of known codon preferences of the intended host where the nucleic acid is to be expressed.

The term "detectable response" refers to any signal or response that may be detected in an assay, which may be performed with or without a detection reagent. Detectable responses include, but are not limited to, radioactive decay and energy (e.g., fluorescent, ultraviolet, infrared, visible) emission, absorption, polarization, fluorescence, phosphorescence, transmission, reflection or resonance transfer. Detectable responses also include chromatographic mobility, turbidity, electrophoretic mobility, mass spectrum, ultraviolet spectrum, infrared spectrum, nuclear magnetic resonance spectrum and x-ray diffraction. Alternatively, a detectable response may be the result of an assay to measure one or more properties of a biologic material, such as melting point, density, conductivity, surface acoustic waves, catalytic activity or elemental composition.

The term "disease" or "disorder", as used herein, refers to an impairment of health or a condition of abnormal functioning.

The term "DLD-1" as used herein refers to a human colon cancer cell line with a truncated APC.

The term "dose" as used herein refers to the quantity of medicine prescribed to be taken at one time.

The term "drug" as used herein refers to a therapeutic agent or any substance used in the prevention, diagnosis, alleviation, treatment, or cure of disease.

The terms "Emopamil Binding Protein" (EBP), "Human Sterol Isomerase" (HIS) and "delta8-delta7 sterol isomerase" are used interchangeably to refer to an integral membrane protein of the endoplasmic reticulum that catalyzes the conversion of delta(8)-sterols into delta(7)-sterols.

The term "effective amount" or "amount effective" refers to the amount necessary or sufficient to realize a desired biologic effect.

The term "effective dose" as used herein refers to the quantity of medicine prescribed to be taken at one time necessary or sufficient to realize a desired biologic effect.

As used herein, the term "enzymatic activity" refers to the amount of substrate consumed (or product formed) in a given time under given conditions. Enzymatic activity also may be referred to as "turnover number."

As used herein, the terms "formulation" and "composition" are used interchangeably to refer to a product of the described invention that comprises all active and inert ingredients.

The term "functional equivalent" or "functionally equivalent" are used interchangeably herein to refer to substances, molecules, polynucleotides, proteins, peptides, or polypeptides having similar or identical biological activity to a reference substance, molecule, polynucleotide, protein, peptide, or polypeptide. Any EBP-modulating anti-cancer compound that retains the biological activity of TASIN-1 may be used as such a functional equivalent.

The term "growth" as used herein refers to a process of becoming larger, longer or more numerous, or an increase in size, number, or volume.

The term "half maximal inhibitory concentration" ("IC50") is a measure of the effectiveness of a compound in inhibiting a biological or biochemical function.

The term "HCT116" as used herein refers to a human colon cancer cell line with wild type APC.

The term "HT29" as used herein refers to a human colon cancer cell line with a truncated APC.

The terms "inhibiting", "inhibit" or "inhibition" are used herein to refer to reducing the amount or rate of a process, to stopping the process entirely, or to decreasing, limiting, or blocking the action or function thereof. Inhibition may include a reduction or decrease of the amount, rate, action function, or process of a substance by at least 5%, at least 10%, at least 15%, at least 20%, at least 25%, at least 30%, at least 40%, at least 45%, at least 50%, at least 55%, at least 60%, at least 65%, at least 70%, at least 75%, at least 80%, at least 85%, at least 90%, at least 95%, at least 98%, or at least 99%.

The term "inhibitor" as used herein refers to a molecule that binds to an enzyme thereby decreasing enzyme activity. Enzyme inhibitors are molecules that bind to enzymes thereby decreasing enzyme activity. The binding of an inhibitor may stop substrate from entering the active site of the enzyme and/or hinder the enzyme from catalyzing its reaction. Inhibitor binding is either reversible or irreversible. Irreversible inhibitors usually react with the enzyme and change it chemically, for example, by modifying key amino acid residues needed for enzymatic activity. In contrast, reversible inhibitors bind non-covalently and produce different types of inhibition depending on whether these inhibitors bind the enzyme, the enzyme-substrate complex, or both. Enzyme inhibitors often are evaluated by their specificity and potency.

The term "injury," as used herein, refers to damage or harm to a structure or function of the body caused by an outside agent or force, which may be physical or chemical.

The term "interfere" or "to interfere with" as used herein refers to the hampering, impeding, dampening, hindering, obstructing, blocking, reducing or preventing of an action or occurrence. By way of example, a receptor antagonist interferes with (e.g., blocks or dampens) an agonist-mediated response rather than provoking a biological response itself.

The term "invasion" or "invasiveness" as used herein refers to a process in malignant cells that includes penetration of and movement through surrounding tissues.

The term "Kaplan Meier plot" or "Kaplan Meier survival curve" as used herein refers to the plot of probability of clinical study subjects surviving in a given length of time while considering time in many small intervals. The Kaplan Meier plot assumes that: (i) at any time subjects who are censored (i.e., lost) have the same survival prospects as subjects who continue to be followed; (ii) the survival probabilities are the same for subjects recruited early and late in the study; and (iii) the event (e.g., death) happens at the time specified. Probabilities of occurrence of events are computed at a certain point of time with successive probabilities multiplied by any earlier computed probabilities to get a final estimate. The survival probability at any particular time is calculated as the number of subjects surviving divided by the number of subjects at risk. Subjects who have died, dropped out, or have been censored from the study are not counted as at risk.

The term "ligand" as used herein refers to a molecule that can bind selectively to a molecule, such that the binding interaction between the ligand and its binding partner is detectable over nonspecific interactions by a quantifiable assay. Derivatives, analogues and mimetic compounds are intended to be included within the definition of this term.

The terms "marker" and "cell surface marker" are used interchangeably herein to refer to a receptor, a combination of receptors, or an antigenic determinant or epitope found on the surface of a cell that allows a cell type to be distinguishable from other kinds of cells. Specialized protein receptors (markers) that have the capability of selectively binding or adhering to other signaling molecules coat the surface of every cell in the body. Cells use these receptors and the molecules that bind to them as a way of communicating with other cells and to carry out their proper function in the body. Cell sorting techniques are based on cellular biomarkers where a cell surface marker(s) may be used for either positive selection or negative selection, i.e., for inclusion or exclusion, from a cell population.

The term "maximum tolerated dose" (MTD) as used herein refers to the highest dose of a drug that does not produce unacceptable toxicity.

The term "median survival" as used herein refers to the time after which 50% of individuals with a particular condition are still living and 50% have died. For example, a median survival of 6 months indicates that after 6 months, 50% of individuals with, e.g., colon cancer would be alive, and 50% would have passed away. Median survival is often used to describe the prognosis (i.e., chance of survival) of a condition when the average survival rate is relatively short, such as for colon cancer. Median survival is also used in clinical studies when a drug or treatment is being evaluated to determine whether or not the drug or treatment will extend life.

The term "metastasis" as used herein refers to the transference of organisms or of malignant or cancerous cells, producing disease manifestations, from one part of the body to other parts.

The term "migration" as used herein refers to a movement of a population of cells from one place to another.

The term "mitotic index" as used herein refers to the ratio of the number of cells undergoing mitosis (cell division) to the number of cells not undergoing mitosis in a population of cells.

The term "modify" as used herein means to change, vary, adjust, temper, alter, affect or regulate to a certain measure or proportion in one or more particulars.

The term "modifying agent" as used herein refers to a substance, composition, therapeutic component, active constituent, therapeutic agent, drug, metabolite, active agent, protein, non-therapeutic component, non-active constituent, non-therapeutic agent, or non-active agent that reduces, lessens in degree or extent, or moderates the form, symptoms, signs, qualities, character or properties of a condition, state, disorder, disease, symptom or syndrome.

The term "modulate" as used herein means to regulate, alter, adapt, or adjust to a certain measure or proportion.

The term "neoplasm" as used herein refers to an abnormal proliferation of genetically altered cells. A malignant neoplasm (or malignant tumor) is synonymous with cancer. A benign neoplasm (or benign tumor) is a tumor (solid neoplasm) that stops growing by itself, does not invade other tissues and does not form metastases.

The term "normal healthy control subject" as used herein refers to a subject having no symptoms or other clinical evidence of a disease.

The term "normal human colonic epithelial cells" (HCECs) as used herein refers to immortalized human colonic epithelial cell (HCEC) lines generated using exogenously introduced telomerase and cdk4 (Fearon, E. R. & Vogelstein, B. A genetic model for colorectal tumorigenesis. Cell 61, 759-767 (1990)). These cells are non-transformed, karyotypically diploid and have multipotent characteristics. When placed in Matrigel® in the absence of a mesenchymal feeder layer, individual cells divide and form self-organizing, crypt-like structures with a subset of cells exhibiting markers associated with mature intestinal epithelium.

The term "outcome" as used herein refers to a specific result or effect that can be measured. Nonlimiting examples of outcomes include decreased pain, reduced tumor size, and survival (e.g., progression-free survival or overall survival).

The term "overall survival" (OS) as used herein refers to the length of time from either the date of diagnosis or the start of treatment for a disease, such as cancer, that patients diagnosed with the disease are still alive.

The term "parenteral" as used herein refers to introduction into the body by way of an injection (i.e., administration by injection), including, for example, subcutaneously (i.e., an injection beneath the skin), intramuscularly (i.e., an injection into a muscle); intravenously (i.e., an injection into a vein), intrathecally (i.e., an injection into the space around the spinal cord or under the arachnoid membrane of the brain), or infusion techniques. A parenterally administered composition is delivered using a needle, e.g., a surgical needle. The term "surgical needle" as used herein, refers to any needle adapted for delivery of fluid (i.e., capable of flow) compositions into a selected anatomical structure. Injectable preparations, such as sterile injectable aqueous or oleaginous suspensions, may be formulated according to the known art using exemplary dispersing or wetting agents and suspending agents.

The terms "pharmaceutical formulation" or "pharmaceutical composition" as used herein refer to a formulation or composition that is employed to prevent, reduce in intensity, cure or otherwise treat a target condition or disease.

The term "pharmaceutically acceptable carrier" as used herein refers to any substantially non-toxic carrier conventionally useable for administration of pharmaceuticals in which the EBP-modulating anti-cancer compound of the described invention will remain stable and bioavailable. The pharmaceutically acceptable carrier must be of sufficiently high purity and of sufficiently low toxicity to render it suitable for administration to the mammal being treated. It further should maintain the stability and bioavailability of an active agent. The pharmaceutically acceptable carrier can be liquid or solid and is selected, with the planned manner of administration in mind, to provide for the desired bulk, consistency, etc., when combined with an active agent and other components of a given composition.

The term "pharmaceutically acceptable salt" as used herein refers to those salts which are, within the scope of sound medical judgment, suitable for use in contact with the tissues of humans and lower animals without undue toxicity, irritation, allergic response and the like and are commensurate with a reasonable benefit/risk ratio. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts may be prepared as alkaline metal or alkaline earth salts, such as sodium, potassium or calcium salts of the carboxylic acid group. By "pharmaceutically acceptable salt" is meant those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, P. H. Stahl, et al. describe pharmaceutically acceptable salts in detail in "Handbook of Pharmaceutical Salts: Properties, Selection, and Use" (Wiley VCH, Zurich, Switzerland: 2002). The salts may be prepared in situ during the final isolation and purification of the compounds described within the described invention or separately by reacting a free base function with a suitable organic acid. Representative acid addition salts include, but are not limited to, acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate(isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid. Basic addition salts may be prepared in situ during the final isolation and purification of compounds described within the invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Pharmaceutically acceptable salts also may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium or magnesium) salts of carboxylic acids may also be made.

The terms "primary tumor" or "primary cancer" are used interchangeably to refer to the original, or first, tumor in the body. Cancer cells from a primary cancer may spread to other parts of the body and form new, or secondary tumors. This is called metastasis. The secondary tumors are the same type of cancer as the primary cancer.

The term "progression" as used herein refers to the course of a disease as it becomes worse or spreads in the body.

The term "progression-free survival" (PFS) as used herein refers to the length of time during and after the treatment of a disease that a patient lives with the disease but it does not get worse.

The term "proliferation" as used herein refers to expansion of a population of cells by the continuous division of single cells into identical daughter cells, leading to a multiplying or increasing in the number of cells.

The term "recurrence" as used herein refers to a disease (e.g., cancer) that has come back, usually after a period of time during which the disease could not be detected.

The term "reduce" or "reducing" as used herein refers to limit occurrence of a disorder in individuals at risk of developing the disorder.

The terms "refractory" or "resistant" are used interchangeably herein refers to a disease or condition that does not respond to treatment. The disease may be resistant at the beginning of treatment or it may become resistant during treatment.

The term "remission" as used herein refers to a decrease in or disappearance of signs and symptoms of a disease. In partial remission, some, but not all, signs and symptoms have disappeared. In complete remission, all signs and symptoms have disappeared although the disease may still be in the body.

The term Response Evaluation Criteria in Solid Tumors (or "RECIST") as used herein refers to a standard way to measure how well a cancer patient responds to treatment. It is based on whether tumors shrink, stay the same, or get bigger. To use RECIST, there must be at least one tumor that can be measured on x-rays, CT scans, or MRI scans. The types of response a patient can have are a complete response (CR), a partial response (PR), progressive disease (PD), and stable disease (SD).

Rho Associated Coiled Coil Kinase (ROCK) Proteins. Cancer-associated changes in cellular behavior, such as modified cell-cell contact, increased migratory potential, and generation of cellular force, all require alteration of the cytoskeleton. ROCK proteins belong to the protein kinase A, G, and C family (AGC family) of classical serine/threonine protein kinases, a group that also includes other regulators of cell shape and motility, such as citron Rho-interacting kinase (CRIK), dystrophia myotonica protein kinase (DMPK), and the myotonic dystrophy kinase-related Cdc42-binding kinases (MRCKs). The main function of ROCK signaling is regulation of the cytoskeleton through the phosphorylation of downstream substrates, leading to increased actin filament stabilization and generation of actin-myosin contractility. (Morgan-Fisher, M. et al., 61:185-198, at 185).

Two homologous mammalian serine/threonine kinases, Rho-associated protein kinases I and II (ROCK I and II), are key regulators of the actin cytoskeleton acting downstream of the small GTPase Rho. ROCK I (alternatively called ROK β) and ROCK II (also known as Rho kinase or ROK α) are 160-kDa proteins encoded by distinct genes. The mRNA of both kinases is ubiquitously expressed, but ROCK I protein is mainly found in organs such as liver, kidney, and lung, whereas ROCK II protein is mainly expressed in muscle and brain tissue. The two kinases have the same overall domain structure and have 64% overall identity in humans, with 89% identity in the catalytic kinase domain. Both kinases contain a coiled-coil region (55% identity) containing a Rho-binding domain (RBD) and a pleckstrin homology (PH) domain split by a C1 conserved region (80% identity) (See FIG. 1). Despite a high degree of homology between the two ROCKs, as well as the fact that they share several common substrates, studies have shown that the two ROCK isoforms also have distinct and non-redundant functions. For example, ROCK I has been shown to be essential for the formation of stress fibers and focal adhesions, whereas ROCK II is required for myosin II-dependent phagocytosis.

ROCKs exist in a closed, inactive conformation under quiescent conditions, which is changed to an open, active conformation by the direct binding of guanosine triphosphate (GTP)-loaded Rho. (Id.). Rho is a small GTPase which functions as a molecular switch, cycling between guanosine diphosphate (GDP) and guanosine triphosphate (GTP) bound states under signaling through growth factors or cell adhesion receptors. (Id.). GTPases are hydrolase enzymes that bind and hydrolyze GTP. In a similar way to ATP, GTP can act as an energy carrier, but it also has an active role in signal transduction, particularly in the regulation of G protein activity. G proteins, including Rho GTPases, cycle between an inactive GDP-bound and an active GTP-bound conformation. The transition between the two conformational states occurs through two distinct mechanisms: activation by GTP loading and inactivation by GTP hydrolysis. GTP loading is a two-step process that requires the release of bound GDP and its replacement by a GTP molecule. Nucleotide release is a spontaneous but slow process that has to be catalyzed by RHO-specific guanine nucleotide exchange factors (RHOGEFs), which associate with RHO GTPases and trigger release of the nucleotide. The resulting nucleotide-free binary complex has no particular nucleotide specificity. However, the cellular concentration of GTP is markedly higher than that of GDP, which favors GTP loading, resulting in the activation of RHO GTPases.

Conversely, to turn off the switch, GTP has to be hydrolyzed. This is facilitated by RHO-specific GTPase-activating proteins (RHOGAPs), which stimulate the intrinsically slow hydrolytic activity of RHO proteins. Although guanine nucleotide exchange factors (GEFs) and GTPase-activating proteins (GAPs) are the canonical regulators of this cycle, several alternative mechanisms, such as post-translational modifications, may fine-tune the RHO switch. In addition, inactive RHO GTPases are extracted by RHO-specific guanine nucleotide dissociation inhibitors (RHOGDIs) from cell membranes to prevent their inappropriate activation and to protect them from misfolding and degradation. (Garcia-Mata, R. et al. "The 'invisible hand': regulation of RHO GTPases by RHOGDIs." Nature Reviews Molecular Cell Biology. (2011) 12:493-504; at 494).

Many proteins aid in activating and inhibiting ROCK I and ROCK II. Table A shows molecules that regulate ROCK by direct binding. (Morgan-Fisher, M. et al., 61:185-198, at 188). For example, small GTP-binding proteins RhoA (which controls cell adhesion and motility through organization of the actin cytoskeleton and regulation of actomyosin contractility) (Yoshioka, K. et al., "Overexpression of Small GTP-binding protein RhoA promotes Invasion of Tumor Cells," J. Cancer Res. (1999) 59: 2004-2010), RhoB (which is localized primarily on endosomes, has been shown to regulate cytokine trafficking and cell survival) and RhoC (which may be more important in cell locomotion) (Wheeler, A. P., Ridley, A. J., "Why three Rho proteins? RhoA, RhoB, RhoC and cell motility," Exp. Cell Res. (2004) 301(1): 43-49) associate with and activate the ROCK proteins. Other GTP binding proteins, such as RhoE, Ras associated with diabetes (Rad) and Gem (a member of the RGK family of GTP-binding proteins within the Ras superfamily possessing a ras-like core and terminal extensions whose expression inhibited ROK beta-mediated phosphorylation of myosin light chain and myosin phosphatase, but not LIM kinase, (see Ward Y., et al., J. Cell Biol. (2002) 157(2): 291-302), inhibit ROCK, binding at sites distinct from the canonical Ras binding domain (RBD). Association with the PDK1 kinase promotes ROCK I activity by blocking RhoE association.

TABLE A

| Partner | Binding Site on ROCK | Outcome of Interaction | Cell Types | References |
|---------|----------------------|------------------------|------------|------------|
| ROCK1 | | | | |
| PDK1 | aa 375-415 | Retention of ROCK I at the plasma membrane. Increases cortical actin-myosin contractility and increases amoeboid migration. Prevents negative regulation of ROCKI activity by RhoE. PDK1 does not affect ROCK I kinase activity. | (H) Malignant melanoma, (R) breast cancer, (H) squamous cell carcinoma | Pinner and Sahal 2008 |
| MYBPH | aa 17-535 | Reduces MLC phosphorylation. Decreases single-cell motility leading to reduced lung adenocarcinoma invasion and metastasis. | (H) Lung adenocarcinoma | Hosono et al. 2011 |
| RhoE | aa 1-420 | Stress fiber disassembly and suppresses hepatocellular carcinoma motility and invasiveness. In competition with PDK1 for the same binding site on ROCK I. Regulates ROCK I kinase activity. | (H) Squamous cell and (H) hepatocellular carcinoma, (H) malignant melanoma | Riento et al. 2003; Pinner and Sahal 2008; Ma W et al. 2012 |
| Shroom2 | aa 593-1062 | Shroom2 and ROCK interact and regulate endothelial cell contractility. Reduced Shroom 2 mRNA levels have been linked to human colorectal cancer. | (H, M) Endothelial cells | Dunlop et al. 2012; Farber et al. 2011 |
| ROCKII | | | | |
| Coronin IB | aa 1135-1381 | Inhibits ROCK II signaling to myosin | (H) Breast adenocarcinoma | Rana and Worthylake 2012 |
| CRMP-2L and -2S | aa 1-543 | CRMP-2(L) inhibits ROCK II activity, resulting in alteration of cell migration, actin cytoskeleton organization, and decreased fibronectin matrix assembly | (H) Colon and breast adenocarcinoma, (R) fibroblasts, (Ca) kidney epithelial cells | Yoneda et al. 2012 |
| Raf1 | aa 1-543 | Reduces ROCK kinase activity. Promotes STAT3/myc activation and dedifferentiation in Ras-induced skin tumors. Regulates cell motility. | (M) Skin carcinoma, (M) primary keratinocytes, (M) fibroblasts | Ehrenreiter et al. 2005, 2009; Piazzolla et al., 2005; Niault et al. 2009 |
| Dynamin 1 | aa 1135-1381 | Overexpression studies showed that dynamin I is necessary for appropriate ROCK II action on the actin cytoskeleton in neuronal cells. | (R) Brain extract | Turnuslime et al. 2009 |

TABLE A-continued

| Partner | Binding Site on ROCK | Outcome of Interaction | Cell Types | References |
|---|---|---|---|---|
| MLCP | aa 354-775 | ROCK II phosphorylates MBS and inactivates MLCP. | (R) Smooth muscle cells | Kimura et al. 1996; Wang et al. 2009 |
| Myosin II | aa 1152-1388 | Overexpression studies showed myosin II to anchor ROCK II to stress fibers | (P)Brain extract, (M, R) fibroblasts | Kawabata et al. 2004 |
| NPM/B23 | aa 5-553 | Enhances ROCK II activity. Leads to centrosome amplification. | (M) Fibroblasts | Ma Z et al. 2006; Ferretti et al. 2010 |
| P80 CRMP-1 | aa 1-543 | Overexpression studies showed p80 CRMP-1 inhibits activity of recombinant ROCK II kinase domain. ROCK II phosphorylates p80 CRMP-1. | (R) Brain extract | Leung et al. 2002 |
| ROCK I and II | | | | |
| Gem | aa 787-976 (ROCK I), Full length ROCK II | Overexpression studies showed that Gem abolishes ROCK I-dependent MLC phosphorylation but not LIMK activation. Prevents ROCK I-mediated cell rounding and neurite retraction in neuroblastoma cells. Binds ROCK II. | (H) Neuroblastoma | Ward et al. 2002 |
| Rad | aa 787-976 (ROCK I), aa 807-976 ROCK II | Overexpression studies showed that Rad binding prevents ROCK II-mediated cell rounding and neurite retraction in neuroblastoma cells. Binds ROCK I. | (H) Neuroblastoma | Ward et al. 2002 |
| Morgana/chpI | Full-length | Binds and reduces ROCK II kinase activity. Inhibits ROCK II-NPM interaction. Binds ROCK I containing complexes. | (H) Embryonic kidney cells, (M) embryonic fibroblasts | Ferretti et al. 2010 |
| Shroom 3 | aa 726-926 (ROCK I), aa 698-957 (ROCK II) | Recruitment of the ROCKs to apical junctions. Increases MLC phosphorylation at apical junctions. Shroom3-ROCK interaction is crucial for neuroepithelial cell arrangement and remodeling. | (C, M) Embryos, (Ca) kidney epithelial cells | Nishimura and Takeichi 2008 |

ROCK activation leads to a concerted series of events that promote force generation and morphological changes. These events contribute directly to a number of actin-myosin mediated processes, such as cell motility, adhesion, smooth muscle contraction, neurite retraction and phagocytosis. In addition, ROCK kinases play roles in proliferation, differentiation, apoptosis and oncogenic transformation, although these responses can be cell type-dependent. (Olson, M. F. "Applications for ROCK kinase inhibition" Curr Opin Cell Biol. (2008) 20(2): 242-248, at 242-243).

ROCK I and ROCK II promote actin-myosin mediated contractile force generation through the phosphorylation of numerous downstream target proteins, including ezrin/radixin/moesin (ERM), the LIM-kinases (LIMK), myosin light chain (MLC), and MLOC phosphatase (MLCP). ROCK phosphorylates LIM kinases-1 and -2 (LIMK1 and LIMK2) at conserved Threonines in their activation loops, increasing LIMK activity and the subsequent phosphorylation of cofilin proteins, which blocks their F-actin-severing activity. ROCK also directly phosphorylates the myosin regulatory light chain, myosin light chain II (MLC), and the myosin binding subunit (MYPT1) of the MLC phosphatase to inhibit catalytic activity. Many of these effects are also amplified by ROCK-mediated phosphorylation and activation of the Zipper-interacting protein kinase (ZIPK), a serine/threonine kinase which is involved in the regulation of apoptosis, autophagy, transcription, translation, actin cytoskeleton reorganization, cell motility, smooth muscle contraction and mitosis, which phosphorylates many of the same substrates as ROCK.

The phosphorylation of MLC by ROCK provides the chemical energy for actin-myosin ratcheting, and also phosphorylates myosin light chain phosphatase (MLCP), thereby inactivating MLCP and preventing its dephosphorylation of MLC. Thus, ROCK promotes actin-myosin movement by activation and stabilization. Other known substrates of ROCK include the cytoskeleton related proteins such as the ERM proteins, and focal adhesion kinase (FAK). The ERM proteins function to connect transmembrane proteins to the cytoskeleton. (Street, C. A. and Bryan, B. A. "Rho Kinase Proteins-Pleiotropic Modulators of Cell Survival and Apoptosis" Anticancer Res. (2011) 31(11): 3645-3657, at 3650).

ROCK has been linked to apoptosis, cell survival, and cell cycle progression.

Rho-ROCK signaling has been implicated in cell cycle regulation. Rho-ROCK signaling increases cyclin D1 and Cip1 protein levels, which stimulate G1/S cell cycle progression. (Morgan-Fisher, M. et al., 61:185-198, at 189). Polyploidization naturally occurs in megakaryocytes due to an incomplete mitosis, which is related to a partial defect in Rho-ROCK activation, and leads to an abnormal contractile ring lacking myosin IIA.

Rho-ROCK signaling also has been linked to apoptosis and cell survival. During apoptosis, ROCK I and ROCK II are altered to become constitutively-active kinases. Through proteolytic cleavage by caspases (ROCK I) or granzyme B (ROCK II), a carboxyl-terminal portion is removed that normally represses activity. Interaction with phosphatidyl inositol (3,4,5)-triphosphate (PIP3) provides an additional regulatory mechanism by localizing ROCK II to the plasma membrane where it can undertake spatially restricted activities, i.e. the regulation by localization of enzymatic activity. Phosphorylation at multiple specific sites by polo-like kinase 1 was found to promote ROCK II activation by RhoA. (Olson, M. F., 20(2): 242-248, at 242). Additional Serine/Threonine and Tyrosine kinases may also regulate ROCK activity given that more phosphorylations have been identified. (Id.). Specifically, protein oligomerization induces N-terminal trans-phosphorylation. (Riento, K. and Ridley, A. J., "ROCKs: multifunction kinases in cell behavior." Nat Rev Mol Cell Biol. (2003) 4:446-456). Other direct activators include intracellular second messengers such as arachodonic acid and sphingosylphosphorylcholine which can activate ROCK independently of Rho. Furthermore, ROCK1 activity can be induced during apoptosis. (Mueller, B. K. et al., "Rho Kinase, a promising drug target for neurological disorders." (2005) Nat Rev Mol Cell Biol. 4(6): 387-398).

ROCK protein signaling reportedly acts in either a pro- or anti-apoptotic fashion depending on cell type, cell context and microenvironment. For instance, ROCK proteins are essential for multiple aspects of both the intrinsic and extrinsic apoptotic processes, including regulation of cytoskeletal-mediated cell contraction and membrane blebbing, nuclear membrane disintegration, modulation of Bcl2-family member and caspase expression/activation and phagocytosis of the fragmented apoptotic bodies (Mueller, B. K., et al., 4:387-398). ROCK signaling also exhibits pro-survival roles. Though a wealth of data exists to suggest both pro- and anti-survival roles for ROCK proteins, the molecular mechanisms that modulate these pleitropic roles are largely unknown. (Street, C. A. and Bryan, B. A., 31(11): 3645-3657

The term "sign" as used herein refers to something found during a physical exam or from a laboratory test that shows that a person may have a condition or disease.

The terms "subject" or "individual" or "patient" are used interchangeably to refer to a member of an animal species of mammalian origin, including but not limited to, a mouse, a rat, a cat, a goat, sheep, horse, hamster, ferret, platypus, pig, a dog, a guinea pig, a rabbit and a primate, such as, for example, a monkey, ape, or human.

The term "subject in need of such treatment" as used herein refers to a patient who suffers from a disease, disorder, condition, or pathological process, e.g., a cancer. According to some embodiments, the term "subject in need of such treatment" also is used to refer to a patient whose cancer comprises a population of cancer cells sensitive to an EBP-modulating anti-cancer compound (i) who will be administered an EBP modulating anti-cancer compound; (ii) is receiving an EBP modulating anti-cancer compound; or (iii) has received an EBP-modulating anti-cancer compound, unless the context and usage of the phrase indicates otherwise.

The terms "substantial inhibition", "substantially inhibited" and the like as used herein refer to inhibition of at least 50%, inhibition of at least 55%, inhibition of at least 60%, inhibition of at least 65%, inhibition of at least 70%, inhibition of at least 75%, inhibition of at least 80%, inhibition of at least 85%, inhibition of at least 90%, inhibition of at least 95%, or inhibition of at least 99%.

The term "survival rate" as used herein refers to the percent of individuals who survive a disease (e.g., cancer) for a specified amount of time. For example, if the 5-year survival rate for a particular cancer is 34%, this means that 34 out of 100 individuals initially diagnosed with that cancer would be alive after 5 years.

The term "symptom" as used herein refers to a sign or a disease or condition. The terms "symptom management", "palliative care," and "supportive care" are used interchangeably herein to refer to care given to improve the quality of life (QOL) of patients who have a serious or life-threatening disease.

The term "therapeutic agent" as used herein refers to a drug, molecule, nucleic acid, protein, metabolite, composition or other substance that provides a therapeutic effect. The term "active" as used herein refers to the ingredient, component or constituent of the compositions of the described invention responsible for the intended therapeutic effect. The terms "therapeutic agent" and "active agent" are used interchangeably herein.

The terms "therapeutically effective amount", an "amount effective", or "pharmaceutically effective amount" of one or more of the active agents and used interchangeably to refer to an amount that is sufficient to provide the intended benefit of treatment. An effective amount of the active agents that can be employed according to the described invention generally ranges from generally about 0.001 mg/kg body weight to about 1000 mg/kg body weight. However, dosage levels are based on a variety of factors, including the type of injury, the age, weight, sex, medical condition of the patient, the severity of the condition, the route of administration, and the particular active agent employed. Thus the dosage regimen may vary widely, but can be determined routinely by a physician using standard methods. Additionally, the terms "therapeutically effective amounts" and "pharmaceutically effective amounts" include prophylactic or preventative amounts.

The term "therapeutic component" as used herein refers to a therapeutically effective dosage (i.e., dose and frequency of administration) that eliminates, reduces, or prevents the progression of a particular disease manifestation in a percentage of a population. An example of a commonly used therapeutic component is the ED50, which describes the dose in a particular dosage that is therapeutically effective for a particular disease manifestation in 50% of a population.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect may also include, directly or indirectly, the arrest reduction or elimination of the progression of a disease manifestation.

The term "sterol" as used herein refers to a steroid alcohol, which contains a common steroid nucleus (a fused, reduced 17-carbon-atom ring system, cyclopentanoperhydrophenantrene) and a hydroxyl group.

As used herein the term "treating" includes abrogating, substantially inhibiting, slowing or reversing the progression of a condition, substantially ameliorating clinical symptoms of a condition, or substantially preventing the appearance of clinical symptoms of a condition. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously asymptomatic for the disorder(s).

The term "truncated" as used herein refers to shortened by cutting off residues; being cut short.

The term "tumor" as used herein refers to a diseases involving abnormal cell growth in numbers (proliferation) or in size with the potential to invade or spread to other parts of the body (metastasis).

The term "tumor burden" or "tumor load" are used interchangeably herein refers to the number of cancer cells, the size of a tumor, or the amount of cancer in the body.

According to one aspect, the described invention provides a composition comprising a therapeutic amount of an emopamil binding protein (EBP) modulating anti-cancer compound. According to some embodiments, in a cancer cell sensitive to the EBP modulating anti-cancer compound, the effective amount of the EBP-modulating anti-cancer compound is effective to cause accumulation of Δ8 sterol intermediates, e.g., 5α-cholest-8-(9)-en-3β-ol (Δ8-cholestenol). According to some embodiments, the cancer cell sensitive to the EBP-modulating anticancer compound is characterized by downregulation of SREBP-2. According to some embodiments, the cancer cell sensitive to the EBP-modulating anti-cancer compound is characterized by downregulation of SREBP-2 genes. According to some embodiments, the cancer cell sensitive to the EBP-modulating anti-cancer compound is characterized by downregulation of SREBP-2 and one or more SREBP-2 target genes of the cholesterol biosynthetic pathway. Exemplary SREBP-2 target genes include ACAT2; MHGCS1; HMGCR; MVK; PMVK; MVD; ID11/ID12; FDFS; GGPS1; FDFT1; SQLE; LSS; CYPS1A1; TM75F2; SCAMOL; NSDHL; HSD17B7; EBP; SC5D; DHCR7; DHCR24. According to some embodiments, the cancer cell sensitive to the EBP-modulating anti-cancer compound comprises a truncated APC protein.

According to some embodiments, in a cancer cell insensitive to the EBP-modulating anti-cancer compound, the amount of the EBP-modulating anti-cancer compound is effective to inhibit EBP and to upregulate endogenous cholesterol synthesis. According to some embodiments, inhibition of EBP is measured as an accumulation of Δ8 sterol intermediates, e.g., 5α-cholest-8-(9)-en-3β-ol (Δ8-cholesetenol). According to some embodiments, the cancer cell insensitive to the EBP-modulating anticancer compound is characterized by upregulation of SREBP-2. According to some embodiments, a cancer cell insensitive to the EBP-modulating anti-cancer compound is characterized by upregulation of SREBP-2 target genes of the cholesterol biosynthetic pathway. Exemplary SREBP-2 target genes include ACAT2; MHGCS1; HMGCR; MVK; PMVK; MVD; ID11/ID12; FDFS; GGPS1; FDFT1; SQLE; LSS; CYPS1A1; TM75F2; SCAMOL; NSDHL; HSD17B7; EBP; SC5D; DHCR7; DHCR24. According to some embodiments, the cancer cell insensitive to the EBP-modulating anti-cancer compound is characterized by upregulation of SREBP-2 and SREBP-2 target genes of the cholesterol biosynthetic pathway. According to some embodiments, the cancer cell insensitive to the EBP-modulating anti-cancer compound comprises a non-truncated wild type APC protein.

According to some embodiments, the composition is in form of a pharmaceutical composition comprising a therapeutic amount of the EBP-modulating anti-cancer compound and a pharmaceutically acceptable carrier. According to some embodiments, administration of the therapeutic amount of the EBP-modulating anti-cancer compound to a subject in need of such treatment is effective to reduce proliferation of the sensitive cancer cell, reduce invasiveness of the sensitive cancer cell, increase apoptosis of the sensitive cancer cell, reduce growth of a tumor comprising the sensitive cancer cell, reduce tumor burden, improve progression free survival, improve overall survival, achieve remission of disease, or a combination thereof.

According to another aspect, the described invention provides a method for identifying a population of cancer cells sensitive to a chemotherapy comprising an EBP-modulating anti-cancer compound. The method comprises (a) providing a test population of cancer cells, a known population of cancer cells containing cancer cells sensitive to an EBP-modulating anticancer compound (positive control), and a known population of cancer cells containing cancer cells insensitive to an EBP-modulating anticancer compound (negative control); (b) administering the known EBP-modulating anticancer compound to the populations of cancer cells; (c) measuring EBP enzyme activity and a parameter of endogenous cholesterol synthesis for each population of cancer cells, wherein an amount of the EBP-modulating anti-cancer compound is effective to decrease EBP enzyme activity and to decrease endogenous cholesterol synthesis in a cancer cell sensitive to the known EBP modulating anti-cancer compound, while an amount of the EBP-modulating anti-cancer compound is effective to increase EBP activity and to increase endogenous cholesterol synthesis in a cancer cell insensitive to the EBP modulating anti-cancer compound.

According to another aspect, the described invention provides a method for identifying EBP-modulating anticancer compounds for their use as a therapeutic agent. The method comprises (a) dividing a population of cancer cells sensitive to a known EBP-modulating anti-cancer compound into aliquoted samples of the population of cancer cells; (b) contacting one sample of the population of sensitive cancer cells with a candidate EBP-modulating anti-cancer compound, contacting a second sample of the sensitive population of cancer cells with a known EBP-modulating anticancer compound (positive control), and contacting a third sample of the sensitive population of cancer cells with a negative control; (c) measuring EBP activity and a parameter of endogenous cholesterol synthesis for the candidate EBP-modulating compound, the positive control and the negative control in (b), wherein an amount of the known EBP-modulating anti-cancer compound is effective to decrease EBP activity and to decrease endogenous cholesterol synthesis in a sensitive cancer cell, while an amount of the known EBP-modulating anti-cancer compound is effective to increase EBP activity and to increase endogenous cholesterol synthesis in a cancer cell insensitive to the known EBP modulating anti-cancer compound; (d) ranking a plurality of candidate EBP-modulating anti-cancer compounds according to the measured effect on EBP activity and the parameter of endogenous cholesterol synthesis in (c); and (e) selecting the top ranked candidate EBP-modulating anti-cancer compound in (d) as a new EBP-modulating anti-cancer compound for use as a therapeutic.

According to another aspect, the described invention provides a method for identifying a subject who will benefit from treatment of a cancer with an EBP-modulating anti-cancer compound. According to some embodiments, the method comprises (a) obtaining a population of cancer cells from the subject; (b) dividing the population of cancer cells into aliquoted samples of the population of cancer cells; (b) contacting a sample of the population of cancer cells with an EBP-modulating anti-cancer compound; (c) measuring EBP enzymatic activity and a parameter of endogenous cholesterol synthesis for each sample of the population of cancer cells, wherein an amount of the EBP-modulating anti-cancer compound is effective to decrease EBP activity and to decrease endogenous cholesterol synthesis in a cancer cell insensitive to the EBP modulating anti-cancer compound, while an amount of the EBP-modulating anti-cancer compound is effective to decrease EBP activity and to increase endogenous cholesterol synthesis in a cancer cell insensitive to the EBP modulating anti-cancer compound, and (d) treating the subject with a composition containing a therapeutic amount of the EBP modulating anti-cancer compound.

Compounds

According to one aspect, the described invention provides an EBP-modulating anti-cancer compound of Formula I:

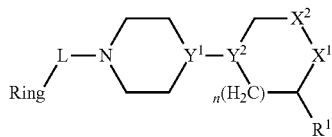
(Formula I)

wherein:
Y1 and Y2 are each independently CH or N;
L is SO2, CO, CH2, or CHMe;
X2 is selected from the group consisting of CH2, CHR2, NR3, O, S;
X1 is selected from the group consisting of CH2, CHR4, NR5, O, S;
n=0, 1, 2
R1 and R2 are each independently selected from the group consisting of H, C1-4 alkyl, C1-4 alkenyl, C1-4 alkynyl, CH2aryl, CH2heteroaryl
R3, R4 and R5 are each independently selected from the group consisting of C1-6 alkyl; C1-6 cycloalkyl, C1-6 alkenyl, C1-6 alkynyl, aryl, heteroaryl, CH2aryl, CH2heteroaryl;
R3 can form a methylene or ethylene bridge to one of the other ring atoms, thus providing a bicyclic ring structure; and
the Ring connected to L can be aryl, heteroaryl, heterocyclyl, fused cycloalkylaryl, fused heterocyclylaryl, fused arylheterocyclyl, fused cycloalkylheteroaryl, fused heterocyclylheteroaryl, fused heteroarylheterocyclyl;
such that all possible stereoisomers, including optically active isomers, are included whenever stereogenic centers are present.

Exemplary small molecule EBP-modulating anti-cancer compounds of formula I are found in Table A (SAR). All possible stereoisomers, including optically active isomers, are included whenever sterogenic centers are present.

According to one embodiment, the described invention provides an EBP-modulating anti-cancer compounds of Formula I-a:

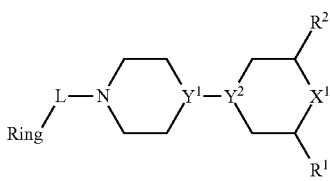
(Formula I-a)

wherein:
Y1 and Y2 are each independently CH or N;
L is SO2, CO, CH2, or CHMe;
X1 is selected from the group consisting of CH2, CHR4, NR5, O, S;
R1 and R2 are each independently H or Me;
R4 and R5 are each independently selected from the group consisting of C1-6 alkyl; C1-6 cycloalkyl, C1-6 alkenyl, C1-6 alkynyl, aryl, heteroaryl, CH2aryl, CH2heteroaryl;
the Ring connected to L can be aryl, heteroaryl, fused heterocyclylaryl;
such that all possible stereoisomers, including optically active isomers, are included whenever stereogenic centers are present.

According to another embodiment, the described invention provides an EBP modulating anti-cancer compound of Formula I-b:

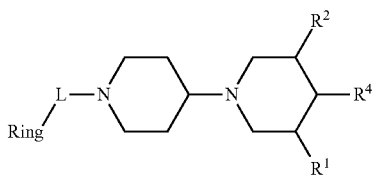
(Formula I-b)

wherein:
L is SO2, CO, CH2, or CHMe
R1 and R2 are each independently H or Me;
R4 selected from the group consisting of C1-6 alkyl; C1-6 alkynyl, aryl, CH2aryl;
the Ring connected to L can be aryl, heteroaryl, fused heterocyclylaryl;
such that all possible stereoisomers, including optically active isomers, are included whenever sterogenic centers are present.

According to another embodiment, an EBP modulating anti-cancer compound of the described invention is represented by Formula I-c:

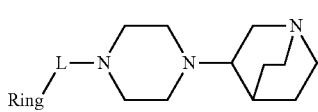
(Formula I-c)

wherein:
L is SO2, CH2, or CHMe;
the Ring connected to L can be aryl, heteroaryl, fused heterocyclylaryl;
such that all possible stereoisomers, including optically active isomers, are included whenever stereogenic centers are present.

According to another embodiment, an EBP modulating anti-cancer compound of the described invention is represented by Formula I-d:

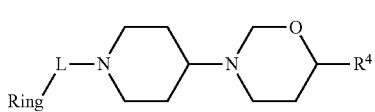
(Formula I-d)

wherein:

L is SO2, CH2, or CHMe;

R4 selected from the group consisting of C1-6 alkyl; C1-6 alkynyl, aryl, CH2aryl;

the Ring connected to L can be aryl, heteroaryl, fused heterocyclylaryl;

such that all possible stereoisomers, including optically active isomers, are included whenever stereogenic centers are present.

According to another embodiment, an EBP modulating anti-cancer compound of the described invention is represented by Formula I-e:

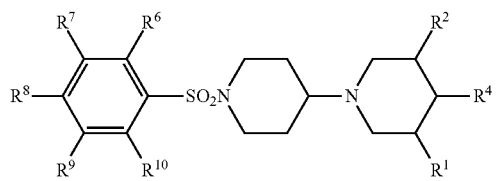

(Formula I-e)

wherein:

R1 and R2 are each independently H or Me;

R4 is selected from the group consisting of H, Me, propargyl, isopropyl, cyclopropyl, CH2aryl;

R6-10 are each independently selected from the group consisting of H, F, Cl, Br, Me, Et, CF3, cyclopropyl, isopropyl, tert-butyl, aryl, OMe, OCF3, OCHF2, OAryl, CN, N3, COAryl, CO2H, CO2R, CHO, CONH2, CONR2, CONHR. In the context of this paragraph, R is independently selected from the group consisting of H, C1-4 alkyl, C1-4 cycloalkyl, Aryl, CH2Aryl, CH2Heteroaryl;

such that all possible stereoisomers, including optically active isomers, are included whenever stereogenic centers are present.

According to one embodiment of EBP modulating anti-cancer compounds represented by Formula I-e, R1 and R2 are each independently H or Me; R4 is selected from H, Me, propargyl, isopropyl, cyclopropyl, CH2aryl; R6-10 are each independently selected from H, F, Cl, Br, Me, Et, CF3, cyclopropyl, isopropyl, aryl, OMe, OCF3, OCHF2, OAryl;

According to another embodiment of EBP modulating anti-cancer compounds represented by Formula I-e, R1 and R2 are each independently H or Me; R4 is selected from H, Me, propargyl, isopropyl, cyclopropyl, CH2aryl; R6 is Aryl, R7-10 are each independently selected from H, F, Cl, CF3, Me, cyclopropyl, isopropyl, OMe, OCF3, OCHF2;

According to another embodiment of EBP modulating anti-cancer compounds represented by Formula I-e, R1 and R2 are each independently H or Me; R4 is selected from H, Me, propargyl, isopropyl, cyclopropyl, CH2aryl; R7 is Aryl, R6, R8, R9 and R10 are each independently selected from H, F, Cl, CF3, Me, cyclopropyl, isopropyl, OMe, OCF3, OCHF2;

According to another embodiment of EBP modulating anti-cancer compounds represented by Formula I-e, R1 and R2 are each independently H or Me; R4 is selected from H, Me, propargyl, isopropyl, cyclopropyl, CH2aryl; R8 is Aryl, R6, R7, R9 and R10 are each independently selected from H, F, Cl, CF3, Me, cyclopropyl, isopropyl, OMe, OCF3, OCHF2;

According to another embodiment of EBP modulating anti-cancer compounds represented by Formula I-e, R1 and R2 are each independently H or Me; R4 is selected from H, Me, propargyl, isopropyl, cyclopropyl, CH2aryl; R7 is COAryl, R6, R8, R9 and R10 are each independently selected from H, F, Cl, CF3, Me, cyclopropyl, isopropyl, OMe, OCF3, OCHF2;

According to another embodiment, a small molecule EBP modulating anti-cancer compound of the described invention is represented by Formula I-f:

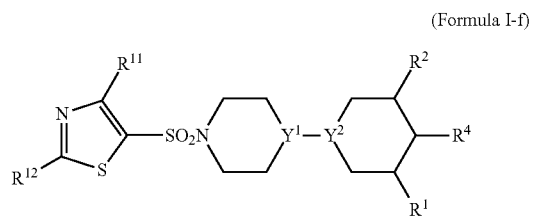

(Formula I-f)

wherein:

Y1 and Y2 are each independently CH or N;

R1 and R2 are each independently H or Me;

R4 is selected from the group consisting of C1-6 alkyl; C1-6 cycloalkyl, C1-6 alkenyl, C1-6 alkynyl, CH2aryl;

R11 and R12 are each independently selected from H, F, Cl, Br, Me, CF3, cyclopropyl, aryl, heteroaryl;

such that all possible stereoisomers, including optically active isomers, are included whenever stereogenic centers are present.

According to an embodiment of EBP modulating small molecule anti-cancer compounds represented by Formula I-f, Y1 is CH; Y2 is N; R1 and R2 are each independently H or Me; R4 is selected from H, Me, propargyl, isopropyl, cyclopropyl, CH2aryl; R11 is H, Me, CF3, cyclopropyl, aryl; and $R^{12}$ is selected from H, F, Cl, $CF_3$, Aryl.

Chemical Substituents and Stereochemistry

The term "Aliphatic" as used herein, denotes a straight— or branched-chain arrangement of constituent carbon atoms, including, but not limited to paraffins (alkanes), which are saturated, olefins (alkenes or alkadienes), which are unsaturated, and acetylenes (alkynes), which contain a triple bond. In complex structures, the chains may be branched or cross-linked.

The term "lower" as used herein refers to a group having between one and six carbons.

As used herein, the term "alkyl" refers to a straight or branched chain hydrocarbon having from 1 to 25 carbon atoms, or of the numbers of carbon atoms specified (e.g. C1-6 alkyl) or any numbers within this range. It is implicitly implied within the context of this application that such alkyl groups can be optionally substituted with substituents such as, but not limited to, halogen, perfluoroalkyl, lower alkyl, lower alkenyl, lower alkynyl, lower cycloalkyl, lower alkoxy, lower cycloalkoxy, lower alkylsulfanyl, oxo, hydroxyl. Examples of "alkyl" as used herein include, but are not limited to, methyl, trifluoromethyl, ethyl, propyl, n-butyl, t-butyl, n-pentyl, isobutyl, and isopropyl, methoxymethyl, methoxyethyl, isopropoxybutyl, propynyloxyethyl, and the like.

The term "Alkenyl," as used herein, denotes a monovalent, straight (unbranched) or branched hydrocarbon chain having one or more double bonds therein where the double bond can be unconjugated or conjugated to another unsaturated group (e.g., a polyunsaturated alkenyl) and can be unsubstituted or substituted, with multiple degrees of substitution being allowed. It may be optionally substituted with substituents such as, but not limited to, halogen, perfluoroalkyl, lower alkyl, lower alkenyl, lower alkynyl, lower cycloalkyl, lower alkoxy, lower cycloalkoxy, lower alkylsulfanyl, oxo, hydroxyl. For example, and without limitation, the alkenyl can be vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, 6-methoxyhexenyl, 2-trifluoromethyl-3-butenyl, and the like.

As used herein, the term "alkynyl" refers to a hydrocarbon radical having at least one carbon-carbon triple bond, optionally substituted with substituents such as, without limitation, halogen, perfluoroalkyl, lower alkyl, lower alkenyl, lower alkynyl, lower cycloalkyl, lower alkoxy, lower cycloalkoxy, lower alkylsulfanyl, oxo, hydroxyl.

The term "aryl" as used herein refers to a benzene ring or to an optionally substituted benzene ring system fused to one or more optionally substituted benzene rings, with multiple degrees of substitution being allowed. Substituents include, but are not limited to, cyano, halogen, perfluoroalkyl, aryl, heteroaryl, heterocyclyl, cycloalkyl, lower alkyl, lower alkoxy, lower alkylsulfanyl, oxo, hydroxy, amino optionally substituted by alkyl or aryl or heteroaryl or heterocyclyl or cycloalkyl, aminocarbonyl (—NRC(O)R) optionally substituted by alkyl or aryl or heteroaryl or heterocyclyl or cycloalkyl, carboxy, acyl, acyloxy, alkoxycarbonyl, aryloxy, heteroaryloxy, heterocyclyloxy, aroyloxy, heteroaroyloxy, heterocycloyloxy, carbamoyl optionally substituted by alkyl or cycloalkyl or aryl or heteroaryl or heterocyclyl, aminosulfonyl optionally substituted by alkyl or cycloalkyl or aryl or heteroaryl or heterocyclyl. Examples of aryl include, but are not limited to, phenyl, 2-napthyl, 1-naphthyl, 1-anthracenyl, and the like.

It should be understood that wherever the terms "alkyl" or "aryl" or either of their prefix roots appear in a name of a substituent, they are to be interpreted as including those limitations given above for alkyl and aryl. Designated numbers of carbon atoms (e.g. C1-10) shall refer independently to the number of carbon atoms in an alkyl, alkenyl or alkynyl or cyclic alkyl moiety or to the alkyl portion of a larger substituent in which the term "alkyl" appears as its prefix root.

As used herein, "cycloalkyl" (used interchangeably with "aliphatic cyclic" herein) refers to a non-aromatic monovalent, monocyclic or polycyclic ring structure having a total of from 3 to 10 carbon ring atoms (but no heteroatoms) optionally possessing one or more degrees of unsaturation, optionally substituted with substituents such as, without limitation, halogen, perfluoroalkyl, cycloalkyl, lower alkyl, lower alkoxy, lower alkylsulfanyl, oxo, hydroxyl. "Cycloalkyl" includes by way of example cyclopropyl, cyclobutyl, cyclopentyl, cyclopentenyl, cyclohexyl, cyclohehexenyl, adamantanyl, norbornyl, nobornenyl, cycloheptyl, or cyclooctyl, and the like.

The terms "heterocycle" and "heterocyclic" as used herein are used interchangeably to refer to a three to twelve-membered heterocyclic ring optionally possessing one or more degrees of unsaturation, containing one or more heteroatomic substitutions selected from —S—, —SO—, —SO2-, —O—, or —N—, optionally substituted with substitutents, including, but not limited to, nitro, cyano, halogen, perfluoroalkyl, aryl, heteroaryl, heterocyclyl, cycloalkyl, lower alkyl, lower alkoxy, lower alkylsulfanyl, lower alkylsulfenyl, lower alkylsulfonyl, oxo, hydroxy, mercapto, amino optionally substituted by alkyl or aryl or heteroaryl or heterocyclyl or cycloalkyl, aminocarbonyl (—NRC(O)R) optionally substituted by alkyl or aryl or heteroaryl or heterocyclyl or cycloalkyl, carboxy, acyl, acyloxy, alkoxycarbonyl, aryloxy, heteroaryloxy, heterocyclyloxy, aroyloxy, heteroaroyloxy, heterocycloyloxy, carbamoyl optionally substituted by alkyl or cycloalkyl or aryl or heteroaryl or heterocyclyl, aminosulfonyl optionally substituted by alkyl or cycloalkyl or aryl or heteroaryl or heterocyclyl, silyloxy optionally substituted by alkyl or aryl, silyl optionally substituted by alkoxy or alkyl or aryl, multiple degrees of substitution being allowed. Such a ring optionally may be fused to one or more of another "heterocyclic" ring(s). Examples of "heterocyclic" include, but are not limited to, pyrrole, furan, thiophene, imidazole, oxazole, thiazole, pyrazole, 3-pyrroline, pyrrolidine, pyridine, pyrimidine, purine, quinoline, isoquinoline, carbazole, tetrahydrofuran, 1,4-dioxane, 1,3-dioxane, piperidine, pyrrolidine, morpholine, piperazine and the like.

Examples of heterocycles include, but are not limited to, pyridyl, thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathiinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, beta-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

As used herein, the term "heteroaryl" refers to a five- to seven-membered aromatic ring, or to a polycyclic heterocyclic aromatic ring, containing one or more nitrogen, oxygen, or sulfur heteroatoms, where N-oxides and sulfur monoxides and sulfur dioxides are permissible heteroaromatic substitutions, optionally substituted with substituents including, but not limited to, nitro, cyano, halogen, perfluoroalkyl, aryl, heteroaryl, heterocyclyl, cycloalkyl, lower alkyl, lower alkoxy, lower alkylsulfanyl, lower alkylsulfenyl, lower alkylsulfonyl, oxo, hydroxy, mercapto, amino optionally substituted by alkyl or aryl or heteroaryl or heterocyclyl or cycloalkyl, aminocarbonyl (—NRC(O)R) optionally substituted by alkyl or aryl or heteroaryl or heterocyclyl or cycloalkyl, carboxy, acyl, acyloxy, alkoxycarbonyl, aryloxy, heteroaryloxy, heterocyclyloxy, aroyloxy, heteroaroyloxy, heterocycloyloxy, carbamoyl optionally substituted by alkyl or cycloalkyl or aryl or heteroaryl or heterocyclyl, aminosulfonyl optionally substituted by alkyl or cycloalkyl or aryl or heteroaryl or heterocyclyl, silyloxy optionally substituted by alkyl or aryl, silyl optionally substituted by alkoxy or alkyl or aryl, multiple degrees of substitution being allowed. For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, quinazoline, benzofuran, benzothiophene, indole, and indazole, and the like.

As used herein, the term "fused cycloalkylaryl" refers to a cycloalkyl group fused to an aryl group, the two having two atoms in common, and wherein the aryl group is the point of substitution. Examples of "fused cycloalkylaryl" used herein include, but are not limited to, 5-indanyl, 5,6,7,8-tetrahydro-2-naphthyl,

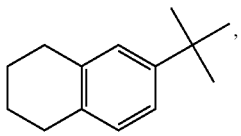

and the like.

As used herein, the term "fused arylcycloalkyl" refers to an aryl group fused to a cycloalkyl group, the two having two atoms in common, and wherein the cycloalkyl group is the point of substitution. Examples of "fused arylcycloalkyl" used herein include, but are not limited to, 1-indanyl, 2-indanyl, 1-(1,2,3,4-tetrahydronaphthyl),

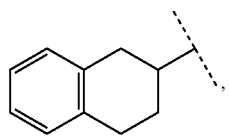

and the like.

As used herein, the term "fused heterocyclylaryl" refers to a heterocyclyl group fused to an aryl group, the two having two atoms in common, and wherein the aryl group is the point of substitution. Examples of "fused heterocyclylaryl" used herein include, but are not limited to, 3,4-methylenedioxy-1-phenyl,

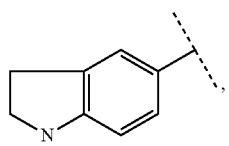

and the like.

As used herein, the term "fused arylheterocyclyl" refers to an aryl group fused to a heterocyclyl group, the two having two atoms in common, and wherein the heterocyclyl group is the point of substitution. Examples of "fused arylheterocyclyl" used herein include, but are not limited to, 2-(1,3-benzodioxolyl),

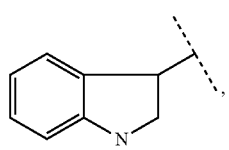

and the like.

As used herein, the term "fused cycloalkylheteroaryl" refers to a cycloalkyl group fused to a heteroaryl group, the two having two atoms in common, and wherein the heteroaryl group is the point of substitution. Examples of "fused cycloalkylheteroaryl" used herein include, but are not limited to, 5-aza-6-indanyl,

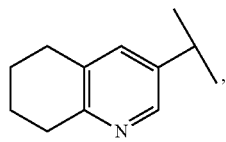

and the like.

As used herein, the term "fused heteroarylcycloalkyl" refers to a heteroaryl group fused to a cycloalkyl group, the two having two atoms in common, and wherein the cycloalkyl group is the point of substitution. Examples of "fused heteroarylcycloalkyl" used herein include, but are not limited to, 5-aza-1-indanyl,

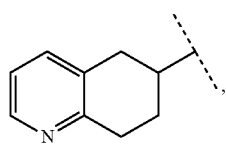

and the like.

As used herein, the term "fused heterocyclylheteroaryl" refers to a heterocyclyl group fused to a heteroaryl group, the two having two atoms in common, and wherein the heteroaryl group is the point of substitution. Examples of "fused heterocyclylheteroaryl" used herein include, but are not limited to, 1,2,3,4-tetrahydro-beta-carbolin-8-yl,

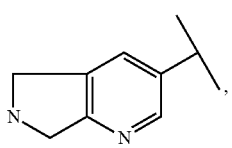

and the like.

As used herein, the term "fused heteroarylheterocyclyl" refers to a heteroaryl group fused to a heterocyclyl group, the two having two atoms in common, and wherein the heterocyclyl group is the point of substitution. Examples of "fused heteroarylheterocyclyl" used herein include, but are not limited to, -5-aza-2,3-dihydrobenzofuran-2-yl,

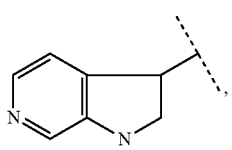

and the like.

As used herein, the term "direct bond", where part of a structural variable specification, refers to the direct joining of the substituents flanking (preceding and succeeding) the variable taken as a "direct bond".

As used herein, the term "O-linked moiety" means a moiety that is bonded through an oxygen atom. Thus, when an R group is an O-linked moiety, that R is bonded through oxygen and it thus can be an ether, an ester (e.g., —O—C (O)-optionally substituted alkyl), a carbonate or a carbamate (e.g., —O—C(O)—NH2 or —O—C(O)—NH-optionally substituted alkyl). Similarly, the term "S-linked moiety"

means a moiety that is bonded through a sulfur atom. Thus, when an R group is an S-linked moiety, that R is bonded through sulfur and it thus can be a thioether (e.g., —S-optionally substituted alkyl), a thioester (—S—C(O)-optionally substituted alkyl) or a disulfide (e.g., —S—S-optionally substituted alkyl). The term "N-linked moiety" means a moiety that is bonded through a nitrogen atom. Thus, when an R group is an N-linked moiety, the R group is bonded through nitrogen and one or more of these can thus be an N-linked amino acid such as —NH—CH2-COOH, a carbamate such as —NH—C(O)—O-optionally substituted alkyl, an amine such as —NH-optionally substituted alkyl, an amide such as —NH—C(O)-optionally substituted alkyl or —N3. The term "C-linked moiety" means a moiety that is bonded through a carbon atom. When one or more R group is bonded through carbon, one or more of these thus can be—optionally substituted alkyl such as —CH2-CH2-O—CH3, —C(O)-optionally substituted alkyl hydroxyalkyl, mercaptoalkyl, aminoalkyl or =CH-optionally substituted alkyl.

The term "alkoxy" as used herein refers to the group RaO—, where Ra is alkyl.

The term "alkenyloxy" as used herein refers to the group RaO—, where Ra is alkenyl.

The term "alkynyloxy" as used herein refers to the group RaO—, where Ra is alkynyl.

The term "alkylsulfanyl" as used herein refers to the group RaS—, where Ra is alkyl.

The term "alkenylsulfanyl" as used herein refers to the group RaS—, where Ra is alkenyl.

The term "alkynylsulfanyl" as used herein refers to the group RaS—, where Ra is alkynyl.

The term "alkylsulfenyl" as used herein refers to the group RaS(O)—, where Ra is alkyl.

The term "alkenylsulfenyl" as used herein refers to the group RaS(O)—, where Ra is alkenyl.

The term "alkynylsulfenyl" as used herein refers to the group RaS(O)—, where Ra is alkynyl.

The term "alkylsulfonyl" as used herein refers to the group RaSO2-, where Ra is alkyl.

The term "alkenylsulfonyl" as used herein refers to the group RaSO2-, where Ra is alkenyl.

The term "alkynylsulfonyl" as used herein refers to the group RaSO2-, where Ra is alkynyl.

The term "acyl" as used herein refers to the group RaC(O)—, where Ra is alkyl, alkenyl, alkynyl, cycloalkyl, cycloalkenyl, aryl, heteroaryl, or heterocyclyl.

The term "aroyl" as used herein refers to the group RaC(O)—, where Ra is aryl.

The term "heteroaroyl" as used herein refers to the group RaC(O)—, where Ra is heteroaryl.

The term "heterocycloyl" as used herein refers to the group RaC(O)—, where Ra is heterocyclyl.

The term "alkoxycarbonyl" as used herein refers to the group RaOC(O)—, where Ra is alkyl.

The term "acyloxy" as used herein refers to the group RaC(O)O—, where Ra is alkyl, alkenyl, alkynyl, cycloalkyl, cycloalkenyl, aryl, heteroaryl, or heterocyclyl.

The term "aroyloxy" as used herein refers to the group RaC(O)O—, where Ra is aryl.

The term "heteroaroyloxy" as used herein refers to the group RaC(O)O—, where Ra is heteroaryl.

The term "heterocycloyloxy" as used herein refers to the group RaC(O)O—, where Ra is heterocyclyl.

The term "substituted" as used herein refers to substitution with the named substituent or substituents, multiple degrees of substitution being allowed unless otherwise stated.

The terms "contain" or "containing" can as used herein refers to in-line substitutions at any position along the above defined alkyl, alkenyl, alkynyl or cycloalkyl substituents with one or more of any of O, S, SO, SO2, N, or N-alkyl, including, for example, —CH2-O—CH2, —CH2-SO2-CH2, —CH2-NH—CH3 and so forth.

The term "oxo" as used herein refers to the substituent =O.

The term "halogen" or "halo" as used herein includes iodine, bromine, chlorine and fluorine.

The term "mercapto" as used herein refers to the substituent —SH.

The term "carboxy" as used herein refers to the substituent —COOH.

The term "cyano" as used herein refers to the substituent —CN.

The term "aminosulfonyl" as used herein refers to the substituent —SO2NH2.

The term "carbamoyl" as used herein refers to the substituent —C(O)NH2.

The term "sulfanyl" as used herein refers to the substituent —S—.

The term "sulfenyl" as used herein refers to the substituent —S(O)—.

The term "sulfonyl" as used herein refers to the substituent —S(O)2-.

The term "ethoxy" as used herein refers to the substituent —O—CH2CH3.

The term "methoxy" as used herein refers to the substituent —O—CH3.

As used herein, the term "optionally" means that the subsequently described event(s) may or may not occur, and includes both event(s) which occur and events that do not occur.

Compounds of structural formula I and formulas Ia-f may contain one or more asymmetric centers and can thus occur as racemates and racemic mixtures, single enantiomers, diastereomeric mixtures and individual diastereomers. The described invention is meant to comprehend all such isomeric forms of the compounds of structural formula I and formulas Ia-f.

Compounds of structural formula I and formulas Ia-f may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general structural formula I and formulas Ia-f may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the described invention.

In the compounds of generic Formula I and formulas Ia-f, the atoms may exhibit their natural isotopic abundances, or one or more of the atoms may be artificially enriched in a particular isotope having the same atomic number, but an atomic mass or mass number different from the atomic mass or mass number predominantly found in nature. The described invention is meant to include all suitable isotopic variations of the compounds of generic Formula I and formulas Ia-g. For example, different isotopic forms of hydrogen (H) include protium (1H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I and formulas Ia-f can be prepared without undue experimentation by conventional techniques well known to those skilled in the art or by processes analogous to those described in the Schemes and Examples herein using appropriate isotopically-enriched reagents and/or intermediates.

It will be understood that, as used herein, references to the compounds of structural formula I and formulas Ia-f are meant to also include the pharmaceutically acceptable salts, and also salts that are not pharmaceutically acceptable when they are used as precursors to the free compounds or their pharmaceutically acceptable salts or in other synthetic manipulations.

Other exemplary EBP-modulating anti-cancer compounds include, without limitation, SR31747A, trifluoroperazine, ifenprodil, tridemorph, cis-flupentixol, 7-ketocholesetanol, tamoxifen, emopamil, verapamil, a conjugate of dendrogenin A, 5, 6 alpha-epoxycholesterol and histamine, haloperidol, fenpropimorph, etc.

Compositions

Compositions useful in the described invention may be in the form of a sterile injectable aqueous solution or oleaginous suspension. A solution generally is considered as a homogeneous mixture of two or more substances; it is frequently, though not necessarily, a liquid. In a solution, the molecules of the solute (or dissolved substance) are uniformly distributed among those of the solvent. A suspension is a dispersion in which a finely-divided species is combined with another species, with the former being so finely divided and mixed that it doesn't rapidly settle out. The term "dispersion", as used herein, refers to a two-phase system, in which one phase is distributed as particles or droplets in the second, or continuous phase. In these systems, the dispersed phase frequently is referred to as the discontinuous or internal phase, and the continuous phase is called the external phase or dispersion medium. For example, in coarse dispersions, the particle size is 0.5 mm. In colloidal dispersions, size of the dispersed particle is in the range of approximately 1 nm to 0.5 mm. Molecular dispersion is a dispersion, in which the dispersed phase consists of individual molecules; if the molecules are less than colloidal size, the result is a true solution.

Compositions useful in the described invention also may be in the form of an emulsion. An emulsion is a two-phase system prepared by combining two immiscible liquid carriers, one of which is disbursed uniformly throughout the other and consists of globules that have diameters equal to or greater than those of the largest colloidal particles. The globule size is critical and must be such that the system achieves maximum stability. Usually, separation of the two phases will not occur unless a third substance, an emulsifying agent, is incorporated. Thus, a basic emulsion contains at least three components, the two immiscible liquid carriers and the emulsifying agent, as well as the active ingredient. Most emulsions incorporate an aqueous phase into a non-aqueous phase (or vice versa). However, it is possible to prepare emulsions that are basically non-aqueous, for example, anionic and cationic surfactants of the non-aqueous immiscible system glycerin and olive oil. Thus, the compositions of the invention may be in the form of an oil-in-water emulsion. The oily phase may be a vegetable oil, for example, olive oil or arachis oil, or a mineral oil, for example a liquid paraffin, or a mixture thereof. Exemplary emulsifying agents may be naturally-occurring gums, for example, gum acacia or gum tragacanth, naturally-occurring phosphatides, for example soy bean, lecithin, and esters or partial esters derived from fatty acids and hexitol anhydrides, for example sorbitan monooleate, and condensation products of the partial esters with ethylene oxide, for example, polyoxyethylene sorbitan monooleate.

According to some embodiments, compositions useful in the described invention may be formulated for parenteral administration by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Exemplary lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension also may contain exemplary stabilizers or agents, which increase the solubility of the compounds to allow for the preparation of highly concentrated solutions. Alternatively, the active compounds may be in powder form for constitution with an exemplary vehicle, e.g., sterile pyrogen-free water, before use.

The pharmaceutical compositions also may comprise exemplary solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Exemplary liquid or solid pharmaceutical preparation forms are, for example, microencapsulated, and if appropriate, with one or more excipients, encochleated, coated onto microscopic gold particles, contained in liposomes, pellets for implantation into the tissue, or dried onto an object to be rubbed into the tissue. Such pharmaceutical compositions also may be in the form of granules, beads, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, or solubilizers are customarily used as described above. The pharmaceutical compositions are exemplary for use in a variety of drug delivery systems. For a brief review of methods for drug delivery, see Langer 1990 Science 249, 1527-1533, which is incorporated herein by reference.

Depending upon the structure, an EBP-modulating anti-cancer compound, and optionally at least one additional active agent, may be administered per se (neat) or, depending upon the structure of the inhibitor, in the form of a pharmaceutically acceptable salt. The EBP-modultaing anti-cancer compound may form pharmaceutically acceptable salts with organic or inorganic acids, or organic or inorganic bases. When used in medicine the salts should be pharmaceutically acceptable, but non-pharmaceutically acceptable salts conveniently may be used to prepare pharmaceutically acceptable salts thereof.

The formulations may be presented conveniently in unit dosage form and may be prepared by any of the methods well known in the art of pharmacy. All methods include the step of bringing into association a composition, or a pharmaceutically acceptable salt or solvate thereof ("active compound") with the carrier which constitutes one or more accessory agents. In general, the formulations are prepared by uniformly and intimately bringing into association the active agent with liquid carriers or finely divided solid carriers or both and then, if necessary, shaping the product into the desired formulation.

The pharmaceutical agent or a pharmaceutically acceptable ester, salt, solvate or prodrug thereof may be mixed with other active materials that do not impair the desired action, or with materials that supplement the desired action. Solutions or suspensions used for parenteral, intradermal, subcutaneous, intrathecal, or topical application may include, but are not limited to, for example, the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation may be enclosed in ampoules, disposable syringes or multiple dose vials made of glass or plastic. Administered intravenously, particular carriers are physiological saline or phosphate buffered saline (PBS).

For use in chemotherapy, a therapeutic amount of a small molecule EBP-modulating anti-cancer compound may be administered to a subject by any mode. Administering the pharmaceutical composition may be accomplished by any means known to the skilled artisan. Routes of administration include, but are not limited to, parenteral, oral, buccal, topical, by inhalation or insufflation (i.e., through the mouth or through the nose), or rectal.

Pharmaceutical compositions for parenteral injection comprise pharmaceutically acceptable sterile aqueous or nonaqueous solutions, dispersions, suspensions or emulsions and sterile powders for reconstitution into sterile injectable solutions or dispersions. Examples of exemplary aqueous and nonaqueous carriers, diluents, solvents or vehicles include water, ethanol, polyols (propylene glycol, polyethylene glycol, glycerol, and the like), exemplary mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

The compositions also may contain adjuvants including preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It also may be desirable to include isotonic agents, for example, sugars, sodium chloride and the like. Prolonged absorption of the injectable pharmaceutical form may be brought about by the use of agents delaying absorption, for example, aluminum monostearate and gelatin.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

The therapeutic agent(s), including the described composition(s) useful in the described invention may be provided in the form of particles. The term "particles" as used herein refers to nano or microparticles (or in some instances larger) that may contain in whole or in part the composition or the other therapeutic agent(s) as described herein. The particles may contain the therapeutic agent(s) in a core surrounded by a coating. The therapeutic agent(s) also may be dispersed throughout the particles. The therapeutic agent(s) also may be adsorbed into the particles. The particles may be of any order release kinetics, including zero order release, first order release, second order release, delayed release, sustained release, immediate release, etc., and any combination thereof. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules that contain the composition in a solution or in a semi-solid state. The particles may be of virtually any shape.

Both non-biodegradable and biodegradable polymeric materials may be used in the manufacture of particles for delivering the therapeutic agent(s). Such polymers may be natural or synthetic polymers. The polymer is selected based on the period of time over which release is desired. For example, bioadhesive polymers include bioerodible hydrogels as described by Sawhney et al in Macromolecules (1993) 26, 581-587, the teachings of which are incorporated herein by reference. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. In order to prolong the effect of a drug, it often is desirable to slow the absorption of the drug from subcutaneous, intrathecal, or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. The term "controlled release" is intended to refer to any drug-containing formulation in which the manner and profile of drug release from the formulation are controlled. This refers to immediate as well as non-immediate release formulations, with non-immediate release formulations including, but not limited to, sustained release and delayed release formulations. The term "sustained release" (also referred to as "extended release") is used herein in its conventional sense to refer to a drug formulation that provides for gradual release of a drug over an extended period of time, and that can result in substantially constant blood levels of a drug over an extended time period. Alternatively, delayed absorption of a parenterally administered drug form is accomplished by dissolving or suspending the drug in an oil vehicle. The term "delayed release" is used herein in its conventional sense to refer to a drug formulation in which there is a time delay between administration of the formulation and the release of the drug there from. "Delayed release" may or may not involve gradual release of drug over an extended period of time, and thus may or may not be "sustained release."

According to some embodiments, use of a long-term sustained release implant may be desirable for treatment of chronic conditions. The term "long-term" release, as used herein, means that the implant is constructed and arranged to deliver therapeutic levels of the active ingredient for at least 7 days, and preferably about 30 to about 60 days. Long-term sustained release implants are well-known to those of ordinary skill in the art and include some of the release systems described above.

Injectable depot forms are made by forming microencapsulated matrices of a described inhibitor in biodegradable polymers such as polylactide-polyglycolide. Depending upon the ratio of inhibitor to polymer and the nature of the particular polymer employed, the rate of drug release may be controlled. Such long acting formulations may be formulated with appropriate polymeric or hydrophobic materials (for example as an emulsion in an acceptable oil) or ion exchange resins, or as sparingly soluble derivatives, for example, as a sparingly soluble salt. Examples of other biodegradable polymers include poly(orthoesters) and poly(anhydrides). Depot injectable formulations also are prepared by entrapping the inhibitor of the described invention in liposomes or microemulsions, which are compatible with body tissues.

The injectable formulations may be sterilized, for example, by filtration through a bacterial-retaining filter or by incorporating sterilizing agents in the form of sterile solid compositions that may be dissolved or dispersed in sterile water or other sterile injectable medium just prior to use. Injectable preparations, for example, sterile injectable aqueous or oleaginous suspensions may be formulated according to the known art using suitable dispersing or wetting agents and suspending agents. The sterile injectable preparation also may be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils conventionally are employed or as a solvent or suspending medium. For this purpose any bland fixed oil may be employed including synthetic mono- or diglycerides. In addition, fatty acids such as oleic acid are used in the preparation of injectables.

Formulations for parenteral (including but not limited to, subcutaneous, intradermal, intramuscular, intravenous, intrathecal and intraarticular) administration include aqueous and non-aqueous sterile injection solutions that may contain anti-oxidants, buffers, bacteriostats and solutes, which render the formulation isotonic with the blood of the intended recipient; and aqueous and non-aqueous sterile suspensions, which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Exemplary buffering agents include: acetic acid and a salt (1-2% w/v); citric acid and a salt (1-3% w/v); boric acid and a salt (0.5-2.5% w/v); and phosphoric acid and a salt (0.8-2% w/v). Exemplary preservatives include benzalkonium chloride (0.003-0.03% w/v); chlorobutanol (0.3-0.9% w/v); parabens (0.01-0.25% w/v) and thimerosal (0.004-0.02% w/v).

For oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents also may be incorporated in the mixture. Powders and tablets may be comprised of from about 5 to about 95 percent of the described composition. Exemplary binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate.

The compositions also may be formulated as syrups and elixirs. Syrups and elixirs may be formulated with sweetening agents, for example, glycerol, propylene glycol, sorbitol or sucrose. Such formulations also may contain a demulcent, a preservative, and flavoring and coloring agents. Demulcents are protective agents employed primarily to alleviate irritation, particularly mucous membranes or abraded tissues. A number of chemical substances possess demulcent properties. These substances include the alginates, mucilages, gums, dextrins, starches, certain sugars, and polymeric polyhydric glycols. Others include acacia, agar, benzoin, carbomer, gelatin, glycerin, hydroxyethyl cellulose, hydroxypropyl cellulose, hydroxypropyl methylcellulose, propylene glycol, sodium alginate, tragacanth, hydrogels and the like.

For buccal administration, the compositions of the described invention may take the form of tablets or lozenges formulated in a conventional manner for this route.

Liquid form preparations include solutions, suspensions and emulsions. Liquid form preparations also may include solutions for intranasal administration.

The compositions of the described invention may be in the form of a dispersible dry powder for delivery by inhalation or insufflation (either through the mouth or through the nose). Dry powder compositions may be prepared by processes known in the art, such as lyophilization and jet milling, as disclosed in International Patent Publication No. WO 91/16038 and as disclosed in U.S. Pat. No. 6,921,527, the disclosures of which are incorporated by reference. The composition of the described invention is placed within an exemplary dosage receptacle in an amount sufficient to provide a subject with a unit dosage treatment. The dosage receptacle is one that fits within an exemplary inhalation device to allow for the aerosolization of the dry powder composition by dispersion into a gas stream to form an aerosol and then capturing the aerosol so produced in a chamber having a mouthpiece attached for subsequent inhalation by a subject in need of treatment. Such a dosage receptacle includes any container enclosing the composition known in the art such as gelatin or plastic capsules with a removable portion that allows a stream of gas (e.g., air) to be directed into the container to disperse the dry powder composition. Such containers are exemplified by those shown in U.S. Pat. Nos. 4,227,522 ; 4,192,309; and 4,105,027. Exemplary containers also include those used in conjunction with Glaxo's Ventolin® Rotohaler brand powder inhaler or Fison's Spinhaler® brand powder inhaler. Another exemplary unit-dose container which provides a superior moisture barrier is formed from an aluminum foil plastic laminate. The pharmaceutical-based powder is filled by weight or by volume into the depression in the formable foil and hermetically sealed with a covering foil-plastic laminate. Such a container for use with a powder inhalation device is described in U.S. Pat. No. 4,778,054 and is used with Glaxo's Diskhaler® (U.S. Pat. Nos. 4,627,432; 4,811,731; and 5,035,237). Each of these references is incorporated herein by reference.

Compositions useful in the described invention may be in the form of suppositories for rectal administration of the composition. "Rectal" or "rectally" as used herein refers to introduction into the body through the rectum where absorption occurs through the walls of the rectum. These compositions can be prepared by mixing the drug with an exemplary nonirritating excipient such as cocoa butter and polyethylene glycols which are solid at ordinary temperatures but liquid at the rectal temperature and will therefore melt in the rectum and release the drug. When formulated as a suppository the compositions of the invention may be formulated with traditional binders and carriers, such as triglycerides.

Topical administration may also involve the use of transdermal administration such as transdermal patches or iontophoresis devices which are prepared according to techniques and procedures well known in the art. The terms "transdermal delivery system", transdermal patch" or "patch" refer to an adhesive system placed on the skin to deliver a time released dose of a drug(s) by passage from the dosage form through the skin to be available for distribution via the systemic circulation. Transdermal patches are a well-accepted technology used to deliver a wide variety of pharmaceuticals, including, but not limited to, scopolamine for motion sickness, nitroglycerin for treatment of angina pectoris, clonidine for hypertension, estradiol for post-menopausal indications, and nicotine for smoking cessation.

Exemplary patches for use in the described invention include, but are not limited to, (1) the matrix patch; (2) the reservoir patch; (3) the multi-laminate drug-in-adhesive patch; and (4) the monolithic drug-in-adhesive patch; TRANSDERMAL AND TOPICAL DRUG DELIVERY SYSTEMS, pp. 249-297 (Tapash K. Ghosh et al. eds., 1997), hereby incorporated herein by reference. These patches are well known in the art and generally available commercially.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the described invention, exemplary methods and materials have been described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise.

The publications discussed herein are provided solely for their disclosure prior to the filing date of the present application and each is incorporated by reference in its entirety. Nothing herein is to be construed as an admission that the described invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Identification of Small Molecules that Target Truncated APC Proteins

Mutations in the human APC tumor suppressor gene are linked to Familial Adenomatous Polyposis (FAP), an inherited cancer-prone condition in which numerous polyps are formed in the epithelium of the large intestine (See Kinzler et al., Science, 1991; 253:661-665; Kinzler and Vogelstein, Cell, 1996; 87:159-170; Half et al., Orphanet Journal of Rare Diseases, 2009; 4:22). The development of colorectal cancer (CRC) is initiated by the aberrant outgrowth of adenomatous polyps from the colonic epithelium that ultimately evolve into aggressive carcinomas (See Kinzler and Vogelstein, Cell, 1996; 87: 159-170). About 85% of sporadic colorectal cancers have been reported to harbor APC truncating mutations (See Kinzler and Vogelstein, Cell, 1996; 87:159-170). The growth of the polyps is associated in most cases with alterations of both alleles of the Adenomatous Polyposis Coli (APC) gene. A first mutational hit occurs roughly in the middle of the open reading frame, generating a truncated APC molecule lacking the C-terminal half. Such truncation mutations are located in the so-called mutation cluster region (MCR) (See Schneikert et al., Human Molecular Genetics, 2006; 16: 199-209). The second mutational hit involves either deletion of the second allele or a mutation that leads to the synthesis of a truncated product, almost never occurring after the MCR (See Schneikert et al., Human Molecular Genetics, 2006; 16: 199-209). Thus, colon cancer cells express at least a truncated APC molecule whose length is defined by the position of the MCR and, occasionally, an additional but shorter fragment.

Adenomatous Polyposis Coli (APC) Gene

APC, which does not act as a classical tumor suppressor, influences Wnt signaling thereby regulating gene transcription. Wnts are a family of secreted cysteine-rich glycoproteins that have been implicated in the regulation of stem cell maintenance, proliferation, and differentiation during embryonic development. Canonical Wnt signaling increases the stability of cytoplasmic β-catenin by receptor-mediated inactivation of GSK-3 kinase activity and promotes β-catenin translocation into the nucleus. The canonical Wnt signaling pathway also functions as a stem cell mitogen via the stabilization of intracellular β-catenin and activation of the β-catenin/TCF/LEF transcription complex, resulting in activated expression of cell cycle regulatory genes, such as Myc, cyclin D1, EPhrinB (EPhB) and Msx1, which promote cell proliferation (See Cayuso and Marti, Journal of Neurobiology, 2005; 64:376-387).

APC is the negative regulator of Wnt signaling. Without this negative regulation, the Wnt pathway is more active and is important in cancer (See Polakis, Current Opinion in Genetics & Development, 2007; 17: 45-51). Studies comparing tumor cells with mutations in both APC alleles to correlate levels of Wnt signaling and severity of disease in both humans and mice have aided in establishing a model in which gene dosage effects generate a defined window of enhanced Wnt signaling, leading to polyp formation in the intestine. Combinations of 'milder' APC mutations, associated with weaker enhancement of Wnt signaling, give rise to tumors in extra-intestinal tissues. According to this model, the nature of the germline mutation in APC determines the type of somatic mutation that occurs in the second allele. (See Minde et al. Molecular Cancer, 2011; 10:101).

APC Protein

The APC gene product is a 312 kDa protein consisting of multiple domains, which bind to various proteins, including beta-catenin, axin, C-terminal binding protein (CtBP), APC-stimulated guanine nucleotide exchange factors (Asefs), Ras GTPase-activating-like protein (IQGAP1), end binding-1 (EB1) and microtubules. Studies using mutant mice and cultured cells demonstrated that APC suppresses canonical Wnt signaling, which is essential for tumorigenesis, development and homeostasis of a variety of cell types, including epithelial and lymphoid cells. Further studies have suggested that the APC protein functions in several other fundamental cellular processes. These cellular processes include cell adhesion and migration, organization of actin and microtubule networks, spindle formation and chromosome segregation. Deregulation of these processes caused by mutations in APC is implicated in the initiation and expansion of colon cancer (See Aoki and Taketo, Journal of Cell Science, 2007; 120:3327-3335).

The APC protein functions as a signaling hub or scaffold, in that it physically interacts with a number of proteins relevant to carcinogenesis. Loss of APC influences cell adhesion, cell migration, the cytoskeleton, and chromosome segregation (See Aoki and Taketo, Journal of Cell Science, 2007; 120:3327-3335).

Most investigators believe that APC mutations cause a loss of function change in colon cancer. Missense mutations yield point mutations in APC, while truncation mutations cause the loss of large portions of the APC protein, including defined regulatory domains. A significant number of APC missense mutations have been reported in tumors originating from various tissues, and have been linked to worse disease outcome in invasive urothelial carcinomas (See Kastritis et al., International Journal of Cancer, 2009; 124:103-108), suggesting the functional relevance of point mutated APC protein in the development of extra-intestinal tumors. The molecular basis by which these mutations interfere with the function of APC remains unresolved.

APC mutation resulting in a change of function can influence chromosome instability in at least three manners: by diminishing kinetochore-microtubule interaction, by the loss of mitotic checkpoint function and by generating polyploid cells. For example, studies have shown that APC bound to microtubules increased microtubule stability in vivo and in vitro, suggesting a role of APC in microtubule stability (See Zumbrunn et al., Current Biology, 2001; 11:44-49). Truncated APC led to chromosomal instability in mouse embryonic stem cells (See Fodde et al., Nature Cell Biology, 2001; 3:433-438), interfered with microtubule plus-end attachments, and caused a dramatic increase in mitotic abnormalities (See Green and Kaplan, Journal of Cell Biology, 2003; 163:949-961). Studies have shown that cancer cells with APC mutations have a diminished capacity to correct erroneous kinetochore-microtubule attachments, which account for the wide-spread occurrence of chromosome instability in tumors (See Bakhoum et al., Current Biology, 2009; 19:1937-1942). In addition, abrogation of the spindle checkpoint function was reported with APC loss of function. Knockdown of APC with siRNA indicated that loss of APC causes loss of mitotic spindle checkpoint function by reducing the association between the kinetochore and checkpoint proteins Bub1 and BubR1. Thus, loss of APC reduces apoptosis and induces polyploidy (See Kaplan et al., Nature Cell Biology, 2001; 3:429-432; Dikovskaya et al., Journal of Cell Biology, 2007; 176:183-195; Rusan and Peifer, Journal of Cell Biology, 2008; 181:719-726). Polyploidy is a major source for aneuploidy since it can lead to multipolar mitosis (See Shi and King, Nature, 2005; 437:1038-1042).

While loss of function due to APC may be partially correct, there are reports showing that a large fraction of colon cancer patients have at least one APC gene product that is truncated, and that this has a gain of function. Thus truncated APC proteins may play an active role in colon cancer initiation and progression as opposed to being recessive; for example, truncated APC, but not full-length APC may activate Asef and promote cell migration.

HCECs isolated from normal colonic biopsies were immortalized by successive infections of CDK4 and hTERT followed by selection with respective antibiotics—G418 (250 μg/mL) and blastocidin (2.5 μg/mL). shRNAs against p53 were introduced with retroviruses and p53 knockdown efficiency was verified by Western analysis. Human colon cancer cell lines (HCT116, DLD-1, RKO) and virus-producing cell lines (293FT, Phoenix A) were cultured in basal medium supplemented with 10% serum. The identity of all cell lines was verified by DNA fingerprinting. 1 μg of shRNA together with 1 μg of helper plasmids (0.4 μg pMD2G and 0.6 μg psPAX2) were transfected into 293FT cells with Polyjet reagent (SignaGen). Viral supernatants were collected 48 hours after transfection and cleared through a 0.45-μm filter. Cells were infected with viral supernatants containing 4 μg/mL polybrene (Sigma) at a multiplicity of infection (MOI) of approximately 1. Successfully infected cells were selected with 1 ug/mL puromycin for 3 days. as described in: Eskiocak U, Kim S B, Ly P, Roig A I, Biglione S, Komurov K, Cornelius C, Wright W E, White M A, Shay J W. Functional parsing of driver mutations in the colorectal cancer genome reveals numerous suppressors of anchorage-independent growth. Cancer Res 2011; 71:4359-65, which is incorporated herein by reference.

Mitotic Index

For determination of the mitotic index, DLD1 cells were methanol fixed 24 h after treatment with TASIN-1 at a concentration of 2.5 □L or 10 □□L or Pitstop2 (abcam, ab120687) at a concentration of 10 μL, DNA was visualized by Hoechst 33342 staining, and cells were imaged on a microscope (Axiovert 200M; Carl Zeiss) using a LD 40x/NA 0.75/Ph2 Plan-Neofluor objective. Mitotic cells were identified in the UV channel by their condensed DNA content.

HCECs with TP53, APC knockdown, KRASV12 mutation (1CTRPA) together with ectopic expression of APC truncation 1309 (hereinafter "1CTRPA A1309") (Table 1) have been developed (see Eskiocak U, Kim S B, Ly P, Roig A I, Biglione S, Komurov K, Cornelius C, Wright W E, White M A, Shay J W. Functional parsing of driver mutations in the colorectal cancer genome reveals numerous suppressors of anchorage-independent growth. Cancer Res 2011; 71:4359-65; Ly, P. Eskiocak, U., Parker, C. R., Harris, K. J., Wright, W. E. and Shay, J. W. RNAi screening of the human colorectal cancer genome identifies multifunctional tumor suppressors regulating epithelial cell invasion. Cell Res. 22:1605-1608, 2012, PubMed PMID: 23044803; Zhang, L., Komurov, K., Wright, W. E. and Shay, J. W. Identification of novel driver tumor suppressors through functional interrogation of putative passenger mutations in colorectal cancer. Int J Cancer. 132(3):732-7, 2013. doi: 10.1002/ijc.27705. Epub 2012 Jul. 21. PMID: 22753261, each of which is incorporated herein by reference.) This APC mutation is strongly selected for in colon cancers and has been shown to be more resistant to caspase cleavage than other truncated forms of APC. APC-truncated HCEC cell line 1CTRPA A1309 exhibits an increase in growth rate, enhancement of soft agar growth and invasion through Matrigel® compared to matched parental HCECs (1CTRPA). However, knockdown of wt APC alone (1CTRPA) did not cause HCECs to gain oncogenic properties (data unpublished).

These isogenic cell lines with defined genetic alterations have been used as a cellular model for identification of small molecules that target truncated APC proteins.

TABLE 1

Summary of the isogenic Human Colonic Epithelial Cells (HCECs) used in this screen

| Cell lines | Genetic alterations |
|---|---|
| 1CT | HCECs immortalized with CDK4 and hTERT |
| 1CTRPA | $Kras^{v12}$, shTP53, shAPC |
| 1CTRPA A1309 | $Kras^{v12}$, shTP53, shAPC, APC mutation (aa 1-1309) |

C: CDK4, T: hTERT, R: $Kras^{V12}$, P: shTP53, A: shAPC

Isogenic cell lines were used to carry out a cell-based high-throughput screen designed to identify small molecules and/or natural product fractions from within the University of Texas Southwestern (UTSW) compound file that can selectively inhibit cell growth of APC-truncated HCECs. This compound library encompasses ~200,000 synthetic compounds that represent a large chemical space from several commercial vendors, including 1200 marketed drugs from the Prestwick Chemical Library®, and 600 compounds that went to pre-clinical tests from the NIH library. The isogenic cell lines used in the screen are listed in Table 1.

A primary screen was performed in 1CTRPA A1309. For the screen, cells were seeded as a monolayer at a density of 400 cells/well in 384 well plates [in Colonic Epithelial Cell Medium (CoEpiCM (ScienCell Research Laboratories; Innoprot, etc.)], which are commercially available (Invitrogen; BioRad; Corning etc.). Twenty four hours later candidate compounds were added at a concentration of 2.5 μM per well and cells were incubated for 4 days at physiologic oxygen conditions (~3-5% O2). A luminescence-based Celltiter-Glo® assay was performed to measure cell viability, using ATP levels as the readout. In brief, opaque-walled multiwell plates with mammalian cells in culture medium (25 μl per well, 384-well plates) were prepared. Control wells containing medium without cells were prepared to obtain a value for background luminescence. Test compounds were added to experimental wells, and incubated according to culture protocol. The plate and its contents were incubated at room temperature for approximately 30 minutes. An ATP standard curve was generated immediately prior to adding the CellTiter-Glo® Reagent. A volume of CellTiter-Glo® Reagent equal to the volume of cell culture medium present in each well (25 μl of reagent to 25 μl of medium containing cells for a 384-well plate) was added. The contents were mixed for 2 minutes on an orbital shaker to induce cell lysis. The plate was allowed to incubate at room temperature for 10 minutes to stabilize the luminescent signal and luminescence recorded. (e.g. GloMax®, Lumistar, SPECTROstar, PHERAstar FS). The primary screen yielded 6704 positive hits (based on a z-score of <−3, which means that the z-score of −3 was 3 standard deviations below the mean).

Compounds that inhibited >40% of the proliferation of normal human epithelial cells were excluded based on the screening facility database and previous experience. The remaining 5381 compounds were re-screened against 1CTRPA A1309 (to validate the primary screen results) and 1CTRPA (to exclude those compounds that are not specific to APC truncations). To eliminate the possible general toxicity properties of these compounds, the compounds were also counter screened against normal diploid HCECs (1CT). This counter screen identified 126 compounds that inhibit cell growth of CTRPA A1309>50% more than that of 1CTRPA and 1CT. An additional screen of these selectively toxic compounds was carried out against the same panel of HCECs at a 1:3 fold dilution series of concentrations, ranging from 2.5 um to 30 nm. This secondary counter screen yielded 14 candidate compounds that showed selective inhibition of 1CTRPA A1309 cells at concentrations of 30 nm or 90 nm but without noticeable impact on 1CTRPA or 1CT cells. The overall screening strategy is shown in the flow chart below:

These 14 compounds then were obtained commercially and their $IC_{50}$ determined by performing dose response studies with half log dilution series at 12 concentration points in two authentic CRC lines: HCT116 (wt APC) and DLD1 (truncated APC). Anti-cancer compounds A and B showed selective toxicity towards DLD1 with $IC_{50}$ 63 nm and 131 nm, respectively. These two compounds served as initial lead compounds for analog development and for additional studies.

Exemplary compounds resulting from these substitutions are shown in Table B.

In Vitro APC Inhibition Assay

The small molecule anti-cancer compounds were evaluated for the ability to inhibit the activity of APC in an in vitro assay. Table B shows the $IC_{50}$ measured for each exemplified compound.

Reagents required for the assay are: (3-[4,5-Dimethylthiazol-2-yl]-2,5-diphenyltetrazolium bromide; Thiazolyl blue; RPI corp., cat# M92050); RPMI-1640 or Medium of Choice (i.e. DMEM) without phenol red; 1M Hepes; 100 mM NaPyruvate; 1000× Gentamicin (50 mg/ml); 100× Penicillin/Streptomycin/Fungizone; 1×PBS; Triton X-100; 1N HCl and Isopropanol. To make the MTT solution (10×), MTT powder was dissolved into complete RPMI (or DMEM solution) to a final concentration of 5 mg/mL and was sterilized by filtration with a 0.2 μm filter. The MTT solubilization solution contained 10% Triton X-100, 0.1N and 80% isopropanol. MTT solution was diluted to 1× with complete medium at 12 mL per plate. The culture dishes (96 wells) were removed from the incubator and the media was discarded. The plates were washed three times with 1×PBS. 100 μl of 1×MTT solution was added to each well and the plates were incubated in a tissue culture incubator for 2-4 hours, depending on the cell line. The cells were removed from the incubator and the MTT solution was discarded. 200 μl of 1×MTT solubilization solution was added to each well using a multi-channel pipetor and the cells were placed on an orbital shaker for 10 minutes. The results were read on a microtiter plate reader (absorbance=570 nm, reference=700 nm) and data was exported.

Percent inhibition was determined relative to control reactions without inhibitor, and half maximal inhibitory concentration (IC50) values were determined using a standard four parameter fit to the inhibition data. The term "IC50" as used herein refers to a quantitative measure of the effectiveness of a compound in inhibiting biological or biochemical function that indicates the amount that is needed to inhibit a given biological process (or component of a process) by 50%.

TABLE B

Small molecule anti-cancer analogs.

| Structure | MW | $IC_{50}$ (nM) in HCT-116 | $IC_{50}$ (nM) in DLD-1 | $IC_{50}$ (nM) in HT-29 | S9 $T_{1/2}$ (min) |
|---|---|---|---|---|---|
| 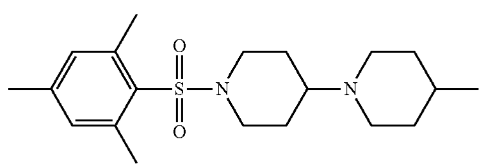 | 364.6 |  | 0.03 |  | 5 |
| 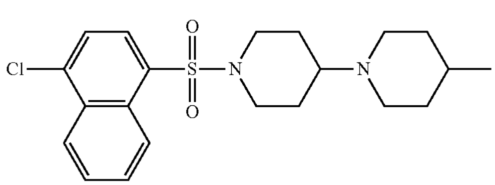 [SMILES: CC1CCN(C2CCN(S(=O)(=O)c3ccc(Cl)c4ccccc34)CC2)CC1] | 407 |  | 0.1 |  | 14 |
| 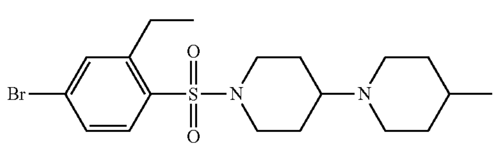 [SMILES: CCc1cc(Br)ccc1S(=O)(=O)N1CCC(N2CCC(C)CC2)CC1] | 429.4 |  | 0.6 |  | 9.1 |
| 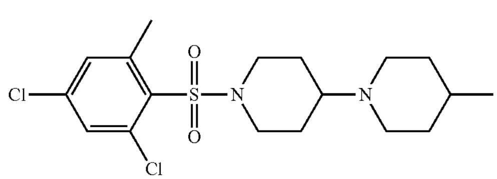 [SMILES: Cc1cc(Cl)cc(Cl)c1S(=O)(=O)N1CCC(N2CCC(C)CC2)CC1] | 405.4 |  | 0.6 |  | 9.1 |

TABLE B-continued

Small molecule anti-cancer analogs.

| Structure | MW | IC$_{50}$ (nM) in HCT-116 | IC$_{50}$ (nM) in DLD-1 | IC$_{50}$ (nM) in HT-29 | S9 T$_{1/2}$ (min) |
|---|---|---|---|---|---|
| 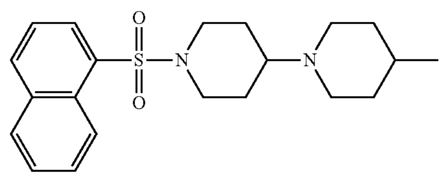 [SMILES: CC1CCN(C2CCN(S(=O)(=O)c3cccc4ccccc34)CC2)CC1] | 372.5 | | 0.65 | | <5 |
| 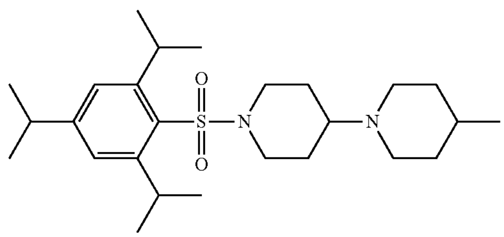 [SMILES: CC1CCN(C2CCN(S(=O)(=O)c3c(C(C)C)cc(C(C)C)cc3C(C)C)CC2)CC1] | 448.7 | | 0.7 | | 59 |
| 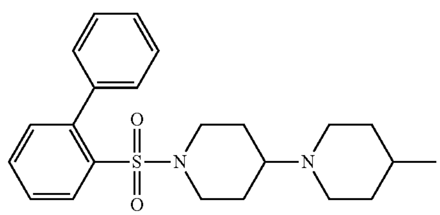 [SMILES: CC1CCN(C2CCN(S(=O)(=O)c3ccccc3-c3ccccc3)CC2)CC1] | 398.6 | | 0.96 | | <6 |
| 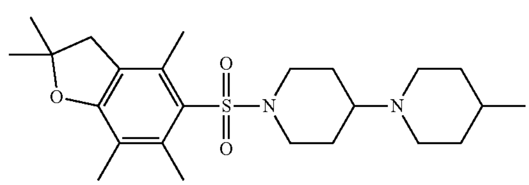 | 434.6 | | 1.2 | | 67 |
| 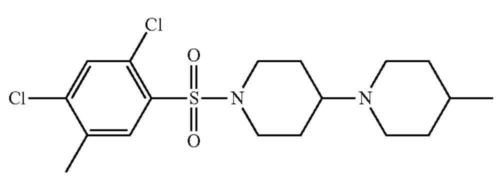 [SMILES: Cc1cc(S(=O)(=O)N2CCC(N3CCC(C)CC3)CC2)c(Cl)cc1Cl] | 405.4 | | 2 | | 6.5 |
| 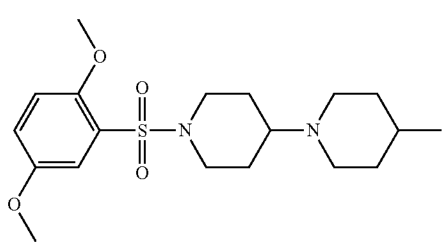 [SMILES: COc1ccc(OC)c(S(=O)(=O)N2CCC(N3CCC(C)CC3)CC2)c1] | 382.5 | | 4.5 | | 9.4 |
| 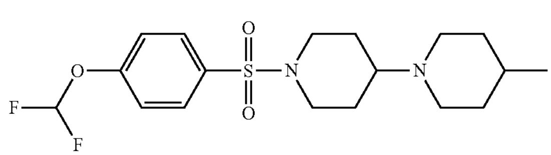 | 388.5 | | 4.8 | | 144 |

TABLE B-continued

Small molecule anti-cancer analogs.

| Structure | MW | IC$_{50}$ (nM) in HCT-116 | IC$_{50}$ (nM) in DLD-1 | IC$_{50}$ (nM) in HT-29 | S9 T$_{1/2}$ (min) |
|---|---|---|---|---|---|
| (structure) | 380.5 | | 10 | | 22.6 |
| (structure) | 356.4 | | 19 | | |
| (structure) | 390.5 | | 29 | | |
| (structure) | 485.4 | | 29 | | |
| (structure) | 406.5 | | 31 | | |
| (structure) | 382.5 | | 41 | | |
| (structure) | 406.5 | | 56 | | |
| (structure) | 478.4 | | 69 | | |

TABLE B-continued

Small molecule anti-cancer analogs.

| Structure | MW | IC$_{50}$ (nM) in HCT-116 | IC$_{50}$ (nM) in DLD-1 | IC$_{50}$ (nM) in HT-29 | S9 T$_{1/2}$ (min) |
|---|---|---|---|---|---|
| 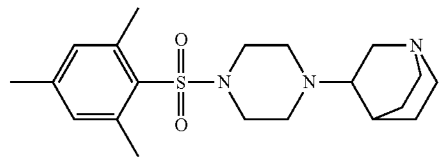 [SMILES: Cc1cc(C)c(S(=O)(=O)N2CCN(C3CN4CCC3CC4)CC2)c(C)c1] | 377.5 | | 84 | | |
| 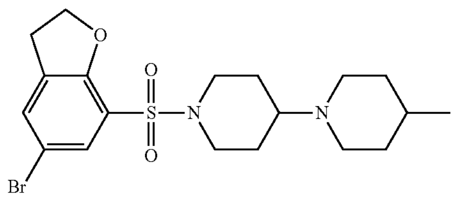 [SMILES: CC1CCN(C2CCN(S(=O)(=O)c3cc(Br)cc4c3OCC4)CC2)CC1] | 443.4 | | 96 | | |
| 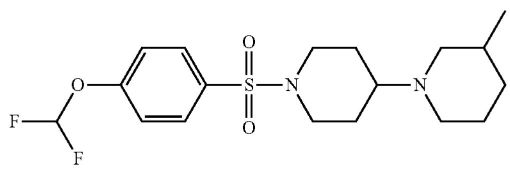 [SMILES: CC1CCCN(C2CCN(S(=O)(=O)c3ccc(OC(F)F)cc3)CC2)C1] | 388.5 | | 105 | | |
| 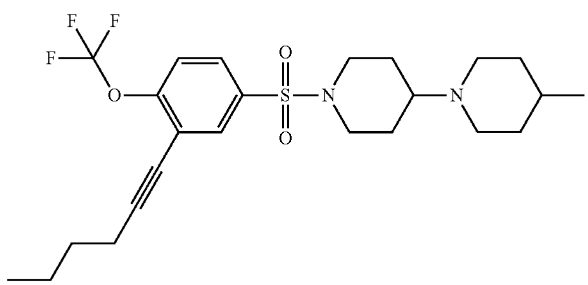 [SMILES: CCCCC#Cc1cc(S(=O)(=O)N2CCC(N3CCC(C)CC3)CC2)ccc1OC(F)(F)F] | 486.6 | | 147 | | |
| 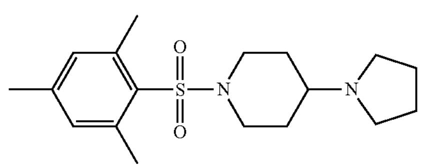 [SMILES: Cc1cc(C)c(S(=O)(=O)N2CCC(N3CCCC3)CC2)c(C)c1] | 336.5 | | 172.2 | | |
| 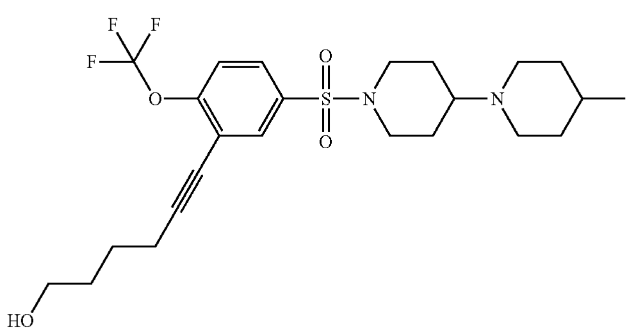 [SMILES: CC1CCN(C2CCN(S(=O)(=O)c3ccc(OC(F)(F)F)c(C#CCCCCO)c3)CC2)CC1] | 502.6 | | 205 | | |
| 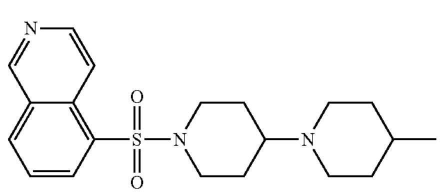 [SMILES: CC1CCN(C2CCN(S(=O)(=O)c3cccc4cnccc34)CC2)CC1] | 373.5 | | 225 | | |

TABLE B-continued

Small molecule anti-cancer analogs.

| Structure | MW | IC$_{50}$ (nM) in HCT-116 | IC$_{50}$ (nM) in DLD-1 | IC$_{50}$ (nM) in HT-29 | S9 T$_{1/2}$ (min) |
|---|---|---|---|---|---|
| (4-phenoxyphenyl)sulfonyl-piperidin-4-yl-(3-methylpiperidin-1-yl) | 414.6 | | 244 | | |
| (4-phenoxyphenyl)sulfonyl-piperidin-4-yl-(4-methylpiperidin-1-yl) | 414.6 | | 253 | | |
| (4-fluorophenyl)sulfonyl-piperidin-4-yl-(3-methylpiperidin-1-yl) | 340.5 | | 255 | | |
| phenylsulfonyl-piperidin-4-yl-(4-methylpiperidin-1-yl) | 322.5 | | 293.9 | | |
| (4-nitrophenyl)sulfonyl-piperidin-4-yl-(3-methylpiperidin-1-yl) | 367.5 | | 366 | | |
| (2,4,6-triisopropylphenyl)sulfonyl-piperidin-4-yl-pyrrolidin-1-yl | 420.7 | | 374 | | |
| (2-(trifluoromethoxy)phenyl)sulfonyl-piperidin-4-yl-(4-methylpiperidin-1-yl) | 406.5 | | 421 | | |
| (4-(trifluoromethoxy)phenyl)carbonyl-piperidin-4-yl-(4-methylpiperidin-1-yl) | 370.4 | | 426 | | |

TABLE B-continued

Small molecule anti-cancer analogs.

| Structure | MW | IC$_{50}$ (nM) in HCT-116 | IC$_{50}$ (nM) in DLD-1 | IC$_{50}$ (nM) in HT-29 | S9 T$_{1/2}$ (min) |
|---|---|---|---|---|---|
| 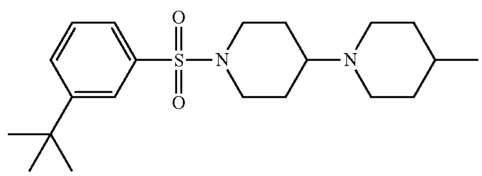 [SMILES: CC1CCN(C2CCN(S(=O)(=O)c3cccc(C(C)(C)C)c3)CC2)CC1] | 378.6 | | 463 | | |
| 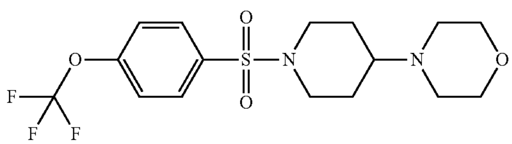 [SMILES: O=S(=O)(c1ccc(OC(F)(F)F)cc1)N1CCC(N2CCOCC2)CC1] | 394.4 | | 501 | | |
| 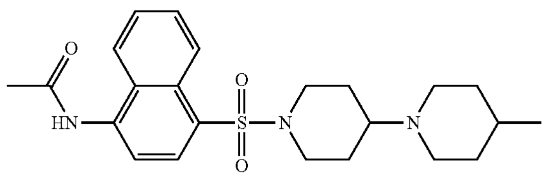 [SMILES: CC(=O)Nc1ccc(S(=O)(=O)N2CCC(N3CCC(C)CC3)CC2)c2ccccc12] | 429.6 | | 1100 | | |
| 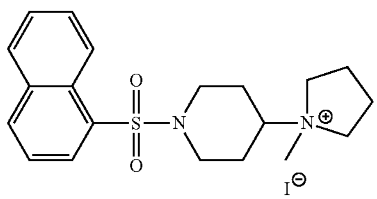 [SMILES: C[N+]1(C2CCN(S(=O)(=O)c3cccc4ccccc34)CC2)CCCC1 ; [I-]] | 486.4 | | 2300 | | |
| 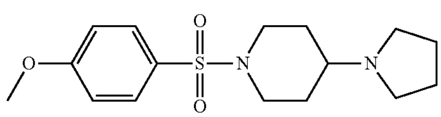 [SMILES: COc1ccc(S(=O)(=O)N2CCC(N3CCCC3)CC2)cc1] | 324.4 | | 3203 | | |
| 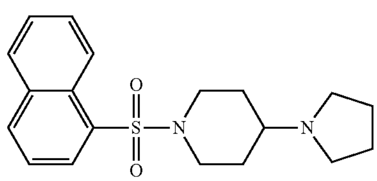 [SMILES: O=S(=O)(c1cccc2ccccc12)N1CCC(N2CCCC2)CC1] | 344.5 | | 3896 | | |
| | 464.4 | | ~7963 | | |
| | 464.4 | | >10,000 | | |
| 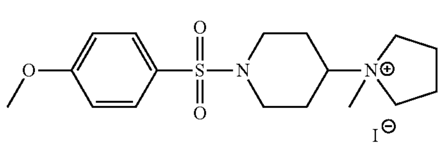 [SMILES: COc1ccc(S(=O)(=O)N2CCC([N+]3(C)CCCC3)CC2)cc1 ; [I-]] | 466.4 | | >10,000 | | |

TABLE B-continued

Small molecule anti-cancer analogs.

| Structure | MW | IC$_{50}$ (nM) in HCT-116 | IC$_{50}$ (nM) in DLD-1 | IC$_{50}$ (nM) in HT-29 | S9 T$_{1/2}$ (min) |
|---|---|---|---|---|---|
| (structure) | 352.5 | >10,000 | 63 | 53 | |
| (structure) | 346.5 | >10,000 | 5300 | 1100 | |
| (structure) | 390.5 | >10,000 | 85 | 35 | |
| (structure) | 390.5 | >10,000 | 7900 | 2300 | |
| (structure) | 346.5 | >10,000 | 18 | 4 | 25.2 |
| (structure) | 480.6 | >10,000 | 504 | 185 | |
| (structure) | 367.5 | >10,000 | 921 | 437 | |

TABLE B-continued

Small molecule anti-cancer analogs.

| Structure | MW | IC$_{50}$ (nM) in HCT-116 | IC$_{50}$ (nM) in DLD-1 | IC$_{50}$ (nM) in HT-29 | S9 T$_{1/2}$ (min) |
|---|---|---|---|---|---|
| 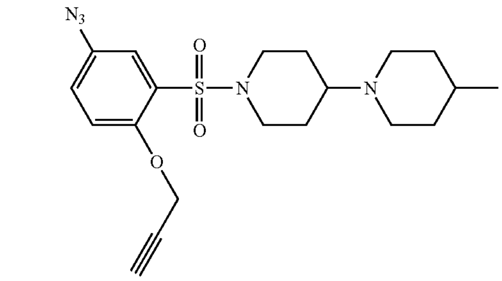 [SMILES: C#CCOc1ccc(N=[N+]=[N-])cc1S(=O)(=O)N1CCC(N2CCC(C)CC2)CC1] | 417.5 | >10,000 | 15000 | 4500 | |
| 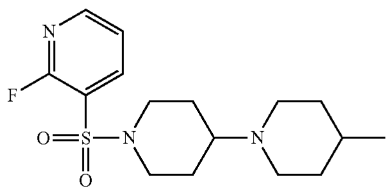 [SMILES: CC1CCN(C2CCN(S(=O)(=O)c3cccnc3F)CC2)CC1] | 341.4 | | >10,000 | | |
| 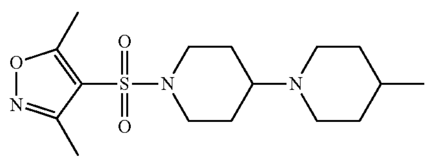 [SMILES: Cc1noc(C)c1S(=O)(=O)N1CCC(N2CCC(C)CC2)CC1] | 341.5 | | >10,000 | | |
| 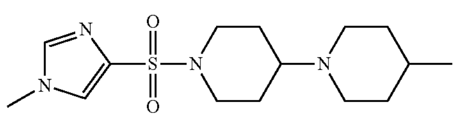 | 326.5 | | >10,000 | | |
| 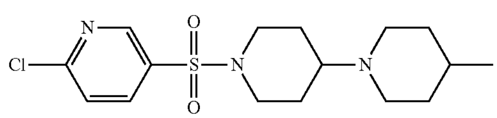 [SMILES: CC1CCN(C2CCN(S(=O)(=O)c3ccc(Cl)nc3)CC2)CC1] | 357.9 | | 3700 | | |
| 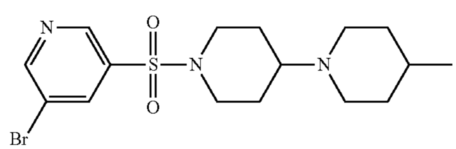 [SMILES: CC1CCN(C2CCN(S(=O)(=O)c3cncc(Br)c3)CC2)CC1] | 402.4 | | 7200 | | |
| 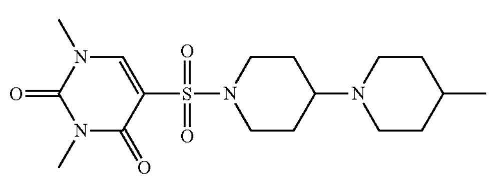 [SMILES: CC1CCN(C2CCN(S(=O)(=O)c3cn(C)c(=O)n(C)c3=O)CC2)CC1] | 384.5 | | >10,000 | | |
| | 387.5 | | 5300 | | |
| | 387.5 | | 235 | | |

TABLE B-continued

Small molecule anti-cancer analogs.

| Structure | MW | IC$_{50}$ (nM) in HCT-116 | IC$_{50}$ (nM) in DLD-1 | IC$_{50}$ (nM) in HT-29 | S9 T$_{1/2}$ (min) |
|---|---|---|---|---|---|
| 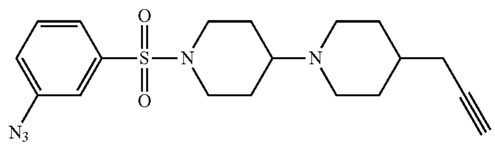 | 387.5 | | 1900 | | |
| | 365.5 | | 1100 | | |
| | 365.5 | | 426 | | |
| 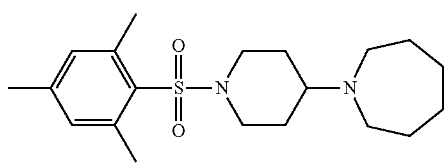 [SMILES: Cc1cc(C)c(S(=O)(=O)N2CCC(N3CCCCCC3)CC2)c(C)c1] | 364.6 | | 3300 | | |
| 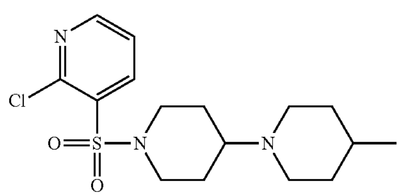 [SMILES: CC1CCN(C2CCN(S(=O)(=O)c3cccnc3Cl)CC2)CC1] | 357.9 | | >10,000 | | |
| 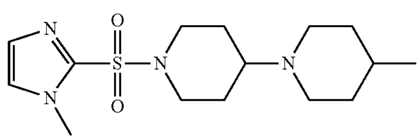 [SMILES: CC1CCN(C2CCN(S(=O)(=O)c3nccn3C)CC2)CC1] | 326.5 | | >10,000 | | |
| 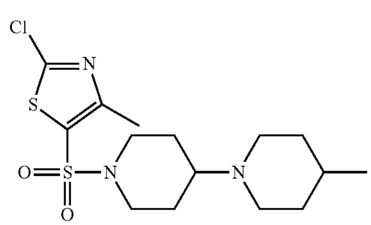 [SMILES: Cc1nc(Cl)sc1S(=O)(=O)N1CCC(N2CCC(C)CC2)CC1] | 378 | >10,000 | 1.6 | 1.5 | |
| 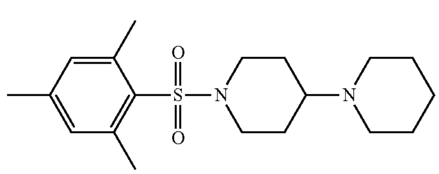 [SMILES: Cc1cc(C)c(S(=O)(=O)N2CCC(N3CCCCC3)CC2)c(C)c1] | 350.5 | >10,000 | 2200 | | |

TABLE B-continued

Small molecule anti-cancer analogs.

| Structure | MW | IC$_{50}$ (nM) in HCT-116 | IC$_{50}$ (nM) in DLD-1 | IC$_{50}$ (nM) in HT-29 | S9 T$_{1/2}$ (min) |
|---|---|---|---|---|---|
| 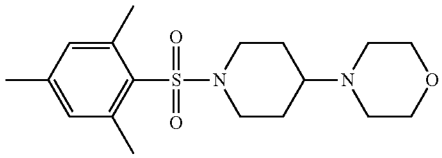 [SMILES: Cc1cc(C)c(S(=O)(=O)N2CCC(N3CCOCC3)CC2)c(C)c1] | 352.5 | >10,000 | 3100 | | |
| 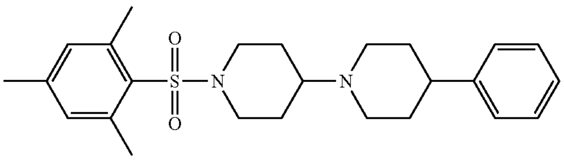 [SMILES: Cc1cc(C)c(S(=O)(=O)N2CCC(N3CCC(c4ccccc4)CC3)CC2)c(C)c1] | 426.6 | >10,000 | 865 | | |
| 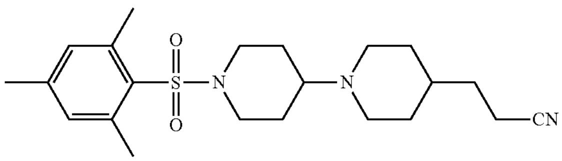 [SMILES: Cc1cc(C)c(S(=O)(=O)N2CCC(N3CCC(CCC#N)CC3)CC2)c(C)c1] | 403.6 | >10,000 | 7400 | | |
| 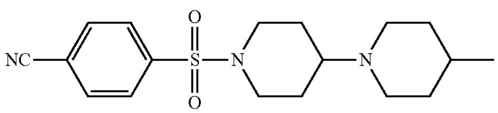 | 347.5 | >10,000 | 2800 | | |
| 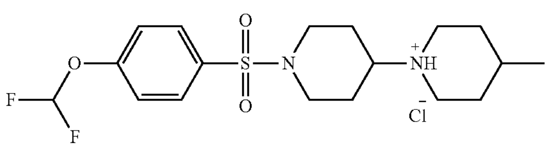 [SMILES: CC1CCN(C2CCN(S(=O)(=O)c3ccc(OC(F)F)cc3)CC2)CC1 ; Cl] | 424.9 | >10,000 | 63 | 79 | |
| 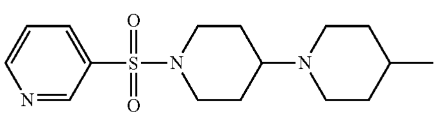 [SMILES: CC1CCN(C2CCN(S(=O)(=O)c3cccnc3)CC2)CC1] | 323.5 | >10,000 | 2400 | 2,200 | |
| 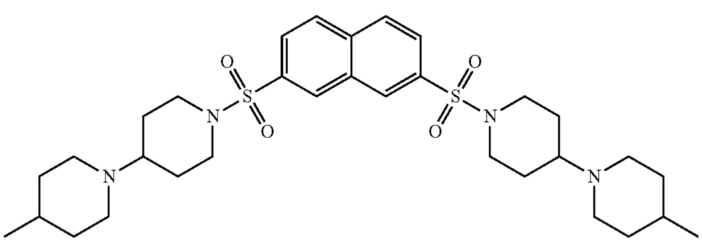 | 616.9 | TBD | TBD | | |
| 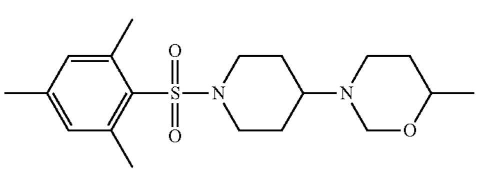 | 366.5 | >10,000 | 92 | 61 | |
| 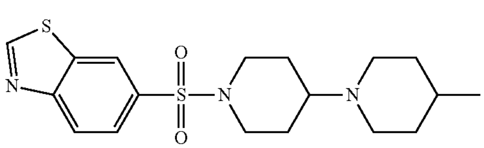 [SMILES: CC1CCN(C2CCN(S(=O)(=O)c3ccc4ncsc4c3)CC2)CC1] | 379.5 | >10,000 | 38 | 26 | |

TABLE B-continued
Small molecule anti-cancer analogs.
| Structure | MW | IC$_{50}$ (nM) in HCT-116 | IC$_{50}$ (nM) in DLD-1 | IC$_{50}$ (nM) in HT-29 | S9 T$_{1/2}$ (min) |
|---|---|---|---|---|---|
| 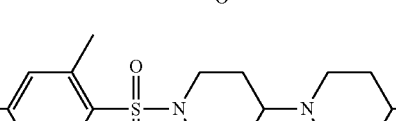 | 401.4 | >10,000 | 3.1 | 1.2 | |
| 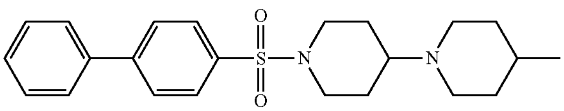 [SMILES: CC1CCN(C2CCN(S(=O)(=O)c3ccc(-c4ccccc4)cc3)CC2)CC1] | 398.6 | >10,000 | 258 | 234 | |
| 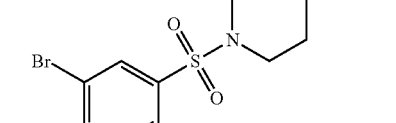 | 440.6 | >10,000 | 3.5 | 3 | |
| 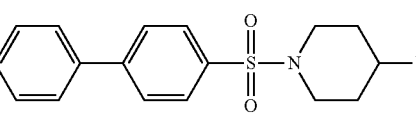 | 431.4 | >10,000 | 2 | 2 | |
| 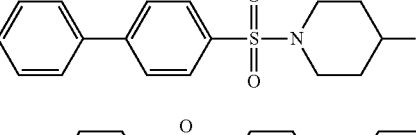 | 433 | >10,000 | 105 | 112 | |
| 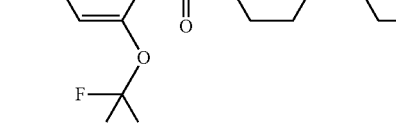 | 428.6 | >10,000 | 263 | 288 | |
| 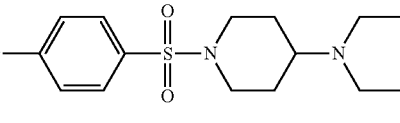 | 485.4 | >10,000 | 5 | 4 | |
| 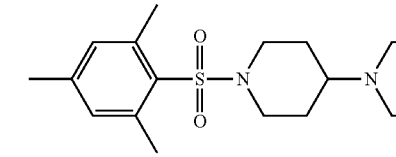 | 425.4 | >10,000 | 0.2 | 0.12 | |
| 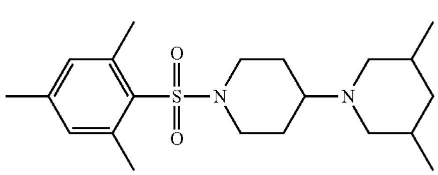 | 378.6 | >10,000 | 17 | 15 | |

TABLE B-continued

Small molecule anti-cancer analogs.

| Structure | MW | IC$_{50}$ (nM) in HCT-116 | IC$_{50}$ (nM) in DLD-1 | IC$_{50}$ (nM) in HT-29 | S9 T$_{1/2}$ (min) |
|---|---|---|---|---|---|
| (2,4,6-trimethylphenyl)sulfonyl-piperidine-piperidine-isopropyl | 392.6 | >10,000 | 0.3 | 0.2 | |
| (3-bromophenyl)sulfonyl-piperidine-(4-methylpiperidine) | 401.4 | >10,000 | 3.2 | 1.2 | |
| (4-bromophenyl)sulfonyl-piperidine-piperidine-CH₂-C≡C-TMS | 497.6 | >10,000 | 2.9 | 1.7 | |
| (4-chlorophenyl)sulfonyl-piperidine-(4-methylpiperidine) | 356.9 | >10,000 | 2.2 | 5.6 | |
| (4-methylphenyl)sulfonyl-piperidine-(4-methylpiperidine) | 336.5 | >10,000 | 9.1 | 14 | |
| (3,4-dichlorophenyl)sulfonyl-piperidine-(4-methylpiperidine) | 391.4 | >10,000 | 2.9 | 2.2 | |
| (4-benzoylphenyl)sulfonyl-piperidine-piperidine-CH₂-C≡CH | 450.6 | >10,000 | 4.8 | 5.2 | |
| (2-bromophenyl)sulfonyl-piperidine-(4-methylpiperidine) | 401.4 | >10,000 | 3 | 3 | |
| (4'-trifluoromethyl-biphenyl-2-yl)sulfonyl-piperidine-(4-methylpiperidine) | 466.6 | >10,000 | 122 | 57 | |

TABLE B-continued

Small molecule anti-cancer analogs.

| Structure | MW | IC$_{50}$ (nM) in HCT-116 | IC$_{50}$ (nM) in DLD-1 | IC$_{50}$ (nM) in HT-29 | S9 T$_{1/2}$ (min) |
|---|---|---|---|---|---|
| 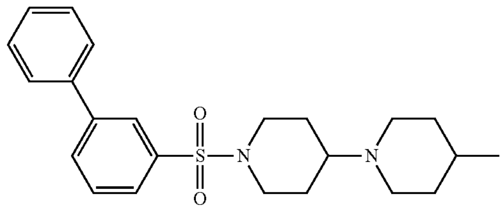 [SMILES: CC1CCN(C2CCN(S(=O)(=O)c3cccc(-c4ccccc4)c3)CC2)CC1] | 398.6 | >10,000 | 2 | 2 | |
| 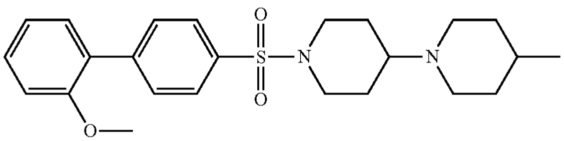 [SMILES: COc1ccccc1-c1ccc(S(=O)(=O)N2CCC(N3CCC(C)CC3)CC2)cc1] | 428.6 | >10,000 | 26 | 19 | |
| 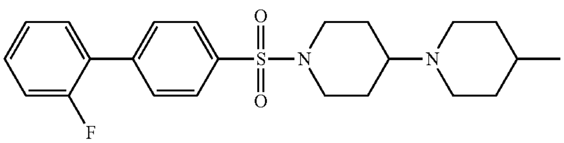 [SMILES: CC1CCN(C2CCN(S(=O)(=O)c3ccc(-c4ccccc4F)cc3)CC2)CC1] | 416.6 | >10,000 | 5 | 6 | |
| 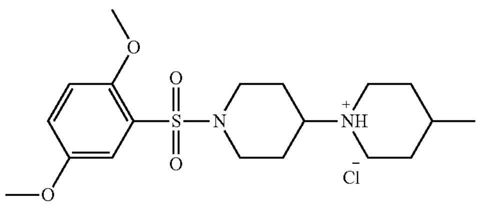 | 419 | | 45 | 7 | |
| 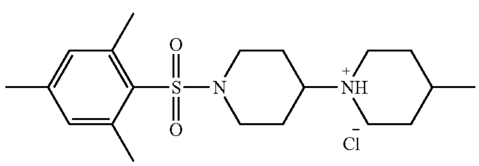 | 401 | | 908 | 2 | |
| 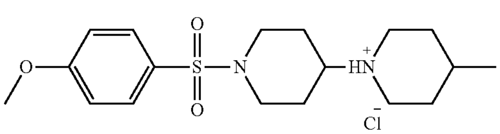 | 389 | | 494 | 6 | |

Analogs with an IC50 under 100 nM in DLD-1 are indicated in bold typeface.

Truncated APC Selective Inhibitor-1 (TASIN-1) Kills CRC Lines with APC Truncations while Sparing Normal Human Colonic Epithelial Cells (HCECs) and Other Cancer Cells with Wild Type (WT) APC, Interferes with Proper Mitotic Spindle Formation, and Induces JNK-Dependent Apoptotic Cell Death in APC Truncated Cells.

Dose response analysis in two authentic CRC cell lines: HCT116 (WT APC) and DLD1 (truncated APC), led to identification of the lead compound TASIN-1 (truncated APC selective inhibitor-1):

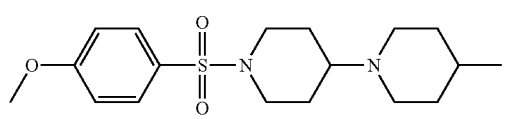

TASIN-1

As previously reported, this compound exhibited potent and selective toxicity towards DLD1 cells (IC50=63 nM) but not towards HCT116 cells (IC50>10 μM). Sustained treatment of TASIN-1 inhibited soft agar growth in DLD1 but not in HCT116 cells.

In Vivo Antitumor Activity of TASIN-1 in a Xenograft Mouse Model.

The in vivo antitumor activity of TASIN-1 was examined in a xenograft mouse model. Nude mice with established DLD1 tumors were injected intraperitoneally with either solvent (control) or 40 mg/kg of TASIN-1 twice daily for 18 days. TASIN-1 treatment reduced the size of tumor xenografts and reduced tumor growth rates compared with control mice. As previously reported, no overt toxicity and no statistically significant differences were observed in the body weights of mice between control group and TASIN-1 treated group. Similar antitumor activity was observed in HT29 xenografts, which also harbors truncated APC and demonstrated a similar sensitivity as DLD1 in vitro. However, TASIN-1 did not inhibit tumor growth in HCT116 (WT APC) xenografts, demonstrating that TASIN-1 maintains selectivity in vivo. Immunohistochemistry analysis of excised tumors showed that TASIN-1 induced a significant increase in the apoptotic marker, cleaved caspase 3 in TASIN-1 treated DLD1 tumors compared with control tumors. Induction of apoptosis was confirmed by detection of cleaved PARP1 in tumor lysates from control and TASIN-1 treated DLD1 xenografts (data not shown).

Anti-Tumor Effects of TASIN-1 in CPC;Apc Mice

The antitumor effects of TASIN-1 in CPC;Apc mice, a genetically engineered mouse model that mainly develops colorectal tumors, were further tested. These mice carry a CDX2P-NLS Cre recombinase transgene and a loxP-targeted Apc allele that deletes exon 14, leading to a frame shift at codon 580 and a truncated APC protein (Hinoi, T. et al. Mouse model of colonic adenoma-carcinoma progression based on somatic Apc inactivation. *Cancer Res* 67, 9721-9730 (2007)). Mice ~110 days old were injected intraperitoneally with either solvent or 20 mg/kg/injection of TASIN-1 twice a week for 90 days. Weights were measured every 15 days over the treatment period. These studies were performed according to the guidelines of the UT Southwestern Institutional Animal Care and Use Committee.

Figure 5:
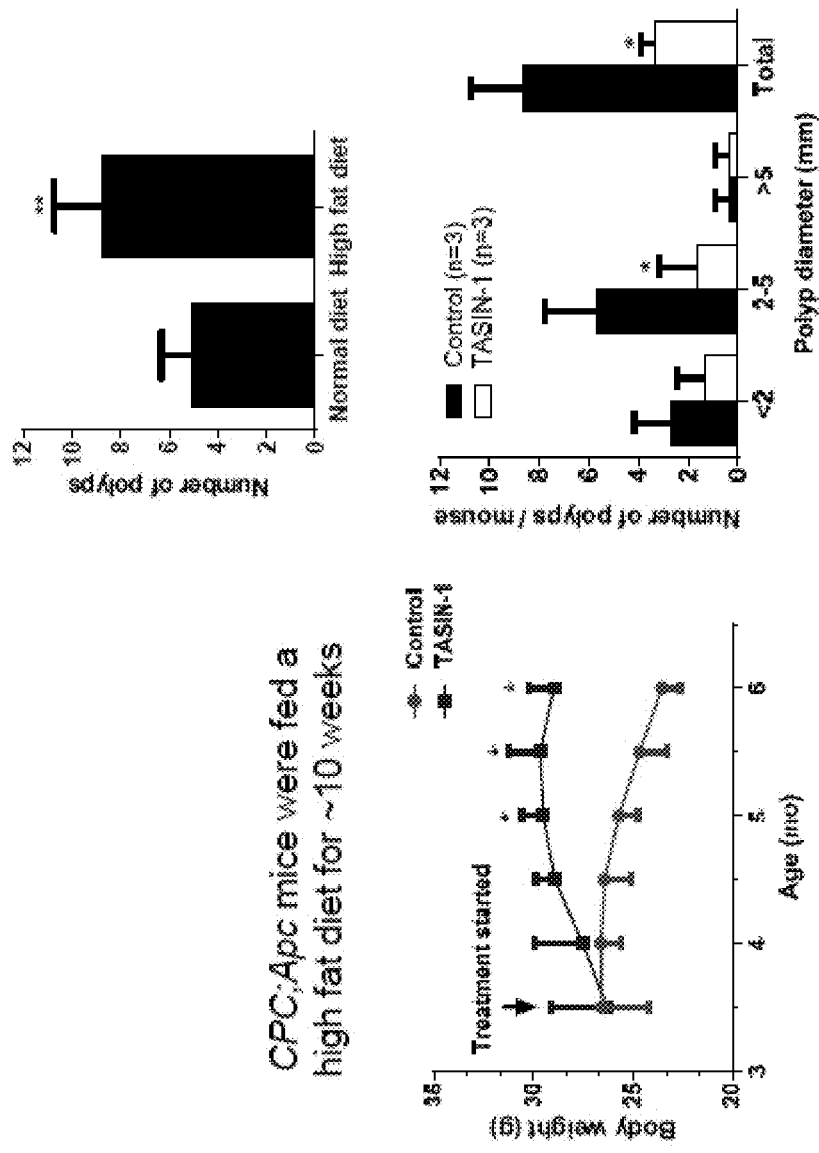
FIG. 5 shows that TASIN-1 prevents colon cancer progression, which otherwise is accelerated by a high fat diet in CPC/Apc mice.

As previously reported, TASIN-1 treatment resulted in significant reduction in tumor formation in the colon of CPC;Apc mice. Benign tumors (polyps) that developed in TASIN-1 treated CPC;Apc mice were much smaller compared to the control group (FIG. 5). Additionally, TASIN-1 treated mice with less tumor burden gained weight to a level similar to WT mice over the 90 days' treatment. Finally, TASIN-1 treated mice showed suppressed expression of a panel of inflammatory response genes and reduced staining for Ki67 and cyclin D1, accompanied by increased staining for cleaved caspase 3 in colon tumor sections (data not shown). Taken together, these in vivo experiments show that TASIN-1 efficiently attenuates tumorigenesis in both human xenografts and genetically engineered CRC mouse models without noticeable toxicity.

Example 2

TASIN-1 is Selectively Toxic to HCECs and CRC Cell Lines with APC Truncation when Tested in Physiological Levels of Serum DLD-1 cells normally are cultured in 10% serum medium, and they are rapidly shifted to 0.2% serum medium for dose response studies. All experiments were performed in normoxic condition (21% O2).

Figure 2:
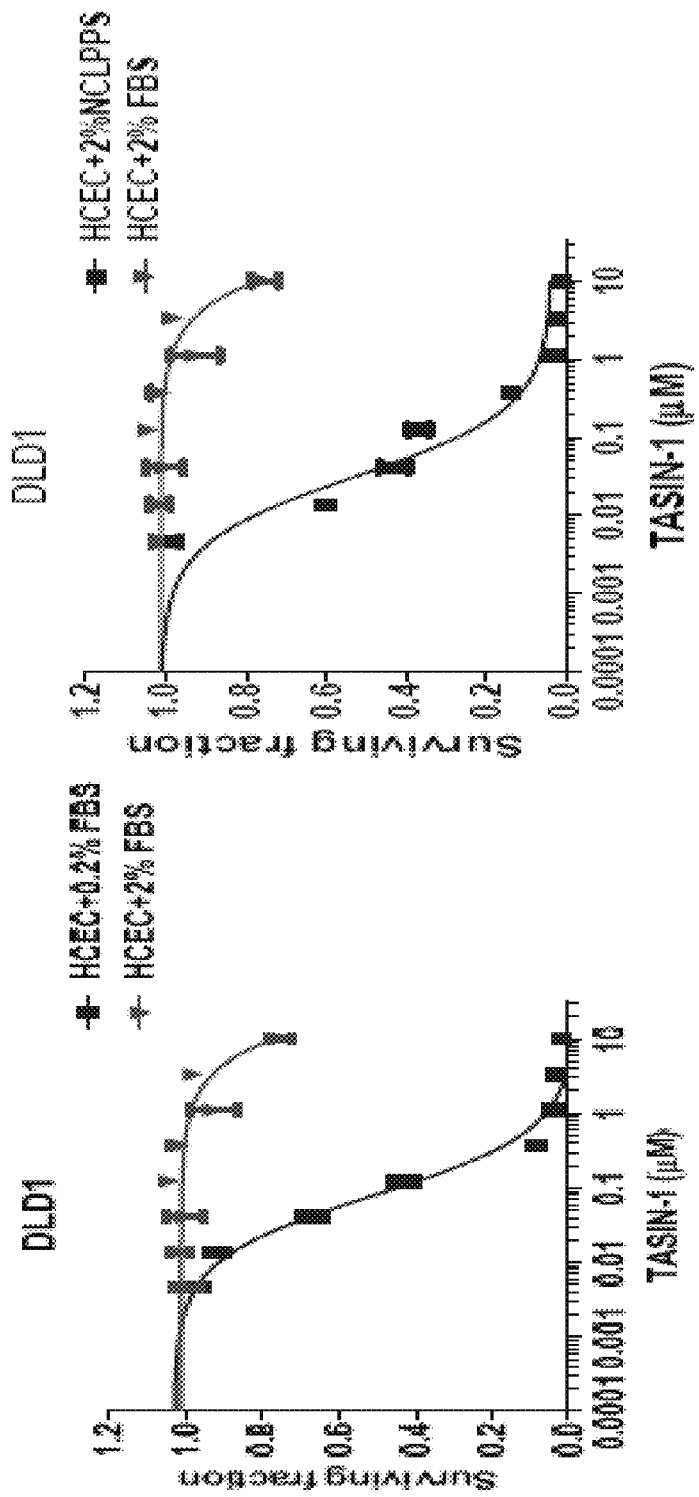
FIG. 2 shows that DLD1 cells cultured in 0.2% serum or 2% lipoprotein deficient serum (LPPS) are sensitive to TASIN-1.

FIG. 2 shows that TASIN-1 is active only in 0.2% serum or 2% lipoprotein deficient serum (LPPS) media conditions. DLD-1 cells have a truncated APC and are sensitive to TASIN-1 only in low (0.2%) serum (left panel). However, if one uses 2% lipoprotein deficient newborn calf lipoprotein-poor serum (NCLPPS) (right panel), the cells remain sensitive to TASIN.

Figure 3:
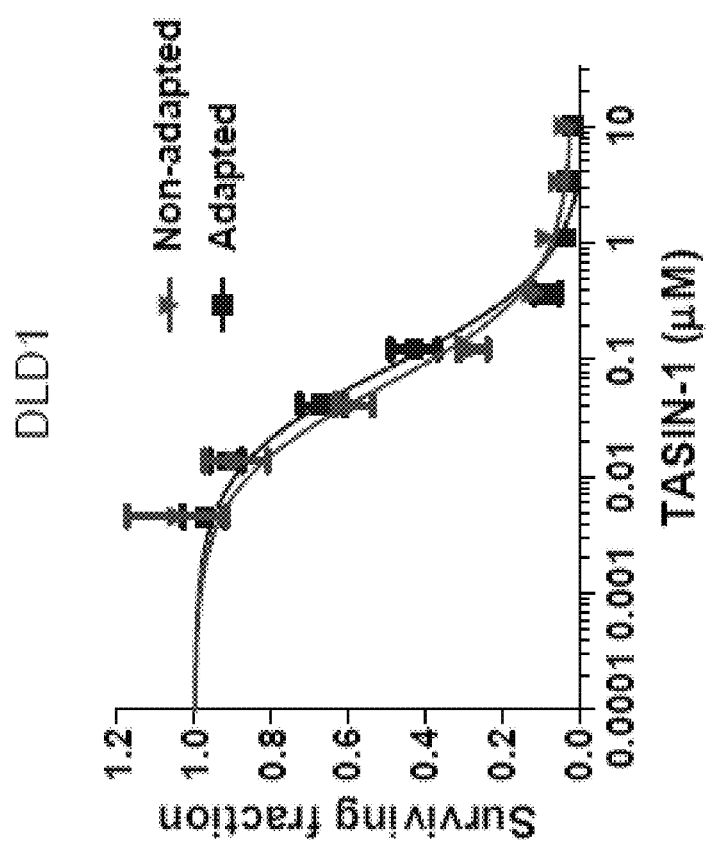
FIG. 3 shows that DLD1 cells adapted to 0.2% serum medium and non-adapted cells rapidly changed from 10% to low serum have similar sensitivity to TASIN-1.

As shown in FIG. 3, the sensitivity of DLD1 cells TASIN-1 was the same if the cells were not gradually adapted to low serum but instead the serum content was rapidly changed from 10% to low serum during drug testing. Adapted DLD1 cells were adapted to medium containing 0.2% serum by gradually decreasing serum from 10%, 5%, 2% to 0.2%. Non-adapted DLD1 cells were rapidly changed from 10% serum to low serum. It was concluded that the effects of TASIN-1 are not due to rapid shifting of cells from high to low serum. It is believed that the tumor microenvironment is only exposed to very low cerum amounts (see Semin. Oncol. 41: 281 (2014)).

Figure 4:
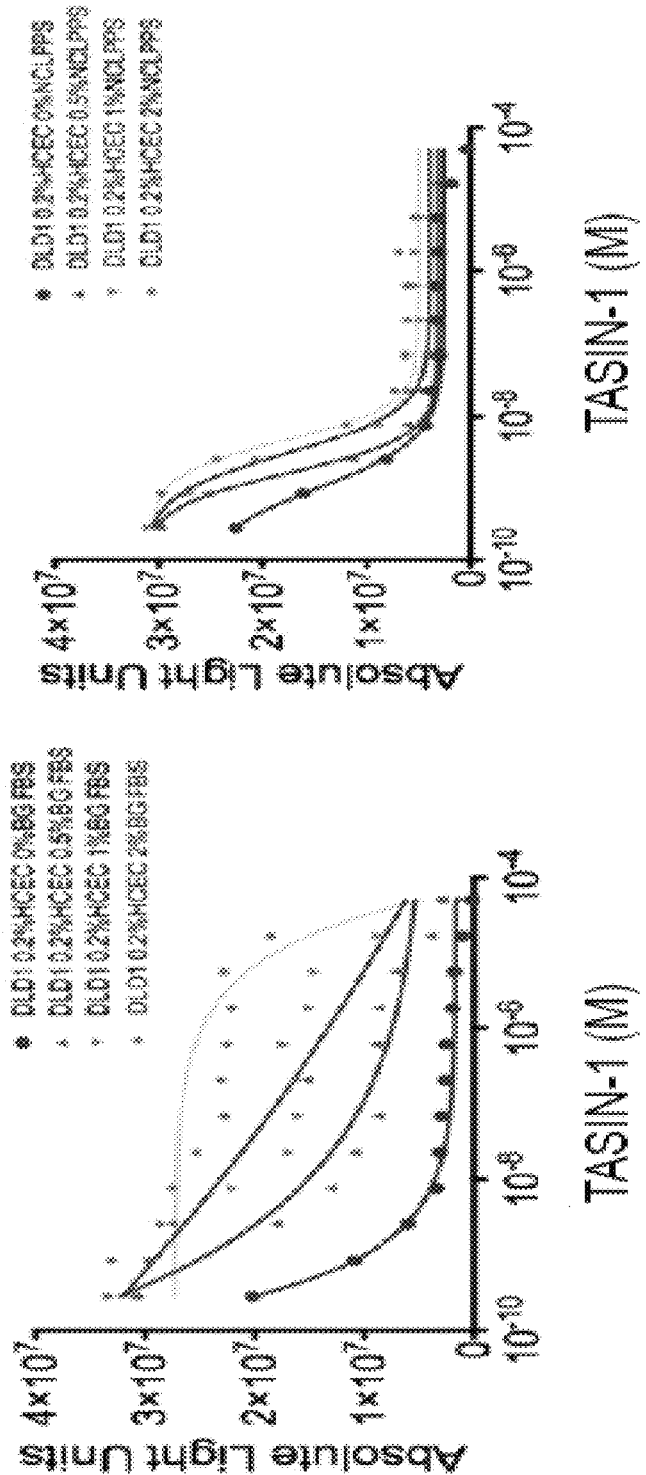
FIG. 4 shows that sensitivity of DLD1 cells to TASIN-1 is gradually lost by increasing serum level, but not by increasing the amount of lipoprotein poor serum.

As shown in FIG. 4, TASIN1-treated cells are rescued with FBS but not with LPPS. The panel on the left (4A) shows that the sensitivity of DLD1 cells to TASIN-1 is gradually lost by increasing serum level using fetal bovine serum (FBS). The right panel (4B) shows that increasing the amount of lipoprotein poor serum does not change the sensitivity of DLD1 cells to TASIN-1 concentration.

Example 3

TASIN-1 Prevents Colon Cancer Progression Under High Fat Diet Conditions

Normal diet for CPC;Apc mice is 5.7% fat, while a high fat atherogenic diet is 12.8% fat (see Harlan, T. D. 120156 Hepatology 46: 1392 (2007)). CPC;Apc mice were fed a high fat diet for about 10 weeks; half the mice received TASIN-1 (dose), the other half did not (control). As shown in FIG. 5, left panel, body weight for the control group decreased over time, compared to the TASIN-1 group. As shown in FIG. 5, right panel top, colon cancer progression was accelerated by the high fat diet. As shown in FIG. 5, right panel, bottom, TASIN-1 reduced polyp formation and size, even in mice fed a high fat diet.

Example 4

EBP is the Direct Target of TASIN-1

Emodampil binding protein (EBP) was identified as the target of TASIN-1 using photoaffinity probes. Photoaffinity probes containing an alkyne group (to be used for click chemistry) and either benzophenone moieties or aryl azides, which in response to UV light have the potential to form a covalent bond with the protein target.

Figure 6:
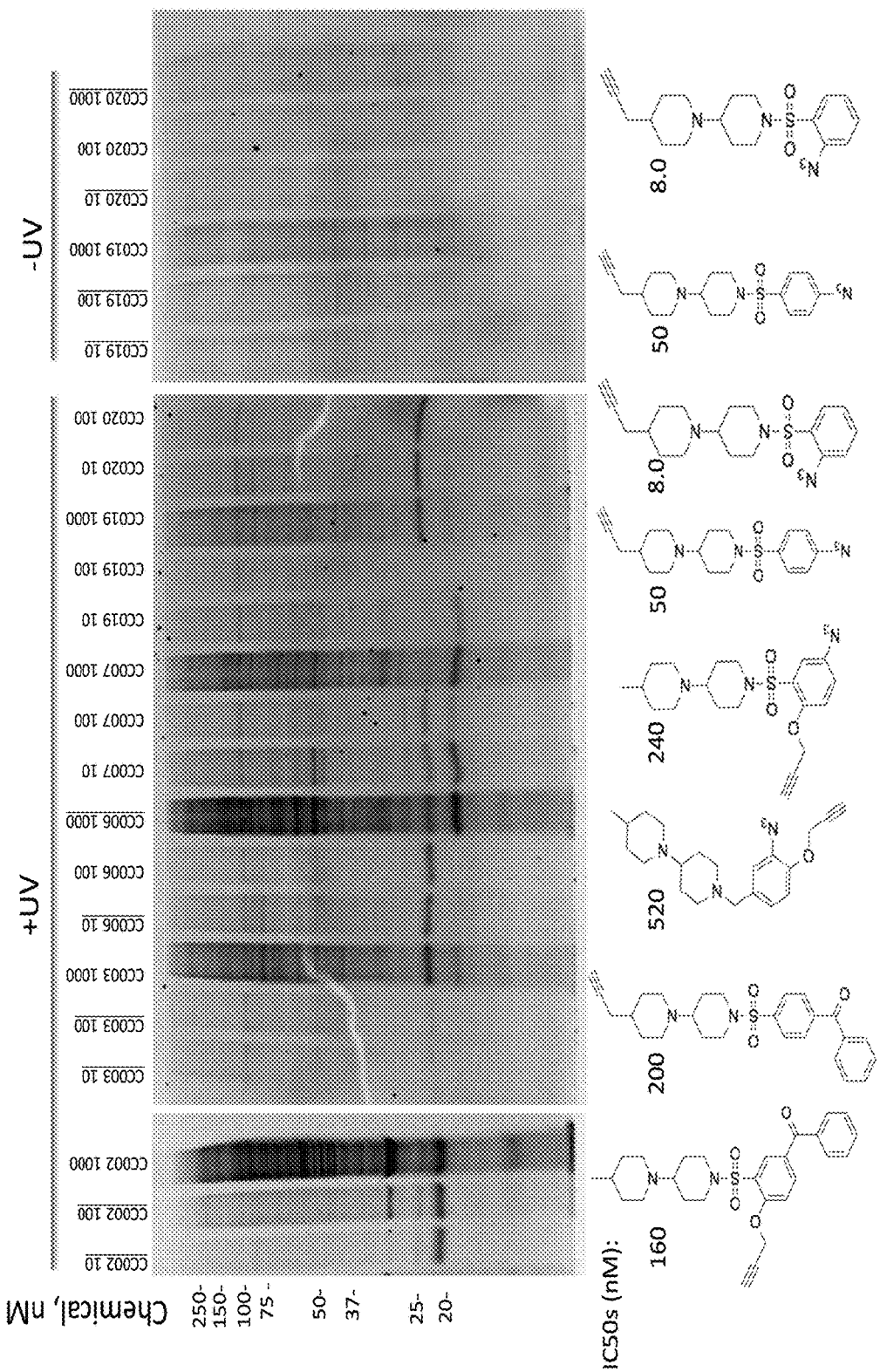
FIG. 6 shows SDS PAGE of TASIN competitor compounds with DLD-1 cells in the presence and absence of UV light.

DLD-1 cells were incubated with a photoaffinity probe at varying concentrations and then exposed to UV light. Lysate was collected from the cells, conjugated to a alexa fluor 532 dye azide using standard protocols for copper dependent click chemistry, and then analyzed by SDS-PAGE. FIG. 6 shows the SDS PAGE profile of DLD-1 cells treated with a TASIN probe as shown in the presence and absence of UV light. A 22 kD band representing a protein bound to the compound in multiple photocrosslinkers was detected. This band was dependent on the UV treatment, thus reflecting a non-covalent bond.

Figure 7:
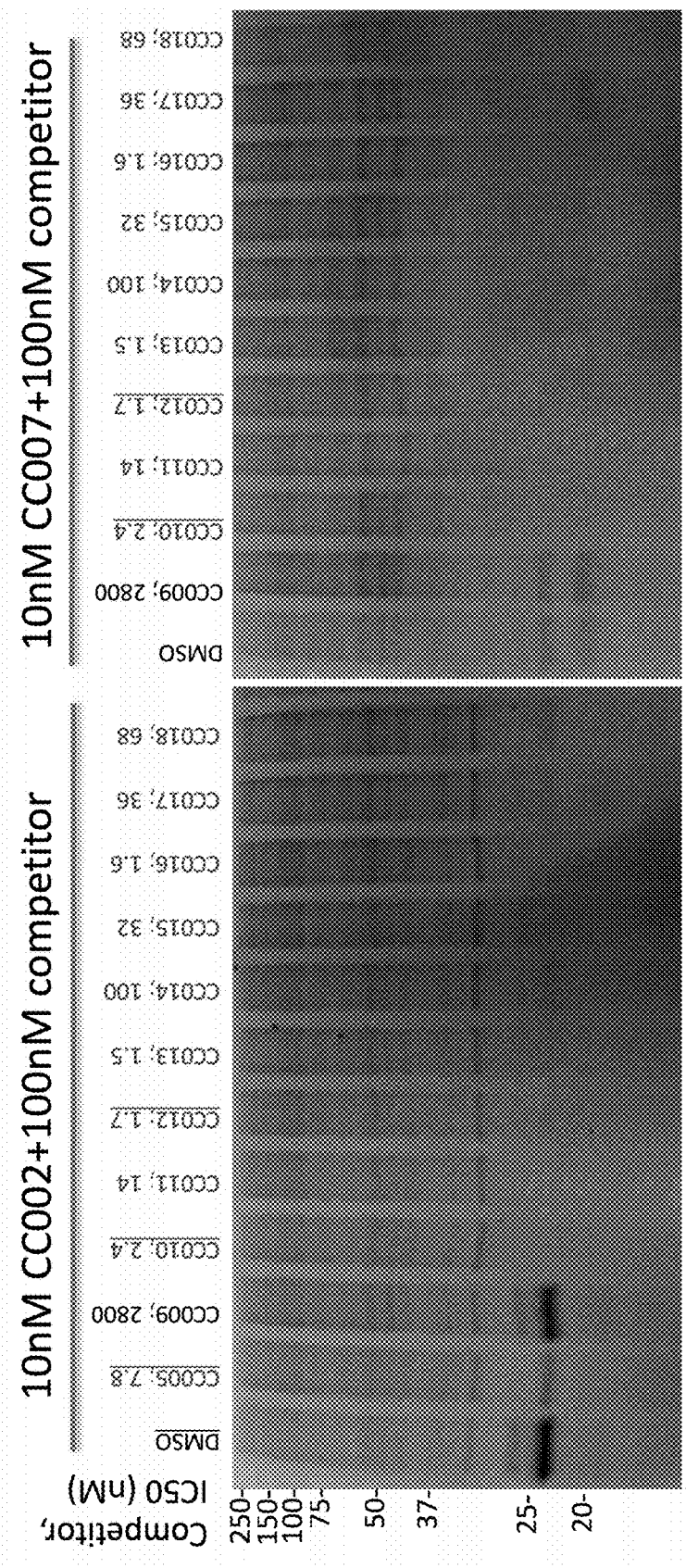
FIG. 7 shows that a series of UV-dependent bands are competed by active TASIN analogues but not by inactive analogues. Band p2'7, p22 and p18 are competing, of which p22 is the strongest with CC002.

To determine whether this 22 kD band reflected the functional target of the TASIN probes, the TASIN probe (10 nM) was co-incubated with 100 nM of various competitor probes as shown. Since the amount of each competitor probe is in excess, binding of the competitor probe is detected as loss of signal or reduced intensity of the TASIN probe. FIG. 7 shows that co-incubation with active analogues of TASIN blocked probe binding whereas less active analogues did not. These results suggested that the functional activity of the compounds correlated with binding to the 22 kD protein band.

Figure 8:
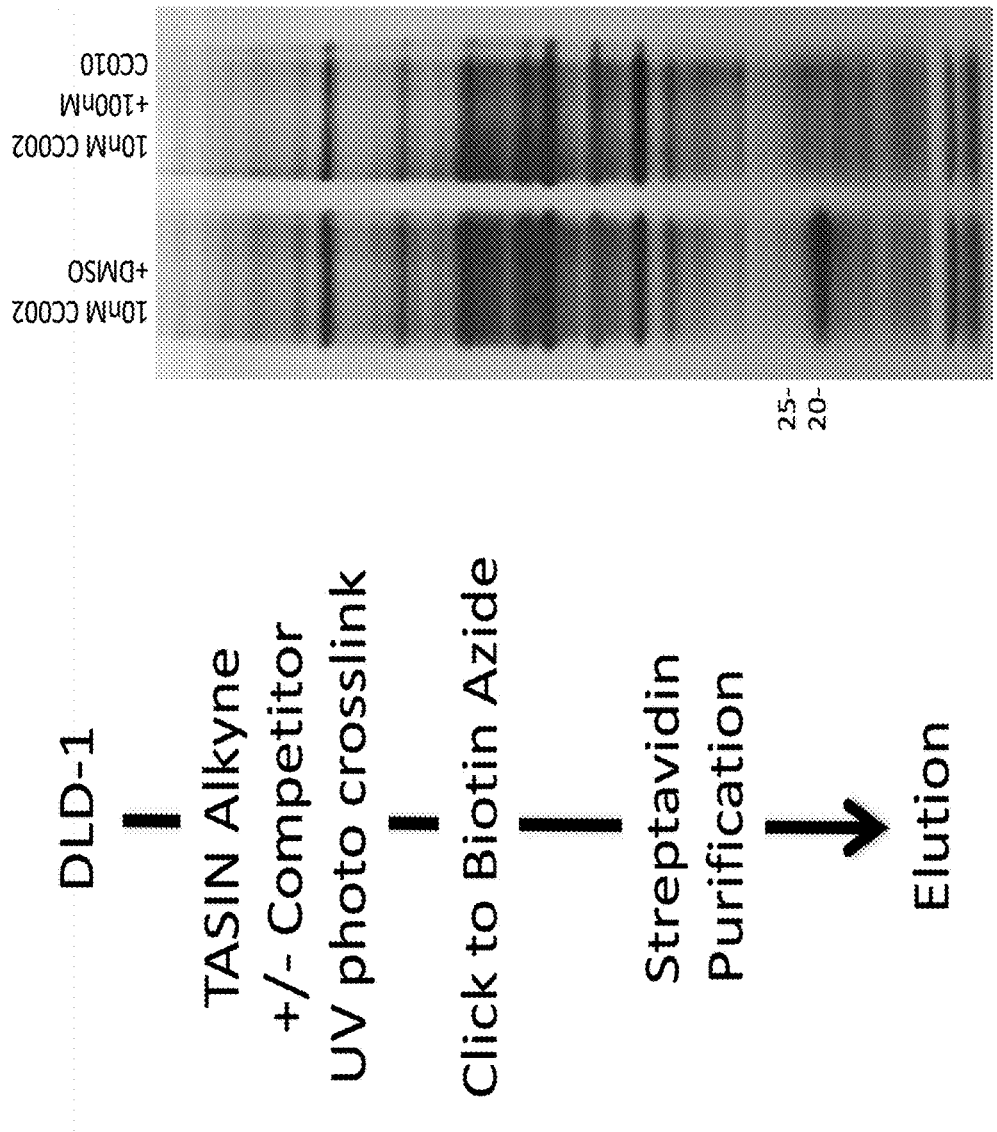
FIG. 8 shows a scheme for purification of p22 for mass spectrometry.

As shown in FIG. 8, lysate from DLD-1 cells treated with the TASIN probe +/−an excess amount of competitor was collected and conjugated to a biotin azide using copper dependent click chemistry. Streptavidin beads were used to purify biotin bound proteins and the resulting precipitate was analyzed by SDS-PAGE stained with silver. The results shown in the right panel revealed a 22 kD protein whose signal intensity was reduced when a competitor was added, consistent with the predicted functional target. The 22 kD band, along with the analogous region in the competitor lane was excised from the SDS-PAGE gel and submitted to trypsin digestion and peptide analysis by tandem mass spectrometry. Proteins were identified based on mapping peptides and ranked by the ratio of spectral index between the sample with competitor and the sample without competitor. Spectral index is a semi-quantitative analysis of protein abundance. Table $2_{13}$ shows that the highest ranking protein (i.e., most abundant) with a ratio of 0.01 was EBP).

TABLE 2

3-beta-hydroxysteroid-delta(8), delta(7)-isomerase (EBP) is a top hit for competition and one of the top hits for spectral intensity.

| Description | Mw (Da) | Spectral Index (MIC Sin) | | Ratio +comp/ −comp |
|---|---|---|---|---|
| | | CC002 + CC010 | CC002 + DMSO | |
| EBP_HUMAN 2-beta-hydroxysteroid-Delta(8), Delta(7)-isomerase OS = Homo sapiens GN = EBP PE = 1 SV = 3 | 26389.80 | 8.37E−06 | 5.95E−04 | 0.01 |
| TPIS_HUMAN Triosephosphate isomerase OS = Homo sapiens GN = TPI1 PE = 1, SV = 3 | 26724.80 | 1.58E−07 | 1.17E−06 | 0.14 |
| LGUL_HUMAN Lactoylglutathione lyuase OS = Homo sapiens GN = GLO1 PE = 1 SV = 4 | 19066.60 | 7.93E−07 | 2.99E−06 | 0.27 |
| RAB8A_HUMAN Ras-related protein Rab-8A OS = Homo sapiens GN = RAB8A PE = 1 SV = 1 | 23707.20 | 4.68E−07 | 1.7E−06 | 0.27 |
| [1] B3KSH1_HUMAN Eukaryotic translation initiation factor 3 subunit FOS = Homo sapiens GN = EIF3F PE = 2 SV = 1 | [2] 37630.20 | [3] 1.36E−07 | [4] 5.03E−07 | [5] 0.27 |

Figure 9:
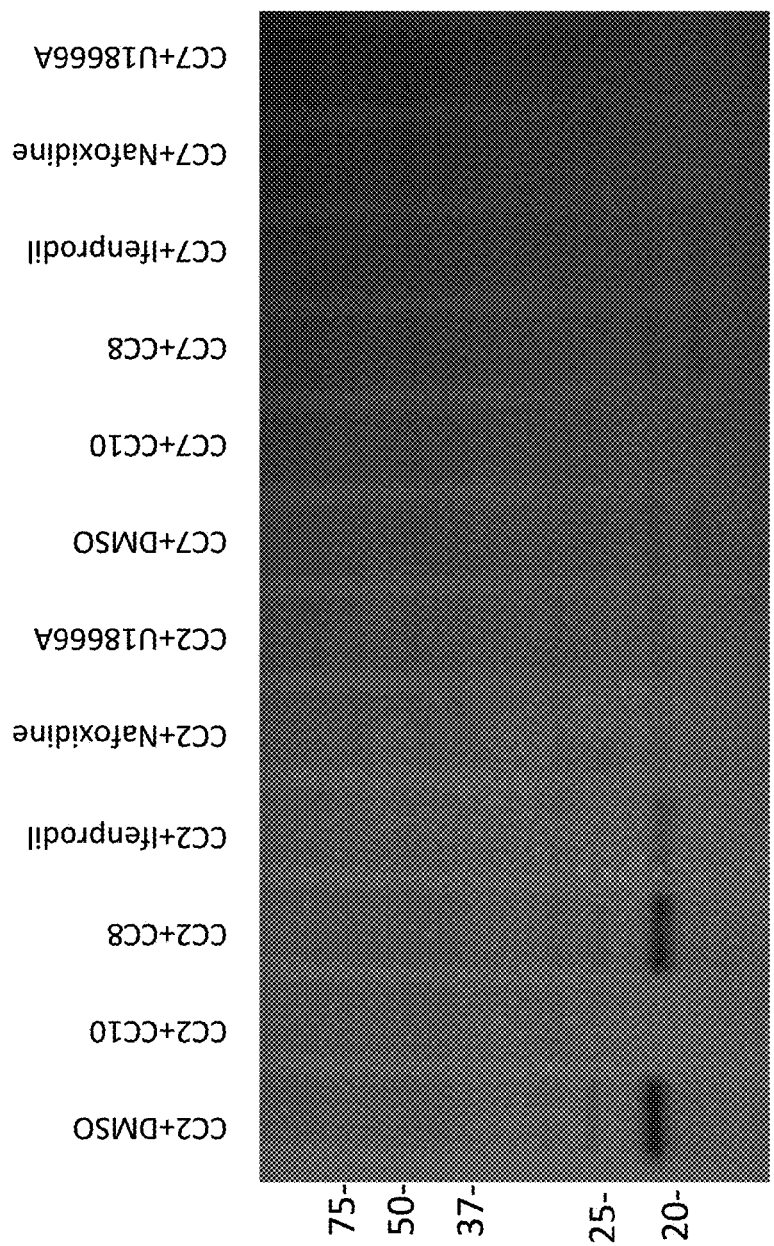
FIG. 9 shows that known EBP antagonists nafoxidine, ifenprodil, and U18666A compete with p22 (EBP).

To confirm that EBP was the target of TASIN, chemically distinct scaffolds that are known to bind EBP (e.g., Ifenprodil, Nafoxidine, and U18666A) were used as competitors for TASIN probes CC002 and CC007. In all three cases, these known EBP binders competed for CC002 or CC007 binding (FIG. 9). These results confirmed that the 22 kD protein band that bound to the TASIN probes is EBP.

Figure 10:
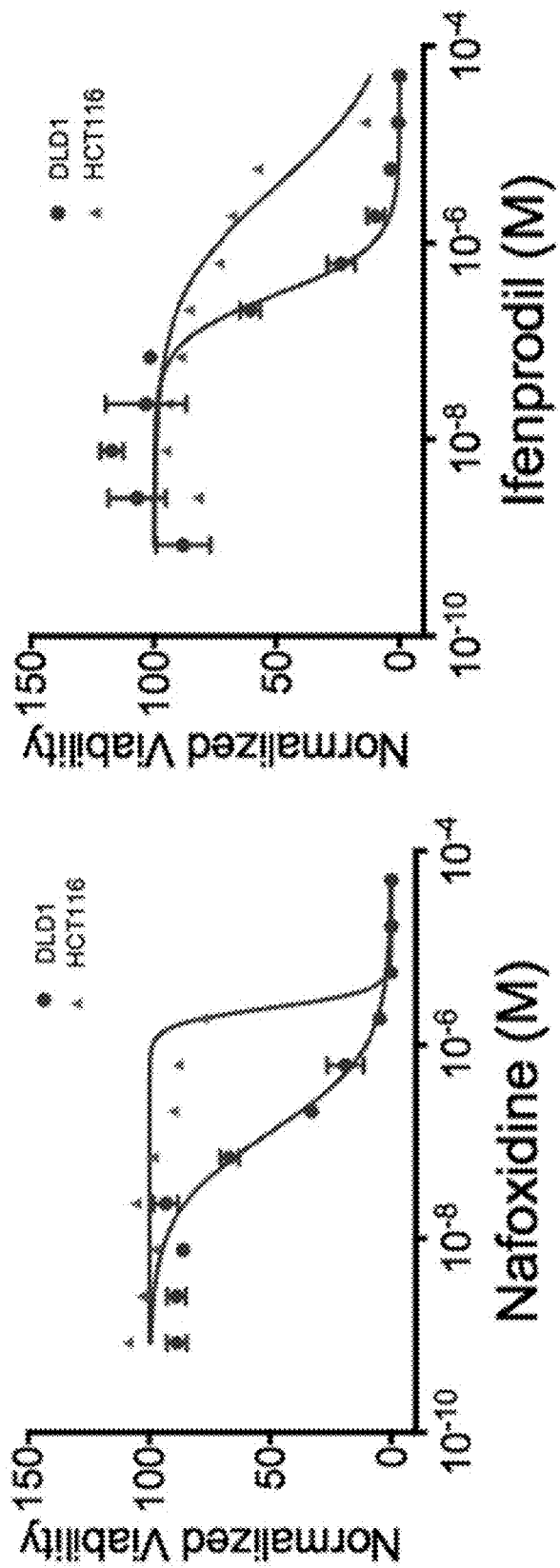
FIG. 10 shows that known EBP antagonists nafoxidine and ifenprodil recapitulate selectivity but are less potent than TASIN.

To test whether inhibitors of EBP generally confer the same selectivity to cancer cell lines that harbor APC truncation mutations, HCT-116 and DLD-1 cells were incubated with Nafoxidine and Ifenprodil at varying doses. As shown in FIG. 10, DLD-1 cells were selectively sensitive to these EBP inhibitors, just as they were to TASIN.

Figure 11:
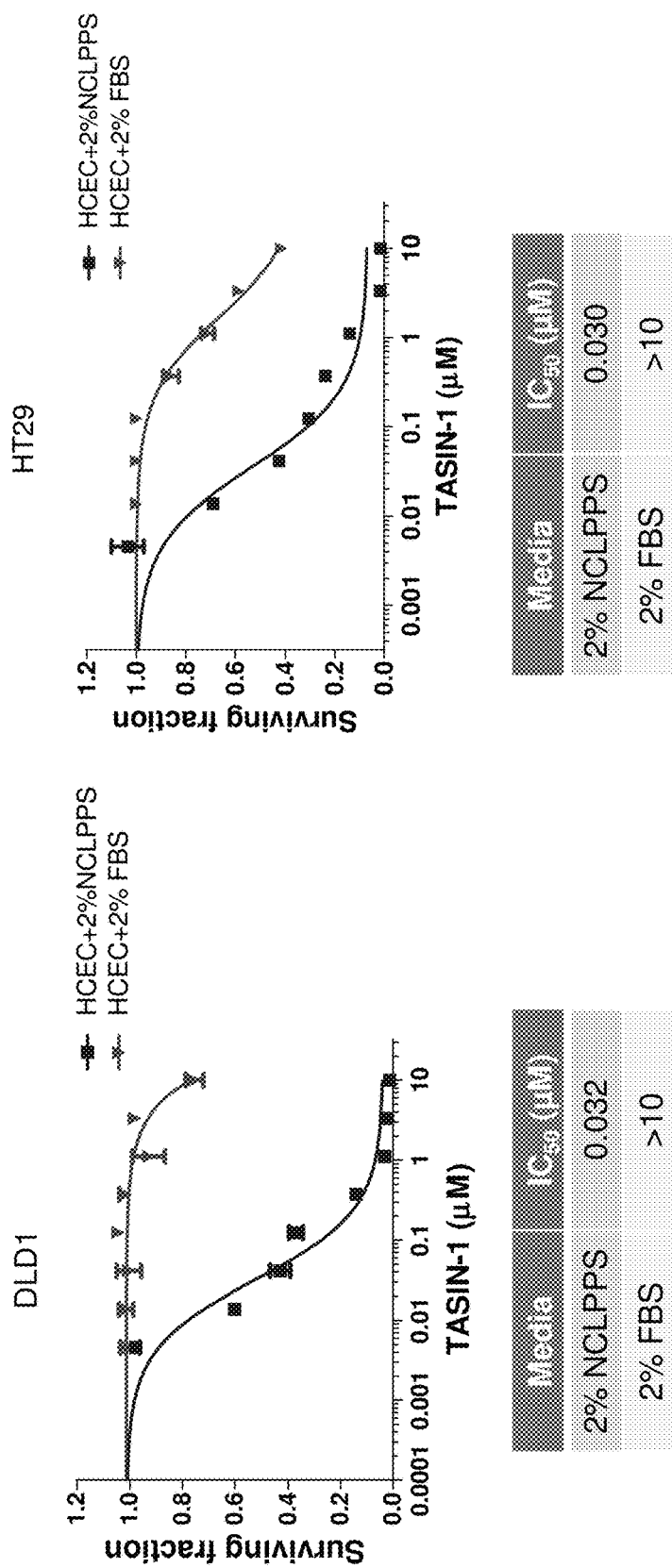
FIG. 11 shows that TASIN-1 kills DLD-1 and HT29 cells in 2% Lipoprotein deficient serum (LPPS) but not in 2% FBS media.

Without being bound by theory, these results suggest that DLD-1 cells may die as a result of cholesterol deficiency. To determine whether DLD-1 cells die as a result of cholesterol deficiency, DLD-1 cells were incubated with standard media containing increasing concentrations of Fetal Bovine Serum (FBS) or lipoprotein-depleted FBS. FBS is a rich source of low-density lipoprotein (LDL) receptor and cholesterol. The results of this experiment showed that FBS rescued DLD-1 cells from the toxicity of TASIN whereas lipoprotein-depleted FBS did not (FIG. 4). These results indicate that DLD-1 cells die as a result of a block in cholesterol synthesis. As shown in FIG. 11, HT29 cells, another cancer cell line with an APC truncation, are also rescued from TASIN by FBS but not lipoprotein-deficient serum.

Figure 12:
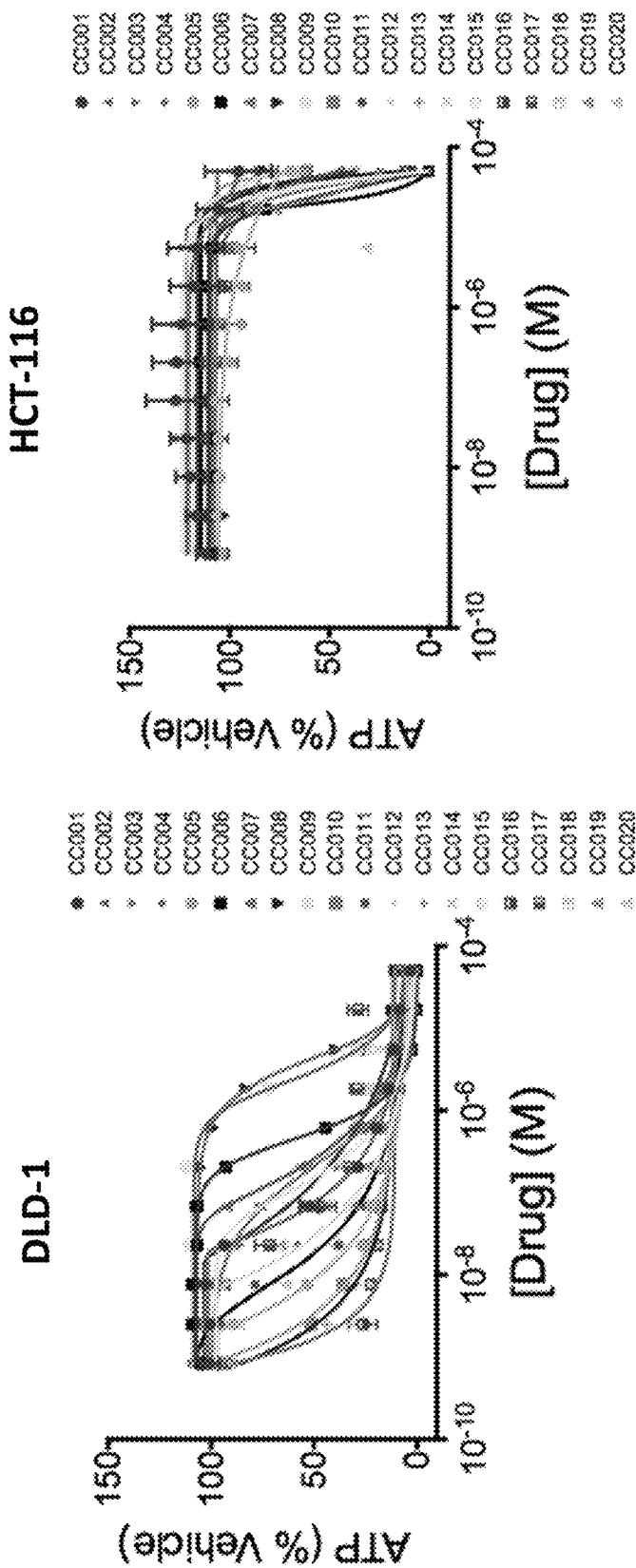
FIG. 12 shows that exemplary TASIN analogues are toxic and selective for DLD-1 in 0.2% HCEC medium.

FIG. 12 shows that exemplary TASIN analogues are toxic and selective for DLD-1 in 0.2% HCEC medium.

Figure 13:
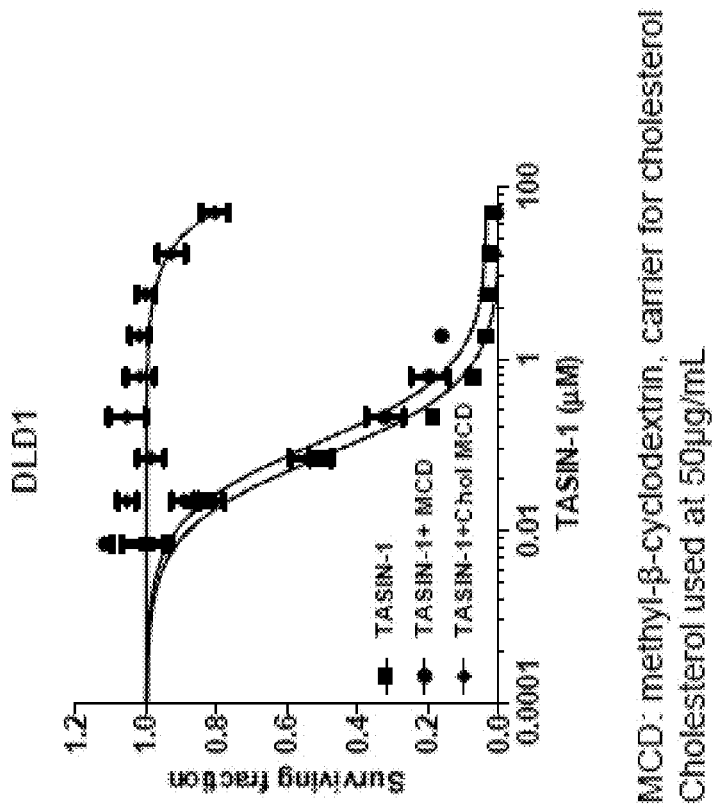
FIG. 13- shows that exogenous addition of purified lipoproteins or cholesterol to the medium decreases sensitivity of DLD1 cells to TASIN-1.
Figure 13:
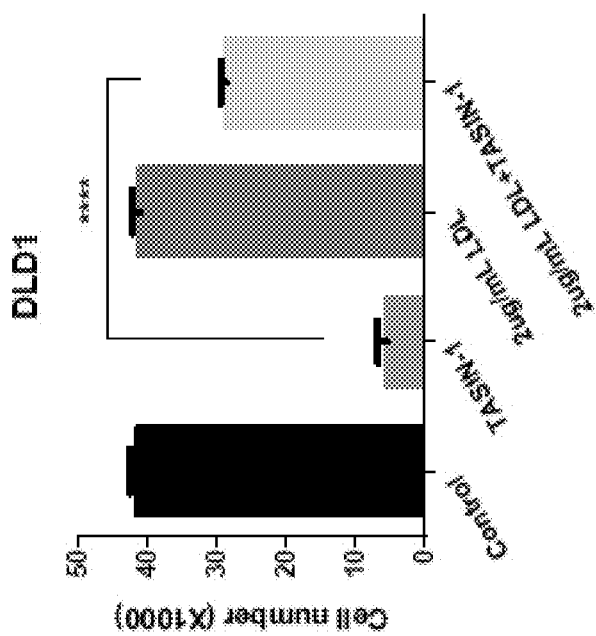

FIG. 13 shows that exogenous addition of LDL or cholesterol rescues TASIN-1 induced cell death. Adding purified lipoproteins to the medium (left panel) or cholesterol (right panel) decreases the sensitivity of DLD-1 cells to TASIN-1. These results implicate cholesterol biosynthesis or metabolism as being important, and help explain that TASIN-1 targeting EBP upstream of cholesterol is effective, but not if cholesterol downstream of EBP is provided.

Stable Knockdown of EBP Recapitulates the Effects of TASIN-1 in DLD-1 Cells—

Figure 14:
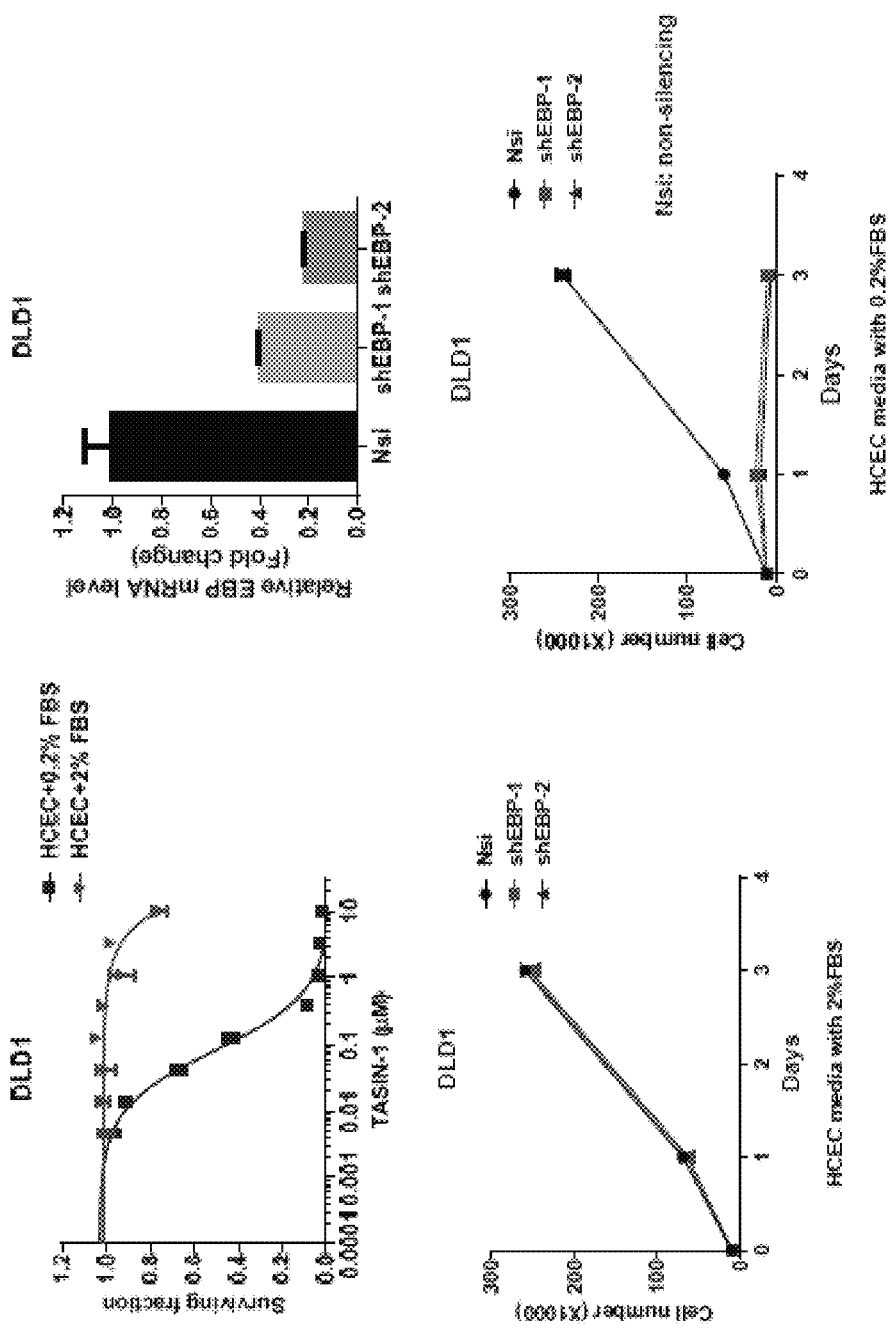
FIG. 14 shows that stable knockdown of EBP, like TASIN-1, affects growth of DLD1 cells in 0.2% FBS.

FIG. 14 panels A-D show that shRNA knockdown of EBP has no effect on cells grown in 2% FBS, but does affect cell growth in 0.2% FBS. FIG. 14A is a plot of surviving fraction (y-axis) versus µM TASIN-1 (x axis) for HCEC cells in 0.2% (triangles) and 2% (squares) FBS. FIG. 14B is a bar graph showing fold change of relative EBP mRNA level for shEBP-1, shEBP-2, and a nonsilencing control. FIG. 14C is a plot of cell number (y axis) versus days in HCEC media with 2% FBS) for shEBP-1, shEBP-2, and a nonsilencing control. D is a plot of cell number (y axis) versus days in HCEC media with 0.2% FBS) for shEBP-1, shEBP-2, and a nonsilencing control.

Figure 15:
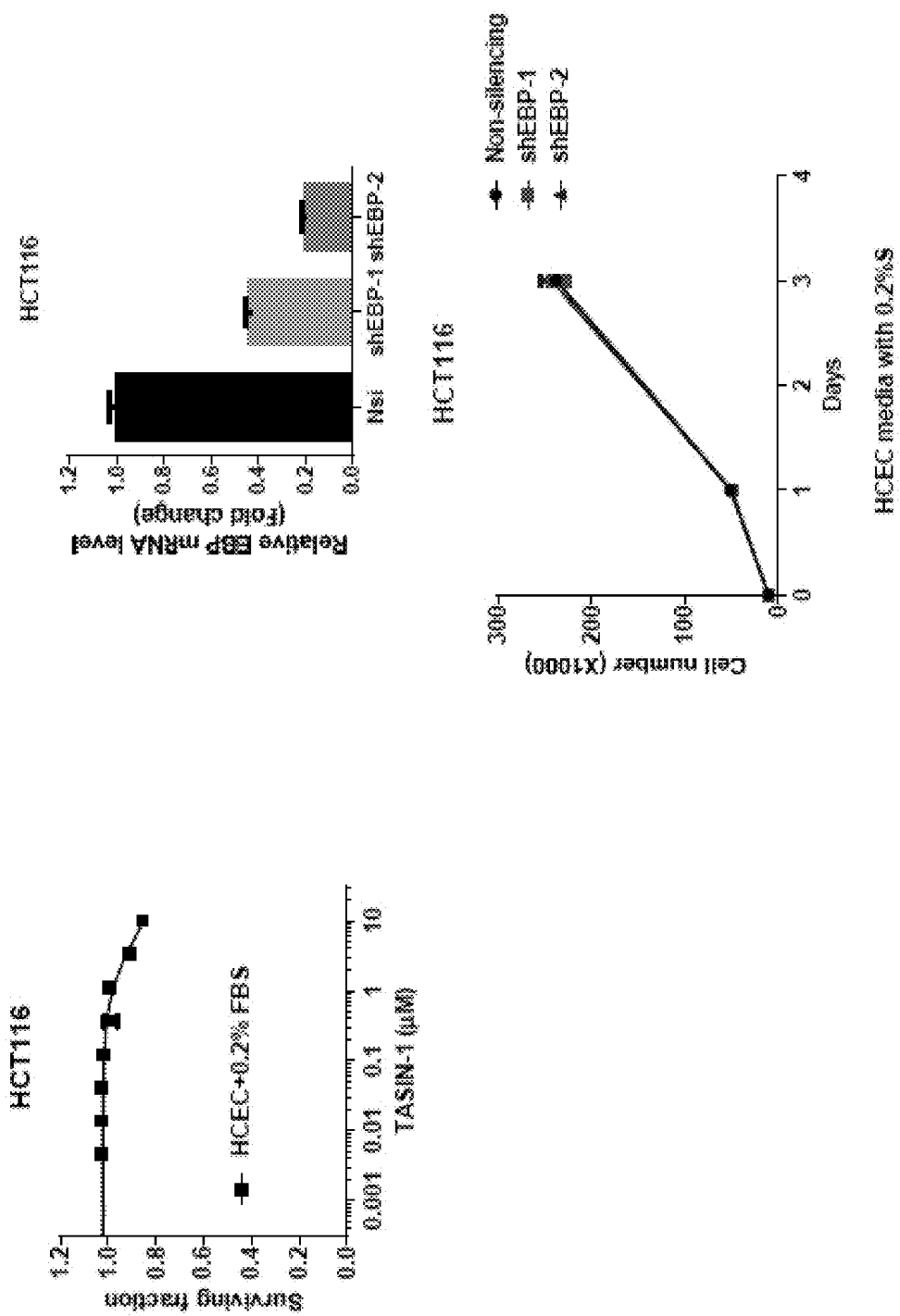
FIG. 15 shows that stable knockdown of EBP does not affect growth of HCT116 cells in 0.2% FBS.

FIG. 15 A-C show that in the absence of truncated APC, stable knockdown of EBP has no effect on HCT116 cell growth rates. A is a plot of surviving fraction (y-axis) vs. µM TASIN-1 (x axis) for HCT116 HCEC cells in 0.2% FBS. B is a bar graph showing fold change of relative EBP mRNA level for shEBP-1, shEBP-2, and a nonsilencing control. C is a plot of cell number (y axis) versus days in HCEC media with 0.2% FBS) for shEBP-1, shEBP-2, and a nonsilencing control.

EBP also was confirmed as the functional target of TASIN by demonstrating that ectropic over-expression of EBP leads to TASIN resistance.

Figure 16:
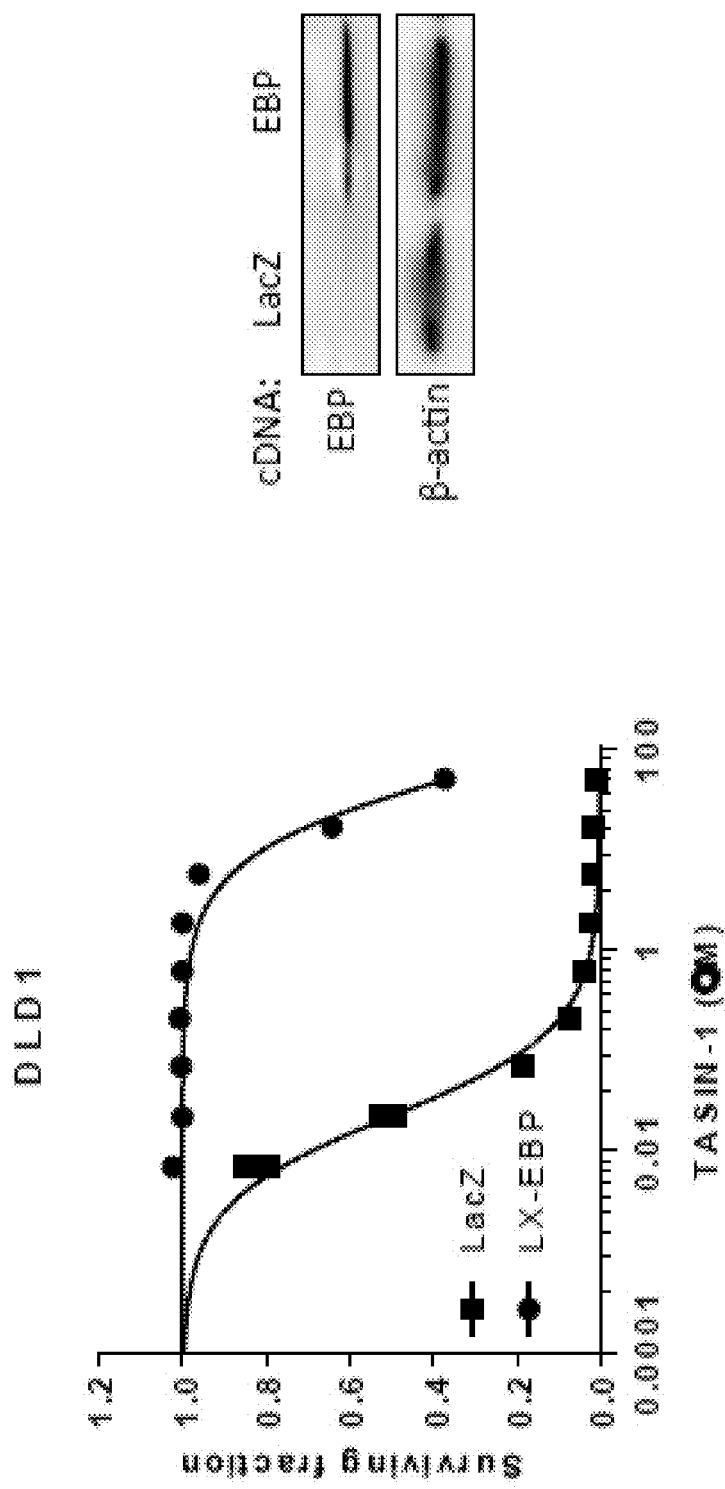
FIG. 16 shows that overexpression of EBP confers resistance to TASIN-1 in DLD-1 cells.

FIG. 16 shows that overexpression of EBP confers resistance to TASIN-1 in DLD-1 cells.

Figure 17:
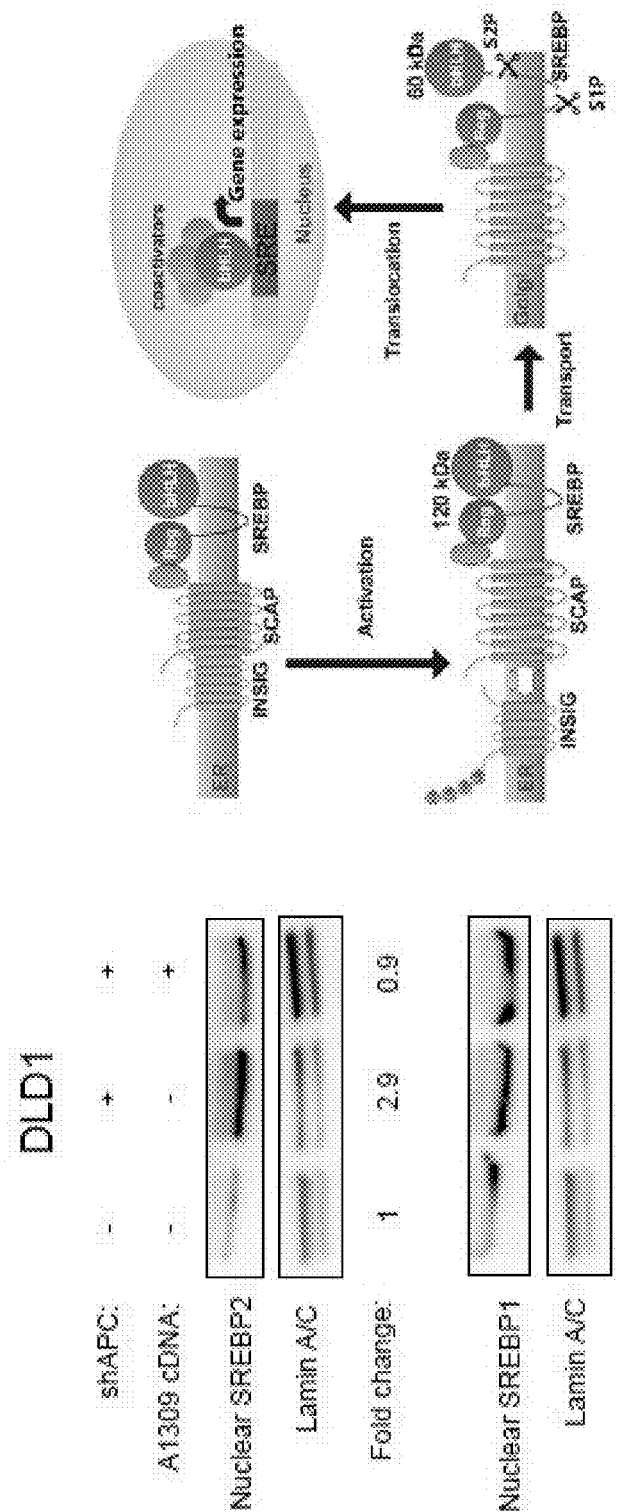
FIG. 17 shows that APC truncation expression reduces SREBP1 & 2 cleavage in DLD-1 cells.

FIG. 17 shows that APC truncation expression reduces SREBP1 & 2 cleavage in DLD-1 cells.

Figure 18:
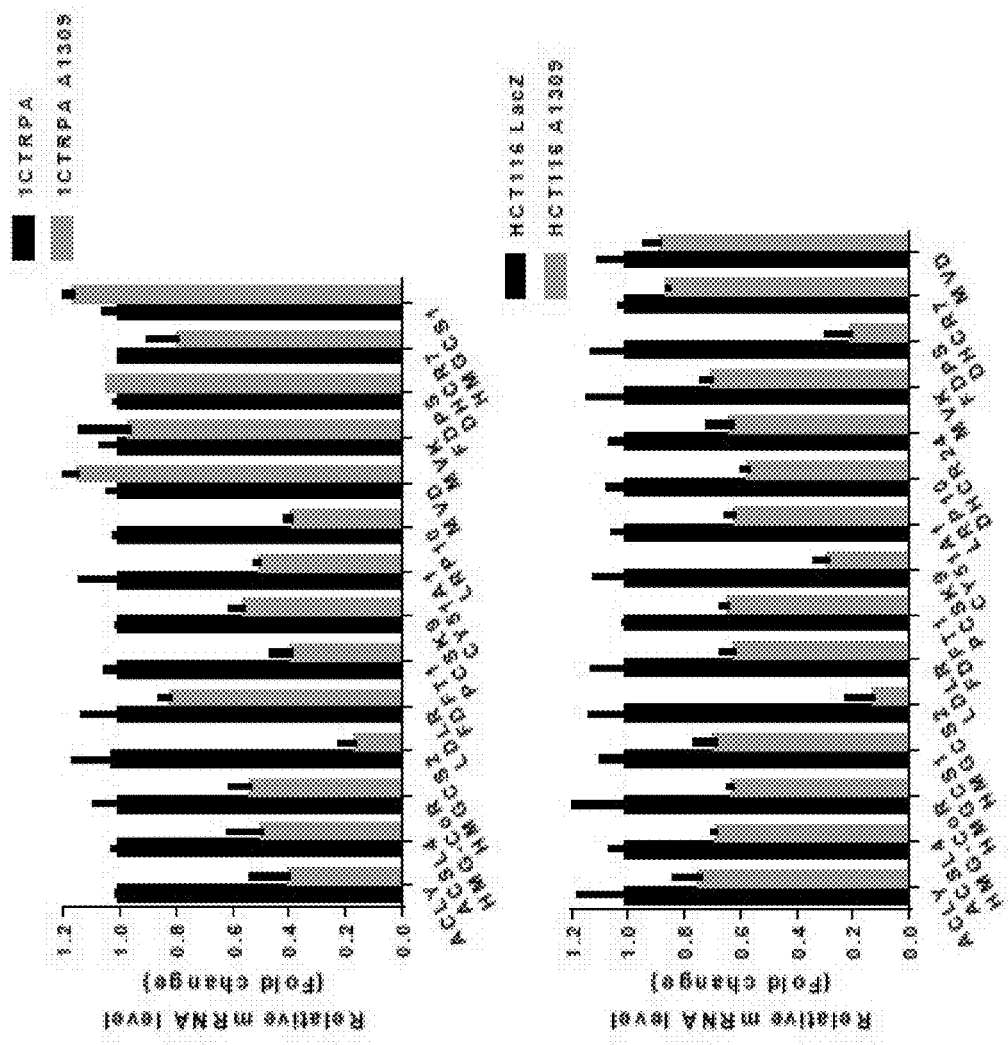
FIG. 18 shows that APC truncation expression downregulates a panel of genes involved in cholesterol homeostasis.

FIG. 18 shows that APC truncation expression down-regulates a panel of genes involved in cholesterol homeostasis.

Figure 19:
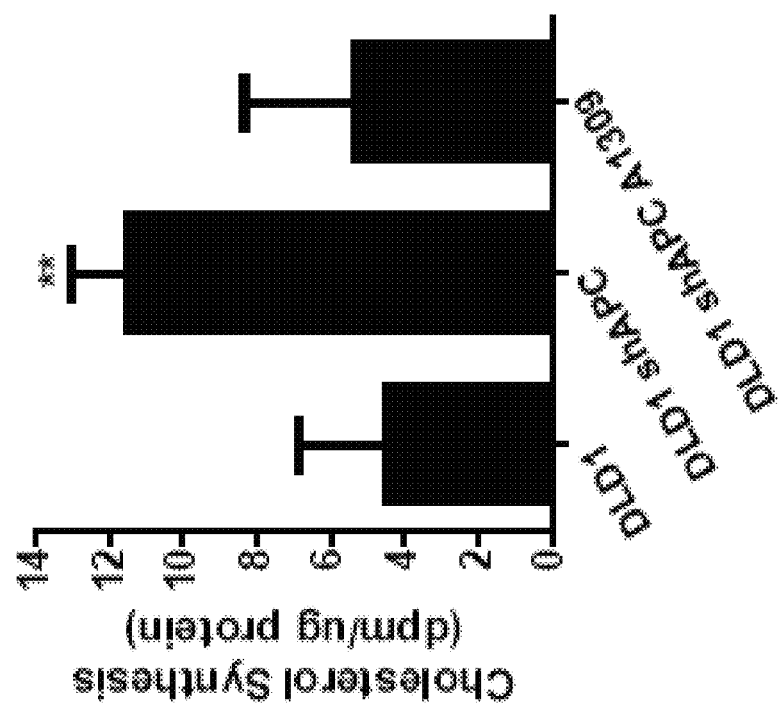
FIG. 19 shows that knockdown of truncated APC significantly increases endogenous cholesterol biosynthesis, but reintroduction of truncated APC returns the rate of cholesterol synthesis in DLD1 cells back to DLD1 levels.

FIG. 19, a bar graph showing the effects of knockdown of truncated APC on endogenous cholesterol biosynthesis, is a plot of cholesterol synthesis (dpm/µg protein) versus untreated DLD1 cells, DLD1 cells treated with shAPC, and DLD1 cells treated with shAPC A1309 in HCEC media with 0.2% FBS. APC truncation reduced the endogenous cholesterol biosynthesis rate in DLD cells. Knockdown of truncated APC significantly increased endogenous cholesterol biosynthesis, but reintroduction of truncated APC returned the cholesterol synthesis rate back to DLD levels.

Figure 20:
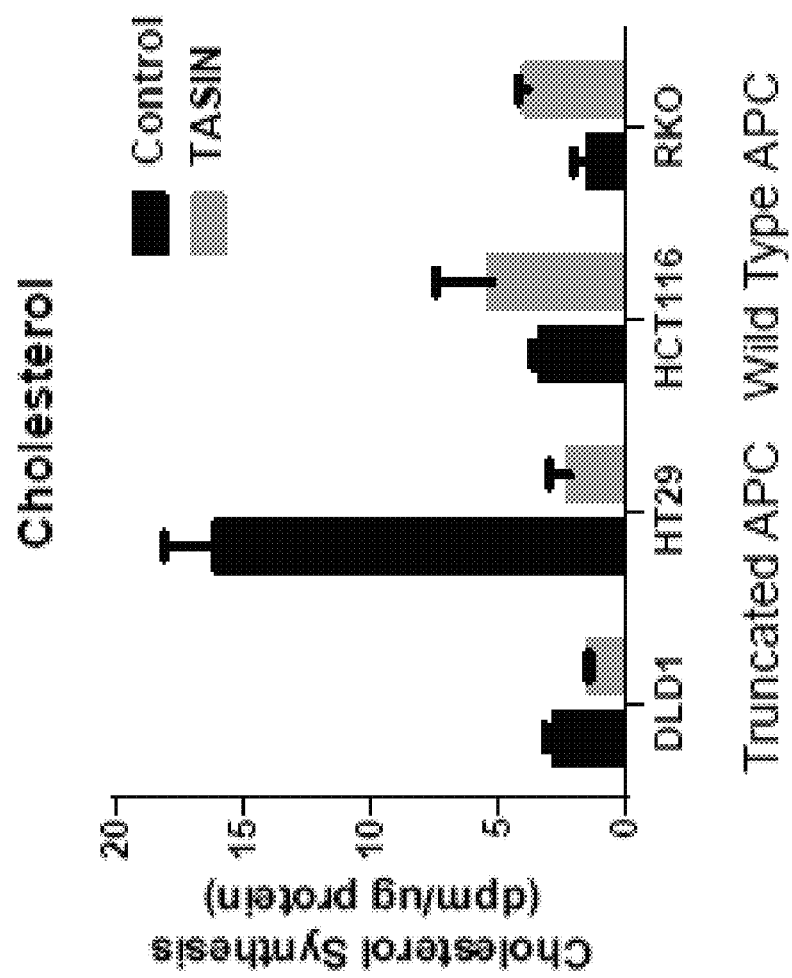
FIG. 20 shows that TASIN-1 further reduces endogenous cholesterol biosynthesis (dpm/μg protein) in cells containing truncated APC, but not in cells with wild type APC.

FIG. 20 shows that TASIN-1 further reduces endogenous cholesterol biosynthesis in cells containing truncated APC. Two cell lines expressing a truncated APC (DLD1 and HT29), and two cell lines expressing wild type APC (HCT116 and RKO colon cancer cells) were incubated with TASIN-1 for 40 h, and then labeled for 8 hours with 14C acetate. Choelseterol was extracted from the cells and cholesterol synthesis quantitated. The result show that TASIN-1 reduces cholesterol biosynthesis in cells expressing truncated APC, but not in cells expressing wild type APC.

Figure 21:
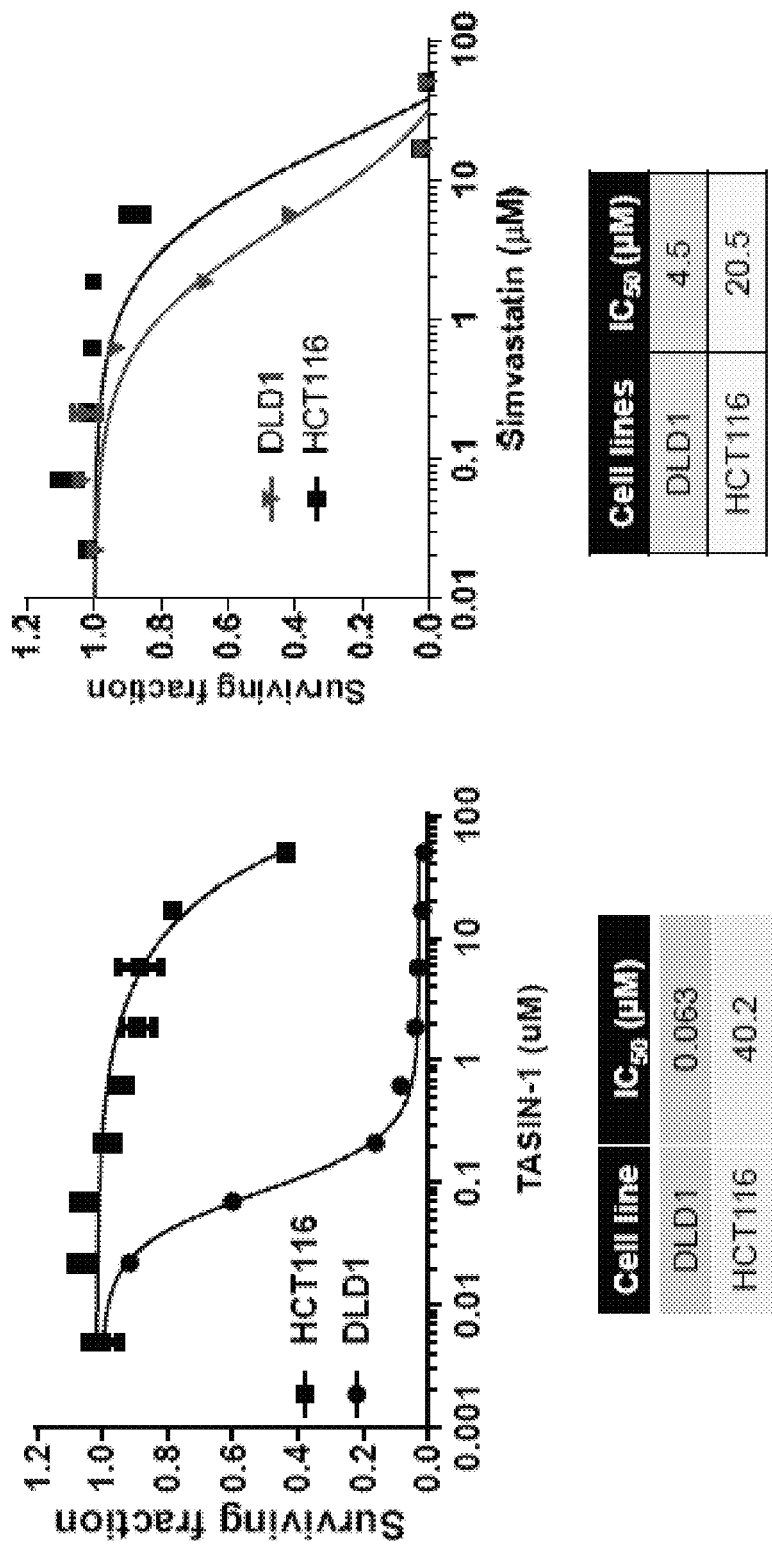
FIG. 21 shows that simvastatin has only a slight effect on survival of DLD-1 cells, and is significantly less potent (IC50 4.5 μM) than TASIN-1 (IC50 0.063 μM).

As shown in FIG. 21, a known cholesterol lowering drug (simvastatin, IC50 4.5 μM) has a slight effect on DLD1 cells (truncated APC), and is significantly less potent than TASIN-1 (IC50 0.063 μM). HCT116 cells (wild type APC) served as a control.

Figure 22:
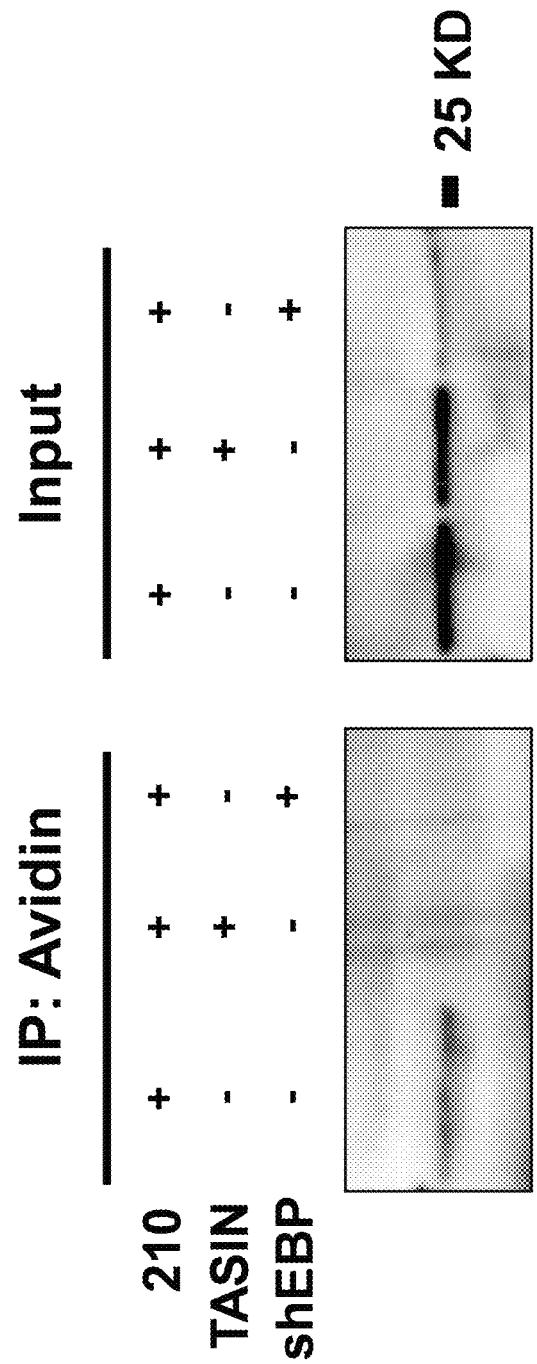
FIG. 22 shows that 210, a biotin-labeled potent TASIN analog, interacts with EBP in DLD1 cells. DLD1 cells were incubated with 210 in the presence or absence of TASIN-1 and pulled down by streptavidin beads. Bound EBP was detected by Western Blot. EBP is not pulled down in DLD1shEBP cells. These results confirm the interaction between TASIN-1 and EBP in DLD-1 cells.

FIG. 22 shows that 210, a biotin-labeled potent TASIN analog, interacts with EBP in DLD1 cells. DLD1 cells were incubated with 210 in the presence or absence of TASIN-1 and pulled down by streptavidin beads. Bound EBP was detected by Western Blot. EBP is not pulled down in DLD1shEBP cells. These results confirm the interaction between TASIN-1 and EBP in DLD-1 cells.

Figure 23:
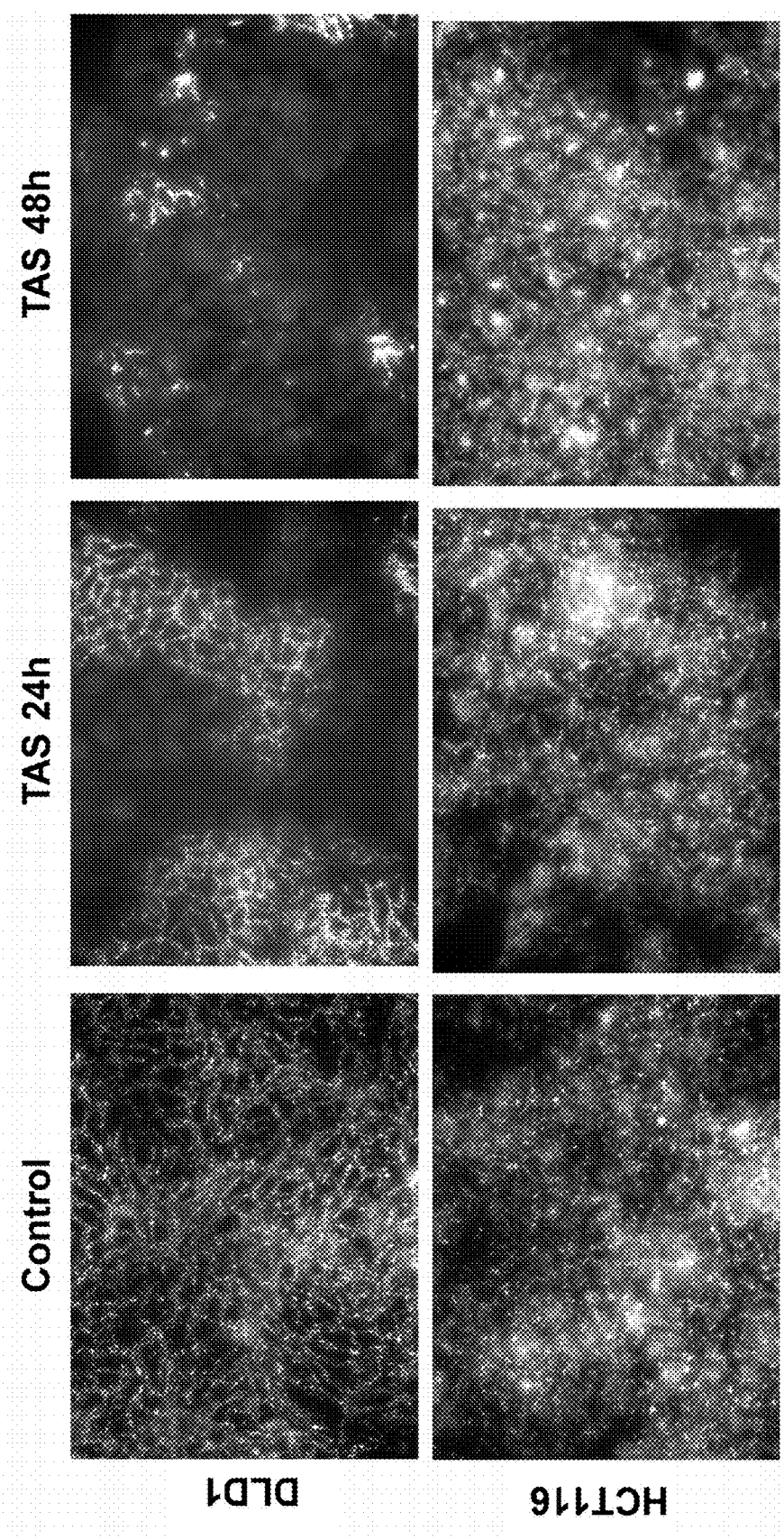
FIG. 23 shows that TASIN-1 decreases intracellular cholesterol level in DLD1 but not in HCT116 cells. Cells were treated with DMSO or 2.5 μM of TASIN-1 for 24 or 48 hours. Cholesterol levels were determined by Filipin III staining. Fipipin is a fluorescent chemical that specifically binds to cholesterol.

FIG. 23 shows that TASIN-1 decreases intracellular cholesterol level in DLD1 but not in HCT116 cells. Cells were treated with DMSO or 2.5 μM of TASIN-1 for 24 or 48 hours. Cholesterol levels were determined by Filipin III staining. Fipipin is a fluorescent chemical that specifically binds to cholesterol.

Figure 24:
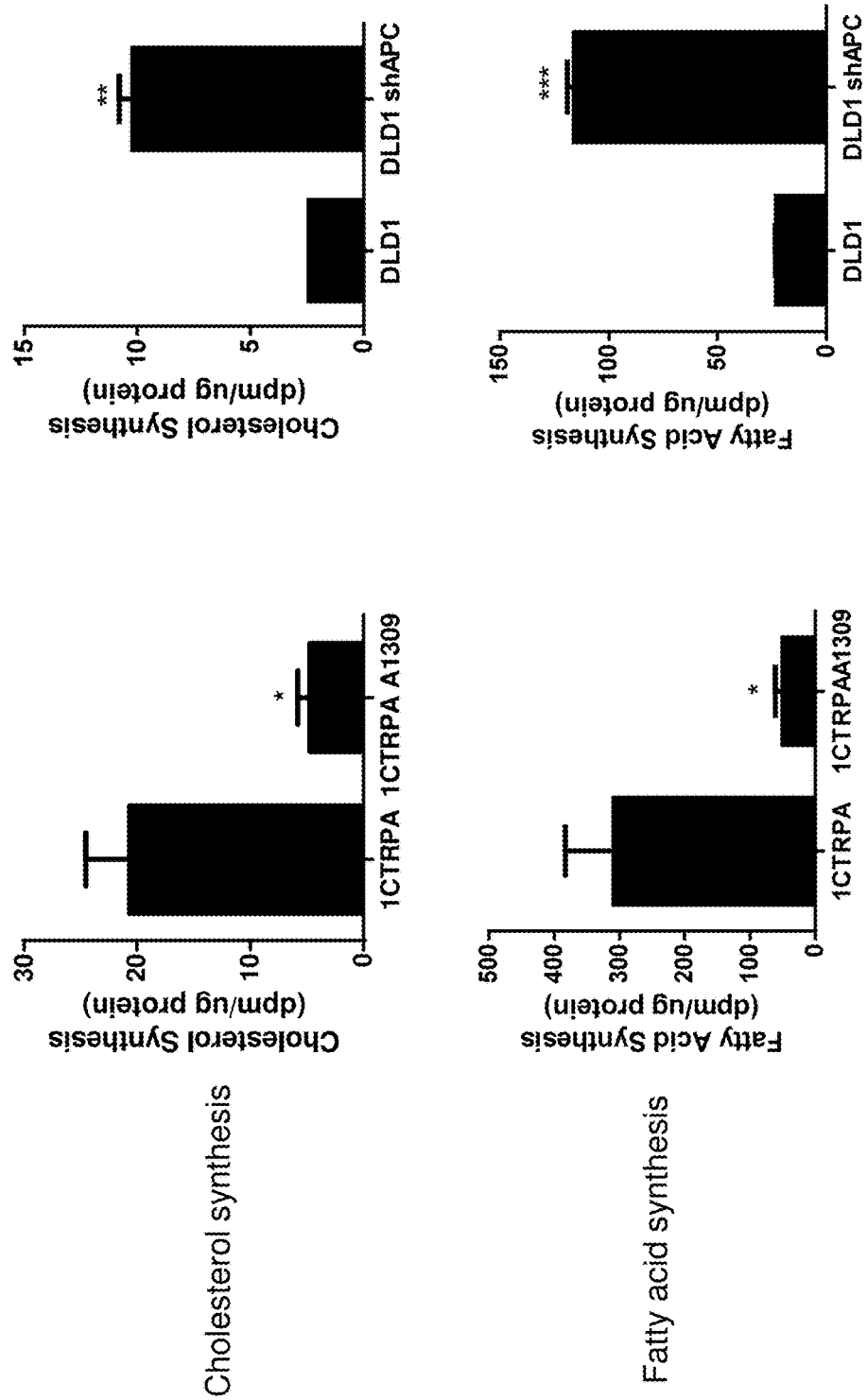
FIG. 24 shows that APC truncated protein is involved in cholesterol homeostasis. Cholesterol and fatty acid synthesis rates were measured in isogenic HCEC (1CTRPA, 1CTRPA A1309) and DLD1 cell lines (DLD1, DLD1 APC knockdown). Data represent mean±s.d., n=2. Student's t-test, *P<0.05, **P<0.01. APC truncation expression affects cholesterol and fatty acid biosynthesis rate.

FIG. 24 shows that APC truncated protein is involved in cholesterol homeostasis. Cholesterol and fatty acid synthesis rates were measured in isogenic HCEC (1CTRPA, 1CTRPA A1309) and DLD1 cell lines (DLD1, DLD1 APC knockdown). Data represent mean±s.d., n=2. Student's t-test, *P<0.05, **P<0.01. APC truncation expression affects cholesterol and fatty acid biosynthesis rate.

Figure 25:
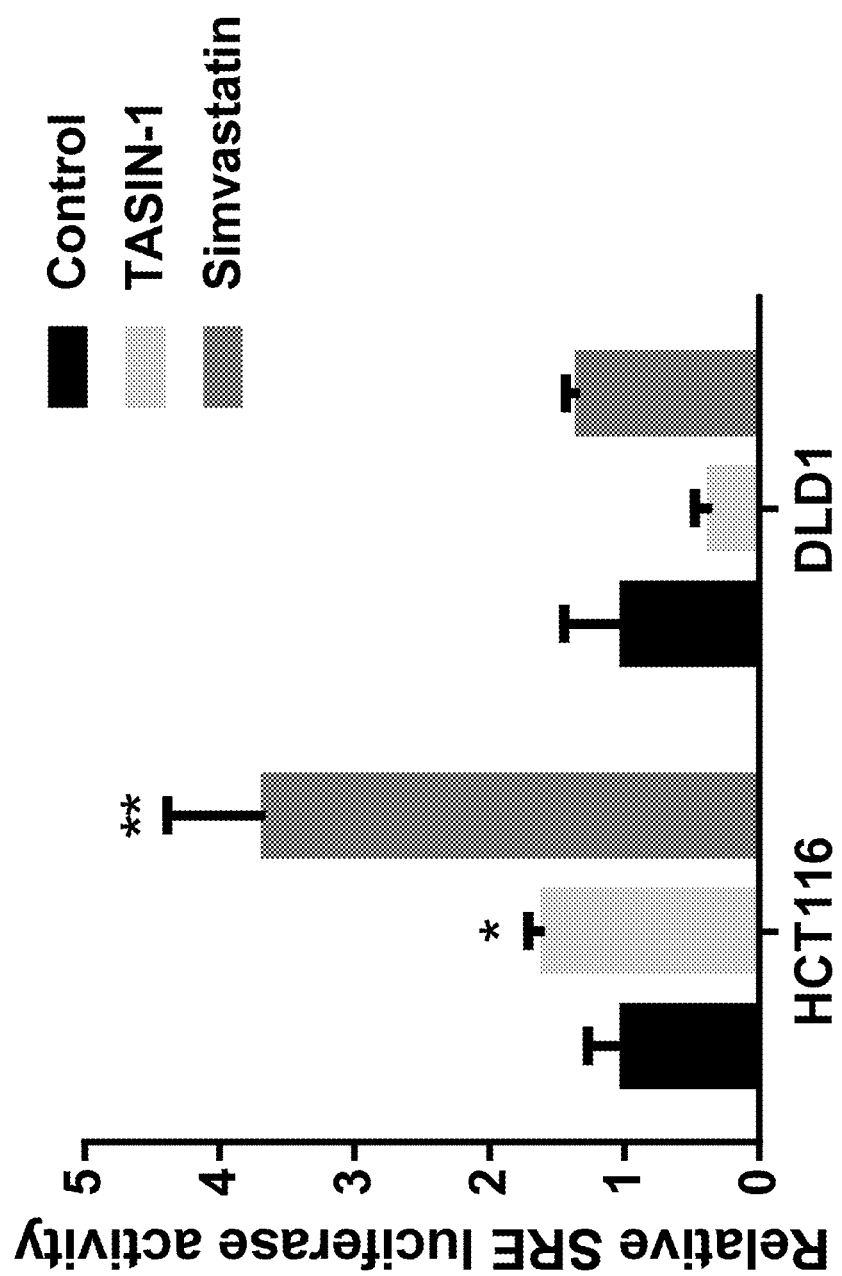
FIG. 25 shows the relative SRE luciferase activity in HCT116 and DLD1 cells treated with 2.5 μM of TASIN-1 or 10 μM of Simvastatin for 24 hours. Data represent mean±s.d., n=2. Student's t-test, **P<0.01. TASIN-1 treatment increased sterol response element (SRE) luciferase activity only in HCT116 cells.

FIG. 25 shows the relative SRE luciferase activity in HCT116 and DLD1 cells treated with 2.5 μM of TASIN-1 or 10 μM of Simvastatin for 24 hours. Data represent mean±s.d., n=2. Student's t-test, **P<0.01. TASIN-1 treatment increased sterol response element (SRE) luciferase activity only in HCT116 cells.

Figure 26:
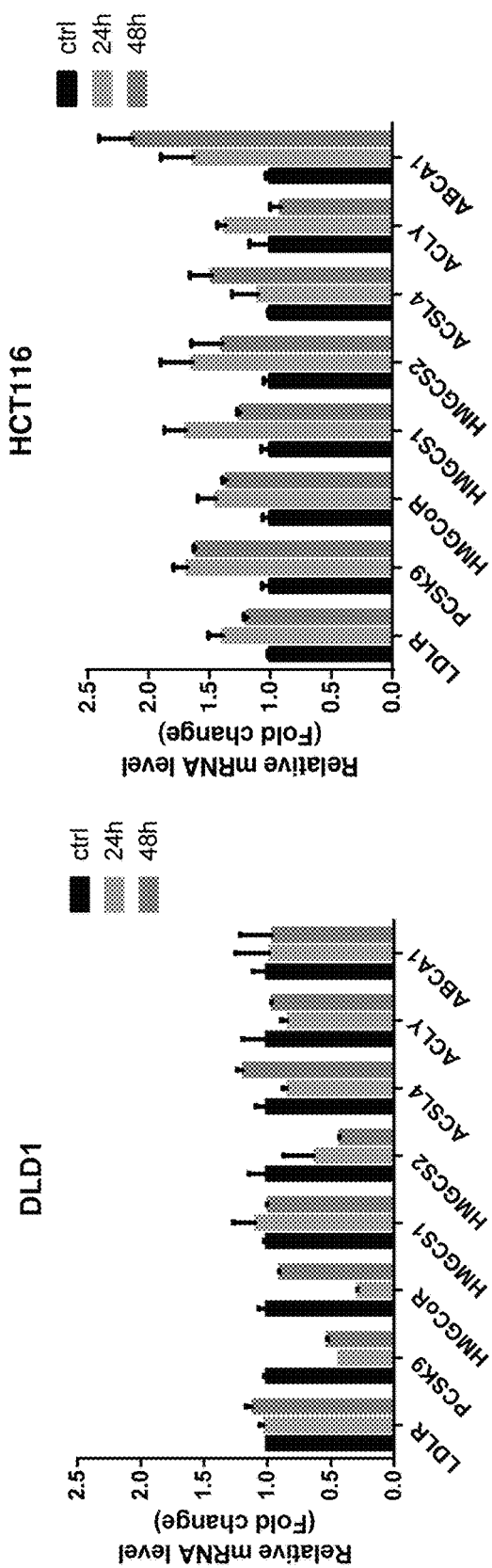
FIG. 26 shows the results of Quantitative PCR analysis of the major target genes regulated by SREBP2 in HCT116 cells or DLD1 cells treated with 2.5 μM of TASIN-1 for 24 and 48 hours. Expression level was normalized to the control cells. Data represent mean±s.d., n=2. TASIN-1 treatment leads to up-regulation of SREBP2 target genes only in HCT116 cells.

FIG. 26 shows the results of Quantitative PCR analysis of the major target genes regulated by SREBP2 in HCT116 cells or DLD1 cells treated with 2.5 μM of TASIN-1 for 24 and 48 hours. Expression level was normalized to the control cells. Data represent mean±s.d., n=2. TASIN-1 treatment leads to up-regulation of SREBP2 target genes only in HCT116 cells.

Figure 27:
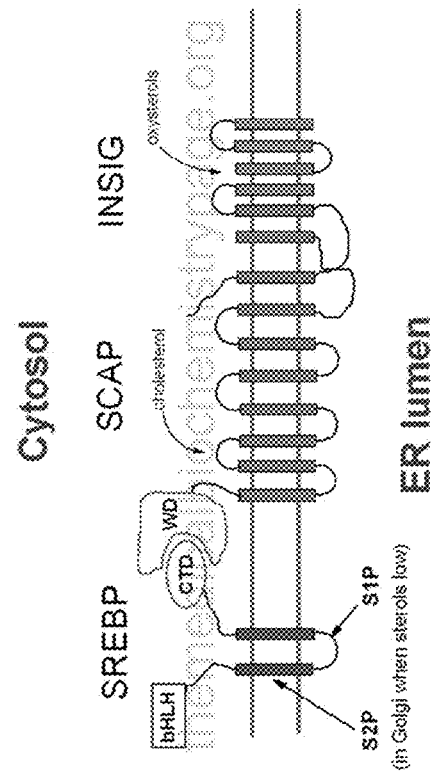
FIG. 27 is a lipoprotein signaling PCR array (Qiagen, 90 genes) showing upregulation and downregulation of a panel of cholesterol signaling related genes in APC knockdown DLD1 cells, which are reversed by ectopic expression of APC 1309. The results deomstrate gain-of-Function of APC truncation in cholesterol signaling and metabolism.
Figure 27:
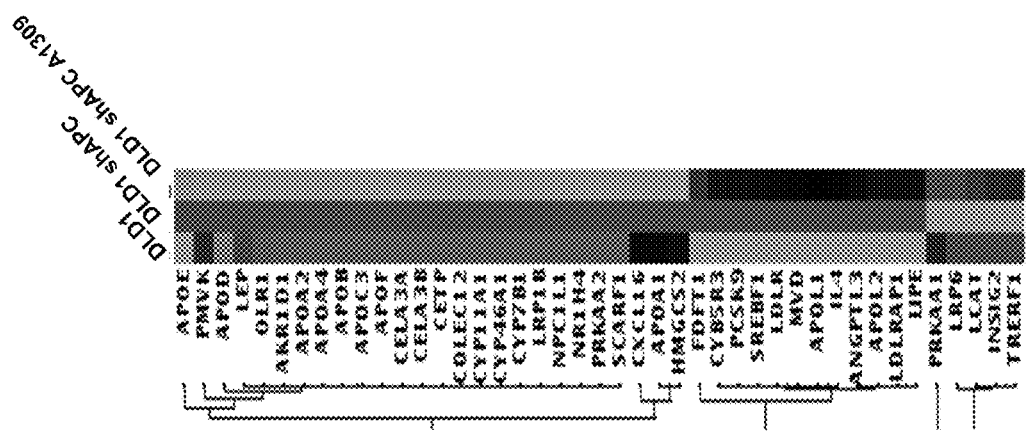

FIG. 27 is a lipoprotein signaling PCR array (Qiagen, 90 genes) showing upregulation and downregulation of a panel of cholesterol signaling related genes in APC knockdown DLD1 cells, which are reversed by ectopic expression of APC 1309. The results demonstrate gain-of-Function of APC truncation in cholesterol signaling and metabolism.

Figure 28:
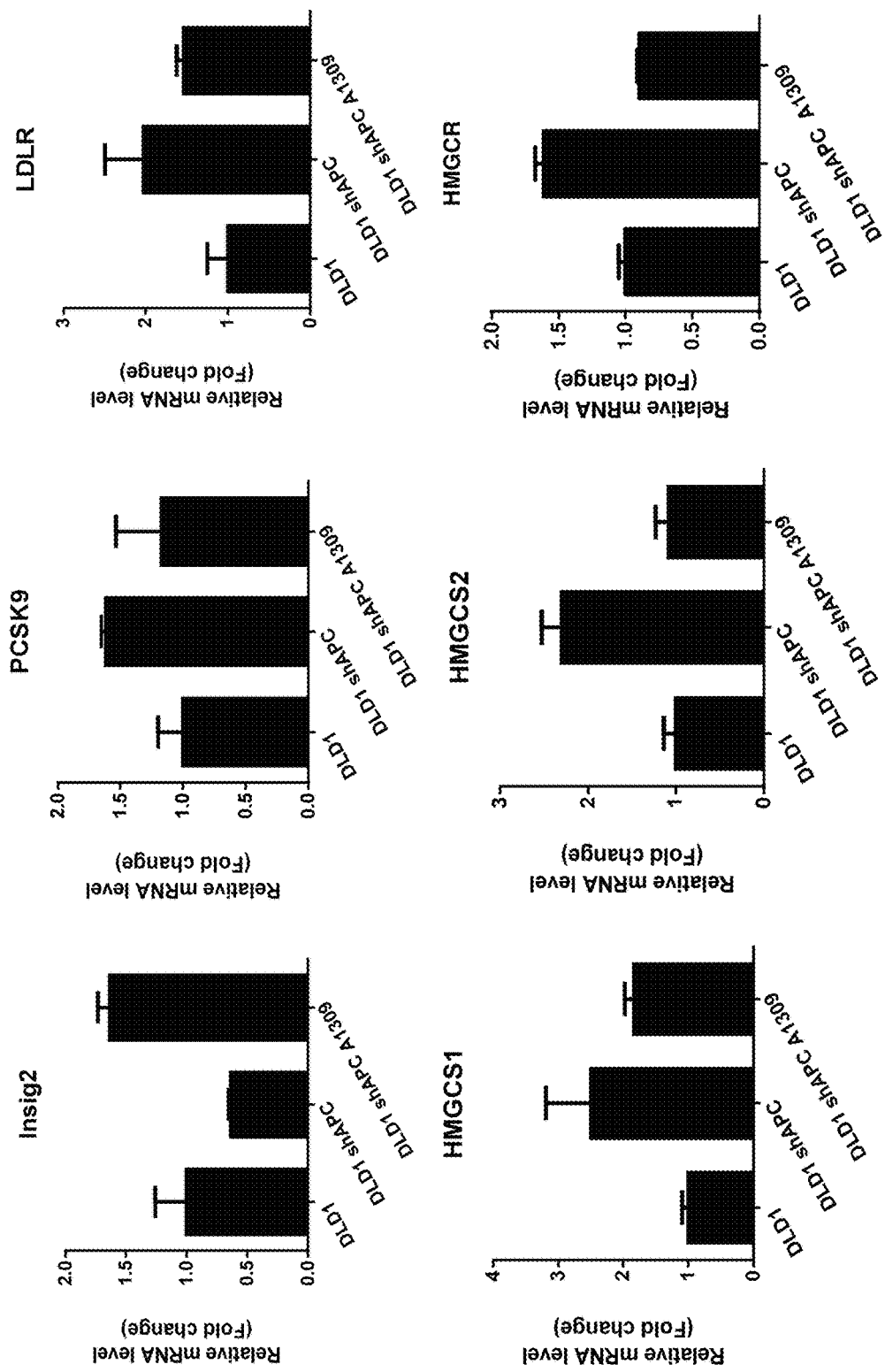
FIG. 28 shows that APC truncation affects expression of SREBP2 target genes. Quantitative PCR was performed on the isogenic DLD1 cell lines with primers against the major target genes regulated by SREBP2. Expression level was normalized to that in DLD1 cells. Data represent mean±s.d., n=2.

FIG. 28 shows that APC truncation affects expression of SREBP2 target genes. Quantitative PCR was performed on the isogenic DLD1 cell lines with primers against the major target genes regulated by SREBP2. Expression level was normalized to that in DLD1 cells. Data represent mean±s.d., n=2.

Figure 29:
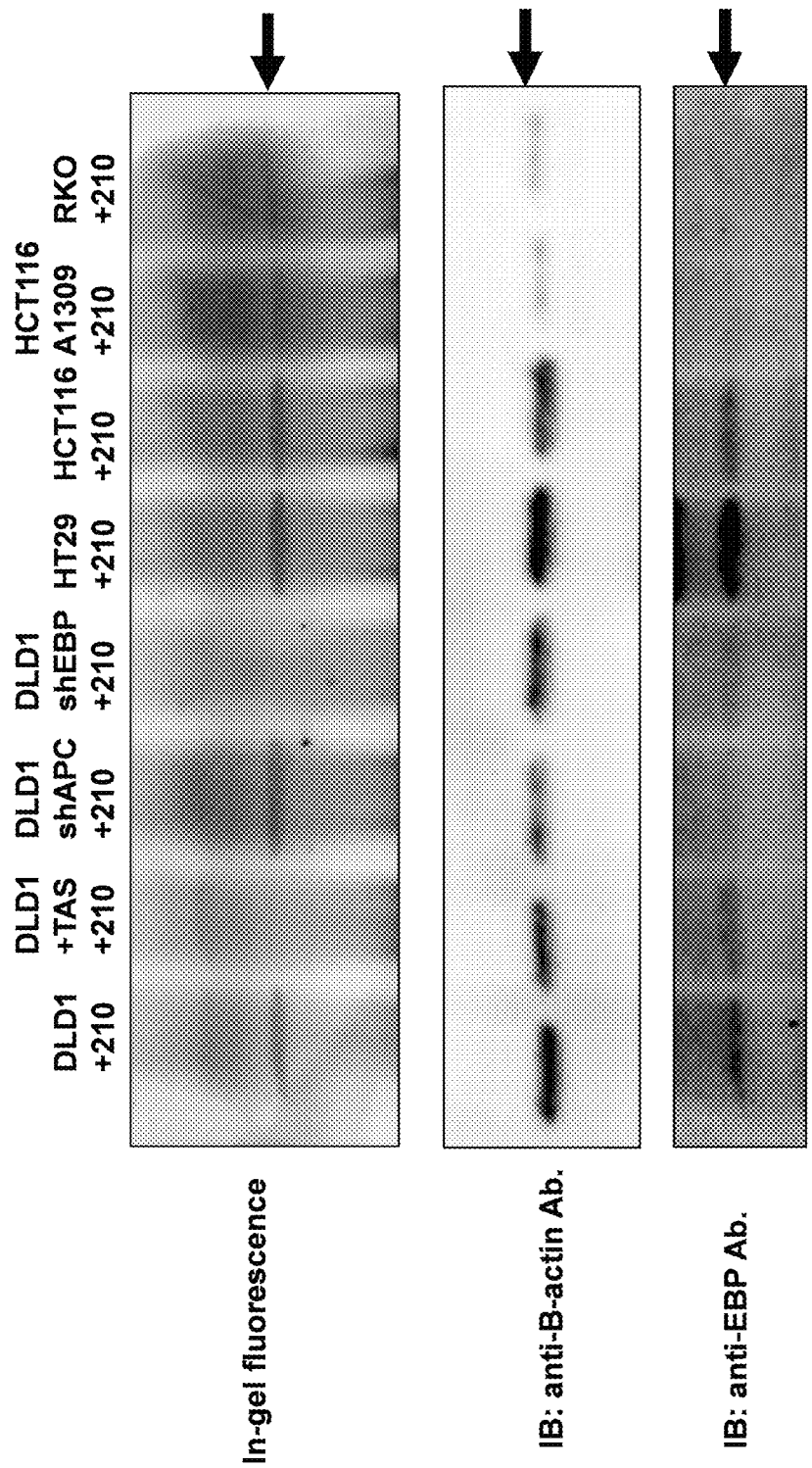
FIG. 29 confirms the interaction between TASIN-1 and EBP in colorectal cancer (CRC) cells. CRC cells were incubated with TASIN-1 analog #210 and labeled with Alexa532 after UV crosslinking via click reaction. Proteins were precipitated using cold acetone and resuspended in Laemmli buffer, followed by in-gel fluorescence and Western blot analysis.
Figure 30:
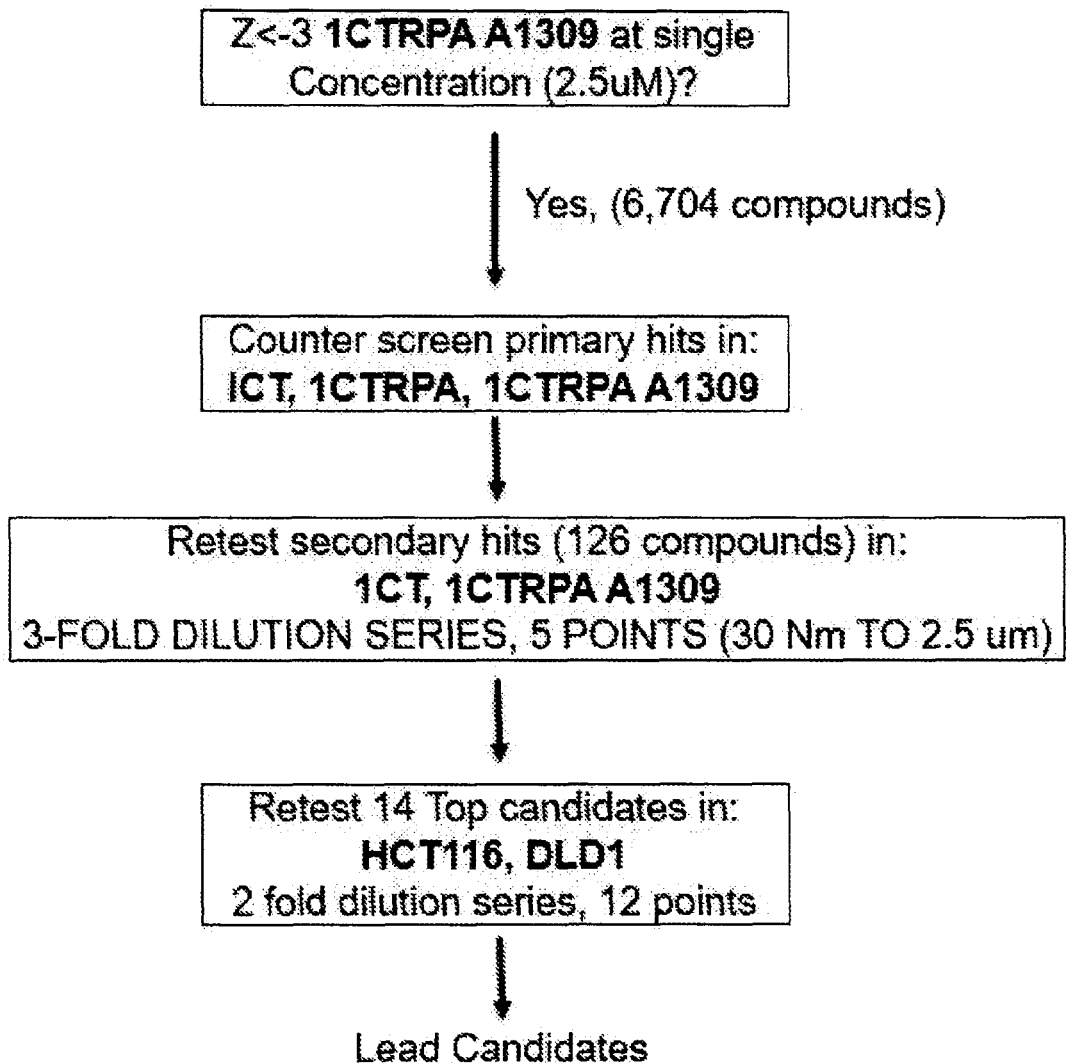
FIG. 30 describes the overall screening strategy for screening for compounds.

FIG. 29 confirms the interaction between TASIN-1 and EBP in colorectal cancer (CRC) cells. CRC cells were incubated with TASIN-1 analog #210 and labeled with Alexa532 after UV crosslinking via click reaction. Proteins were precipitated using cold acetone and resuspended in Laemmli buffer, followed by in-gel fluorescence and Western blot analysis.

While the described invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the described invention. All such modifications are intended to be within the scope of the claims appended hereto.

What is claimed is:

1. A method for targeting emopamil binding protein for treating a subject with colorectal cancer with a pharmaceutical composition comprising an Emopamil binding protein (EBP)-modulating anti-cancer compound, wherein the EBP-modulating anti-cancer compound is

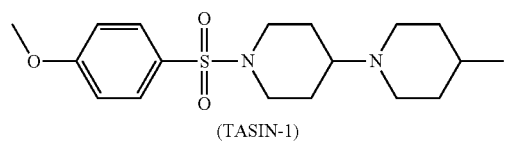

(TASIN-1)

or a functional equivalent selected from the group consisting of:

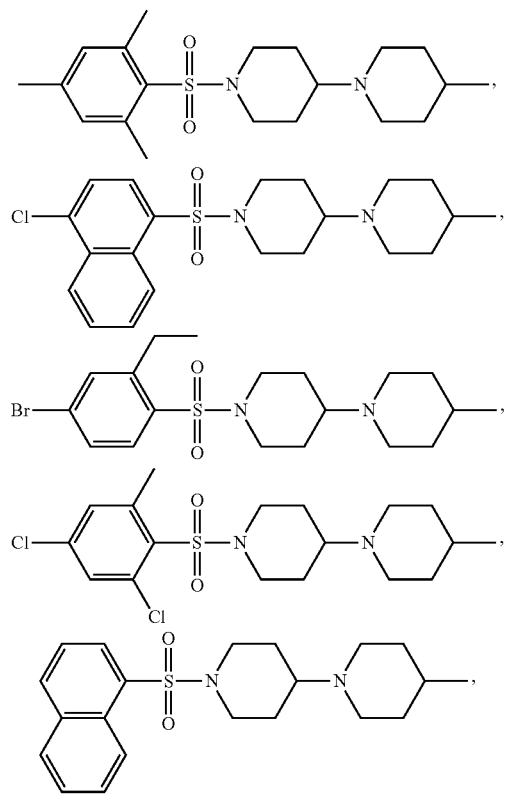

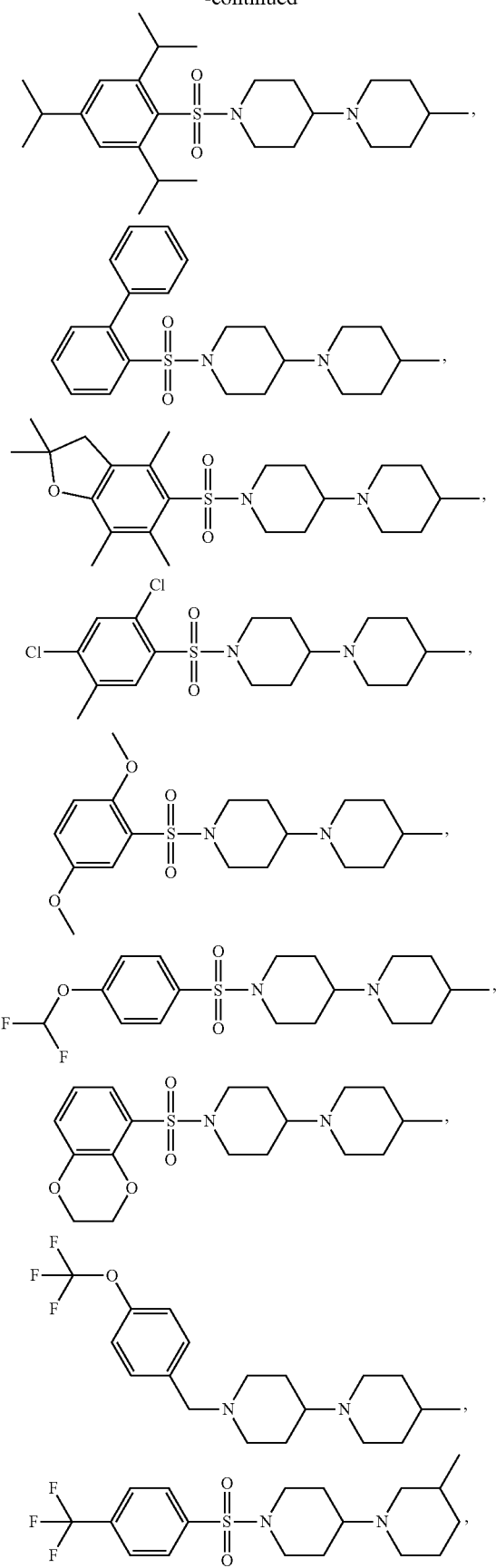
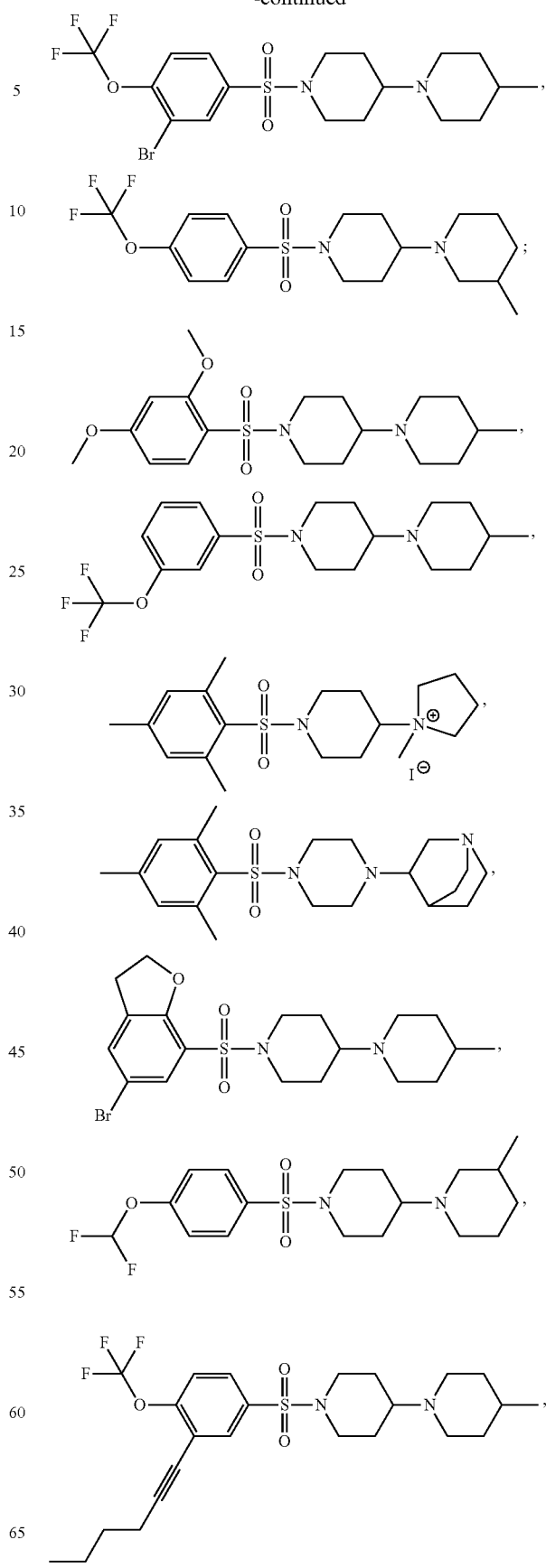

129
-continued
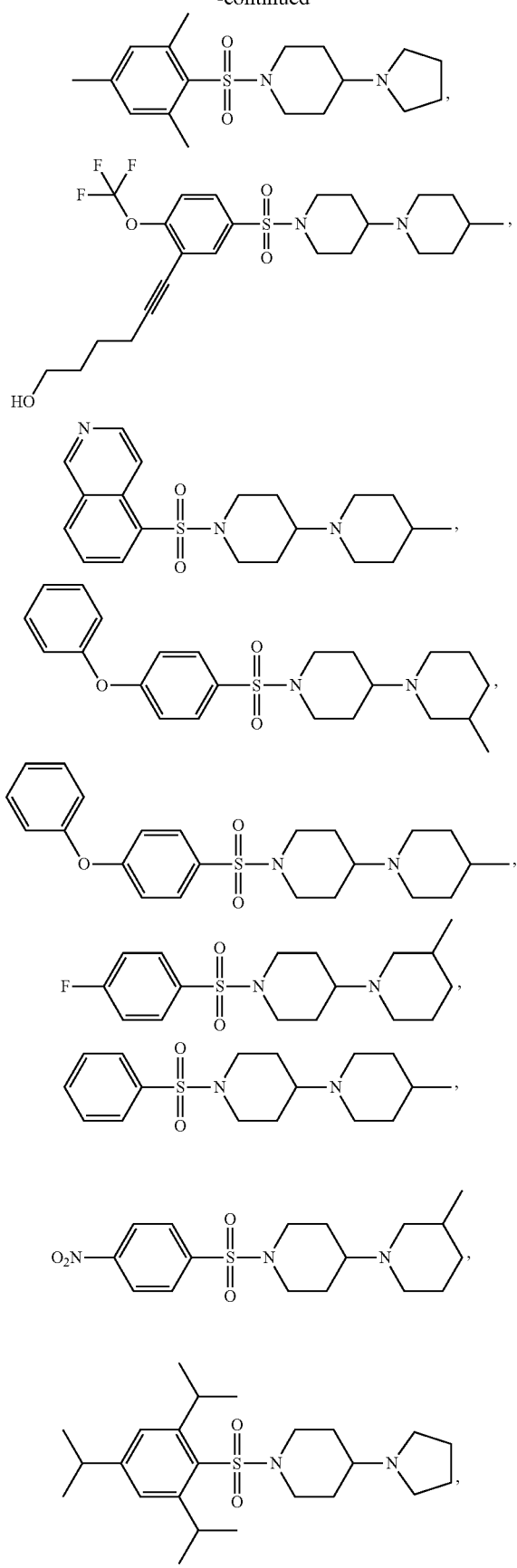
130
-continued
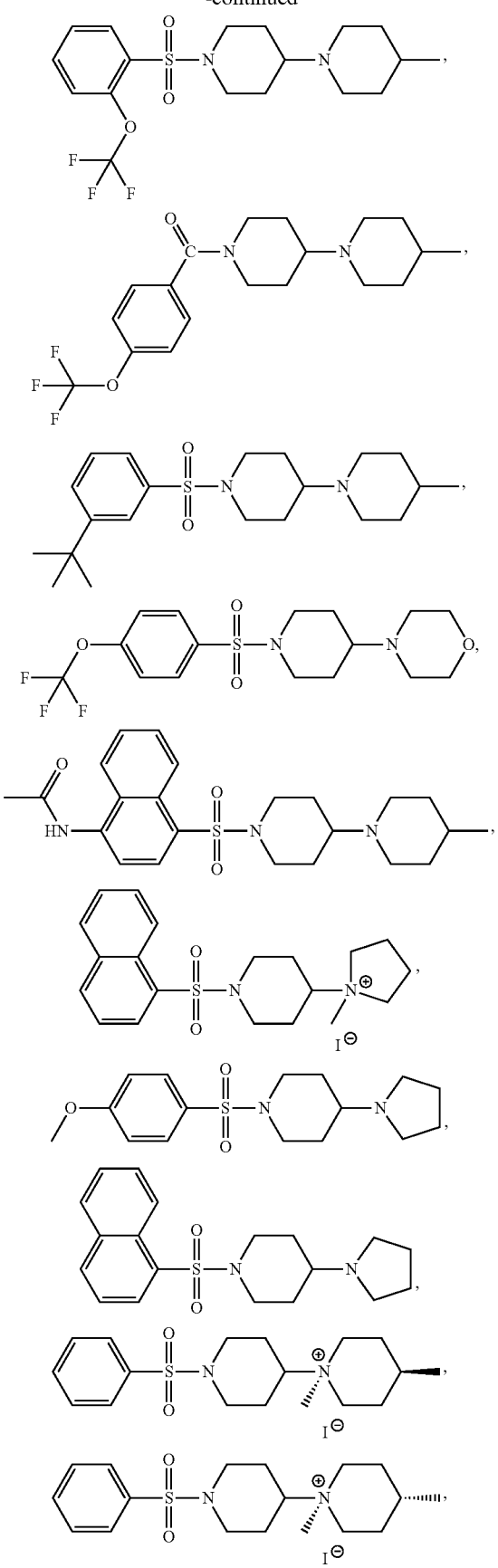

131
-continued
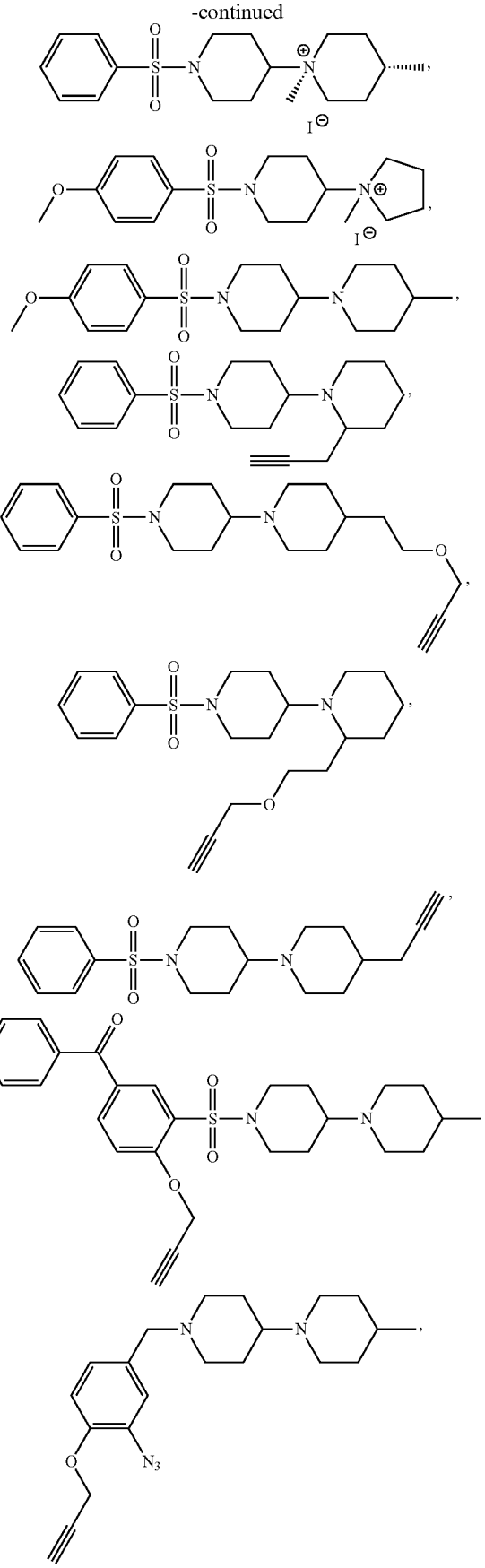
132
-continued
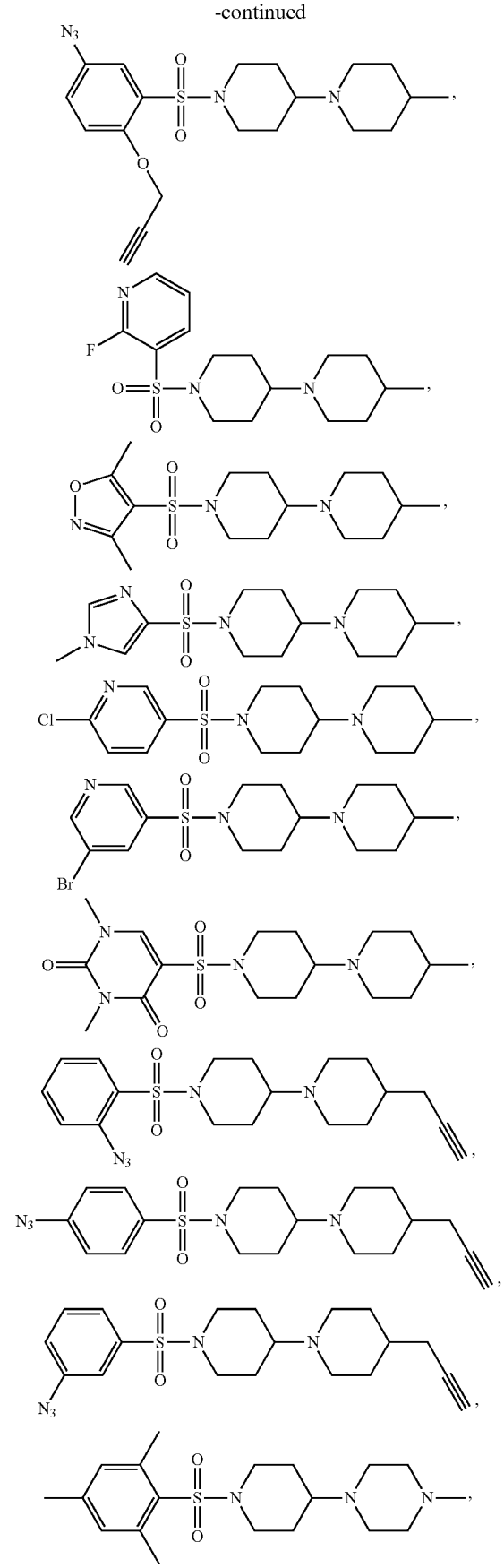

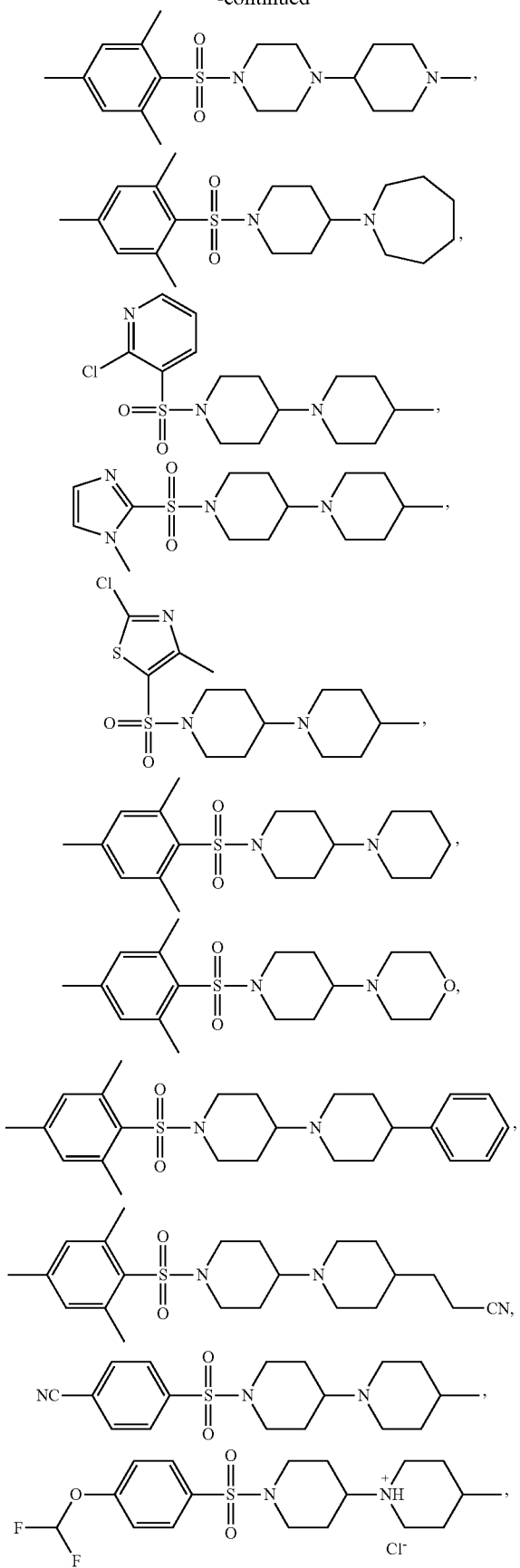
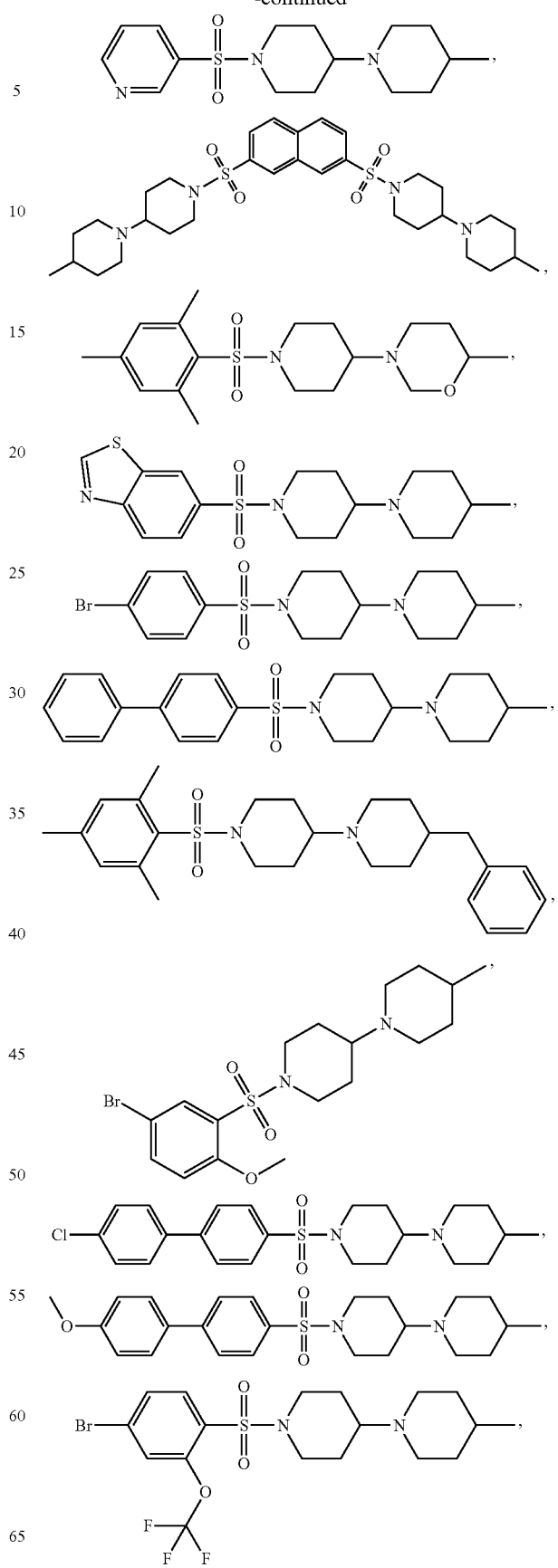

-continued

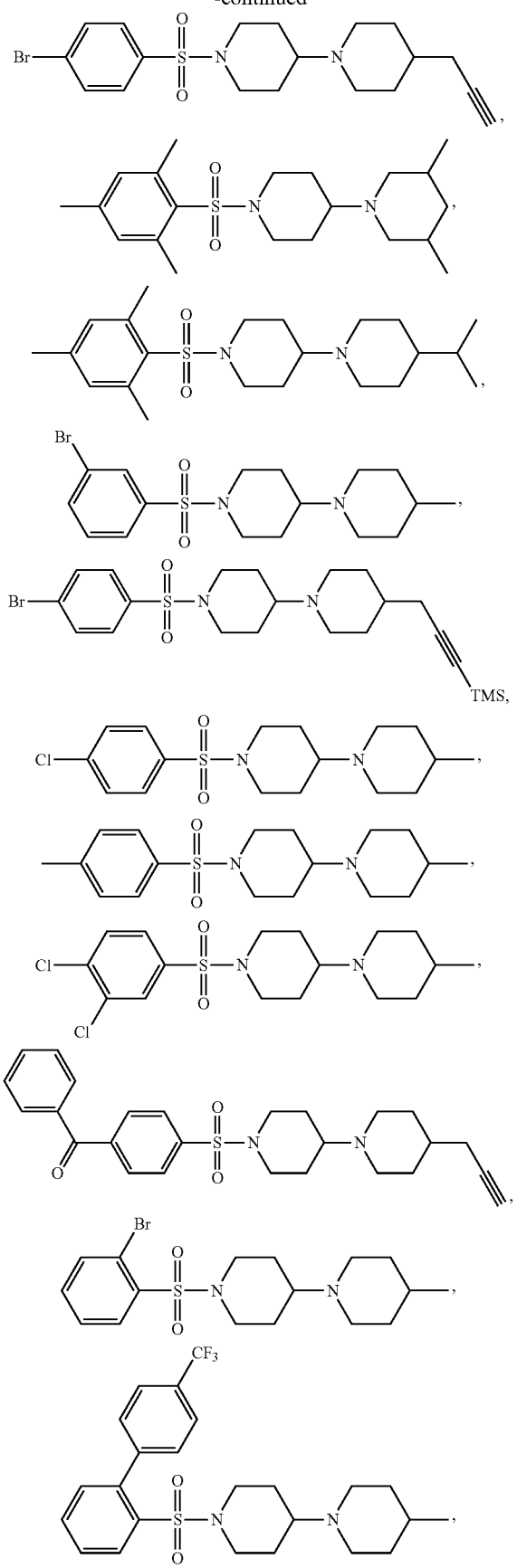

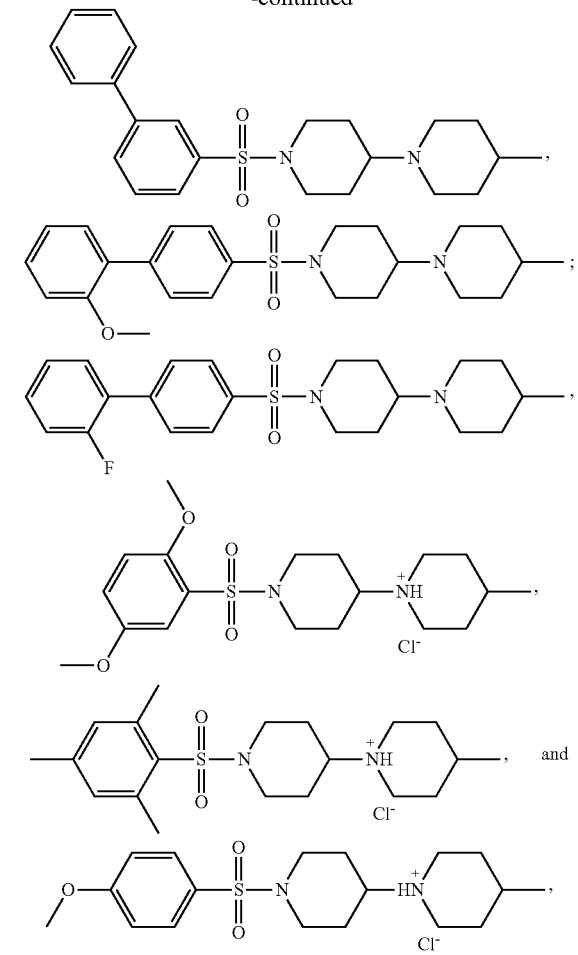

the method comprising
(a) isolating a colorectal tumor sample comprising a population of cancer cells from the subject;
(b) providing (i) an aliquot of the colorectal tumor sample in (a) as a test population of cancer cells, (ii) a known population of cancer cells sensitive to the EBP-modulating anticancer compound (positive control), and (iii) a known population of cancer cells insensitive to the EBP-modulating anticancer compound (negative control),
wherein the known population of cancer cells sensitive to the EBP modulating anti-cancer compound (positive control) is a population of cancer cells selected from the group consisting of DLD1 cells, HT29 cells, SW620 cells, SE480 cells, Caco-2 cells, Lovo cells, and HC116 p53-/-A1309 cells, and
the known population of cancer cells insensitive to the EBP-modulating anticancer compound (negative control) is a population of cancer cells selected from the group consisting of HCT116 cells and RKO cells;
(c) determining whether the aliquot of the colorectal tumor sample contains a subpopulation of cancer cells sensitive to the composition comprising the EBP-modulating anti-cancer compound by
(1) contacting the EBP-modulating anticancer compound to the populations of cancer cells in (b);
(2) measuring EBP enzyme activity and cholesterol synthesis rate for each population of cancer cells, wherein
in a cancer cell sensitive to the EBP modulating anti-cancer compound, an amount of the EBP-modulating anti-cancer compound is effective to decrease EBP enzyme activity and to decrease the rate of endogenous cholesterol synthesis, while
in a cancer cell insensitive to the EBP modulating anti-cancer compound, an amount of the EBP-modulating anti-cancer compound is effective to increase EBP activity and to increase the rate of endogenous cholesterol synthesis;
and
(d) upon determining that the test population of colorectal cancer cells contains a population of cancer cells sensitive to the EBP modulating anti-cancer compound in (c), treating the colorectal tumor by administering to the subject the pharmaceutical composition containing a therapeutic amount of the EBP modulating anti-cancer compound.

2. The method according to claim 1, wherein in the cancer cell sensitive to the EBP modulating anti-cancer compound, the effective amount of the EBP-modulating anti-cancer compound is effective to cause accumulation of a Δ8 sterol intermediate.

3. The method according to claim 2, wherein the Δ8 sterol intermediate is 5α-cholest-8-(9)-en-3β-ol (Δ8 -cholesetenol).

4. The method according to claim 1, wherein in the cancer cell sensitive to the EBP-modulating anticancer compound, the effective amount of the EBP modulating anti-cancer compound is effective to cause downregulation of SREBP-2.

5. The method according to claim 1, wherein in the cancer cell sensitive to the EBP-modulating anticancer compound, the effective amount of the EBP modulating anti-cancer compound is effective to cause downregulation of SREBP-2 genes.

6. The method according to claim 1, wherein in the cancer cell sensitive to the EBP-modulating anticancer compound, the effective amount of the EBP modulating anti-cancer compound is effective to cause downregulation of SREBP-2 and one or more SREBP-2 target genes of the cholesterol biosynthetic pathway selected from the group consisting of ACAT2; MHGCS1; HMGCR; MVK; PMVK; MVD; ID11/ID12; FDFS;
GGPS1; FDFT1; SQLE; LSS; CYPS1A1; TM75F2; SCAMOL; NSDHL; HSD17B7;
EBP; SC5D; DHCR7; and DHCR24.

7. The method according to claim 1, wherein the cancer cell sensitive to the EBP-modulating anti-cancer compound comprises a truncated APC protein.

8. The method according to claim 1, wherein the therapeutic amount of the EBP-modulating anti-cancer compound is effective to reduce proliferation of the cancer cell sensitive to the EBP modulating anti-cancer compound, to reduce invasiveness of the cancer cell sensitive to the EBP modulating anti-cancer compound, increase apoptosis of the cancer cell sensitive to the EBP modulating anti-cancer compound, reduce growth of a tumor comprising the cancer cell sensitive to the EBP modulating anti-cancer compound, reduce tumor burden, improve progression free survival, improve overall survival, achieve remission of disease, or a combination thereof.

9. The method according to claim 1, wherein the pharmaceutical composition comprising a first amount of the EBP-modulating anticancer compound further comprises a second amount of a compound selected from the group consisting of dendrogenin A, SR31747A, tamoxifen, emopamil, verapamil, cis-flupentixol, trifluoroperazine, 7-ketocholestenol, haloperidol, and fenpropimorph.

10. A method for identifying a therapeutic EBP-modulating anticancer compound for targeting emopamil binding protein for treating a subject with colorectal cancer comprising
(a) dividing a population of cancer cells sensitive to a known EBP-modulating anti-cancer compound into aliquoted samples of the population of cancer cells, wherein
the population of cancer cells sensitive to the known EBP-modulating anti-cancer compound is a population of DLD 1 cells or HT29 cells,
the known EBP-modulating anti-cancer compound is

(TASIN-1)

(b) contacting one sample of the population of sensitive cancer cells with a candidate EBP-modulating anti-cancer compound, contacting a second sample of the sensitive population of cancer cells with the known EBP-modulating anticancer compound (positive control), and contacting a third sample of the sensitive population of cancer cells with a compound that does not modulate EBP activity (negative control);
(c) measuring EBP enzyme activity and cholesterol synthesis rate for the candidate EBP-modulating compound, the positive control and the negative control in (b),
wherein
an amount of the known EBP-modulating anti-cancer compound is effective to decrease EBP activity and to decrease the rate of endogenous cholesterol synthesis in a sensitive cancer cell;
(d) ranking a plurality of candidate EBP-modulating anti-cancer compounds according to the measured EBP enzyme activity and endogenous cholesterol synthesis rate in (c):
and
(e) selecting a top-ranked candidate EBP-modulating anti-cancer compound in (d) from the group consisting of:

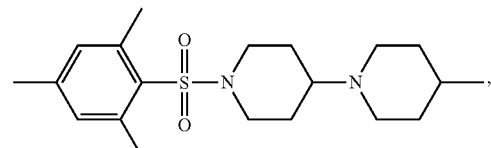

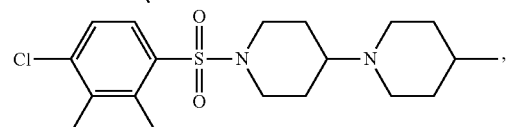

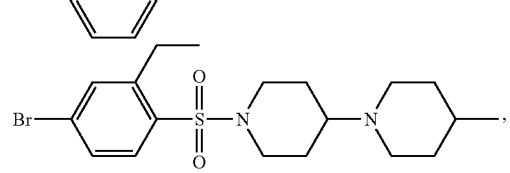

-continued
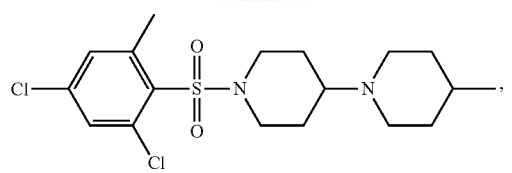
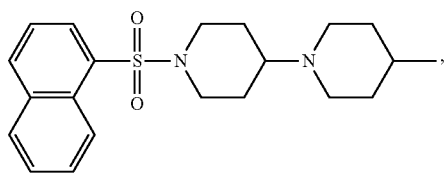
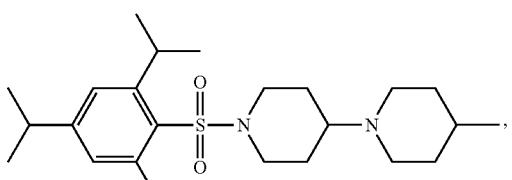
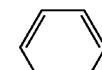
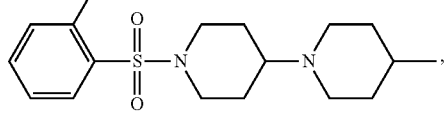
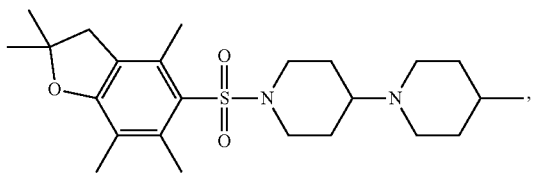
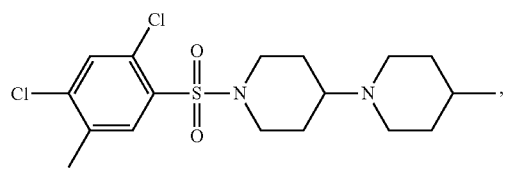
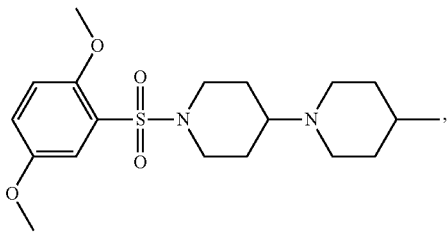
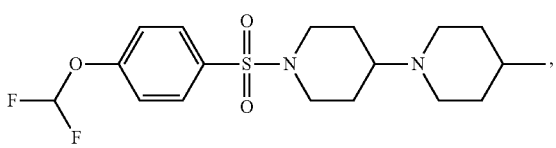
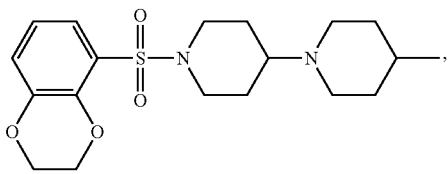
-continued
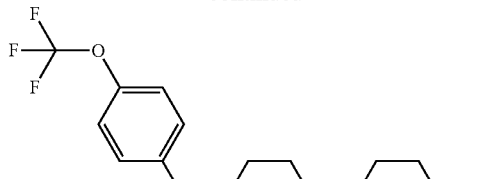
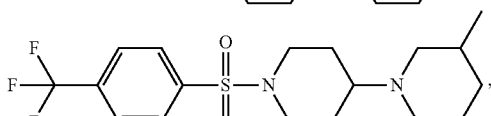
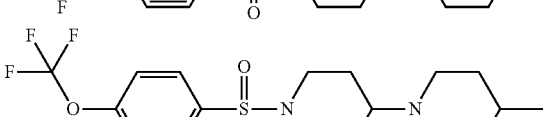
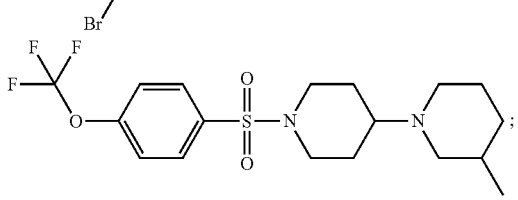
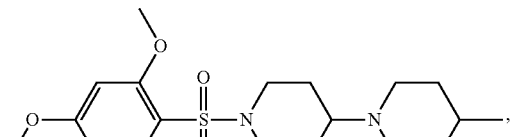
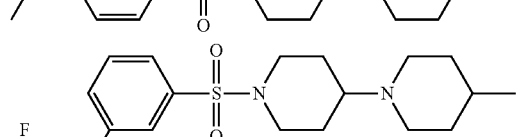
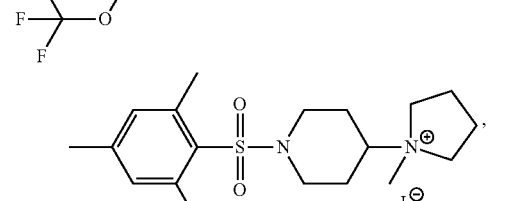
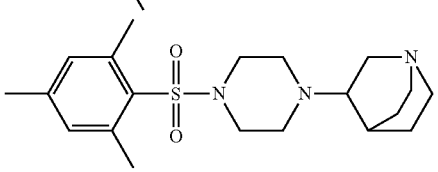
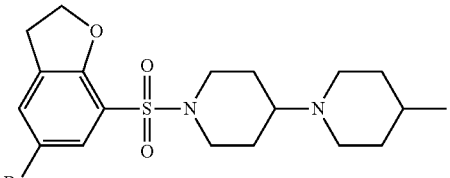
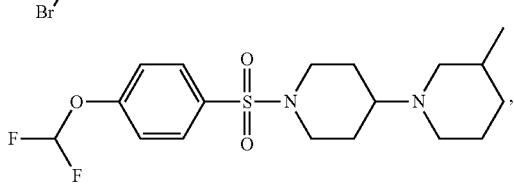

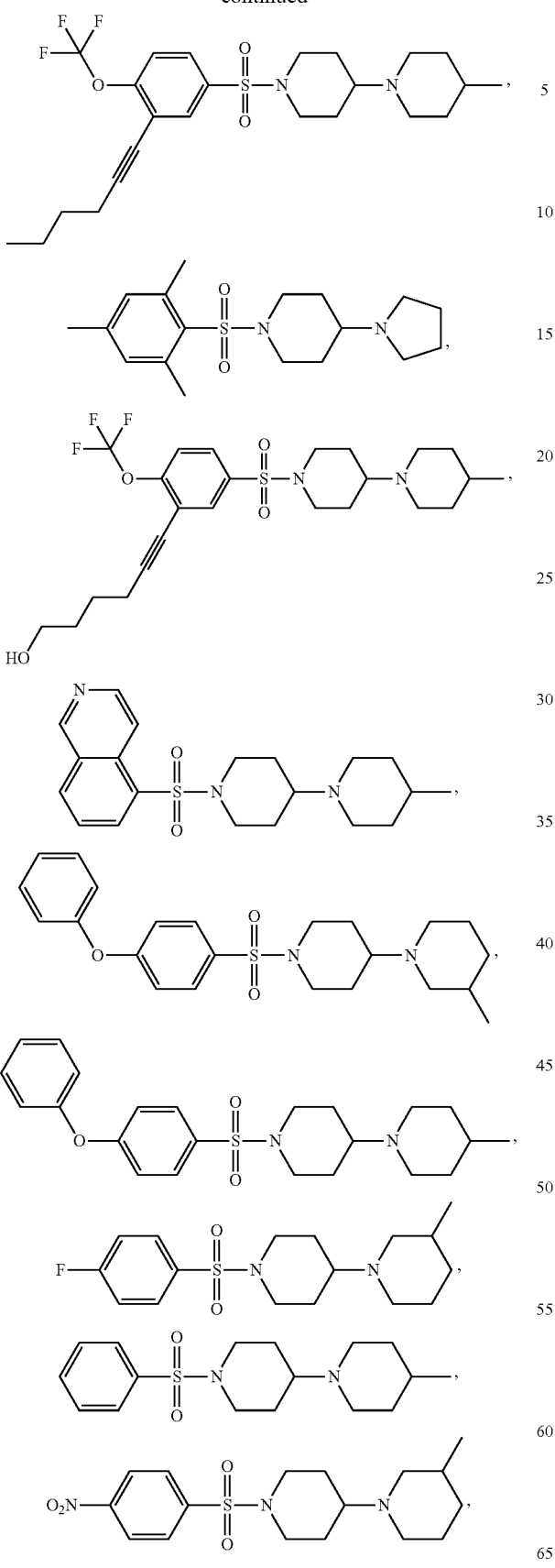
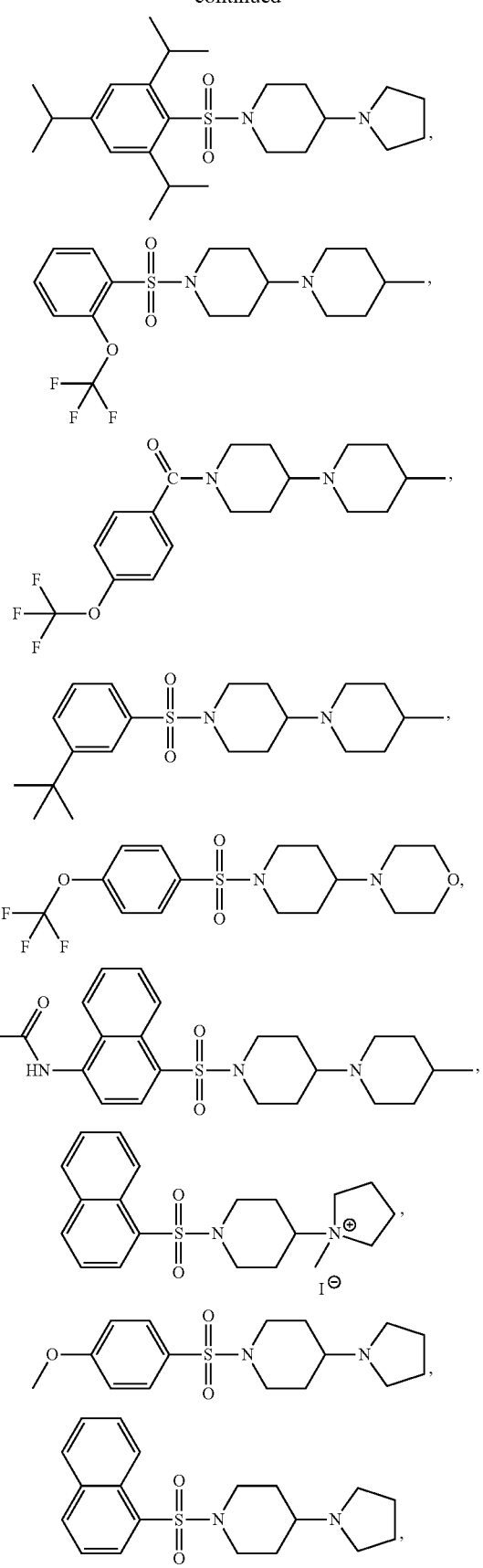

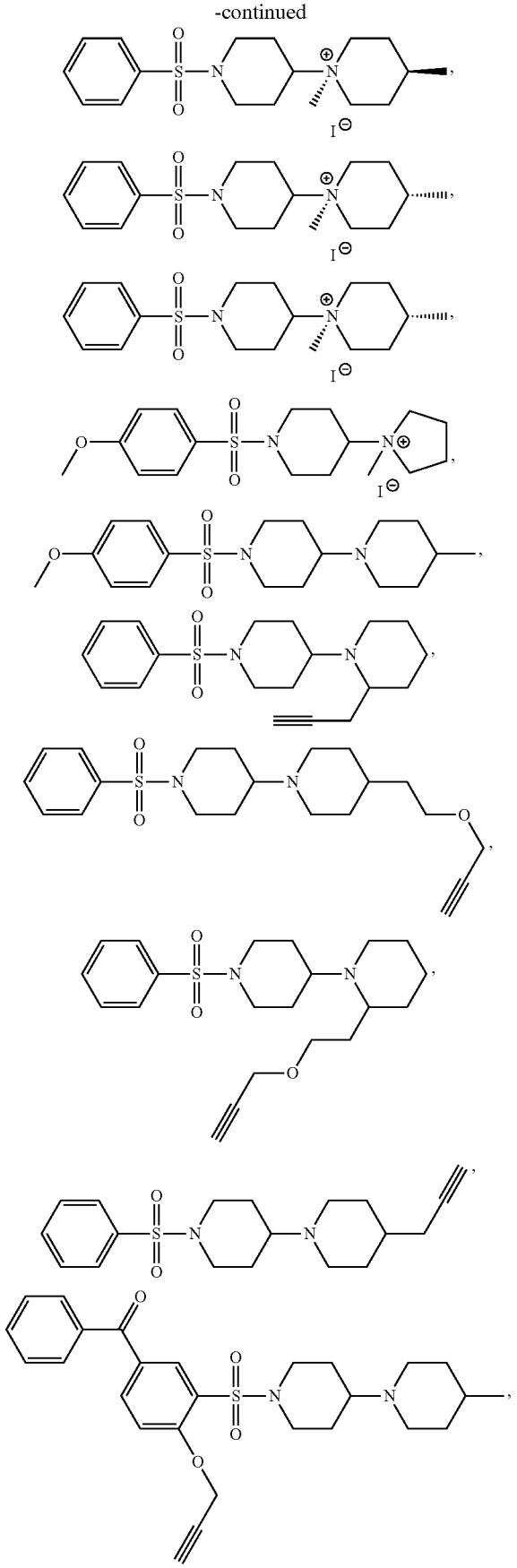
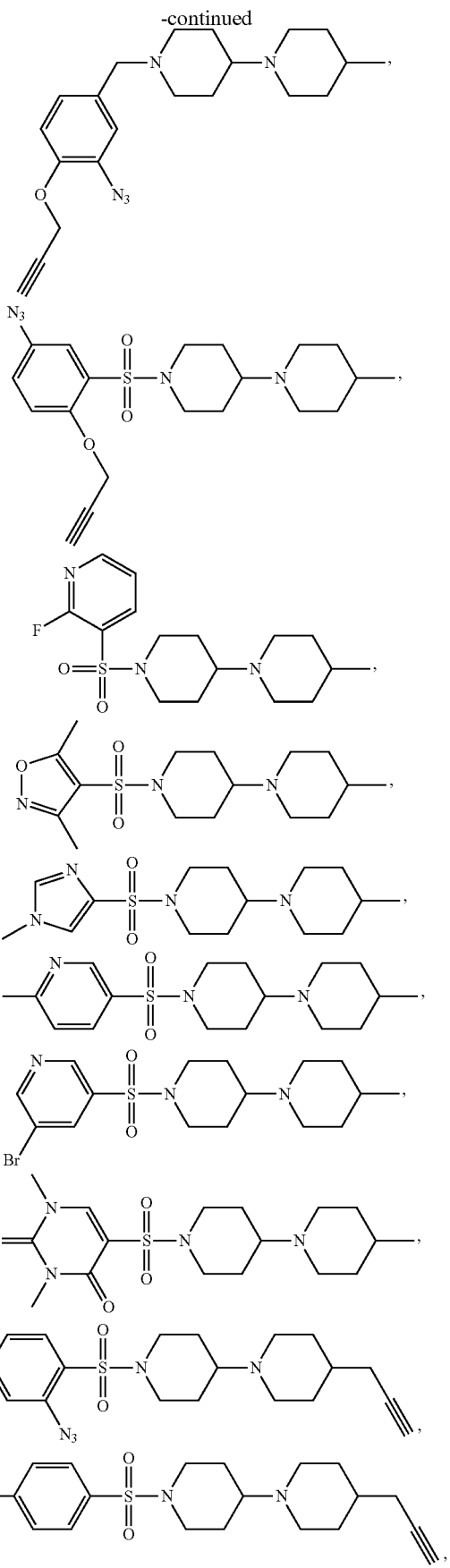

145
-continued
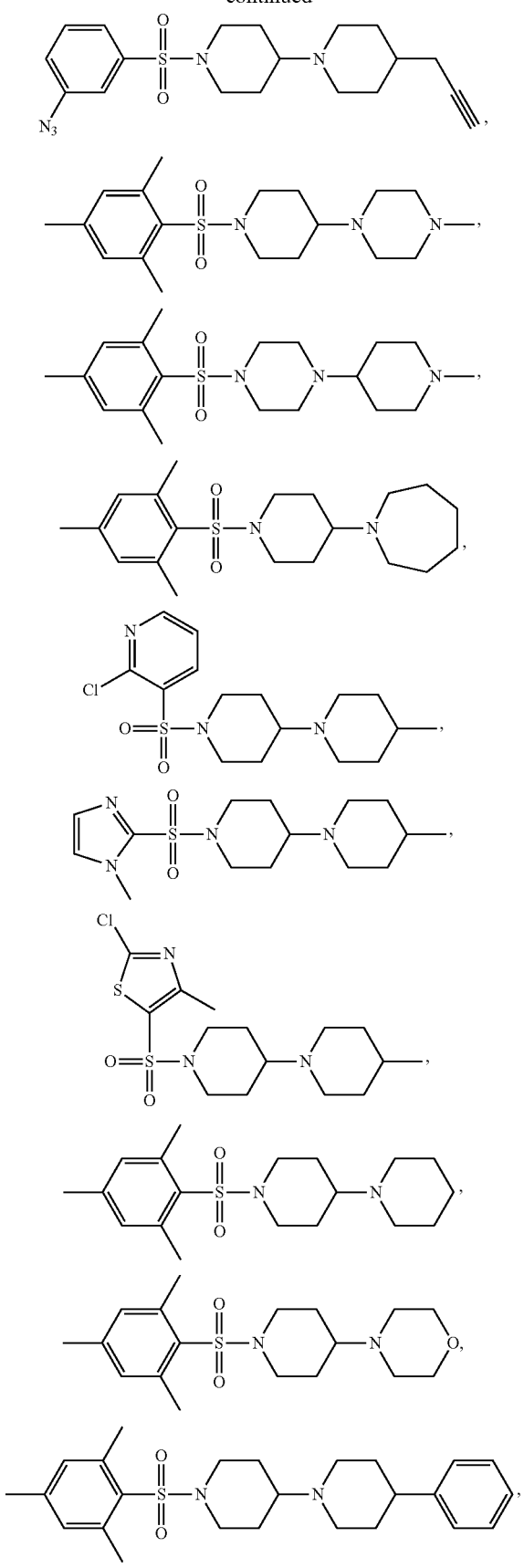
146
-continued
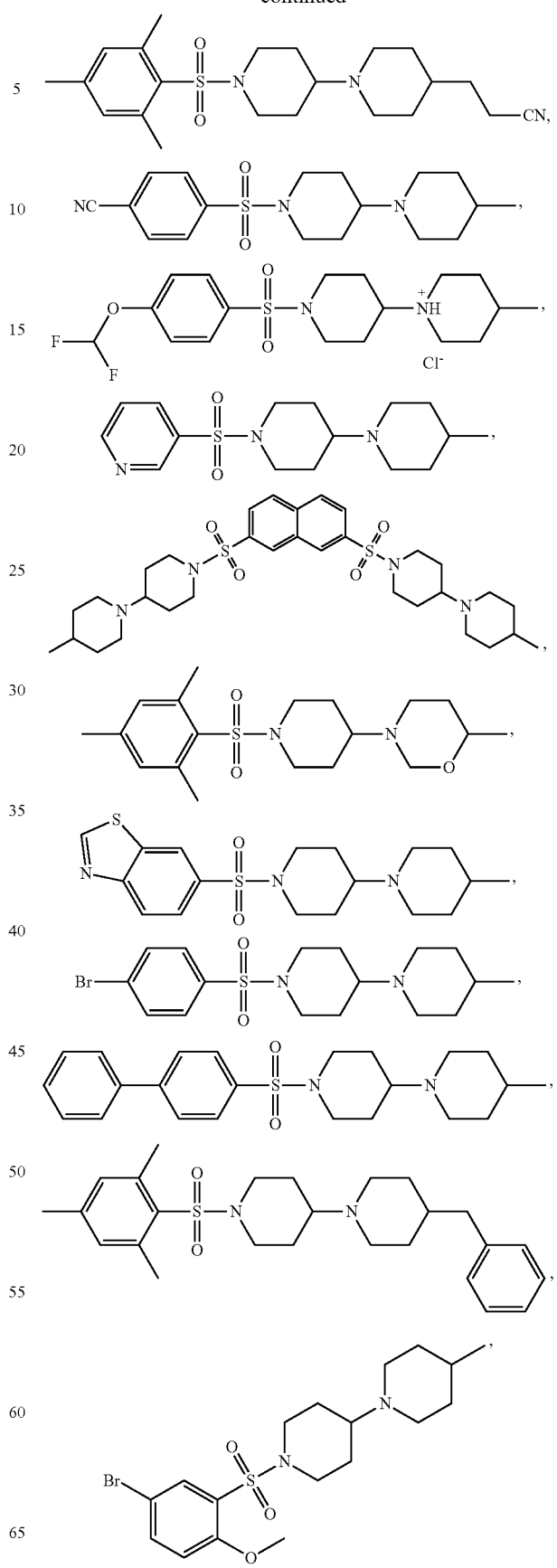

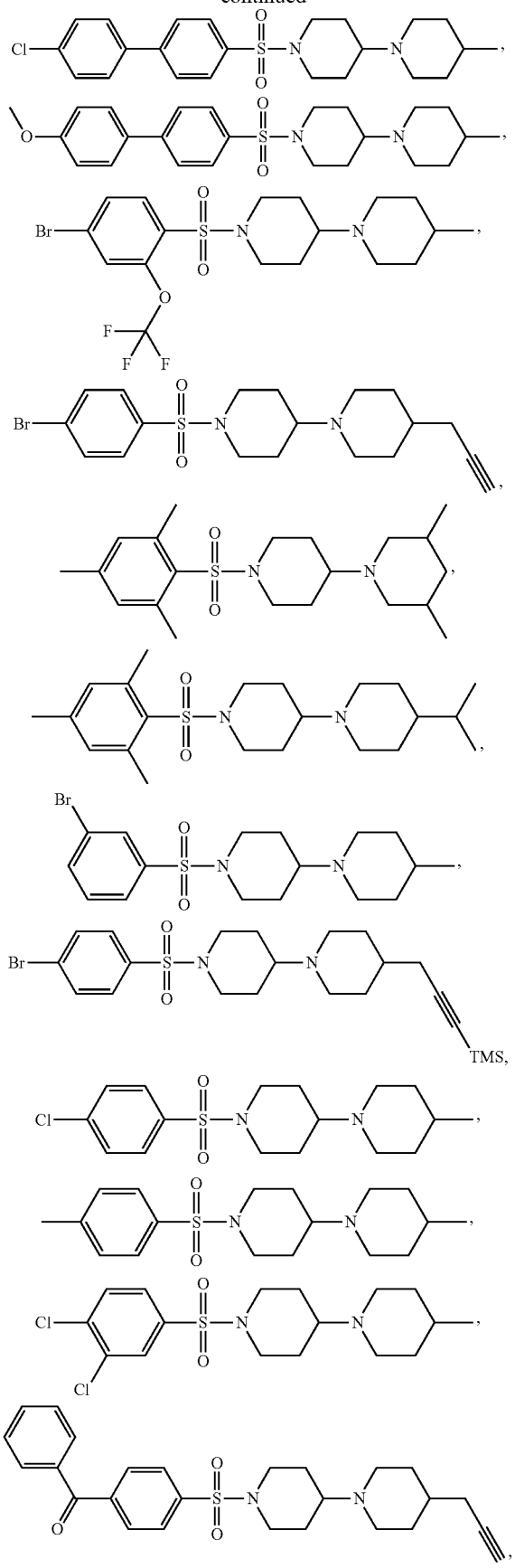
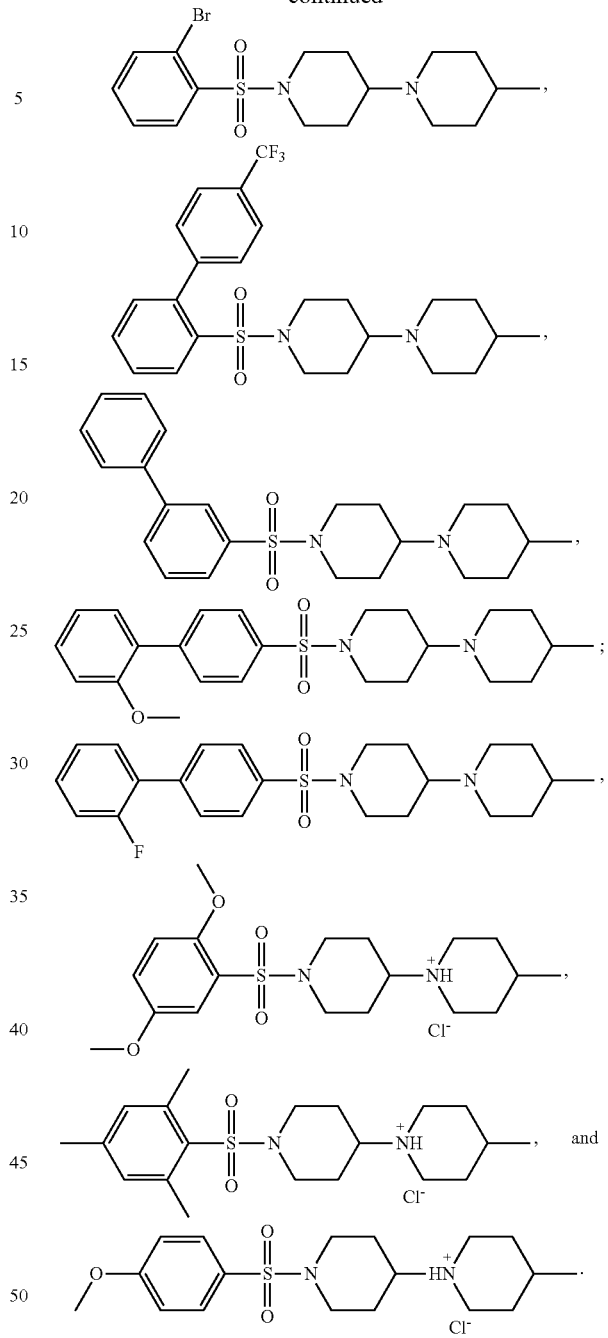

as a new EBP-modulating anti-cancer compound for treating the subject with colorectal cancer.

11. The method according to claim 10, wherein a pharmaceutical composition comprises a first amount of the EBP-modulating anti-cancer compound and a second amount of a compound selected from the group consisting of dendrogenin A, SR31747A, tamoxifen, emopamil, verapamil, cis-flupentixol, trifluoroperazine, 7-ketocholestenol, haloperidol, and fenpropimorp.

12. The method according to claim 10, wherein the decrease in EBP activity is measured as an accumulation of a Δ8 sterol intermediate.

13. The method according to claim 12, wherein the Δ8 sterol intermediate is 5α-cholest-8-(9)-en-3β-ol (Δ8 -cholesetenol).

14. The method according to claim 10, wherein the effective amount of the new EBP modulating anti-cancer compound is effective to cause downregulation of SREBP-2.

15. The method according to claim 10, wherein the effective amount of the new EBP modulating anti-cancer compound is effective to cause downregulation of one or more SREBP-2 target genes of the cholesterol biosynthetic pathway selected from the group consisting of ACAT2; MHGCS1; HMGCR; MVK; PMVK; MVD; ID11/ID12; FDFS; GGPS1; FDFT1; SQLE; LSS; CYPS1A1; TM75F2; SCAMOL; NSDHL; HSD17B7; EBP; SC5D; DHCR7; and DHCR24.

16. The method according to claim 1, wherein the EBP enzyme activity is measured by the amount of the accumulated Δ8 sterol intermediate, and the cholesterol synthesis rate is determined by the rate of $^{14}$C labeled acetate converted to cholesterol.

17. The method according to claim 10, wherein the cholesterol synthesis rate is determined by the rate of $^{14}$C labeled acetate converted to cholesterol.

18. The method according to claim 10, wherein the cancer cell sensitive to the known EBP-modulating anti-cancer compound comprises a truncated APC protein.

19. The method according to claim 10, wherein the therapeutic amount of the top-ranked candidate EBP-modulating anti-cancer compound is effective to reduce proliferation of the cancer cell sensitive to the EBP modulating anti-cancer compound, to reduce invasiveness of the cancer cell sensitive to the EBP modulating anti-cancer compound, increase apoptosis of the cancer cell sensitive to the EBP modulating anti-cancer compound, reduce growth of a tumor comprising the cancer cell sensitive to the EBP modulating anti-cancer compound, reduce tumor burden, improve progression free survival, improve overall survival, achieve remission of disease, or a combination thereof.

* * * * *